US010829777B2

(12) United States Patent
Karchi et al.

(10) Patent No.: US 10,829,777 B2
(45) Date of Patent: Nov. 10, 2020

(54) METHODS OF INCREASING ABIOTIC STRESS TOLERANCE AND/OR BIOMASS IN PLANTS AND PLANTS GENERATED THEREBY

(71) Applicant: Evogene Ltd., Rehovot (IL)

(72) Inventors: Hagai Karchi, Moshav Sitriya (IL); Gil Ronen, Emek Hefer (IL); Rodrigo Yelin, Zur-Yigal (IL); Larisa Rabinovich, Rishon-LeZion (IL)

(73) Assignee: Evogene Ltd., Rehovot (IL)

( * ) Notice: Subject to any disclaimer, the term of this patent is extended or adjusted under 35 U.S.C. 154(b) by 0 days.

(21) Appl. No.: 16/271,934

(22) Filed: Feb. 11, 2019

(65) Prior Publication Data

US 2019/0161767 A1 May 30, 2019

Related U.S. Application Data

(60) Division of application No. 15/256,641, filed on Sep. 5, 2016, now Pat. No. 10,214,749, which is a division of application No. 13/019,317, filed on Feb. 2, 2011, now Pat. No. 9,487,796, which is a continuation of application No. 11/990,386, filed as application No. PCT/IL2006/000947 on Aug. 15, 2006, now Pat. No. 7,910,800.

(60) Provisional application No. 60/707,957, filed on Aug. 15, 2005.

(51) Int. Cl.
*C12N 15/82* (2006.01)
*C07K 14/415* (2006.01)

(52) U.S. Cl.
CPC ........ *C12N 15/8273* (2013.01); *C07K 14/415* (2013.01); *C12N 15/8237* (2013.01); *C12N 15/8261* (2013.01); *C12N 15/8271* (2013.01)

(58) Field of Classification Search
None
See application file for complete search history.

(56) References Cited

U.S. PATENT DOCUMENTS

| | | | | |
|---|---|---|---|---|
| 6,084,153 | A | 7/2000 | Good et al. | |
| 7,910,800 | B2 | 3/2011 | Karchi et al. | |
| 2002/0046419 | A1 | 4/2002 | Choo et al. | |
| 2004/0034888 | A1 | 2/2004 | Liu et al. | |
| 2004/0172684 | A1 | 9/2004 | Kovalic et al. | |
| 2005/0108791 | A1 | 5/2005 | Edgerton | |
| 2006/0123516 | A1 * | 6/2006 | Ronen | C07K 14/415 800/289 |
| 2006/0179511 | A1 | 8/2006 | Chomet et al. | |
| 2007/0271633 | A9 * | 11/2007 | Kovalic | C07H 21/04 800/284 |
| 2009/0089898 | A1 | 4/2009 | Karchi et al. | |
| 2017/0051303 | A1 | 2/2017 | Karchi et al. | |

FOREIGN PATENT DOCUMENTS

| | | |
|---|---|---|
| AU | 2005234725 | 12/2005 |
| AU | 2006281018 | 2/2007 |
| EP | 1225231 | 7/2002 |
| EP | 1945021 | 7/2008 |
| WO | WO 2004/081173 | 9/2004 |
| WO | WO 2004/104162 | 12/2004 |
| WO | WO 2004/111183 | 12/2004 |
| WO | WO 2005/121364 | 12/2005 |
| WO | WO 2007/020638 | 2/2007 |
| WO | WO 2007/049275 | 5/2007 |
| WO | WO 2008/075364 | 6/2008 |
| WO | WO 2008/122980 | 10/2008 |
| WO | WO 2009/013750 | 1/2009 |
| WO | WO 2009/083958 | 7/2009 |
| WO | WO 2009/141824 | 11/2009 |
| WO | WO 2010/020941 | 2/2010 |
| WO | WO 2010/049897 | 5/2010 |
| WO | WO 2010/076756 | 7/2010 |
| WO | WO 2010/100595 | 9/2010 |
| WO | WO 2010/143138 | 12/2010 |
| WO | WO 2011/015985 | 2/2011 |
| WO | WO 2011/080674 | 7/2011 |
| WO | WO 2011/135527 | 11/2011 |
| WO | WO 2012/028993 | 3/2012 |
| WO | WO 2012/085862 | 6/2012 |
| WO | WO 2012/150598 | 11/2012 |
| WO | WO 2013/027223 | 2/2013 |
| WO | WO 2013/078153 | 5/2013 |
| WO | WO 2013/080203 | 6/2013 |
| WO | WO 2013/098819 | 7/2013 |
| WO | WO 2013/128448 | 9/2013 |
| WO | WO 2013/179211 | 12/2013 |
| WO | WO 2014/033714 | 3/2014 |
| WO | WO 2014/102773 | 7/2014 |

(Continued)

OTHER PUBLICATIONS

Wells (Biochemistry 29:8509-8517, 1990).*
Guo et al. (PNAS, 101: 9205-9210, 2004 ).*
Ngo et al., (The Protein Folding Problem and Tertiary Structure Prediction, K. Merz., and S. Le Grand (eds.) pp. 492-495,1994).*
Thornton et al. (Nature structural Biology, structural genomics supplement, Nov. 2000).*
Keskin et al. (Protein Science, 13:1043-1055, 2004).*

(Continued)

*Primary Examiner* — Vinod Kumar

(57) ABSTRACT

Isolated polynucleotides having a nucleic acid sequence at least 80% homologous to SEQ ID NO:1, 3, 5, 7, 9, 11, 158, 159, 160, 161, 162-204, 206-211, 214-287 and/or encoding polypeptides having an amino acid sequence at least 80% homologous to SEQ ID NO: 2, 4, 6, 8, 10, 12, 13-56, 58-63, 66-121, 141-156 or 157 are provided. Also provided are methods of utilizing same for increasing the tolerance of a plant to abiotic stresses and/or increasing the biomass, vigor and/or yield of a plant.

14 Claims, 2 Drawing Sheets

Specification includes a Sequence Listing.

(56) References Cited

FOREIGN PATENT DOCUMENTS

| | | |
|---|---|---|
| WO | WO 2014/102774 | 7/2014 |
| WO | WO 2014/188428 | 11/2014 |
| WO | WO 2015/029031 | 3/2015 |
| WO | WO 2015/181823 | 12/2015 |
| WO | WO 2016/030885 | 3/2016 |
| WO | WO 2017/115353 | 7/2017 |

OTHER PUBLICATIONS

Communication Pursuant to Article 94(3) EPC dated Apr. 3, 2012 From the European Patent Office Re. Application No. 06766224.7.
Communication Pursuant to Article 94(3) EPC dated May 12, 2010 From the European Patent Office Re. Application No. 06766224.7.
Communication Pursuant to Article 94(3) EPC dated Jun. 18, 2014 From the European Patent Office Re. Application No. 06766224.7.
Communication Pursuant to Rule 19(1) EPC dated Mar. 21, 2016 From the European Patent Office Re. Application No. 15186277.8.
Examination Report dated Dec. 9, 2014 From the Institute Mexicano de la Propiedad Industrial Re. Application No. MX/a/2011/007294.
Examination Report dated Jan. 9, 2017 From the Instituto Mexicano de la Propiedad Industrial, IMPI Re. Application No. MX/a/2012/010484 and Its Translation Into English. (6 Pages).
Examination Report dated Jun. 11, 2012 From the Instituto Mexicano de la Propiedad Industrial Re. Application No. MX/a/2011/007294 and Summary in English.
Examination Report dated Apr. 19, 2011 From the Instituto Mexicano de la Propiedad Industrial Re. Application No. MX/a/2011/007294 and Summary in English.
Examination Report dated Jun. 20, 2013 From the Instituto Mexicano de la Propiedad Industrial Re. Application No. MX/a/2011/007294 and Its Translation Into English.
Examination Report dated Mar. 25, 2014 From the Instituto Mexicano de la Propiedad Industrial Re. Application No. MX/a/2011/007294 and Its Translation Into English.
Examination Report dated Jul. 27, 2016 From the Instituto Mexicano de la Propiedad industrial, IMPI Re. Application No. MX/a/2012/010484 and Its Translation Into English.
Examination Report dated Jul. 30, 2014 From the Government of India, Patent Office, Intellectual Property Building Re. Application No. 1286/CHENP/2008.
Examiner's Report dated Oct. 19, 2011 From the Australian Government, IP Australia Re. Application No. 2006281018.
Examiner's Report dated Jun. 24, 2011 From the Australian Government, IP Australia Re. Applicarion No. 2006281018.
Examiner's Report dated Jan. 31, 2012 From the Australian Government, IP Australia Re. Application No. 2006281018.
Hearing Notice in Reference of Application No. 1286/CHENP/2008 dated Aug. 5, 2016 From the Government of India, Patent Office, Intellectual Property Building Re. Application No. 1286/CHENP/2008.
International Preliminary Report on Patentability dated Jan. 22, 2009 From the International Bureau of WIPO Re. Application No. PCT/IL2006/000947.
International Search Report dated Aug. 27, 2008 From the International Searching Authority Re.: Application No. PCT/IL06/00947.
Notice of Non-Compliant Amendment dated Jun. 22, 2015 From the US Patent and Trademark Office Re. U.S. Appl. No. 13/019,317.
Office Action dated Oct. 28, 2013 From the State Intellectual Property Office of the People's Republic of China Re. Application No. 201110104274.1 and Its Translation Into English.
Official Action dated May 15, 2009 From the US Patent and Trademark Office Re. U.S. Appl. No. 11/990,386.
Official Action dated Jul. 16, 2018 From the US Patent and Trademark Office Re. U.S. Appl. No. 15/256,641. (39 pages).
Official Action dated Dec. 22, 2014 From the US Patent and Trademark Office Re. U.S. Appl. No. 13/019,317.
Official Action dated Oct. 22, 2009 From the US Patent and Trademark Office Re. U.S. Appl. No. 11/990,386.
Official Action dated Aug. 24, 2015 From the US Patent and Trademark Office Re. U.S. Appl. No. 13/019,317.
Patent Examination Report dated Jun. 17, 2015 From the Australian Government, IP Australia Re. Application No. 2014203601.
Patent Examination Report dated Jun. 21, 2013 From the Australian Government, IP Australia Re. Application No. 2012241091.
Patent Examination Report dated Dec. 23, 2015 From the Australian Government, IP Australia Re. Application No. 2014203601.
Patent Examination Report dated Feb. 24, 2014 From the Australian Government, IP Australia Re. Application No. 2012241091.
Requisition by the Examiner dated Aug. 7, 2015 From the Canadian Intellectual Property Office Re. Application No. 2,619,114.
Requisition by the Examiner dated Feb. 7, 2017 From the Canadian Intellectual Property Office Re. Application No. 2,619,114.
Requisition by the Examiner dated Mar. 17, 2014 From the Canadian Intellectual Property Office Re. Application No. 2,619,114.
Requisition by the Examiner dated Mar. 22, 2018 From the Innovation, Science and Economic Development Canada, Canadian Intellectual Property Office Re. Application No. 2,619,114. (4 Pages).
Requisition by the Examiner dated Mar. 25, 2013 From the Canadian Intellectual Property Office Re. Application No. 2,619,114.
Restriction Official Action dated Sep. 15, 2014 From the US Patent and Trademark Office Re. U.S. Appl. No. 13/019,317.
Restriction Official Action dated Apr. 23, 2018 From the US Patent and Trademark Office Re. U.S. Appl. No. 15/256,641. (7 pages).
Supplementary European Search Report and the European Search Opinion dated Feb. 1, 2010 From the European Patent Office Re. Application No. 06766224.7.
Translation dated Jan. 6, 2015 of Examination Report dated Dec. 9, 2014 From the Instituto Mexicano de la Propiedad Industrial Re. Application No. MX/a/2011/007294.
Translation of Office Action dated Jan. 17, 2012 From the State Intellectual Property Office of the People's Republic of China Re. Application No. 201110104274.1.
Translation of Office Action dated Jan. 17, 2013 From the State Intellectual Property Office of the People's Republic of China Re. Application No. 201110104274.1.
Translation of Office Action dated Oct. 19, 2010 From the State Intellectual Property Office of the People's Republic of China Re. Application No. 200680038391.X.
Translation of Search Report dated Jan. 17, 2013 From the State Intellectual Property Office of the People's Republic of China Re. Application No. 201110104274.1.
Written Opinion dated Aug. 27, 2008 From the International Searching Authority Re.: Application No. PCT/IL06/00947.
Cheng et al. "RecName: Full=Probable Aquaporin TIP4-1; AltName: Full=Tonoplast Intrinsic Protein 4-1; Short=OsTIP4;1 [*Oryza sativa* Japonica Group]", NCBI Database UniProtKB/Swiss-Prot [Online], Locus: TIP41_ORYSJ, GenBank Sequence UniProtKB/Swiss-Prot: Q75GA5.1, Database Accession No. Q75GA5, Oct. 29, 2014.
Guo et al. "Protein Tolerance to Random Amino Acid Change", Proc. Natl. Acad. Sci. USA, PNAS, 101(25): 9205-9210, Jun. 22, 2004.
Invitrogen "SuperScript® Plasmid System With Gateway® Technology for cDNA Synthesis and Cloning", Invitrogen by Life Technologies, User Manual, Catalog No. 18248-013, Manual Part No. 11108, 44 P., Dec. 22, 2010.
Kaldenhoff et al. "Functional Aquaporin Diversity in Plants", Biochimica et Biophysica Acta, 1758: 1134-1141, Available Online Apr. 5, 2006.
Keskin et al. "A New, Structurally Nonredundant, Diverse Data Set of Protein-Protein Interfaces and Its Implications", Protein Science, 13: 1043-1055, 2004.
Kikuchi et al. "*Oryza sativa* Japonica Group cDNA Clone:J023131004, Full Insert Sequence", GenBank Database Accession No. AK072531, Jul. 2, 2013.
Ngo et al. "Computational Complexity, Protein Structure Prediction, and the Levinthal Paradox", The Protein Folding Problem and Tertiary Structure Prediction, Chap.14: 433, 492-495, 1994.
Nuccio et al. "Metabolic Engineering of Plants for Osmotic Stress Resistance", Current Opinion in Plant Biology, XP002216348, 2(2): 128-134, Apr. 1, 1999.

(56) References Cited

OTHER PUBLICATIONS

Thornton et al. "From Structure to Function: Approaches and Limitations", Nature Structural Biology—Structural Genomic Supplement, 7(Suppl.): 991-994, Nov. 2000.
Wells "Additivity of Mutational Effects in Proteins", Biochemistry, 29(37): 8509-8517, Sep. 18, 1990.
Yanagisawa et al. "Metabolic Engineering With Dof1 Transcription Factor in Plants: Improved Nitrogen Assimilation and Growth Under Low-Nitrogen Conditions", Proc. Natl. Acad. Sci USA, PNAS, 101(20): 7833-7838, May 18, 2004.
Formal Office Action dated Mar. 29, 2019 from National Institute of Industrial Property of Brazil Re. Application No. PI061523-0. (2 pages).
Requisition by the Examiner dated Dec. 30, 2019 From the Canadian Intellectual Property Office Re. Application No. 3,034,043. (3 pages).
Search Report dated Sep. 10, 2019 from National Institute of Industrial Property of Brazil Re. Application No. PI0616523-0 and its Summary in English. (5 pages).
Rensink et al. "EM_EST: CK263168. SV 1; Linear; mRNA; EST; PLN; 710 BP" Published Dec. 13, 2013, 2 pages.

* cited by examiner

METHODS OF INCREASING ABIOTIC STRESS TOLERANCE AND/OR BIOMASS IN PLANTS AND PLANTS GENERATED THEREBY

RELATED APPLICATIONS

This application is a division of U.S. patent application Ser. No. 15/256,641 filed on Sep. 5, 2016, which is a division of U.S. patent application Ser. No. 13/019,317 filed on Feb. 2, 2011, now U.S. Pat. No. 9,487,796, which is a continuation of U.S. patent application Ser. No. 11/990,386 filed on Feb. 13, 2008, now U.S. Pat. No. 7,910,800, which is a National Phase of PCT Patent Application No. PCT/IL2006/000947 having International Filing Date of Aug. 15, 2006, which claims the benefit of priority of U.S. Provisional Patent Application No. 60/707,957 filed on Aug. 15, 2005. The contents of the above applications are all incorporated by reference as if fully set forth herein in their entirety.

SEQUENCE LISTING STATEMENT

The ASCII file, entitled 76591SequenceListing.txt, created on Jan. 16, 2019, comprising 454,107 bytes, submitted concurrently with the filing of this application is incorporated herein by reference.

FIELD AND BACKGROUND OF THE INVENTION

The present invention relates to methods of increasing abiotic stress tolerance and/or biomass in plants and, more particularly, to plants expressing exogenous abiotic stress-tolerance genes.

Abiotic stress (also referred to as "environmental stress") conditions such as salinity, drought, flood, suboptimal temperature and toxic chemical pollution, cause substantial damage to agricultural plants. Most plants have evolved strategies to protect themselves against these conditions. However, if the severity and duration of the stress conditions are too great, the effects on plant development, growth and yield of most crop plants are profound. Furthermore, most of the crop plants are very susceptible to abiotic stress (ABS) and thus necessitate optimal growth conditions for commercial crop yields. Continuous exposure to stress causes major alterations in the plant metabolism which ultimately lead to cell death and consequently yield losses. Thus, despite extensive research and the use of sophisticated and intensive crop-protection measures, losses due to abiotic stress conditions remain in the billions of dollars annually (1,2).

The following summarizes the implications of exemplary abiotic stress conditions.

Problems associated with drought. A drought is a period of abnormally dry weather that persists long enough to produce a serious hydrologic imbalance (for example crop damage, water supply shortage, etc.). While much of the weather that we experience is brief and short-lived, drought is a more gradual phenomenon, slowly taking hold of an area and tightening its grip with time. In severe cases, drought can last for many years and can have devastating effects on agriculture and water supplies. With burgeoning population and chronic shortage of available fresh water, drought is not only the number one weather related problem in agriculture, it also ranks as one of the major natural disasters of all time, causing not only economic damage, but also loss of human lives. For example, losses from the US drought of 1988 exceeded $40 billion, exceeding the losses caused by Hurricane Andrew in 1992, the Mississippi River floods of 1993, and the San Francisco earthquake in 1989. In some areas of the world, the effects of drought can be far more severe. In the Horn of Africa the 1984-1985 drought led to a famine that killed 750,000 people.

Problems for plants caused by low water availability include mechanical stresses caused by the withdrawal of cellular water. Drought also causes plants to become more susceptible to various diseases (Simpson (1981). "The Value of Physiological Knowledge of Water Stress in Plants", In Water Stress on Plants, (Simpson, G. M., ed.), Praeger, N.Y., pp. 235-265).

In addition to the many land regions of the world that are too arid for most if not all crop plants, overuse and over-utilization of available water is resulting in an increasing loss of agriculturally-usable land, a process which, in the extreme, results in desertification. The problem is further compounded by increasing salt accumulation in soils, as described above, which adds to the loss of available water in soils.

Problems associated with high salt levels. One in five hectares of irrigated land is damaged by salt, an important historical factor in the decline of ancient agrarian societies. This condition is only expected to worsen, further reducing the availability of arable land and crop production, since none of the top five food crops—wheat, corn, rice, potatoes, and soybean—can tolerate excessive salt.

Detrimental effects of salt on plants are a consequence of both water deficit resulting in osmotic stress (similar to drought stress) and the effects of excess sodium ions on critical biochemical processes. As with freezing and drought, high saline causes water deficit; the presence of high salt makes it difficult for plant roots to extract water from their environment (Buchanan et al. (2000) in Biochemistry and Molecular Biology of Plants, American Society of Plant Physiologists, Rockville, Md.). Soil salinity is thus one of the more important variables that determines where a plant may thrive. In many parts of the world, sizable land areas are uncultivable due to naturally high soil salinity. To compound the problem, salination of soils that are used for agricultural production is a significant and increasing problem in regions that rely heavily on agriculture. The latter is compounded by over-utilization, over-fertilization and water shortage, typically caused by climatic change and the demands of increasing population. Salt tolerance is of particular importance early in a plant's lifecycle, since evaporation from the soil surface causes upward water movement, and salt accumulates in the upper soil layer where the seeds are placed. Thus, germination normally takes place at a salt concentration much higher than the mean salt level in the whole soil profile.

Problems associated with excessive heat. Germination of many crops is very sensitive to temperature. A gene that would enhance germination in hot conditions would be useful for crops that are planted late in the season or in hot climates. Seedlings and mature plants that are exposed to excess heat may experience heat shock, which may arise in various organs, including leaves and particularly fruit, when transpiration is insufficient to overcome heat stress. Heat also damages cellular structures, including organelles and cytoskeleton, and impairs membrane function [Buchanan et al. (2000) in Biochemistry and Molecular Biology of Plants, American Society of Plant Physiologists, Rockville, Md. Heat shock may produce a decrease in overall protein synthesis, accompanied by expression of heat shock proteins. Heat shock proteins function as chaperones and are involved in refolding proteins denatured by heat.

Heat stress often accompanies conditions of low water availability. Heat itself is seen as an interacting stress and adds to the detrimental effects caused by water deficit conditions. Evaporative demand exhibits near exponential increases with increases in daytime temperatures and can result in high transpiration rates and low plant water potentials [Hall et al. (2000) Plant Physiol. 123: 1449-1458]. High-temperature damage to pollen almost always occurs in conjunction with drought stress, and rarely occurs under well-watered conditions. Thus, separating the effects of heat and drought stress on pollination is difficult. Combined stress can alter plant metabolism in novel ways; therefore understanding the interaction between different stresses may be important for the development of strategies to enhance stress tolerance by genetic manipulation.

Problems associated with excessive chilling conditions. The term "chilling sensitivity" has been used to describe many types of physiological damage produced at low, but above freezing, temperatures. Most crops of tropical origins, such as soybean, rice, maize, and cotton are easily damaged by chilling. Typical chilling damage includes wilting, necrosis, chlorosis or leakage of ions from cell membranes. The underlying mechanisms of chilling sensitivity are not completely understood yet, but probably involve the level of membrane saturation and other physiological deficiencies. For example, photoinhibition of photosynthesis (disruption of photosynthesis due to high light intensities) often occurs under clear atmospheric conditions subsequent to cold late summer/autumn nights. For example, chilling may lead to yield losses and lower product quality through the delayed ripening of maize. Another consequence of poor growth is the rather poor ground cover of maize fields in spring, often resulting in soil erosion, increased occurrence of weeds, and reduced uptake of nutrients. A retarded uptake of mineral nitrogen could also lead to increased losses of nitrate into the ground water. By some estimates, chilling accounts for monetary losses in the United States (US) behind only to drought and flooding.

Water deficit is a common component of many plant stresses. Water deficit occurs in plant cells when the whole plant transpiration rate exceeds the water uptake. In addition to drought, other stresses, such as salinity and low temperature, produce cellular dehydration (McCue and Hanson (1990) Trends Biotechnol. 8: 358-362).

Salt and drought stress signal transduction consist of ionic and osmotic homeostasis signaling pathways. The ionic aspect of salt stress is signaled via the SOS pathway where a calcium-responsive SOS3-SOS2 protein kinase complex controls the expression and activity of ion transporters such as SOS1. The pathway regulating ion homeostasis in response to salt stress has been reviewed recently by Xiong and Zhu (2002) Plant Cell Environ. 25: 131-139.

The osmotic component of salt stress involves complex plant reactions that overlap with drought and/or cold stress responses.

Common aspects of drought, cold and salt stress response have been reviewed recently by Xiong and Zhu (2002) supra). Those include:

(a) transient changes in the cytoplasmic calcium levels very early in the signaling event (Knight, (2000) Int. Rev. Cytol. 195: 269-324; Sanders et al. (1999) Plant Cell 11: 691-706);

(b) signal transduction via mitogen-activated and/or calcium dependent protein kinases (CDPKs; see Xiong et al., 2002) and protein phosphatases (Merlot et al. (2001) Plant J. 25: 295-303; Tahtiharju and Palva (2001) Plant J. 26: 461-470);

(c) increases in abscisic acid levels in response to stress triggering a subset of responses (Xiong et al. (2002) supra, and references therein);

(d) inositol phosphates as signal molecules (at least for a subset of the stress responsive transcriptional changes (Xiong et al. (2001) Genes Dev. 15: 1971-1984);

(e) activation of phospholipases which in turn generate a diverse array of second messenger molecules, some of which might regulate the activity of stress responsive kinases (phospholipase D functions in an ABA independent pathway, Frank et al. (2000) Plant Cell 12: 111-124); [0026] (f) induction of late embryogenesis abundant (LEA) type genes including the CRT/DRE responsive COR/RD genes (Xiong and Zhu (2002) supra);

(g) increased levels of antioxidants and compatible osmolytes such as proline and soluble sugars (Hasegawa et al. (2000) Annu. Rev. Plant Mol. Plant Physiol. 51: 463-499); and [0028] (h) accumulation of reactive oxygen species such as superoxide, hydrogen peroxide, and hydroxyl radicals (Hasegawa et al. (2000) supra).

Abscisic acid biosynthesis is regulated by osmotic stress at multiple steps. Both ABA-dependent and -independent osmotic stress signaling first modify constitutively expressed transcription factors, leading to the expression of early response transcriptional activators, which then activate downstream stress tolerance effector genes.

Based on the commonality of many aspects of cold, drought and salt stress responses, it can be concluded that genes that increase tolerance to cold or salt stress can also improve drought stress protection. In fact this has already been demonstrated for transcription factors (in the case of AtCBF/DREB1) and for other genes such as OsCDPK7 (Saijo et al. (2000) Plant J. 23: 319-327), or AVP1 (a vacuolar pyrophosphatase-proton—pump, Gaxiola et al. (2001) Proc. Natl. Acad. Sci. USA 98: 11444-11449).

Developing stress-tolerant plants is a strategy that has the potential to solve or mediate at least some of these problems. However, traditional plant breeding strategies used to develop new lines of plants that exhibit tolerance to ABS are relatively inefficient since they are tedious, time consuming and of unpredictable outcome. Furthermore, limited germplasm resources for stress tolerance and incompatibility in crosses between distantly related plant species represent significant problems encountered in conventional breeding. Additionally, the cellular processes leading to ABS tolerance are complex in nature and involve multiple mechanisms of cellular adaptation and numerous metabolic pathways (4-7).

Genetic engineering efforts, aimed at conferring abiotic stress tolerance to transgenic crops, have been described in the prior art. Studies by Apse and Blumwald (Curr Opin Biotechnol. 13:146-150, 2002), Quesada et al. (Plant Physiol. 130:951-963, 2002), Holmstrom et al. (Nature 379: 683-684, 1996), Xu et al. (Plant Physiol 110: 249-257, 1996), Pilon-Smits and Ebskamp (Plant Physiol 107: 125-130, 1995) and Tarczynski et al. (Science 259: 508-510, 1993) have all attempted at generating stress tolerant plants.

In addition, several U.S. patents and patent applications also describe polynucleotides associated with stress tolerance and their use in generating stress tolerant plants. U.S. Pat. Nos. 5,296,462 and 5,356,816 describe transforming plants with polynucleotides encoding proteins involved in cold adaptation in *Arabidopsis thaliana*, to thereby promote cold tolerance in the transformed plants.

U.S. Pat. No. 6,670,528 describes transforming plants with polynucleotides encoding polypeptides binding to stress responsive elements, to thereby promote tolerance of the transformed plants to abiotic stress.

U.S. Pat. No. 6,720,477 describes transforming plants with a polynucleotide encoding a signal transduction stress-related protein, capable of increasing tolerance of the transformed plants to abiotic stress.

U.S. application Ser. Nos. 09/938,842 and 10/342,224 describe abiotic stress-related genes and their use to confer upon plants tolerance to abiotic stress.

U.S. application Ser. No. 10/231,035 describes overexpressing a molybdenum cofactor sulfurase in plants to thereby increase their tolerance to abiotic stress.

Although the above described studies were at least partially successful in generating stress tolerant plants, there remains a need for stress tolerant genes which can be utilized to generate plants tolerant of a wide range of abiotic stress conditions.

While reducing the present invention to practice, the present inventors have identified through bioinformatic and laboratory studies several novel abiotic stress-tolerance genes, which can be utilized to increase tolerance to abiotic stress and/or biomass, vigor and yield in plants.

SUMMARY OF THE INVENTION

According to one aspect of the present invention there is provided a method of increasing tolerance of a plant to an abiotic stress, comprising expressing within the plant an exogenous polynucleotide encoding a polypeptide having an amino acid sequence at least 90% homologous to SEQ ID NO: 2, 4, 6, 8, 10, 12, 13-56, 58-63, 66-119, 139-154 or 155 thereby increasing the tolerance of the plant to the abiotic stress.

According to still further features in the described preferred embodiments the abiotic stress is selected from the group consisting of salinity, water deprivation, low temperature, high temperature, heavy metal toxicity, anaerobiosis, nutrient deficiency, nutrient excess, atmospheric pollution and UV irradiation.

According to another aspect of the present invention there is provided a method of increasing biomass, vigor and/or yield of a plant, comprising expressing within the plant an exogenous polynucleotide encoding a polypeptide having an amino acid sequence at least 90% homologous to SEQ ID NO: 2, 4, 6, 8, 10, 12, 13-56, 58-63, 66-119, 139-154 or 155, thereby increasing biomass, vigor and/or yield of the plant.

According to still further features in the described preferred embodiments the expressing is effected by:

(a) transforming a cell of the plant with the exogenous polynucleotide;
(b) generating a mature plant from the cell; and
(c) cultivating the mature plant under conditions suitable for expressing the exogenous polynucleotide within the mature plant.

According to still further features in the described preferred embodiments the transforming is effected by introducing to the plant cell a nucleic acid construct including the exogenous polynucleotide and at least one promoter capable of directing transcription of the exogenous polynucleotide in the plant cell.

According to yet another aspect of the present invention there is provided a nucleic acid construct, comprising a nucleic acid sequence at least 90% identical to a nucleotide sequence selected from the group consisting of SEQ ID NOs: 1, 3, 5, 7, 9, 11, 156, 157, 158, 159, 160-202, 204-209, 212-285 and a promoter capable of directing transcription of the nucleic acid sequence in a host cell.

According to still further features in the described preferred embodiments the promoter is a constitutive promoter.

According to still further features in the described preferred embodiments the constitutive promoter is CaMV 35S promoter.

According to still further features in the described preferred embodiments the constitutive promoter is At6669 promoter.

According to still further features in the described preferred embodiments the promoter is an inducible promoter.

According to still further features in the described preferred embodiments the inducible promoter is an abiotic stress inducible promoter.

According to still further features in the described preferred embodiments the host cell is a plant cell.

According to still further features in the described preferred embodiments the plant cell forms a part of a dicotyledonous plant cell.

According to still further features in the described preferred embodiments the plant cell forms a part of a monocotyledonous plant cell.

According to still another aspect of the present invention there is provided an isolated polypeptide, comprising an amino acid sequence at least 90% homologous to the amino acid sequence encoded by a polynucleotide selected from the group consisting of SEQ ID NOs: 1, 3, 5, 7, 9, 11, 156, 157, 158, 159, 160-202, 204-209, 212-285.

According to still further features in the described preferred embodiments the amino acid sequence is at least 90% homologous to SEQ ID NO: 2, 4, 6, 8, 10, 12, 13-56, 58-63, 66-119, 139-154 or 155.

According to an additional aspect of the present invention there is provided a plant cell comprising an exogenous polynucleotide encoding a polypeptide having an amino acid sequence at least 90% homologous to SEQ ID NO: 2, 4, 6, 8, 10, 12, 13-56, 58-63, 66-119, 139-154 or 155 thereby increasing the tolerance of the plant to the abiotic stress.

According to still further features in the described preferred embodiments the plant cell forms a part of a plant.

The present invention successfully addresses the shortcomings of the presently known configurations by providing methods of utilizing novel abiotic stress-tolerance genes to increase plants tolerance to abiotic stress and/or biomass.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE SEVERAL VIEWS OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

FIG. 2A—Plants grown under non-stressing conditions for 7-10 days were transferred to high osmoticum conditions and their growth was followed for 12 days using digital imaging. Processed images of pictures taken at Day 0, Day 5 and Day 12 are shown. Note the control plants in the upper center of each plate and the independent transgenic events surrounding the control plants. FIG. 2B is a graph that describes plant area growth as a function of time using the images shown in panel A. Four of the five events shown are able to grow significantly faster than the wild-type control plants under the same conditions. Statistical analysis of the results is shown further below in Table 5 rows 1-5.

DESCRIPTION OF SPECIFIC EMBODIMENTS OF THE INVENTION

Figure 1:
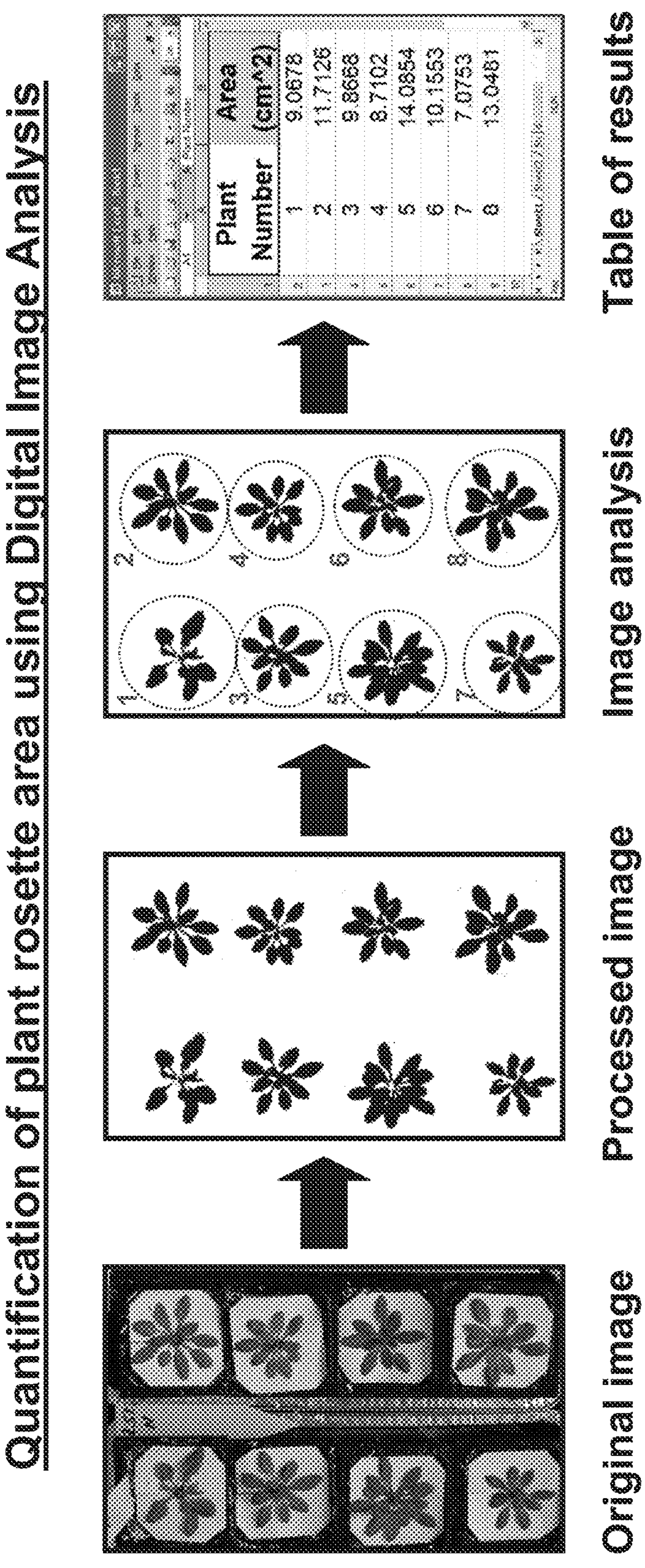
FIG. 1 is a schematic illustration of the methodology used to measure plants' size. Digital pictures are taken using uniform illumination and a tripod set a constant distance. The digital pictures obtained are processed using a "green-based" filter that removes the "non-green parts" of the picture leaving only the plant rosette area for quantification. Following quantification of the rosette area, results are exported to a spreadsheet and analyzed using statistical software.

The present invention is of methods of increasing plants tolerance to abiotic stress and/or biomass by utilizing novel abiotic stress tolerance genes and of plants exhibiting increased tolerance to stress conditions and/or increased capacity to accumulate biomass.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Whilst reducing the present invention to practice, the present inventors while employing bioinformatic techniques, identified polynucleotide sequences which encode putative abiotic-stress tolerance (ABST) proteins (Example 1). Selected sequences were isolated (Example 2), cloned into expression vectors (Example 3-4) and introduced into *Arabidopsis thaliana* plants (Example 5-6). These plants, were grown under salinity stress conditions, or under normal conditions, and checked for increased biomass as compared with similar control plants not carrying the exogenous ABST genes. As is evident from the results shown in Example 8, nucleic acid sequences selected according to the teachings of the present invention were shown to improve the tolerance of transgenic plants transfected therewith to abiotic stress as compared to control plants.

Thus, according to one aspect of the present invention, there is provided a method of increasing tolerance of a plant to an abiotic stress and/or plant biomass. The method includes expressing within the plant an exogenous polynucleotide encoding a polypeptide having an amino acid sequence at least 90% homologous to SEQ ID NO: 2, 4, 6, 8, 10, 12, 13-56, 58-63, 66-119, 139-154 or 155.

According to one preferred embodiment of this aspect of the present invention the isolated polynucleotide is as set forth is SEQ ID NO: 1, 3, 5, 7, 9, 11, 156, 157, 158, 159, 160-202, 204-209, 212-285.

Alternatively, the exogenous polynucleotide of the present invention encodes a polypeptide having an amino acid sequence as further described hereinbelow. at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, or more say 100% homologous to an amino acid sequence selected from the group consisting of SEQ ID NO: 2, 4, 6, 8, 10, 12, 13-56, 58-63, 66-119, 139-154 or 155.

The phrase "abiotic stress" used herein refers to any adverse effect on metabolism, growth, reproduction and/or viability of a plant. Accordingly, abiotic stress can be induced by suboptimal environmental growth conditions such as, for example, salinity, water deprivation, flooding, freezing, low or high temperature, heavy metal toxicity, anaerobiosis, nutrient deficiency, atmospheric pollution or UV irradiation. The implications of abiotic stress are discussed in the Background section.

The phrase "abiotic stress tolerance" as used herein refers to the ability of a plant to endure an abiotic stress without suffering a substantial alteration in metabolism, growth, productivity and/or viability. Preferably, the genetically engineered plants of the present invention exhibit at least about 2% more, 5% more, 10% more, 20% more, 30% more, 40% more, 50% more, 60% more, 70% more, 80% more, 90% more or even higher tolerance to abiotic stress than non-transgenic plants.

As used herein, the term "exogenous polynucleotide" refers to a nucleic acid sequence which is not naturally expressed within the plant but which, when introduced into the plant either in a stable or transient manner, produces at least one polypeptide product.

Homology (e.g., percent homology) can be determined using any homology comparison software, including for example, the BlastP software of the National Center of Biotechnology Information (NCBI) such as by using default parameters.

Identity (e.g., percent homology) can be determined using any homology comparison software, including for example, the BlastN software of the National Center of Biotechnology Information (NCBI) such as by using default parameters.

The polynucleotide of the present invention refers to a single or double stranded nucleic acid sequences which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase.

Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

Nucleic acid sequences of the polypeptides of the present invention may be optimized for expression. Such optimized sequences are provided in SEQ ID NOs: 156, 157, 158 and 159. Examples of such sequence modifications include, but are not limited to, an altered G/C content to more closely approach that typically found in the plant species of interest, and the removal of codons atypically found in the plant species commonly referred to as codon optimization.

The phrase "codon optimization" refers to the selection of appropriate DNA nucleotides for use within a structural gene or fragment thereof that approaches codon usage within the plant of interest. Therefore, an optimized gene or nucleic acid sequence refers to a gene in which the nucleotide sequence of a native or naturally occurring gene has been modified in order to utilize statistically-preferred or statistically-favored codons within the plant. The nucleotide sequence typically is examined at the DNA level and the coding region optimized for expression in the plant species determined using any suitable procedure, for example as described in Sardana et al. (1996, Plant Cell Reports 15:677-681). In this method, the standard deviation of codon usage, a measure of codon usage bias, may be calculated by first finding the squared proportional deviation of usage of each codon of the native gene relative to that of highly expressed plant genes, followed by a calculation of the average squared deviation. The formula used is: 1 SDCU=n=1 N [(Xn−Yn)/Yn] 2/N, where Xn refers to the frequency of usage of codon n in highly expressed plant genes, where Yn to the frequency of usage of codon n in the gene of interest and N refers to the total number of codons in the gene of interest. A table of codon usage from highly expressed genes of dicotyledonous plants is compiled using the data of Murray et al. (1989, Nuc Acids Res. 17:477-498).

One method of optimizing the nucleic acid sequence in accordance with the preferred codon usage for a particular plant cell type is based on the direct use, without performing any extra statistical calculations, of codon optimization tables such as those provided on-line at the Codon Usage Database through the NIAS (National Institute of Agrobiological Sciences) DNA bank in Japan (Hypertext Transfer Protocol://World Wide Web (dot) kazusa (dot) or (dot) jp/codon/). The Codon Usage Database contains codon usage tables for a number of different species, with each codon usage table having been statistically determined based on the data present in Genbank.

By using the above tables to determine the most preferred or most favored codons for each amino acid in a particular species (for example, rice), a naturally-occurring nucleotide sequence encoding a protein of interest can be codon optimized for that particular plant species. This is effected by replacing codons that may have a low statistical incidence in the particular species genome with corresponding codons, in regard to an amino acid, that are statistically more favored. However, one or more less-favored codons may be selected to delete existing restriction sites, to create new ones at potentially useful junctions (5' and 3' ends to add signal peptide or termination cassettes, internal sites that might be used to cut and splice segments together to produce a correct full-length sequence), or to eliminate nucleotide sequences that may negatively effect mRNA stability or expression.

The naturally-occurring encoding nucleotide sequence may already, in advance of any modification, contain a number of codons that correspond to a statistically-favored codon in a particular plant species. Therefore, codon optimization of the native nucleotide sequence may comprise determining which codons, within the native nucleotide sequence, are not statistically-favored with regards to a particular plant, and modifying these codons in accordance with a codon usage table of the particular plant to produce a codon optimized derivative. A modified nucleotide sequence may be fully or partially optimized for plant codon usage provided that the protein encoded by the modified nucleotide sequence is produced at a level higher than the protein encoded by the corresponding naturally occurring or native gene. Construction of synthetic genes by altering the codon usage is described in for example PCT Patent Application 93/07278.

Thus, the present invention encompasses nucleic acid sequences described hereinabove; fragments thereof, sequences hybridizable therewith, sequences homologous thereto, sequences encoding similar polypeptides with different codon usage, altered sequences characterized by mutations, such as deletion, insertion or substitution of one or more nucleotides, either naturally occurring or man induced, either randomly or in a targeted fashion.

The polynucleotides described above also encode previously uncharacterized polypeptides.

Thus the present invention provides a polypeptide having an amino acid sequence as further described hereinbelow. at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, or more say 100% homologous to an amino acid sequence selected from the group consisting of SEQ ID NO: 2, 4, 6, 8, 10, 12, 13-56, 58-63, 66-119, 139-154 or 155.

The present invention also encompasses fragments of the above described polypeptides and polypeptides having mutations, such as deletions, insertions or substitutions of one or more amino acids, either naturally occurring or man induced, either randomly or in a targeted fashion.

A suitable plant for use with the method of the present invention can be any monocotyledonous or dicotyledonous plant including, but not limited to, maize, wheat, barely, rye, oat, rice, soybean, peanut, pea, lentil and alfalfa, cotton, rapeseed, canola, pepper, sunflower, potato, tobacco, tomato, eggplant, *eucalyptus*, a tree, an ornamental plant, a perennial grass and a forage crop.

Expressing the exogenous polynucleotide of the present invention within the plant can be effected by transforming one or more cells of the plant with the exogenous polynucleotide, followed by generating a mature plant from the transformed cells and cultivating the mature plant under conditions suitable for expressing the exogenous polynucleotide within the mature plant.

Preferably, the transformation is effected by introducing to the plant cell a nucleic acid construct which includes the exogenous polynucleotide of the present invention and at least one promoter capable of directing transcription of the exogenous polynucleotide in the plant cell. Further details of suitable transformation approaches are provided hereinbelow.

As used herein, the term "promoter" refers to a region of DNA which lies upstream of the transcriptional initiation site of a gene to which RNA polymerase binds to initiate transcription of RNA. The promoter controls where (e.g., which portion of a plant, which organ within an animal, etc.) and/or when (e.g., which stage or condition in the lifetime of an organism) the gene is expressed.

Any suitable promoter sequence can be used by the nucleic acid construct of the present invention. Preferably the promoter is a constitutive promoter, a tissue-specific, or an abiotic stress-inducible promoter.

Suitable constitutive promoters include, for example, CaMV 35S promoter (SEQ ID NO: 120; Odell et al., Nature 313:810-812, 1985); *Arabidopsis* At6669 promoter (SEQ ID NO: 121, patent No WO2004/104162); maize Ubi 1 (Christensen et al., Plant Sol. Biol. 18:675-689, 1992); rice actin (McElroy et al., Plant Cell 2:163-171, 1990); pEMU (Last et al., Theor. Appl. Genet. 81:581-588, 1991); and Synthetic Super MAS (Ni et al., The Plant Journal 7: 661-76, 1995). Other constitutive promoters include those in U.S. Pat. Nos. 5,659,026, 5,608,149; 5,608,144; 5,604,121; 5,569,597: 5,466,785; 5,399,680; 5,268,463; and 5,608,142.

Suitable tissue-specific promoters include, but not limited to, leaf-specific promoters such as described, for example, by Yamamoto et al., Plant J. 12:255-265, 1997; Kwon et al., Plant Physiol. 105:357-67, 1994; Yamamoto et al., Plant Cell Physiol. 35:773-778, 1994; Gotor et al., Plant J. 3:509-18, 1993; Orozco et al., Plant Mol. Biol. 23:1129-1138, 1993; and Matsuoka et al., Proc. Natl. Acad. Sci. USA 90:9586-9590, 1993.

Suitable abiotic stress-inducible promoters include, but not limited to, salt-inducible promoters such as RD29A (Yamaguchi-Shinozalei et al., Mol. Gen. Genet. 236:331-340, 1993); drought-inducible promoters such as maize rab17 gene promoter (Pla et. al., Plant Mol. Biol. 21:259-266, 1993), maize rab28 gene promoter (Busk et. al., Plant J. 11:1285-1295, 1997) and maize Ivr2 gene promoter (Pelleschi et. al., Plant Mol. Biol. 39:373-380, 1999); and heat-inducible promoters such as heat tomato hsp80-promoter from tomato (U.S. Pat. No. 5,187,267).

The nucleic acid construct of the present invention preferably further includes an appropriate selectable marker and/or an origin of replication. Preferably, the nucleic acid construct utilized is a shuttle vector, which can propagate both in *E. coli* (wherein the construct comprises an appropriate selectable marker and origin of replication) and be compatible with propagation in cells. The construct according to the present invention can be, for example, a plasmid, a bacmid, a phagemid, a cosmid, a phage, a virus or an artificial chromosome.

The nucleic acid construct of the present invention can be utilized to stably or transiently transform plant cells. In stable transformation, the exogenous polynucleotide of the present invention is integrated into the plant genome and as such it represents a stable and inherited trait. In transient transformation, the exogenous polynucleotide is expressed by the cell transformed but it is not integrated into the genome and as such it represents a transient trait.

There are various methods of introducing foreign genes into both monocotyledonous and dicotyledonous plants (Potrykus, I., Annu. Rev. Plant. Physiol., Plant. Mol. Biol. (1991) 42:205-225; Shimamoto et al., Nature (1989) 338: 274-276).

The principle methods of causing stable integration of exogenous DNA into plant genomic DNA include two main approaches:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Arntzen, C. J., Butterworth Publishers, Boston, Mass. (1989) p. 93-112.

(ii) Direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of transgenic dicotyledonous plants.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Following stable transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the transformed plants.

Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

Preferably, mature transformed plants generated as described above are further selected for abiotic stress tolerance. Accordingly, transformed and non-transformed (wild type) plants are exposed to an abiotic stress condition, such as water depravation, suboptimal temperature, nutrient deficiency, or preferably a salt stress condition. Salt stress can be effected in many ways such as, for example, by irrigating the plants with a hyperosmotic solution, by cultivating the plants hydroponically in a hyperosmotic growth solution (e.g., Hoagland solution), or by culturing the plants in a hyperosmotic growth medium (e.g., MS medium). Since different plants vary considerably in their tolerance to salinity, the salt concentration in the irrigation water, growth solution, or growth medium is preferably adjusted according to the specific characteristics of the specific plant cultivar or variety, so as to inflict a mild or moderate effect on the physiology and/or morphology of the plants (for guidelines as to appropriate concentration please see, Bernstein and Kafkafi, Root Growth Under Salinity Stress In: Plant Roots, The Hidden Half 3rd ed. Waisel Y, Eshel A and Kafkafi U. (editors) Marcel Dekker Inc., New York, 2002, and reference therein). Following exposure to the stress condition the plants are frequently monitored until substantial physiological and/or morphological effects appear in wild type plants. Subsequently, transformed plants not exhibiting substantial physiological and/or morphological effects, or exhibiting higher biomass than wild-type plants, are identified as abiotic stress tolerant plants.

Although stable transformation is presently preferred, transient transformation of leaf cells, meristematic cells or the whole plant is also envisaged by the present invention.

Transient transformation can be effected by any of the direct DNA transfer methods described above or by viral infection using modified plant viruses.

Viruses that have been shown to be useful for the transformation of plant hosts include CaMV, TMV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants, is described in WO 87/06261.

Preferably, the virus of the present invention is avirulent and thus is incapable of causing severe symptoms such as reduced growth rate, mosaic, ring spots, leaf roll, yellowing, streaking, pox formation, tumor formation and pitting. A suitable avirulent virus may be a naturally occurring avirulent virus or an artificially attenuated virus. Virus attenuation may be effected by using methods well known in the art including, but not limited to, sub-lethal heating, chemical treatment or by directed mutagenesis techniques such as described, for example, by Kurihara and Watanabe (Molecular Plant Pathology 4:259-269, 2003), Gal-on et al. (1992), Atreya et al. (1992) and Huet et al. (1994).

Suitable virus strains can be obtained from available sources such as, for example, the American Type culture Collection (ATCC) or by isolation from infected plants. Isolation of viruses from infected plant tissues can be effected by techniques well known in the art such as described, for example by Foster and Tatlor, Eds. "Plant Virology Protocols: From Virus Isolation to Transgenic Resistance (Methods in Molecular Biology (Humana Pr), Vol 81)", Humana Press, 1998. Briefly, tissues of an infected plant believed to contain a high concentration of a suitable virus, preferably young leaves and flower petals, are ground in a buffer solution (e.g., phosphate buffer solution) to produce a virus infected sap which can be used in subsequent inoculations.

Construction of plant RNA viruses for the introduction and expression of non-viral exogenous polynucleotide sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; and Takamatsu et al. FEBS Letters (1990) 269:73-76.

When the virus is a DNA virus, suitable modifications can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

Construction of plant RNA viruses for the introduction and expression in plants of non-viral exogenous polynucleotide sequences such as those included in the construct of the present invention is demonstrated by the above references as well as in U.S. Pat. No. 5,316,931.

In one embodiment, a plant viral polynucleotide is provided in which the native coat protein coding sequence has been deleted from a viral polynucleotide, a non-native plant viral coat protein coding sequence and a non-native promoter, preferably the subgenomic promoter of the non-native coat protein coding sequence, capable of expression in the plant host, packaging of the recombinant plant viral polynucleotide, and ensuring a systemic infection of the host by the recombinant plant viral polynucleotide, has been inserted. Alternatively, the coat protein gene may be inactivated by insertion of the non-native polynucleotide sequence within it, such that a protein is produced. The recombinant plant viral polynucleotide may contain one or more additional non-native subgenomic promoters. Each non-native subgenomic promoter is capable of transcribing or expressing adjacent genes or polynucleotide sequences in the plant host and incapable of recombination with each other and with native subgenomic promoters. Non-native (foreign) polynucleotide sequences may be inserted adjacent the native plant viral subgenomic promoter or the native and a non-native plant viral subgenomic promoters if more than one polynucleotide sequence is included. The non-native polynucleotide sequences are transcribed or expressed in the host plant under control of the subgenomic promoter to produce the desired products.

In a second embodiment, a recombinant plant viral polynucleotide is provided as in the first embodiment except that the native coat protein coding sequence is placed adjacent one of the non-native coat protein subgenomic promoters instead of a non-native coat protein coding sequence.

In a third embodiment, a recombinant plant viral polynucleotide is provided in which the native coat protein gene is adjacent its subgenomic promoter and one or more non-native subgenomic promoters have been inserted into the viral polynucleotide. The inserted non-native subgenomic promoters are capable of transcribing or expressing adjacent genes in a plant host and are incapable of recombination with each other and with native subgenomic promoters. Non-native polynucleotide sequences may be inserted adjacent the non-native subgenomic plant viral promoters such that the sequences are transcribed or expressed in the host plant under control of the subgenomic promoters to produce the desired product.

In a fourth embodiment, a recombinant plant viral polynucleotide is provided as in the third embodiment except that the native coat protein coding sequence is replaced by a non-native coat protein coding sequence.

The viral vectors are encapsidated by the coat proteins encoded by the recombinant plant viral polynucleotide to produce a recombinant plant virus. The recombinant plant viral polynucleotide or recombinant plant virus is used to infect appropriate host plants. The recombinant plant viral polynucleotide is capable of replication in the host, systemic spread in the host, and transcription or expression of foreign gene(s) (exogenous polynucleotide) in the host to produce the desired protein.

Techniques for inoculation of viruses to plants may be found in Foster and Taylor, eds. "Plant Virology Protocols: From Virus Isolation to Transgenic Resistance (Methods in Molecular Biology (Humana Pr), Vol 81)", Humana Press, 1998; Maramorosh and Koprowski, eds. "Methods in Virology" 7 vols, Academic Press, New York 1967-1984; Hill, S. A. "Methods in Plant Virology", Blackwell, Oxford, 1984; Walkey, D. G. A. "Applied Plant Virology", Wiley, New York, 1985; and Kado and Agrawa, eds. "Principles and Techniques in Plant Virology", Van Nostrand-Reinhold, New York.

In addition to the above, the polynucleotide of the present invention can also be introduced into a chloroplast genome thereby enabling chloroplast expression.

A technique for introducing exogenous polynucleotide sequences to the genome of the chloroplasts is known. This technique involves the following procedures. First, plant cells are chemically treated so as to reduce the number of chloroplasts per cell to about one. Then, the exogenous polynucleotide is introduced via particle bombardment into the cells with the aim of introducing at least one exogenous polynucleotide molecule into the chloroplasts. The exogenous polynucleotides selected such that it is integratable into the chloroplast's genome via homologous recombination which is readily effected by enzymes inherent to the chloroplast. To this end, the exogenous polynucleotide includes, in addition to a gene of interest, at least one polynucleotide stretch which is derived from the chloroplast's genome. In addition, the exogenous polynucleotide includes a selectable marker, which serves by sequential selection procedures to ascertain that all or substantially all of the copies of the chloroplast genomes following such selection will include the exogenous polynucleotide. Further details relating to this technique are found in U.S. Pat. Nos. 4,945,050; and 5,693,507 which are incorporated herein by reference. A polypeptide can thus be produced by the protein expression system of the chloroplast and become integrated into the chloroplast's inner membrane.

Since abiotic stress tolerance in plants can involve multiple genes acting additively or in synergy (see, for example, in Quesda et al., Plant Physiol. 130:951-063, 2002), the present invention also envisages expressing a plurality of exogenous polynucleotides in a single host plant to thereby achieve superior abiotic stress tolerance.

Expressing a plurality of exogenous polynucleotides in a single host plant can be effected by co-introducing multiple nucleic acid constructs, each including a different exogenous polynucleotide, into a single plant cell. The transformed cell can than be regenerated into a mature plant using the methods described hereinabove.

Alternatively, expressing a plurality of exogenous polynucleotides in a single host plant can be effected by co-introducing into a single plant-cell a single nucleic-acid construct including a plurality of different exogenous polynucleotides. Such a construct can be designed with a single promoter sequence which can transcribe a polycistronic message including all the different exogenous polynucleotide sequences. To enable co-translation of the different polypeptides encoded by the polycistronic message, the polynucleotide sequences can be inter-linked via an internal ribosome entry site (IRES) sequence which facilitates translation of polynucleotide sequences positioned downstream of the IRES sequence. In this case, a transcribed polycistronic RNA molecule encoding the different polypeptides described above will be translated from both the capped 5' end and the two internal IRES sequences of the polycistronic RNA molecule to thereby produce in the cell all different polypeptides. Alternatively, the construct can include several promoter sequences each linked to a different exogenous polynucleotide sequence.

The plant cell transformed with the construct including a plurality of different exogenous polynucleotides, can be regenerated into a mature plant, using the methods described hereinabove.

Alternatively, expressing a plurality of exogenous polynucleotides in a single host plant can be effected by introducing different nucleic acid constructs, including different exogenous polynucleotides, into a plurality of plants. The regenerated transformed plants can then be cross-bred and resultant progeny selected for superior abiotic stress tolerance and/or biomass traits, using conventional plant breeding techniques.

Hence, the present application provides methods of utilizing novel abiotic stress-tolerance genes to increase tolerance to abiotic stress and/or biomass in a wide range of economical plants, in a safe and cost effective manner.

Plants are subject to a range of environmental challenges. Several of these, including salt stress, general osmotic stress, drought stress and freezing stress, have the ability to impact whole plant and cellular water availability. Not surprisingly, then, plant responses to this collection of stresses are related. In a recent review, Zhu notes that "most studies on water stress signaling have focused on salt stress primarily because plant responses to salt and drought are closely related and the mechanisms overlap" (Zhu (2002) Ann. Rev. Plant Biol. 53: 247-273). Many examples of similar responses and pathways to this set of stresses have been documented. For example, the CBF transcription factors have been shown to condition resistance to salt, freezing and drought (Kasuga et al. (1999) Nature Biotech. 17: 287-291). The *Arabidopsis* rd29B gene is induced in response to both salt and dehydration stress, a process that is mediated largely through an ABA signal transduction process (Uno et al. (2000) Proc. Natl. Acad. Sci. USA 97: 11632-11637), resulting in altered activity of transcription factors that bind to an upstream element within the rd29B promoter. In *Mesembryanthemum crystallinum* (ice plant), Patharker and Cushman have shown that a calcium-dependent protein kinase (McCDPK1) is induced by exposure to both drought and salt stresses (Patharker and Cushman (2000) Plant J. 24: 679-691). The stress-induced kinase was also shown to phosphorylate a transcription factor, presumably altering its activity, although transcript levels of the target transcription factor are not altered in response to salt or drought stress. Similarly, Saijo et al. demonstrated that a rice salt/drought-induced calmodulin-dependent protein kinase (OsCDPK7) conferred increased salt and drought tolerance to rice when overexpressed (Saijo et al. (2000) Plant J. 23: 319-327).

Exposure to dehydration invokes similar survival strategies in plants as does freezing stress (see, for example, Yelenosky (1989) Plant Physiol 89: 444-451) and drought stress induces freezing tolerance (see, for example, Siminovitch et al. (1982) Plant Physiol 69: 250-255; and Guy et al. (1992) Planta 188: 265-270). In addition to the induction of cold-acclimation proteins, strategies that allow plants to survive in low water conditions may include, for example, reduced surface area, or surface oil or wax production.

It will be appreciated that some pathways involved in resistance to one stress (as described above), will also be involved in resistance to other stresses, regulated by the same or homologous genes. Of course, the overall resistance pathways are related, not identical, and therefore not all genes controlling resistance to one stress will control resistance to the other stresses. Nonetheless, if a gene conditions resistance to one of these stresses, it would be apparent to one skilled in the art to test for resistance to these related stresses. Methods of assessing stress resistance are further provided in the Examples section which follows.

Polynucleotide sequences of the present invention are capable of increasing a biomass of a plant. It will be appreciated that the ability of the polypeptides of the present invention to increase plant yield/biomass/vigor is inherent to their ability to promote the increase in plant cell-size (as shown in Example 8 and FIG. 2).

Thus, the present invention also envisages a method of increasing a biomass/vigor/yield of a plant (coniferous plants, moss, algae, monocot or dicot, as well as other plants listed in Hypertext Transfer Protocol://World Wide Web (dot) nationmaster (dot) com/encyclopedia/Plantae).

As used herein the phrase "plant biomass" refers to the amount or quantity of tissue produced from the plant in a growing season, which could also determine or affect the plant yield or the yield per growing area.

As used herein the phrase "plant vigor" refers to the amount or quantity of tissue produced from the plant in a given time. Hence increase vigor could determine or affect the plant yield or the yield per growing time or growing area.

As used herein the phrase "plant yield" refers to the amount or quantity of tissue produced and harvested as the plant produced product. Hence increase yield could affect the economic benefit one can obtain from the plant in a certain growing are and/or growing time.

Preferably, the genetically engineered plants of the present invention exhibit at least about 2% more, 5% more, 10% more, 20% more, 30% more, 40% more, 50% more, 60% more, 70% more, 80% more, 90% more or even greater biomass, vigor and/or yield than non-transgenic plants.

Methods of assaying plant vigor, yield and biomass are well known in the art (see Example 10).

Thus, the present invention is of high agricultural value for promoting the yield of commercially desired crops (e.g., biomass of vegetative organ such as poplar wood, or reproductive organ such as number of seeds or seed biomass).

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

Example 1

Identifying Putative Abiotic Stress—Tolerance Genes from Monocots

Abiotic stress-tolerance (ABST) genes were identified and validated in vivo as previously described WO2004/104162 to the present assignee. A number of ABS genes and polypeptides encoded thereby were identified from dicot plants (SEQ ID NOs. 122-126 and 127-131, respectively). Screen for orthologous sequences was performed on monocot genomic databases, NCBI (Hypertext Transfer PrOtocol://World Wide Web (dot) ncbi (dot) nlm (dot) nih (dot) gov),) and TIGR (Hypertext Transfer Protocol://World Wide Web (dot) tigr (dot) org/) databases of Maize, *Sorghum*, Rice and Barley.

The expressed sequence tags (ESTs) and cDNA sequences were clustered and assembled using the LEADS™ software (Compugen) and compared to the TIGR (Hypertext Transfer Protocol://World Wide Web (dot) tigr (dot) org/) databases of the above monocots. Overall, clustering of 372,000 maize ESTs resulted in 41,990 clusters among them 19,870 singletones. In *Sorghum* about 190,000 ESTs were clustered into 39,000 clusters, while in barley 370,500 ESTs generated 50,000 different clusters each representing a different gene. Similar number of sequences and clustered genes were found in the rice genomic database.

A digital expression profile summary was compiled for each cluster according to all keywords included in the sequence records comprising the cluster. Digital expression, also known as electronic northern blot, is a tool that displays virtual expression profile based on the EST sequences forming the gene cluster. The tool can provide the expression profile of a cluster in terms of plant anatomy (in what tissues/organs is the gene expressed), developmental stage (the developmental stages at which a gene can be found) and profile of treatment (provides the physiological conditions under which a gene is expressed such as drought, cold, pathogen infection, etc). Given a random distribution of ESTs in the different clusters, the digital expression provides a probability value that describes the probability of a cluster having a total of N ESTs to contain X ESTs from a certain collection of libraries. For the probability calculations are taken into consideration: a) the number of ESTs in the cluster, b) the number of ESTs of the implicated and related libraries, c) the overall number of ESTs available representing the species. Thereby clusters with low probability values are highly enriched with ESTs from the group of libraries of interest indicating a specialized expression.

The concepts of orthology and paralogy have recently been applied to functional characterizations and classifications on the scale of whole-genome comparisons Orthologs and paralogs constitute two major types of homologs: The first evolved from a common ancestor by specialization, and the latter are related by duplication events. It is assumed that paralogs arising from ancient duplication events are likely to have diverged in function while true orthologs are more likely to retain identical function over evolutionary time.

To further investigate and identify the ABST putative ortholog genes from monocot species, two computational methods were integrated:

(i) Method for alignments of ortholog sequences—the method is effected by constructing ortholog groups across multiple eukaryotic taxa, using modifications on the Markov cluster algorithm to group putative orthologs and paralogs. These putative orthologs were further organized under Phylogram—a branching diagram (tree) assumed to be an estimate of a phylogeny of the genes.

(ii) Method for generating genes expression profile "Digital Expression"—The present inventors have performed considerable work aimed at annotating sequences. Expression data was analyzed and the EST libraries were classified using a fixed vocabulary of custom terms such as experimental treatments. The annotations from all the ESTs clustered to a gene were analyzed statistically by comparing their frequency in the cluster versus their abundance in the database, allowing to construct a numeric and graphic expression profile of that gene, which is termed "digital expression".

The rationale of using these two complementary methods is based on the assumption that true orthologs are likely to retain identical function over evolutionary time. These two methods (sequence and expression pattern) provide two different sets of indications on function similarities between two homologous genes, similarities in the sequence level—identical amino acids in the protein domains and similarity in expression profiles.

While comparing the sequences from monocots to the tomato ABST genes, homology levels between the tomato genes and their best orthologue gene from monocot differed dramatically, ranging from 45% to 88%. Moreover, the in-silico expression profile of the monocot genes does not always fit to a gene involved in ABS tolerance. Hence, an extensive search for the monocot functional orthologue of each tomato gene (SEQ ID NO: 122-131) was effected.

In attempt to identify the best orthologues of the tomato ABST genes, two sets of analyses were performed. First, the sequences of 5 tomato ABST genes (SEQ ID NO: 122-126) and their deduced polypeptide sequences (SEQ ID NO: 127-131) were compared to all monocot putative proteins, encoded by DNA sequences of gene clusters mentioned above. The comparison was done on the protein level looking for identity higher than 45% along the entire protein sequence.

Table 1 below shows the best homologous genes and their identity level to the tomato ABST proteins. Next, these monocot proteins originated from different monocot species (barley, *sorghum* and maize) were screened based on their expression pattern during the development of several monocot species. This screening was based on digital expression of the genes, as described above. The digital expression represents the distribution of the ESTs composing each in silico gene and the deviation of the actual distribution from random distribution. The genes were selected based on three criteria: genes with higher expression in roots, roots and leaves and/or induced by treatments representing soil stress conditions (drought, salinity, soil deficiencies). An increase in expression was considered only in cases were greater than 2 folds (relative to the random EST distribution) increase was evident with significance probability lower than 0.05. Table 2 below summarizes the expression profile of the genes in different organ or tissues and the treatments that set off significant elevation in their expression level.

TABLE 1

The level of homology between the tomato ABST genes and their homologes genes from monocot.

| Tomato gene SEQ ID NO | TIGR Name/Acc No of Homologous gene | Plant origin | Level of homology (e value) | % Identity (Percenrtage from the entire protein sequence) |
|---|---|---|---|---|
| 122 | TC104838 SEQ ID NO 1 | *Sorghum* | 2E−70 | 88% |
| | TC103857 | *Sorghum* | 2E−70 | 88% |
| | TC258871 | Maize | 1E−69 | 86% |
| | TC139195 | Barley | 5E−69 | 86% |
| 123 | TC94284 SEQ ID NO 3 | *Sorghum* | 3E−43 | 45% |
| | TCI32394 | Barley | 6E−40 | 44% |
| 124 | TC102291 SEQ ID NO 5 | *Sorghum* | 1E−72 | 54% |
| | TC146720 | Barley | 3E−99 | 58% |
| 125 | TC92953 SEQ ID NO 7 | *Sorghum* | 7E−59 | 47% |
| | TC91426 SEQ ID NO 9 | *Sorghum* | 4E−98 | 74% |
| | TC91474 | *Sorghum* | 5E−98 | 72% |
| | TC263205 | Maize | 2E−97 | 74% |
| 126 | TC103772 SEQ ID NO 11 | *Sorghum* | 1E−52 | 49% |
| | TC148356 | Barley | 1E−54 | 46% |
| | TC260731 | Maize | 1E−54 | 46% |

TABLE 2

The expression profile of the ABST homologous in silico genes as it represented by statistical analysis of their ESTs distribution

| Name of Homologous gene | Plant species | Organs/tissues with the highest gene expression | Fold increase (All results are singnificant in P value > 0.05) | Treatments that induce th expression level | Fold increase (all results are singnificant in P value > 0.05) |
|---|---|---|---|---|---|
| TC104838 SEQ ID NO 1 | *Sorghum* | Pollen preanthesis stage | 3 | Ethylene, drought | 2 |
| TC103857 | *Sorghum* | Diverse expression | 2 | None* | None* |
| TC258871 | Maize | Diverse expression, preferentially in cell lignification region of leaves | 2 | None* | None* |
| TC139195 | Barley | In various grain tissues | 2-3.5 | None | None |
| TC94284 SEQ ID NO 3 | *Sorghum* | Leaves, roots during fruit loading | 4.5 2 | Drought, nitrogen deficiencies, soil acidity | 4 2 2 |
| TC132394 | Barley | Leaves, coleoptile mainly during fruit development | 2.5 3 | None | None |

TABLE 2-continued

The expression profile of the ABST homologous in silico genes as it represented by statistical analysis of their ESTs distribution

| Name of Homologous gene | Plant species | Organs/tissues with the highest gene expression | Fold increase (All results are singnificant in P value > 0.05) | Treatments that induce th expression level | Fold increase (all results are singnificant in P value > 0.05) |
|---|---|---|---|---|---|
| TC102291 SEQ ID NO 5 | *Sorghum* | Callus and cell suspension | 3 | Salinity and drought stress | 3 |
| TC146720 | Barley | Seeds preferentially in the embryo and scutellum during ripening | 2 | Cold stress, *Fusarium* infection | 3<br>3.5 |
| TC92953 SEQ ID NO 7 | *Sorghum* | Leaves during fruit loading | 2 | Drought, Nitrogen-deficiency, salinity (150 Mm) | 4<br>4<br>2.5 |
| TC91426 SEQ ID NO 9 | *Sorghum* | Young roots | 12 | Ethylene, etiolation, soil acidity | 4<br>3<br>12 |
| TC91474 | *Sorghum* | Entire seedling | 2 | Etiolation | 16 |
| TC263205 | Maize | Primary root system in seedling stage | 3 | Drought | 2 |
| TC103772 SEQ ID NO 11 | *Sorghum* | Young roots | 2 | Drought, soil acidity | 2<br>2 |
| TC148356 | Barley | Callus, leaves in the vetatative stage | 4, 2 | Infection by *Blumeria graminis* | 2 |
| TC260731 | Maize | Root preferntialy primary roots | 2.5 | None | None |

None*- None of the treatments with significant elevation in digital expression could be considered as soil stress treatment Combination of the above screening as it is described in Table 1 and in Table 2 above revealed the final list of five monocot genes that are predicted to be the most related to the tomato ABST genes (SEQ ID NOs. 1, 3, 5, 7, 9).

The selected polynucleotide sequences (Table 3 below) were analyzed for presence of ORFs using Vector NTI suite (InforMax, U.K.) version 6 (Hasting Software, Inc: World Wide Web (dot) generunner (dot) com/). ORFs identified in each of these polynucleotide sequences were compared to Genbank database sequences, using Blast (World Wide Web (dot) ncbi (dot) nlm (dot) nih (dot) gov/BLAST/); the ORF displaying the highest homology to a GenBank sequence or sequences, was mapped in order to identify an ATG start codon. The position of the ATG start codon of this ORF was then compared with that of the identified polynucleotide sequence in order to verify that each of the five sequences described herein includes a full length ORF and an ATG start codon (thus qualifies as a "putative monocot ABST gene").

TABLE 3

Monocot ABST genes

| Tomato ABST SEQ ID NO. | Homologous Monocot ABST Gene SEQ ID NO: | Artificially optimized ABST* Gene SEQ ID NO: |
|---|---|---|
| 122 | 1 | 156 |
| 123 | 3 | 157 |
| 124 | 5 | 158 |
| 125 | 7 | |
| 125 | 9 | |
| 126 | 11 | 159 |

*Further described in Example 2 below.

Polypeptides with significant homology to the Monocot ABST genes have been identified from the NCBI databases using BLAST software (Table 4).

TABLE 4

ABST homologues

| Monocot ABST Putative Gene SEQ ID No. | ABST Polypeptide Homologue, encoded by TIGR Accession No/SEQ ID NO: | Source Organism | ABST Polypeptide Homologue SEQ ID No. | Homology in Polypeptide sequence (%) |
|---|---|---|---|---|
| 1 | TC270110/160 | *Zea mays* | 13 | 100 |
| 1 | TC56855/161 | *Saccharum officinarum* | 14 | 100 |
| 1 | TC104838/162 | *sorghum* | 15 | 100 |
| 1 | TC57929/163 | *Saccharum officinarum* | 16 | 98 |
| 1 | TC103857/164 | *sorghum* | 17 | 98 |
| 1 | TC262554/165 | *Oryza sativa* | 18 | 98 |
| 1 | TC258871/166 | *Zea mays* | 19 | 97 |
| 1 | TC139195/167 | *Hordeum vulgare* | 20 | 96 |
| 1 | TC262556/168 | *Oryza sativa* | 21 | 95 |
| 1 | TC232174/169 | *Triticum aestivum* | 22 | 95 |
| 1 | TC232139/170 | *Triticum aestivum* | 23 | 95 |
| 1 | TC139194/171 | *Hordeum vulgare* | 24 | 95 |
| 1 | CA486561/172 | *Triticum aestivum* | 25 | 100 |
| 1 | TC258873/173 | *Zea mays* | 26 | 100 |
| 1 | CA187014/174 | *Saccharum officinarum* | 27 | 90 |
| 1 | TC233455/175 | *Triticum aestivum* | 28 | 96 |
| 1 | CF063450/176 | *Zea mays* | 29 | 98 |
| 1 | CA617041/177 | *Triticum aestivum* | 30 | 100 |
| 3 | TC94284/178 | *sorghum* | 31 | 100 |
| 3 | TC49791/179 | *Saccharum officinarum* | 32 | 95 |
| 180 | TC93449/180 | *sorghum* | 33 | 100 |
| 180 | TC49718/181 | *Saccharum officinarum* | 34 | 95 |
| 180 | TC49720/182 | *Saccharum officinarum* | 35 | 96 |
| 7 | TC92953/183 | *sorghum* | 36 | 100 |
| 7 | TC66617/184 | *Saccharum officinarum* | 37 | 90 |
| 7 | TC273860/185 | *Zea mays* | 38 | 91 |
| 7 | TC253191/186 | *Zea mays* | 39 | 90 |
| 11 | TC103772/187 | *sorghum* | 40 | 100 |
| 11 | TC272084/188 | *Zea mays* | 41 | 92 |
| 11 | TC60928/189 | *Saccharum officinarum* | 42 | 94 |
| 1 | TC5422/190 | canola | 43 | 88 |
| 1 | TC904/191 | canola | 44 | 88 |
| 1 | TC121774/192 | *Solanum tuberosum* | 45 | 88 |
| 1 | TC40342/193 | *Gossypium* | 46 | 88 |
| 1 | TC40115/194 | *Gossypium* | 47 | 88 |
| 1 | TC155918/195 | *Lycopersicon esculentum* | 48 | 88 |
| 1 | TC154398/196 | *Lycopersicon esculentum* | 49 | 88 |
| 1 | TC154397/197 | *Lycopersicon esculentum* | 50 | 88 |
| 1 | TC153989/198 | *Lycopersicon esculentum* | 51 | 88 |
| 1 | TC120511/199 | *Solanum tuberosum* | 52 | 88 |
| 1 | TC113582/200 | *Solanum tuberosum* | 53 | 88 |
| 1 | TC112701/201 | *Solanum tuberosum* | 54 | 88 |
| 1 | TC111912/202 | *Solanum tuberosum* | 55 | 88 |
| 1 | TC4674/203 | *Capsicum annum* | 56 | 88 |
| 1 | TC270923/204 | *arabidopsis* | 57 | 87 |
| 1 | CD823817/205 | canola | 58 | 86 |
| 1 | TC526/206 | canola | 59 | 86 |
| 1 | TC525/207 | canola | 60 | 86 |
| 1 | BG442528/208 | *Gossypium* | 61 | 87 |
| 1 | TC33702/209 | *Gossypium* | 62 | 87 |
| 1 | TC32714/210 | *Gossypium* | 63 | 87 |
| 1 | TC270782/211 | *arabidopsis* | 64 | 87 |
| 1 | TC225449/212 | *Glycine max* | 65 | 87 |
| 1 | TC5255/213 | *Capsicum annum* | 66 | 88 |
| 1 | TC28221/214 | *populus* | 67 | 84 |
| 1 | TC108140/215 | *medicago* | 68 | 85 |
| 1 | TC28222/216 | *populus* | 69 | 84 |
| 1 | TC94402/217 | *medicago* | 70 | 84 |
| 1 | TC28223/218 | *populus* | 71 | 83 |
| 1 | TC102506/219 | *medicago* | 72 | 85 |
| 1 | NP890576/222 | *Oryza sativa* | 73 | 76 |
| 1 | TC280376/223 | *Oryza sativa* | 74 | 73 |
| 1 | CN009841/224 | *Triticum aestivum* | 75 | 75 |
| 1 | BI948270/225 | *Hordeum vulgare* | 76 | 75 |
| 1 | TC259334/226 | *arabidopsis* | 77 | 75 |
| 1 | BQ767154/227 | *Hordeum vulgare* | 78 | 73 |
| 1 | TC60345/228 | *Saccharum officinarum* | 79 | 73 |
| 1 | TC138474/229 | *Hordeum vulgare* | 80 | 85 |

TABLE 4-continued

ABST homologues

| Monocot ABST Putative Gene SEQ ID No. | ABST Polypeptide Homologue, encoded by TIGR Accession No/SEQ ID NO: | Source Organism | ABST Polypeptide Homologue SEQ ID No. | Homology in Polypeptide sequence (%) |
|---|---|---|---|---|
| 1 | TC41472/230 | *populus* | 81 | 72 |
| 1 | BJ458177/231 | *Hordeum vulgare* | 82 | 72 |
| 1 | CB674176/232 | *Oryza sativa* | 83 | 82 |
| 1 | TC216405/233 | *Glycine max* | 84 | 88 |
| 1 | AJ777371/234 | *Populus* | 85 | 70 |
| 1 | CV019213/235 | Tobacco | 86 | 85 |
| 1 | CK215690/236 | *Triticum aestivum* | 87 | 80 |
| 1 | CD830784/237 | canola | 88 | 85 |
| 1 | CA624722/238 | *Triticum aestivum* | 89 | 85 |
| 1 | TC32906/239 | *populus* | 90 | 76 |
| 1 | CR285127/240 | *Oryza sativa* | 91 | 89 |
| 1 | TC251945/241 | *Triticum aestivum* | 92 | 72 |
| 3 | TC274823/242 | *Oryza sativa* | 93 | 77 |
| 3 | TC132394/243 | *Hordeum vulgare* | 94 | 75 |
| 3 | TC267180/244 | *Triticum aestivum* | 95 | 77 |
| 3 | TC261921/245 | *Zea mays* | 96 | 87 |
| 3 | TC267181/246 | *Triticum aestivum* | 97 | 74 |
| 3 | TC261922/247 | *Zea mays* | 98 | 81 |
| 3 | TC267182/248 | *Triticum aestivum* | 99 | 73 |
| 180 | TC249531/249 | *Zea mays* | 100 | 86 |
| 180 | TC232170/250 | *Triticum aestivum* | 101 | 85 |
| 180 | TC146720/251 | *Hordeum vulgare* | 102 | 85 |
| 180 | TC249329/252 | *Oryza sativa* | 103 | 84 |
| 180 | TC249532/253 | *Zea mays* | 104 | 88 |
| 180 | TC232150/254 | *Triticum aestivum* | 105 | 85 |
| 180 | TC249330/255 | *Oryza sativa* | 106 | 76 |
| 180 | CB672603/256 | *Oryza sativa* | 107 | 71 |
| 180 | TC32440/257 | *Gossypium* | 108 | 81 |
| 180 | TC119105/258 | *Solanum tuberosum* | 109 | 72 |
| 7 | TC247999/259 | *Triticum aestivum* | 110 | 78 |
| 7 | TC247359/260 | *Triticum aestivum* | 111 | 77 |
| 7 | TC132566/261 | *Hordeum vulgare* | 112 | 77 |
| 7 | TC248676/262 | *Triticum aestivum* | 113 | 74 |
| 7 | TC249667/263 | *Oryza sativa* | 114 | 77 |
| 7 | TC66618/264 | *Saccharum officinarum* | 115 | 88 |
| 11 | TC253495/282 | *Oryza sativa* | 116 | 78 |
| 11 | TC267485/283 | *Triticum aestivum* | 117 | 77 |
| 11 | TC148621/284 | *Hordeum vulgare* | 118 | 76 |
| 11 | TC275474/285 | *Oryza sativa* | 119 | 85 |
| 9 | TC275473/265 | *Oryza sativa* | 139 | 89 |
| 9 | TC224823/266 | *Glycine max* | 140 | 75 |
| 9 | TC234990/267 | *Triticum aestivum* | 141 | 74 |
| 9 | TC266178/268 | *Triticum aestivum* | 142 | 73 |
| 9 | TC119051/269 | *Solanum tuberosum* | 143 | 64 |
| 9 | TC56409/270 | *Saccharum officinarum* | 144 | 75 |
| 9 | TC35873/271 | *Populus* | 145 | 80 |
| 9 | TC119052/272 | *Solanum tuberosum* | 146 | 82 |
| 9 | TC204518/273 | *Glycine max* | 147 | 85 |
| 9 | TC112169/274 | *Solanum tuberosum* | 148 | 84 |
| 9 | TC254696/275 | *Zea mays* | 149 | 70 |
| 9 | TC254696/276 | *Zea mays* | 150 | 70 |
| 9 | TC248906/277 | *Oryza sativa* | 151 | 75 |
| 9 | TC154007/278 | *Lycopersicon esculentum* | 152 | 82 |
| 9 | TC6466/279 | *Capsicum annuum* | 153 | 74 |
| 9 | TC131227/280 | *Hordeum vulgare* | 154 | 74 |
| 9 | TC27564/281 | *Gossypium* | 155 | 71 |

Example 2

Generating the Putative Monocot ABST Genes

DNA sequences of the monocot ABST genes were synthesized by GeneArt (Hypertext Transfer Protocol://World Wide Web (dot) geneart (dot) com/). Synthetic DNA was designed in silico, based on the encoded amino-acid sequences of the monocot ABST genes (SEQ ID Nos 2, 4, 6, 12) and using codon-usage tables calculated from plant transcriptomes (example of such tables can be found in the Codon Usage Database available online at Hypertext Transfer Protocol://World Wide Web (dot) kazusa (dot) or (dot) jp/codon/). The optimized coding sequences are designed in a way that no changes are introduced in the encoded amino acid sequence while using codons preferred for expression in dicotyledonous plants (mainly tomato and *Arabidopsis*) and monocotyledonous plants such as maize. At least one silent mutation per 20 nucleotide base pairs was introduced in the sequence compared to the orthologous monocot sequences to avoid possible silencing when over-expressing the gene in monocot species such as maize. To the optimized sequences the following restriction enzymes sites were added—SalI, XbaI, BamHI, SmaI at the 5' end and SacI at the 3' end. The sequences synthesized by the supplier (GeneArt, Gmbh) were cloned in the pCR-Script plasmid. The resulting sequences are SEQ ID Nos 156, 157, 158, 159; representing the original monocot ABST SEQ ID Nos 1, 3, 5, 11 respectively, as described in Table 3, above.

Example 3

Cloning the Putative ABST Genes

The PCR Script plasmids harboring the synthetic, monocot-based ABST genes were digested with the restriction endonucleases XbaI and SacI (Roche). The resulting fragment was purified using Gel extraction Kit (Qiagen, Germany) and ligated using T4 DNA ligase enzyme (Roche) into the plant expression vector pKG(NOSter), (SEQ ID NO 136), excised with the same enzymes. pKG plasmid is based on the PCR Script backbone, with several changes in the polylinker site to facilitate the cloning of genes of interest downstream to a promoter and upstream to a terminator suitable for expression in plant cells. As a result, the inserted gene, together with the promoter and the terminator can be easily moved to a binary vector.

The resulting pKG(NOSter) harboring putative monocot ABST genes were introduced to *E. coli* DH5 competent cells by electroporation, using a MicroPulser electroporator (Biorad), 0.2 cm cuvettes (Biorad) and EC-2 electroporation program (Biorad). The treated cells were cultured in LB liquid medium at 37° C. for 1 hr, then plated over LB agar supplemented with ampicillin (100 mg/L) and incubated at 37° C. for 16 hrs. Colonies that developed on the selective medium were analyzed by PCR using the primers of SEQ ID NO 132 and SEQ ID NO 133 which were designed to span the inserted sequence in the pKG plasmids. The resulting PCR products were separated on 1% agarose gels and "PCR-positive" colonies labeled and further grown. DNA from positive colonies was isolated using (Qiagen) and sequenced using the ABI 377 sequencer (Amersham Biosciences Inc) to verify the lack of mutations in the final sequence.

The At6669 promoter sequence (set forth in SEQ ID NO: 121) was inserted in all the pKG(NOSter) plasmids harboring putative Monocot ABST genes using the restriction enzymes HindIII and SalI (Roche). Colonies were analyzed by PCR using the primers SEQ ID NO: 138 and SEQ ID NO: 133. Positive plasmids were identified, isolated and sequenced as described above.

Example 4

Generating Binary Vectors Comprising Putative Monocot ABST Genes and Plant Promoters for Driving Expression Thereof Generating Binary Vectors Comprising the At6669 Promoter:

The four pKG(At6669+NOSter) constructs harboring putative Monocot ABST genes downstream to At6669 promoter sequence (set forth in SEQ ID NO: 121), and upstream to the Nopaline Synthase (NOS) terminator, were digested with HindIII and EcoRI (Roche) in order to excise the expression cassettes that were ligated into pGI plasmid digested with the same restriction endonucleases. Altogether, four pGI constructs were generated, each comprising the At6669 promoter positioned upstream of a putative Monocot ABST gene having a sequence set forth in SEQ ID NO: 1, 3, 5, 11.

The plasmid pPI was constructed by inserting a synthetic poly-(A) signal sequence, originating from pGL3 basic plasmid vector (Promega, Acc No U47295; bp 4658-4811) into the HindIII restriction site of the binary vector pBI101.3 (Clontech, Acc. No. U12640). In some cases the backbone binary plasmid used was pGI which is similar to pPI but the GUS gene was replaced by the GUS-Intron gene (Vancanneyt. G, et al MGG 220, 245-50, 1990).

The At6669 promoter was isolated from *Arabidopsis thaliana* var Col0 genomic DNA by PCR amplification using the primers set forth in SEQ ID NOs: 134 and 135. The PCR product was purified (Qiagen, Germany) and digested with the restriction endonucleases HindIII and SalI (Roche). The resulting promoter sequence was introduced into the open binary pPI vector digested with the same enzymes, to produce pPI+At6669 plasmid.

Example 5

Transforming *Agrobacterium tumefaciens* Cells with Binary Vectors Harboring Putative Monocot ABST Genes Each of the binary vectors described in Example 4 above were used to transform *Agrobacterium* cells. Two additional binary constructs, having the Luciferase reporter gene replacing the Monocot ABST gene (positioned downstream of the 35S or At6669 promoter), were used as negative controls.

The binary vectors were introduced to *Agrobacterium tumefaciens* GV301, or LB4404 competent cells (about $10^9$ cells/mL) by electroporation. The electroporation was effected by using a MicroPulser electroporator (Biorad), 0.2 cm cuvettes (Biorad) and EC-2 electroporation program (Biorad). The treated cells were cultured in LB liquid medium at 28° C. for 3 hr, then plated over LB agar supplemented with gentamycin (50 mg/L; for *Agrobacterium* strains GV301) or streptomycin (300 mg/L; for *Agrobacterium* strain LB4404) and kanamycin (50 mg/L) at 28° C. for 48 hrs. *Agrobacterium* colonies which developed on the selective media were analyzed by PCR using the primers set forth in SEQ ID NOs: 132 and 138, which were designed to span the inserted sequence in the pPI plasmid. The resulting PCR products were isolated and sequenced as described in Example 4 above, to verify that the correct ABST sequences were properly introduced to the *Agrobacterium* cells.

Example 6

Transformation of *Arabidopsis thaliana* Plants with Putative Monocot ABST Genes

*Arabidopsis thaliana* Columbia plants ($T_0$ plants) were transformed using the Floral Dip procedure described by Clough and Bent (10) and by Desfeux et al. (11), with minor modifications. Briefly, To Plants were sown in 250 ml pots filled with wet peat-based growth mix. The pots were covered with aluminum foil and a plastic dome, kept at 4° C. for 3-4 days, then uncovered and incubated in a growth chamber at 18-24° C. under 16/8 hr light/dark cycles. The $T_0$ plants were ready for transformation six days before anthesis.

Single colonies of *Agrobacterium* carrying the binary constructs, were generated as described in Example 5 above. Colonies were cultured in LB medium supplemented with kanamycin (50 mg/L) and gentamycin (50 mg/L). The cultures were incubated at 28° C. for 48 hrs under vigorous shaking and then centrifuged at 4000 rpm for 5 minutes. The pellets comprising *Agrobacterium* cells were re-suspended in a transformation medium containing half-strength (2.15 g/L) Murashige-Skoog (Duchefa); 0.044 μM benzylamino purine (Sigma); 112 μg/L B5 Gambourg vitamins (Sigma); 5% sucrose; and 0.2 ml/L Silwet L-77 (OSI Specialists, CT) in double-distilled water, at pH of 5.7.

Transformation of $T_0$ plants was effected by inverting each plant into an *Agrobacterium* suspension, such that the above ground plant tissue was submerged for 3-5 seconds. Each inoculated $T_0$ plant was immediately placed in a plastic tray, then covered with clear plastic dome to maintain humidity and was kept in the dark at room temperature for 18 hrs, to facilitate infection and transformation. Transformed (transgenic) plants were then uncovered and transferred to a greenhouse for recovery and maturation. The transgenic $T_0$ plants were grown in the greenhouse for 3-5 weeks until siliques were brown and dry. Seeds were harvested from plants and kept at room temperature until sowing.

For generating $T_1$ and $T_2$ transgenic plants harboring the genes, seeds collected from transgenic $T_0$ plants were surface-sterilized by soaking in 70% ethanol for 1 minute, followed by soaking in 5% sodium hypochloride and 0.05% triton for 5 minutes. The surface-sterilized seeds were thoroughly washed in sterile distilled water then placed on culture plates containing half-strength Murashige-Skoog (Duchefa); 2% sucrose; 0.8% plant agar; 50 mM kanamycin; and 200 mM carbenicylin (Duchefa). The culture plates were incubated at 4° C. for 48 hours then transferred to a growth room at 25° C. for an additional week of incubation. Vital $T_1$ *Arabidopsis* plants were transferred to a fresh culture plates for another week of incubation. Following incubation the $T_1$ plants were removed from culture plates and planted in growth mix contained in 250 ml pots. The transgenic plants were allowed to grow in a greenhouse to maturity. Seeds harvested from $T_1$ plants were cultured and grown to maturity as $T_2$ plants under the same conditions as used for culturing and growing the $T_1$ plants.

Example 7

Evaluating Germination of Transgenic Plants Cultivated Under Abiotic Stress Conditions Tolerance to salinity or osmotic stress is aimed at identifying genes that confer better germination, seedling vigor or growth in high salt, drought or combination of these or other environmental stresses. Plants differ in their tolerance to salt (NaCl) depending on their stage of development, therefore seed germination, seedling vigor, and plant growth responses are evaluated.

A typical salinity tolerance test is effected by taking plants at different developmental stages and irrigating them with increasing concentrations of NaCl (for example 50 mM, 100 mM, 200 mM, 400 mM). Transgenic plants are compared to control plants in their external phenotypic appearance, degree of wilting, and overall success to reach maturity and yield progeny at concentrations inhibitory to control plants. Quantitative parameters of tolerance measured are as for the previous case, the average wet and dry weight, and the weight of the seeds yielded, the average seed size and the number of seeds produced per plant. Osmotic stress assays (including NaCl and mannitol assays) are conducted to determine if an osmotic stress tolerant phenotype is NaCl-specific or if it is a general osmotic stress related phenotype. Plants tolerant to osmotic stress are in general more tolerant to drought, salinity and freezing conditions and therefore are highly valuable in terms of agronomic traits.

Methods:

The method used to test the plants for improved abiotic stress tolerance includes the test of germination and seedling growth under adverse conditions such as high salinity and high osmoticum.

Germination Assay—

Germination tests compare the percentage of seeds from transgenic plants that could complete the germination process (radical protrusion from the seed coat and complete opening of the cotyledons) to the percentage of seeds from control plants treated in the same manner. Evaluation of germination and seedling vigor is conducted for three weeks after planting. To measure germination and seedling growth, seeds from $T_2$ plants are surface sterilized and individually sown on square agar plates containing for example, solidified basal media supplemented with high salinity (for example 50 mM, 100 mM, 200 mM, 400 mM) or high osmoticum (for example 50 mM, 100 mM, 200 mM, 400 mM mannitol). The basal media is 50% Murashige-Skoog medium (MS)+vitamins supplemented with 0.8% plant agar as solidifying agent. After sowing, plates are transferred for 2-3 days at 4° C. for stratification and then grown for three weeks.

To follow the germination and growth at adverse conditions plates are screened manually or automatically and plant size is determined. Five to ten independent transformation events can be analyzed from each construct. Plants expressing the genes from this invention are compared to control plants sown on the same plates under the same conditions or to the average measurement of all the constructs, seeds and events sown.

Example 8

Evaluating Transgenic Plant Growth Under Abiotic Stress Conditions

Methods:

Stress Resistance and Analysis—

A complementary experiment performed with seedlings follows the tolerance of the plants to adverse conditions. Surface sterilized seeds are sown in basal media [50% Murashige-Skoog medium (MS)+vitamins supplemented with 0.8% plant agar as solidifying agent] in the presence of Kanamycin (for transgenic plants) or in its absence (for wild-type control plants). After sowing, plates were transferred for 2-3 days at 4° C. for stratification and then grown at 25° C. under 23-hour light 1-hour dark daily cycles for 7 to 10 days. At this time point, seedlings randomly chosen were carefully transferred to plates containing high salinity conditions (150 mM NaCl) or conditions resembling the high osmolarity found during drought (210 mM mannitol). Plant growth was followed as a function of time using digital imaging. To follow the plant growth at adverse conditions plants were photographed the day they were transferred to the stress conditions (Day 0). Pictures were subsequently taken every few days after transferring the plants to the stress condition and up to 12 days after the transfer. Plant size was determined from the digital pictures taken. ImageJ software was used for quantitate the plant size from the digital pictures (Hypertext Transfer Protocol://rsb (dot) info (dot) nih (dot) gov/ij/). Proprietary scripts were designed to analyze the size of individual plants as a function of time. FIG. 1 shows the methodology used for image area quantitation. Five to ten independent transformation events were analyzed from each construct and at least 6 randomly selected plants from each event were analyzed in each stress experiment. Plants expressing the genes from this invention were compared either to control plants sown on the same stress inducing plates (internal controls) or to the average measurement of all the control plants used in the same experiment (all controls).

Statistical Analysis—

To identify genes conferring tolerance to plants showing significant differences, plant area data was analyzed using the JMP statistics program (Version 5.2.1, SAS Institute Inc., Cary, N.C., USA). A one-way ANOVA (ANalysis Of VAriance) was used in order to detect the variation between the different genes (populations of independent events) and control plants and identify constructs and events showing statistically different outstanding performance. For gene versus control analysis a Students t-test was employed, using significance of $p<0.05$. In order to find significantly different independent transformation events with increased plant area the Tukey's HSD (Honestly Significantly Different) test was employed using significance of $p<0.05$. Two-way ANOVA was used to identify events that showed significant differences in plant area at certain day points compared to the mean area of control plants growing either in the same plates or in all plates of the same experiment. The Student's t-test was utilized to compare independent transformation events to control plants.

Results:

In order to identify genes providing tolerance to salinity or osmoticum, T2 plants were generated from 5 to 10 independent transgenic events from each construct. The seeds were collected from the T2 plants and plants produced therefrom were analyzed. As detailed above the plants were sown on a selective medium in which transgenic plants are able to strive (kanamycin) and after 7-10 days (4-6 leaves stage) the plants were transferred to a stress producing media: high salinity (150 mM) or high osmoticum (210 mM mannitol). Plants size was analyzed since the day of the transfer and up to 12 days thereon. Student's t-test and Tukey HSD test were used to identify the events that show outstanding performance compared to wild type plants.

The results of the transgenic plants expressing SEQ ID Nos 156, 157, 158, 159; representing the original monocot ABST SEQ ID Nos 1, 3, 5, 11 respectively, as described in Table 4 above under the At6669 promoter (Seq ID 121) are shown. Significant differences were found in the ability of the transgenic plants to grow in the presence of a high salinity stress and/or high osmoticum stress. Table 5 below summarizes the findings of outstanding events conferring tolerance to osmotic stress in comparison to control plants. Various constructs included in this application provide the transgenic plants with an improved ability to resist to abiotic stresses.

Figure 2A:
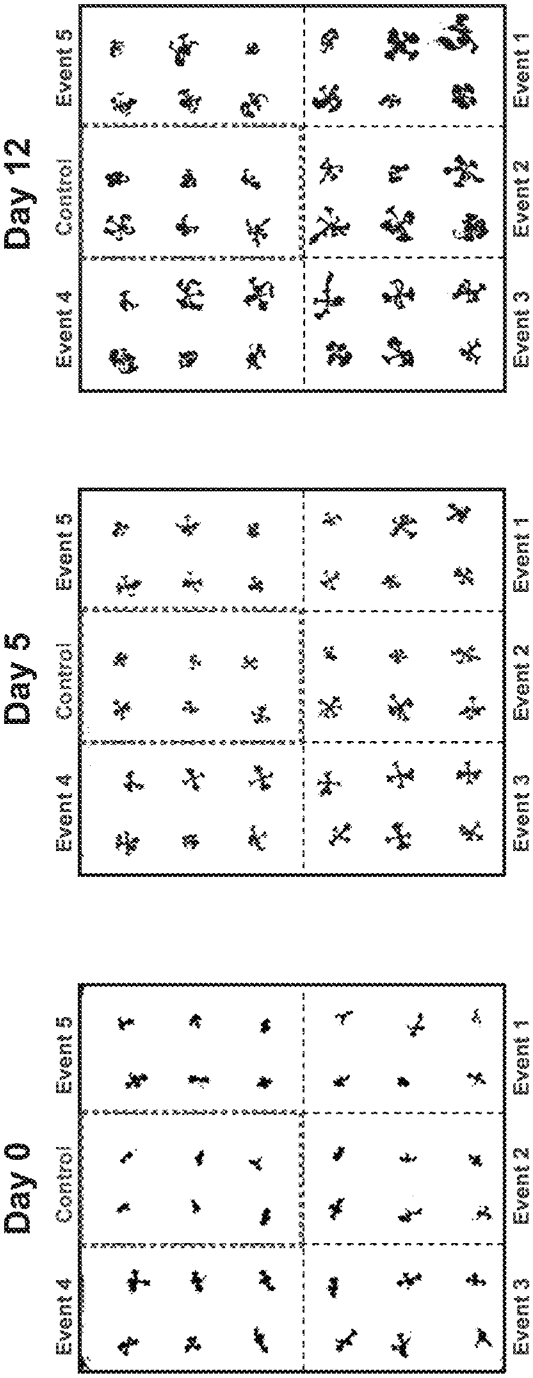
FIGS. 2A-2B are representative results of a gene (SEQ ID 156) that confers abiotic stress tolerance uncovered according to the teachings of the present invention.
Figure 2B:
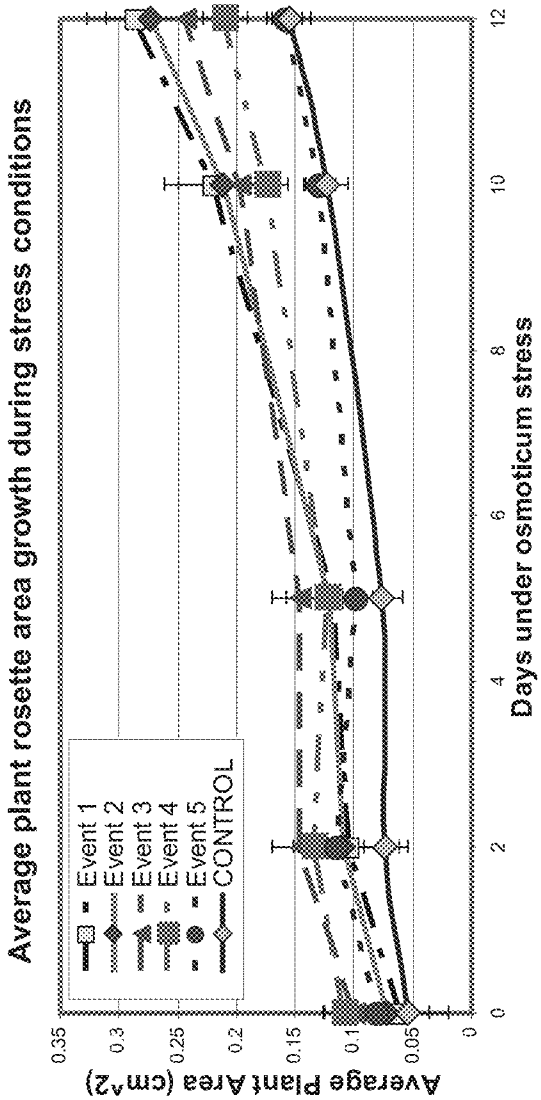

As shown, 4 out of 5 transformation events expressing SEQ ID 156 show significantly improved tolerance to osmoticum as judged by the ability of the transgenic plants to continue developing also at high osmoticum concentration (see Table 5, rows 1-5). The results obtained for SEQ ID 156 are also shown in FIG. 2. In panel A are shown processed images taken at day 0, 5 and 12 from the plate that contained the transgenic and control plants. Panel B shows the average plant area of the different events at the different time points. Events 1, 2, 3 and 4 are significantly more tolerant to osmoticum ($p<0.05$). Other constructs from this application also protect plants from the effects of high osmoticum. Again, four out of five independent transformation events expressing SEQ ID 159 showed significant increased capacity to grow under high osmoticum conditions (Table 5 below, rows 6-10). In addition, one of the events expressing SEQ ID 158 showed significantly high tolerance to high osmoticum than its corresponding control plants.

TABLE 5

LS mean of $T_2$ transgenic *Arabidopsis* plants grown in the presence of 210 mM mannitol

| Row number | Transgene (SEQ ID NO) | Event No | Number of plants tested | Least Square Mean of areas measured ($cm^2$) | Std Error |
|---|---|---|---|---|---|
| 1 | 156 | Event 1 | n = 6 | 0.1635 | 0.0091 |
| 2 | 156 | Event 2 | n = 6 | 0.1566 | 0.0091 |
| 3 | 156 | Event 3 | n = 6 | 0.1547 | 0.0091 |
| 4 | 156 | Event 4 | n = 6 | 0.1480 | 0.0091 |
| 5 | CONTROL of events 1-4 SEQ ID 156, and event 1, SEQ ID 158 | — | n = 6 | 0.1150 | 0.0091 |
| 6 | 159 | Event 1 | n = 6 | 0.1141 | 0.0050 |
| 7 | 159 | Event 2 | n = 6 | 0.1104 | 0.0050 |
| 8 | 159 | Event 3 | n = 6 | 0.1020 | 0.0050 |
| 9 | 159 | Event 4 | n = 6 | 0.0824 | 0.0050 |
| 10 | CONTROL of Event 1-4 SEQ ID 159 | — | n = 6 | 0.0681 | 0.0050 |
| 11 | 158 | Event 1 | n = 6 | 0.1703 | 0.0090 |

The results of salinity tolerance tests are summarized in Table 6 below. As detailed in Table 6 (rows 1-4), three independent transgenic events with a construct containing SEQ ID 156 exhibited a significantly higher tolerance to salinity stress than the control plants in the experiment ($p<0.05$). Similar results were obtained with plants expressing SEQ ID 159. Also in this case, three different transgenic events showed significant increased tolerance to salinity stress compared to their matching control plants (see Table 6, rows 5-9).

TABLE 6

LS mean of $T_2$ transgenic *Arabidopsis* plants grown in the presence of 150 mM NaCl

| Row number | Transgene (SEQ ID NO) | Promoter | Number of plants tested | Least Square Mean of areas measured ($cm^2$) | Std Error |
|---|---|---|---|---|---|
| 1 | 156 | Event 1 | n = 6 | 0.3146 | 0.0112 |
| 2 | 156 | Event 2 | n = 6 | 0.2459 | 0.0112 |
| 3 | 156 | Event 3 | n = 6 | 0.2445 | 0.0112 |
| 4 | CONTROL of all events SEQ ID 156 | — | n = 48 | 0.2165 | 0.003722 |
| 5 | 159 | Event 1 | n = 6 | 0.2541 | 0.0110 |
| 6 | CONTROL of Event 1 SEQ ID 159 | — | n = 6 | 0.2154 | 0.0110 |
| 7 | 159 | Event 2 | n = 6 | 0.2278 | 0.0122 |
| 8 | 159 | Event 3 | n = 6 | 0.2261 | 0.0122 |
| 9 | CONTROL of Event 2 and Event 3 SEQ ID 159 | — | n = 6 | 0.1906 | 0.0122 |

Independent experiments that assess the ability of the constructs to provide salinity and high osmoticum tolerance were carried out as part of this study. Genes were found to protect transgenic plants against the deleterious effects of both stresses. Taken as a whole the results clearly demonstrate the ability of the genes and constructs included in this application to provide abiotic stress tolerance.

Example 9

Evaluating Changes in Root Architecture Due to the Expression of Monocot ABST Genes Many key traits in modern agriculture can be explained by changes in the root architecture. Root size and depth correlates with drought tolerance and fertilizer use efficiency. Deeper root systems can access water in stored in deeper soil layers. Similarly, a highly branched root system provides better coverage of the soil and therefore can effectively absorb all macro and micronutrients available resulting in enhanced fertilizer use efficiency. To test whether the transgenic plants produce a different root structure, plants are grown in agar plates placed vertically. Plates are photographed every few days and the size, length and area covered by the plant roots is assessed. From every construct created, several independent transformation events are checked. To assess significant differences between root features, it is possible to apply one and two-way ANOVA using Students t-test or Tukey HSD test to identify the events showing outstanding root features and to provide a statistical score to the findings (see Example 8 above).

Example 10

Increased Biomass of the Transgenic Plants of the Present Invention $T_1$ or $T_2$ transgenic plants generated as described above are individually transplanted into pots containing a growth mixture of peat and vermiculite (volume ratio 3:2, respectively). The pots are covered for 24 hr period for hardening, then placed in the greenhouse in complete random order and irrigated with tap water (provided from the pots' bottom every 3-5 days) for seven days. Thereafter, half of the plants are irrigated with a salt solution (100 mM NaCl and 5 mM $CaCl_2$) to induce salinity stress (stress conditions). The other half of the plants are continued to be irrigated with tap water (normal conditions). All plants are grown in the greenhouse at 100% RH for 28 days, then harvested (the above ground tissue) and weighted (immediately or following drying in oven at 50° C. for 24 hr).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

REFERENCES CITED

Additional References are Cited Hereinabove

1. World Wide Web (dot) fao (dot) org/ag/agl/agll/spush/degrad (dot) htm.
2. World Wide Web (dot) fao (dot) org/ag/agl/aglw/water-management/introduc (dot) stm
3. McCue K F, Hanson A D (1990). Drought and salt tolerance: towards understanding and application. Trends Biotechnol 8: 358-362.
4. Flowers T J, Yeo Ar (1995). Breeding for salinity resistance in crop plants: where next? Aust J Plant Physiol 22:875-884.

5. Nguyen B D, Brar D S, Bui B C, Nguyen T V, Pham L N, Nguyen H T (2003). Identification and mapping of the QTL for aluminum tolerance introgressed from the new source, *ORYZA* RUFIPOGON Griff., into indica rice (*Oryza sativa* L.). Theor Appl Genet. 106:583-93.

6. Sanchez A C, Subudhi P K, Rosenow D T, Nguyen H T (2002). Mapping QTLs associated with drought resistance in *sorghum* (*Sorghum bicolor* L. Moench). Plant Mol Biol. 48:713-26.

7. Quesada V, Garcia-Martinez S, Piqueras P, Ponce M R, Micol J L (2002). Genetic architecture of NaCl tolerance in *Arabidopsis. Plant Physiol.* 130:951-963.

8. Apse M P, Blumwald E (2002). Engineering salt tolerance in plants. Curr Opin Biotechnol. 13:146-150.

9. Rontein D, Basset G, Hanson A D (2002). Metabolic engineering of osmoprotectant accumulation in plants. Metab Eng 4:49-56

10. Clough S J, Bent A F (1998). Floral dip: a simplified method for *Agrobacterium*-mediated transformation of *Arabidopsis thaliana*. Plant J 16:735-43.

11. Desfeux C, Clough S J, Bent A F (2000). Female reproductive tissues are the primary target of *Agrobacterium*-mediated transformation by the *Arabidopsis* floral-dip method. Plant Physiol 123:895-904.

What is claimed is:

1. A method of producing a plant crop, comprising growing a crop plant transformed with a polynucleotide comprising a nucleic acid sequence encoding a polypeptide comprising an amino acid sequence having at least 95% amino acid sequence identity to the amino acid sequence as set forth in SEQ ID NO: 4, wherein the crop plant is obtained from plants of said plant crop transformed with said polynucleotide, which overexpress said polypeptide, and which have been selected for increased biomass, and/or increased abiotic stress tolerance as compared to a wild type plant of the same species which is grown under the same growth conditions, and thereby producing plant crop having said increased biomass, and/or increased abiotic stress tolerance as compared to said wild type plant.

2. The method of claim 1, wherein said polynucleotide is operably linked to a promoter for directing transcription of said polynucleotide in a plant cell.

3. The method of claim 1, wherein said polypeptide has the amino acid sequence as set forth in SEQ ID NO: 4.

4. The method of claim 1, wherein said polypeptide has the amino acid sequence selected from the group consisting of SEQ ID NO: 4 and SEQ ID NO: 32.

5. The method of claim 1, wherein said plant crop is a dicotyledonous plant crop.

6. The method of claim 1, wherein said plant crop is a monocotyledonous plant crop.

7. The method of claim 2, wherein said polynucleotide comprising said nucleic acid sequence is at least 95% identical to the nucleic acid sequence as set forth in SEQ ID NO: 3.

8. The method of claim 1, wherein said nucleic acid sequence is selected from the group consisting of SEQ ID NO: 157 and SEQ ID NO: 179.

9. A method of increasing biomass, and/or abiotic stress tolerance of a plant as compared to a control plant of the same species which is grown under the same conditions, comprising transforming a plant with a polynucleotide comprising a nucleic acid sequence encoding a polypeptide having an amino acid sequence at least 95% amino acid sequence identity to the amino acid sequence as set forth in SEQ ID NO: 4, wherein overexpression of said polypeptide in said transformed plant results in an increased biomass, and/or an increased abiotic stress tolerance of said transformed plant as compared to a control plant of the same species which is grown under the same conditions.

10. The method of claim 9, further comprising selecting plants transformed with said polynucleotide and overexpressing said polypeptide, resulting in said increased biomass, and/or said increased abiotic stress tolerance in said selected transformed plant as compared to a control plant of the same species which is grown under the same conditions.

11. The method of claim 9, wherein said polypeptide comprises the amino acid sequence selected from the group consisting of SEQ ID NO: 4 and SEQ ID NO: 32.

12. The method of claim 9, further comprising growing the transformed plant under said abiotic stress.

13. The method of claim 9, wherein said abiotic stress is selected from the group consisting of salinity, water deprivation, low temperature, high temperature, heavy metal toxicity, anaerobiosis, nutrient deficiency, nutrient excess, atmospheric pollution and UV irradiation.

14. The method of claim 9, wherein said amino acid sequence is set forth in SEQ ID NO: 4.

* * * * *

SEQUENCE LISTING

<160> NUMBER OF SEQ ID NOS: 285

<210> SEQ ID NO 1
<211> LENGTH: 1037
<212> TYPE: DNA
<213> ORGANISM: Sorghum bicolor

<400> SEQUENCE: 1
acggtaacag agcaatttca gatcagtaga tgcgaacaaa aaccttgctc actcttctct 60
catttcatag cggaaagtaa ccaaagcgga cagtaacatc atcgaacacg ggggtaccaa 120
cacctaatcc aaaggttcaa cggacactaa cacatgggta actcagaatc caacggaacg 180
gtaacacgat actatagata gatagatagc taggataact tggccgaagc cagggtgggc 240
ccacacaatc agttctcgca ctcgcgcgcc tttcccattc gcgccgccgc cgccgccgct 300
gcaagcgcca gctcgccgtc gtccgagcca aacaccccaa cgccgccatg gggcgtatgc 360
acagccgcgg gaagggtatc tcgtcgtcgg cgctgccgta caagaggacg ccgccgacct 420
ggctcaagac cgccgcctcc gacgtggagg agatgatcac taaggcggcg aagaagggtc 480
agatgccgtc gcagatcggc gtcctgctcc gtgaccagca cggtatcccc cttgtcaaga 540
gcgtcacggg cagcaagatc ctccgcatcc tcaaggccca tgggctggcg ccagaaatcc 600
cggaggacct ctacttcctc atcaagaagg cggtggcgat aaggaagcac cttgagagga 660
acaggaagga caaagactcc aaattcaggc tcattcttgt tgagagcagg atccaccgcc 720
ttgcccgcta ctacaagcgc acaaagaagc ttccacccac ctggaagtat gagtcaacca 780
ccgcaagcac tctggtggcc taagtgagga gctcaacatt aggtgcttga agctgggcta 840
ttcttggaat catttttatg taccgtttta tgagtttgga gtgaactaga gatcttgaat 900
gtcctgtgga ggatgccata aacccttttg gttacataga actgcctgtt gttaactttt 960
gctactcggc atccagattt tgtcagctat aatatgatca tttacattac atggtttgcc 1020
cctaccttcc tgcagtc 1037

<210> SEQ ID NO 2
<211> LENGTH: 151
<212> TYPE: PRT
<213> ORGANISM: Sorghum bicolor

<400> SEQUENCE: 2

Met Gly Arg Met His Ser Arg Gly Lys Gly Ile Ser Ser Ser Ala Leu
1 5 10 15

Pro Tyr Lys Arg Thr Pro Pro Thr Trp Leu Lys Thr Ala Ala Ser Asp
20 25 30

Val Glu Glu Met Ile Thr Lys Ala Ala Lys Lys Gly Gln Met Pro Ser
35 40 45

-continued

Gln Ile Gly Val Leu Leu Arg Asp Gln His Gly Ile Pro Leu Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr Phe Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Arg Thr Lys Lys Leu Pro Pro Thr Trp Lys Tyr Glu Ser Thr
    130                 135                 140

Thr Ala Ser Thr Leu Val Ala
145                 150

<210> SEQ ID NO 3
<211> LENGTH: 1346
<212> TYPE: DNA
<213> ORGANISM: Sorghum bicolor

<400> SEQUENCE: 3
aagagaagag cagcagcagc aacagccgcg ccatccgctt gcttccttcc ttcctcttct      60
ctccctccta ccccaccgcc ggcgtcgcct cttcgcgttg cgcgccctcg cgtcgcaccc     120
gtgggtagca gccgcgtacc taccaacctg cgtgctgccg gggggagctct gcacgtctcc     180 tgtcgcctcg cctctcggca tggacgccgg gggagagaag ttcagcgacg cggcggcggc     240
ggagggcggt gagggcggcg gcgacctcta cgccgtcctc gggctcaaga aggagtgctc     300
cgacgccgac ctcaaggtcg cttaccggaa gctcgccaag aaatggcacc cggacaaatg     360
ctcctcctcc agcagcgtga aacacatgga ggaagccaag gagaagttcc aagagatcca     420
gggcgcctat tccgtactct ctgacgccaa taaacggctc ctctacgatg ttggagtata     480
cgacgatgag gacgacgagg atagcatgca ggggatgggt gacttcattg gtgagatggc     540
ccagatgatg agccaggtgc ggccgacgag gcaggaaagc tttgaggagc tgcagcagct     600
ttttgtggac atgttccagt ctgatattga ttcaggattc tgcaacgggt ctgctaagga     660
tcaagttcag gggcaagcca aaagtagaac atgctcgacc tcaccttcat catcaccgtc     720
cccacctcct cctcctacta tagtaaagga ggcagaggtg tcatcatgta atggcttcaa     780
taagcggggt tcatcagcaa tggactcagg gaagcctcca aggcctgttg aaggcggtgc     840
tggtcaggct ggattttgtt ttggggtgag cgatacgaag caaacgccga agccgagagg     900
tccgaacacc agccggagga ggaacggccg gaaacagaag ctgtcatcca agcacgatgt     960
ttcatctgaa gatgaaacgg ccggttccta gcaccagcag ctacggtagc agtttgacct    1020
gtggctttgg tgatatcatt cgttggtcct tggcggtgcc gagggcccta gtagccagca    1080
gcggcaggga ggcacagcat gtcgcttctg ctagctgctg tgatctgaag aggcgtttag    1140
ctcatcatat gccttacctt aggcctgtga gggacttcca ttgaaactcg tcgaggatac    1200
tgcatttttc tttctccatc tgtgtcggtt gtgttgtaca atacattgag tgacttctaa    1260
tcgattcttt ttttttacca ttaattaaca tctggtatat ccgattgatc gatccctagc    1320
cactgattac atgcatgagt tctttg                                         1346

<210> SEQ ID NO 4
<211> LENGTH: 258
<212> TYPE: PRT

-continued

<213> ORGANISM: Sorghum bicolor

<400> SEQUENCE: 4

```
Met Asp Ala Gly Gly Glu Lys Phe Ser Asp Ala Ala Ala Ala Glu Gly
1               5                   10                  15

Gly Glu Gly Gly Gly Asp Leu Tyr Ala Val Leu Gly Leu Lys Lys Glu
            20                  25                  30

Cys Ser Asp Ala Asp Leu Lys Val Ala Tyr Arg Lys Leu Ala Lys Lys
        35                  40                  45

Trp His Pro Asp Lys Cys Ser Ser Ser Ser Ser Val Lys His Met Glu
    50                  55                  60

Glu Ala Lys Glu Lys Phe Gln Glu Ile Gln Gly Ala Tyr Ser Val Leu
65                  70                  75                  80

Ser Asp Ala Asn Lys Arg Leu Leu Tyr Asp Val Gly Val Tyr Asp Asp
                85                  90                  95

Glu Asp Asp Glu Asp Ser Met Gln Gly Met Gly Asp Phe Ile Gly Glu
            100                 105                 110

Met Ala Gln Met Met Ser Gln Val Arg Pro Thr Arg Gln Glu Ser Phe
        115                 120                 125

Glu Glu Leu Gln Gln Leu Phe Val Asp Met Phe Gln Ser Asp Ile Asp
    130                 135                 140

Ser Gly Phe Cys Asn Gly Ser Ala Lys Asp Gln Val Gln Gly Gln Ala
145                 150                 155                 160

Lys Ser Arg Thr Cys Ser Thr Ser Pro Ser Ser Ser Pro Ser Pro Pro
                165                 170                 175

Pro Pro Pro Thr Ile Val Lys Glu Ala Glu Val Ser Ser Cys Asn Gly
            180                 185                 190

Phe Asn Lys Arg Gly Ser Ser Ala Met Asp Ser Gly Lys Pro Pro Arg
        195                 200                 205

Pro Val Glu Gly Gly Ala Gly Gln Ala Gly Phe Cys Phe Gly Val Ser
    210                 215                 220

Asp Thr Lys Gln Thr Pro Lys Pro Arg Gly Pro Asn Thr Ser Arg Arg
225                 230                 235                 240

Arg Asn Gly Arg Lys Gln Lys Leu Ser Ser Lys His Asp Val Ser Ser
                245                 250                 255

Glu Asp
```

<210> SEQ ID NO 5
<211> LENGTH: 1092
<212> TYPE: DNA
<213> ORGANISM: Sorghum bicolor

<400> SEQUENCE: 5

```
atggaaggat acgatagaga gttctggcag ttctctgata ctcttaggct tcagaccgct      60

gctttctctg actttctct cggagattct atctggtctc cagctactgg aggagctgct     120

gctgctgata gaaggaacaa ctctaacgat ctcttcgctg cttctgcttc tccagctgat     180

acaaccgctg ctaagaacaa tggaggagtg ggacttaggc ttaaccttaa cgatggagga     240

ccaggactta ttggatctgg gaagttggct ttcggaggat ctaaggctga taggtacaac     300

aaccttccag ctactactga gaaggctgct tcagcttaca ataacaacat caacgtgaac     360

gctggatacg ctaagaataa caataacaat gctctcgctt tcaacaagat gggaatctat     420

ggatacaaca ctaacaactc aaacatctct aacaactctt catctgggga ggtgaagtct     480

tacttcaata agagtgctgg aagggctgct tctaacaact ctcatggaca tggacatgct     540
```

```
ggaggaaaga agggaggaga gtacggaaat aagaagaagc acgggaagaa cgaaggaaat    600

aacggaggag gaggagctgg agctactgat aagaggttca agacccttcc agcttctgaa    660

gctcttccaa gaggacaagc tatcggaggt tacattttcg tgtgtaataa cgatacaatg    720

gatgagaact tgagaagaga gcttttcgga ctcccatcaa gataccgtga ttcagtgagg    780

gctattagac caggacttcc actcttcttg tacaattact ctacccatca gttgcatggg    840

attttcgagg ctgtttcttt cggaggaact aacatcgatc caaccgcttg ggaagataag    900

aagtgtccag gggagtcaag attcccagct caagtgagag ttgctaccag aaagatctat    960

gatccactcg aggaggatgc tttcagacca atcctccatc attacgatgg accaaagttc   1020

aggcttgagc tttctgttac tgaggctctt gctcttctcg atatctttgc tgataaggat   1080

gatgcttgat ga                                                       1092


<210> SEQ ID NO 6
<211> LENGTH: 362
<212> TYPE: PRT
<213> ORGANISM: Sorghum bicolor

<400> SEQUENCE: 6

Met Glu Gly Tyr Asp Arg Glu Phe Trp Gln Phe Ser Asp Thr Leu Arg
1               5                   10                  15

Leu Gln Thr Ala Ala Phe Ser Gly Leu Ser Leu Gly Asp Ser Ile Trp
            20                  25                  30

Ser Pro Ala Thr Gly Gly Ala Ala Ala Ala Asp Arg Arg Asn Asn Ser
        35                  40                  45

Asn Asp Leu Phe Ala Ala Ser Ala Ser Pro Ala Asp Thr Thr Ala Ala
    50                  55                  60

Lys Asn Asn Gly Gly Val Gly Leu Arg Leu Asn Leu Asn Asp Gly Gly
65                  70                  75                  80

Pro Gly Leu Ile Gly Ser Gly Lys Leu Ala Phe Gly Gly Ser Lys Ala
                85                  90                  95

Asp Arg Tyr Asn Asn Leu Pro Ala Thr Thr Glu Lys Ala Ala Ser Ala
            100                 105                 110

Tyr Asn Asn Asn Ile Asn Val Asn Ala Gly Tyr Ala Lys Asn Asn Asn
        115                 120                 125

Asn Asn Ala Leu Ala Phe Asn Lys Met Gly Ile Tyr Gly Tyr Asn Thr
    130                 135                 140

Asn Asn Ser Asn Ile Ser Asn Asn Ser Ser Ser Gly Glu Val Lys Ser
145                 150                 155                 160

Tyr Phe Asn Lys Ser Ala Gly Arg Ala Ala Ser Asn Asn Ser His Gly
                165                 170                 175

His Gly His Ala Gly Gly Lys Lys Gly Gly Glu Tyr Gly Asn Lys Lys
            180                 185                 190

Lys His Gly Lys Asn Glu Gly Asn Asn Gly Gly Gly Gly Ala Gly Ala
        195                 200                 205

Thr Asp Lys Arg Phe Lys Thr Leu Pro Ala Ser Glu Ala Leu Pro Arg
    210                 215                 220

Gly Gln Ala Ile Gly Gly Tyr Ile Phe Val Cys Asn Asn Asp Thr Met
225                 230                 235                 240

Asp Glu Asn Leu Arg Arg Glu Leu Phe Gly Leu Pro Ser Arg Tyr Arg
                245                 250                 255

Asp Ser Val Arg Ala Ile Arg Pro Gly Leu Pro Leu Phe Leu Tyr Asn
            260                 265                 270
```

-continued

```
Tyr Ser Thr His Gln Leu His Gly Ile Phe Glu Ala Val Ser Phe Gly
        275                 280                 285

Gly Thr Asn Ile Asp Pro Thr Ala Trp Glu Asp Lys Lys Cys Pro Gly
    290                 295                 300

Glu Ser Arg Phe Pro Ala Gln Val Arg Val Ala Thr Arg Lys Ile Tyr
305                 310                 315                 320

Asp Pro Leu Glu Glu Asp Ala Phe Arg Pro Ile Leu His His Tyr Asp
                325                 330                 335

Gly Pro Lys Phe Arg Leu Glu Leu Ser Val Thr Glu Ala Leu Ala Leu
            340                 345                 350

Leu Asp Ile Phe Ala Asp Lys Asp Asp Ala
        355                 360


<210> SEQ ID NO 7
<211> LENGTH: 1726
<212> TYPE: DNA
<213> ORGANISM: Sorghum bicolor

<400> SEQUENCE: 7

aaaaattccc tgcactttat ttcatttaca tcggtggttg tatcttgcac acggttcatt     60

taccatacat acatccaaac tttcctcatc aatttttcgt cgtcaggtac ttctaataaa    120

taccaaaaac ctcgggggca gctcctcttc actgccatga ttttggaagt cgccgcagta    180

gaaactcaaa gtattgtgca cctgttcaag ccaagagacg agaagatcct cctcgcagaa    240

ggccacaagc ggccaagaag cccaggcctc tcttcctcga aggcgtactc tggttctctg    300

gtcggactat ccattgtatt tgcacctcta tcagcacttg ttgcctcatc agagcccatg    360

tcccaccctc ctcctcctcc tgttgatcaa aatatctcgc tgcgcttttg cgagtccttt    420

tccctccaag gaacagaaac acccggcgct tttaccccac ccgcacccgc tttcccctcc    480

cggccaagaa caggagcaac aacaaggctc ctcctcgaga cattccattc atccatggcg    540

aagctcgtga acaagctggt cgattcgttc gaggagcaag acaccccgga cgtcggctgc    600

gtgcgcgccg tgctggccga gctcgtcctc accttcctct tcgtcttcac cggcgtctcc    660

gccgccatgg ccgccgggtc cggcgtgaag cccggcgagg ctatgccgat ggcgacgctg    720

gcggcggtgg caatcgcgca cgcgctggca gccggcgtac tggtgacggc cgggttccac    780

gtctccggcg gccacctcaa ccccgccgtg acggtggggc tcatggtgcg cggccacatc    840

accaagctcc gggcggtgct ctacgtcgcc gcgcaggtgc tggcgtcctc cctcgcctgc    900

atcctgctcc gctacctcag cggcggcatg gtgaccccgg tgcacgccct tggcgcgggc    960

atcagcccga tgcagggcct ggtgatggag gtgatcctca ccttctccct gctcttcgtc   1020

acctacgcca tgatcctgga cccacggagc caggtccgca ccatcggccc gctgctgacc   1080

ggcctcatcg ttggtgccaa cagcctcgcc ggtggcaact tcagcggcgc gtccatgaac   1140

ccggcacggt ccttcgggcc agccctggcc agcggggtct ggacaaacca ctggatctac   1200

tggatcggcc cgctgcttgg cgggcccctg gccgggttca tctacgagtc tttgttcatt   1260

gtgaacaaga cgcacgagcc gctgctcaat ggagacatct gacgaaccat cggcctgccc   1320

tgtggctgtg ggcagggcag tcagcatggt tggttcatgc ttgtttctgt aaaatagttc   1380

attgtctaca agcatgatgg atacatatat tggtcaaggt aattagagag ggttgctgta   1440

aaatagttac cctggtatag gattgttgga tgtagaaatt gttgatgggc tttgtatttt   1500

tttccccctt ttcatgccaa ggaattcttt ttttttaga gggcggggtt ctgtcaagga   1560
```

```
tttgttaagg ctattagtag ttagccatgt agtagaaaac tagagaatgg tatacgtggg   1620

agtgggacct gaagtttttt caggtacact gtagtactat tgtaattttg tcttgaagat   1680

ggaattggat gtacagagta aaaacttctc tttcaagcag taaaaa                   1726


<210> SEQ ID NO 8
<211> LENGTH: 381
<212> TYPE: PRT
<213> ORGANISM: Sorghum bicolor

<400> SEQUENCE: 8

Met Ile Leu Glu Val Ala Ala Val Glu Thr Gln Ser Ile Val His Leu
1               5                   10                  15

Phe Lys Pro Arg Asp Glu Lys Ile Leu Leu Ala Glu Gly His Lys Arg
            20                  25                  30

Pro Arg Ser Pro Gly Leu Ser Ser Ser Lys Ala Tyr Ser Gly Ser Leu
        35                  40                  45

Val Gly Leu Ser Ile Val Phe Ala Pro Leu Ser Ala Leu Val Ala Ser
    50                  55                  60

Ser Glu Pro Met Ser His Pro Pro Pro Pro Pro Val Asp Gln Asn Ile
65                  70                  75                  80

Ser Leu Arg Phe Cys Glu Ser Phe Ser Leu Gln Gly Thr Glu Thr Pro
                85                  90                  95

Gly Ala Phe Thr Pro Pro Ala Pro Ala Phe Pro Ser Arg Pro Arg Thr
            100                 105                 110

Gly Ala Thr Thr Arg Leu Leu Leu Glu Thr Phe His Ser Ser Met Ala
        115                 120                 125

Lys Leu Val Asn Lys Leu Val Asp Ser Phe Glu Glu Gln Asp Thr Pro
    130                 135                 140

Asp Val Gly Cys Val Arg Ala Val Leu Ala Glu Leu Val Leu Thr Phe
145                 150                 155                 160

Leu Phe Val Phe Thr Gly Val Ser Ala Ala Met Ala Ala Gly Ser Gly
                165                 170                 175

Val Lys Pro Gly Glu Ala Met Pro Met Ala Thr Leu Ala Ala Val Ala
            180                 185                 190

Ile Ala His Ala Leu Ala Ala Gly Val Leu Val Thr Ala Gly Phe His
        195                 200                 205

Val Ser Gly Gly His Leu Asn Pro Ala Val Thr Val Gly Leu Met Val
    210                 215                 220

Arg Gly His Ile Thr Lys Leu Arg Ala Val Leu Tyr Val Ala Ala Gln
225                 230                 235                 240

Val Leu Ala Ser Ser Leu Ala Cys Ile Leu Leu Arg Tyr Leu Ser Gly
                245                 250                 255

Gly Met Val Thr Pro Val His Ala Leu Gly Ala Gly Ile Ser Pro Met
            260                 265                 270

Gln Gly Leu Val Met Glu Val Ile Leu Thr Phe Ser Leu Leu Phe Val
        275                 280                 285

Thr Tyr Ala Met Ile Leu Asp Pro Arg Ser Gln Val Arg Thr Ile Gly
    290                 295                 300

Pro Leu Leu Thr Gly Leu Ile Val Gly Ala Asn Ser Leu Ala Gly Gly
305                 310                 315                 320

Asn Phe Ser Gly Ala Ser Met Asn Pro Ala Arg Ser Phe Gly Pro Ala
                325                 330                 335

Leu Ala Ser Gly Val Trp Thr Asn His Trp Ile Tyr Trp Ile Gly Pro
            340                 345                 350
```

-continued

Leu Leu Gly Gly Pro Leu Ala Gly Phe Ile Tyr Glu Ser Leu Phe Ile
        355                 360                 365

Val Asn Lys Thr His Glu Pro Leu Leu Asn Gly Asp Ile
    370                 375                 380

<210> SEQ ID NO 9
<211> LENGTH: 1097
<212> TYPE: DNA
<213> ORGANISM: Sorghum bicolor

<400> SEQUENCE: 9
gcatcagcct gataagctat agccagccat cttctctgaa ttccaactca gtccaagggc 60
tggaagcttg aagtaccgtc agagaaaaag aaaaaaagat ggtgaagctt gcatttggaa 120
gcttgggcga ctctttcagc gccgcgtccc tcaagtccta tgtggccgag ttcattgcca 180
cgctcctctt cgtgttcgcc ggcgtcgggt ccgccattgc ctactcgcaa ttgaccaagg 240
gtggcgctct ggaccccgcc ggcctggtgg ccatcgccat cgcccatgcg ttcgcgctct 300
tcgtcggcgt ctccatggcc gccaacgtct ccggcggcca cctgaacccc gccgtcacct 360
tcggcctcgc cgtcggcggc cacatcacca tcctcaccgg catcttctac tgggtcgccc 420
aggtgctcgg cgcgtccgtg gcgtgccttc tcctgaagta cgtcacccac ggacaggcta 480
tcccgacaca cggcgtgtcc gggatcagcg agatcgaggg cgtggtgatg gagatcgtga 540
tcaccttcgc gctcgtgtac accgtgtacg ccaccgcggc cgaccccaag aaggggtccc 600
tgggcaccat cgcgcccatc gccatcggct tcatcgtcgg cgccaacatc ctggcggccg 660
gacccttcag cggcggctcc atgaacccgg cccgctcctt cggccccgcc gtggccgctg 720
gcaacttcgc cggcaactgg gtctactggg tcggccccct catcggcggc ggcctggccg 780
ggctcgtcta cggcgacgtg ttcatcgcct cctaccagcc cgtcggccag caggatcagt 840
acccatgaag aaagtcgatc cggacccaaa tgcaatgcaa cccgtcgtgt tgatttcacc 900
gtcctcgtcg attcgccgtc gtgtcatcgc ttcgcgcttg tgattatgtt tggtcttgtt 960
tgcattaccc cttctggttt aattttcacc aacggtgtca acatgctgta agcgagagaa 1020
ccgttcgatc tatacctgta taaatgtaat gtacggttca gtatttccaa gtacagtata 1080
tgttccggac ggatttc 1097

<210> SEQ ID NO 10
<211> LENGTH: 249
<212> TYPE: PRT
<213> ORGANISM: Sorghum bicolor

<400> SEQUENCE: 10

Met Val Lys Leu Ala Phe Gly Ser Leu Gly Asp Ser Phe Ser Ala Ala
1               5                   10                  15

Ser Leu Lys Ser Tyr Val Ala Glu Phe Ile Ala Thr Leu Leu Phe Val
            20                  25                  30

Phe Ala Gly Val Gly Ser Ala Ile Ala Tyr Ser Gln Leu Thr Lys Gly
        35                  40                  45

Gly Ala Leu Asp Pro Ala Gly Leu Val Ala Ile Ala Ile Ala His Ala
    50                  55                  60

Phe Ala Leu Phe Val Gly Val Ser Met Ala Ala Asn Val Ser Gly Gly
65                  70                  75                  80

His Leu Asn Pro Ala Val Thr Phe Gly Leu Ala Val Gly Gly His Ile
                85                  90                  95

-continued

```
Thr Ile Leu Thr Gly Ile Phe Tyr Trp Val Ala Gln Val Leu Gly Ala
            100                 105                 110

Ser Val Ala Cys Leu Leu Leu Lys Tyr Val Thr His Gly Gln Ala Ile
        115                 120                 125

Pro Thr His Gly Val Ser Gly Ile Ser Glu Ile Glu Gly Val Val Met
    130                 135                 140

Glu Ile Val Ile Thr Phe Ala Leu Val Tyr Thr Val Tyr Ala Thr Ala
145                 150                 155                 160

Ala Asp Pro Lys Lys Gly Ser Leu Gly Thr Ile Ala Pro Ile Ala Ile
                165                 170                 175

Gly Phe Ile Val Gly Ala Asn Ile Leu Ala Ala Gly Pro Phe Ser Gly
            180                 185                 190

Gly Ser Met Asn Pro Ala Arg Ser Phe Gly Pro Ala Val Ala Ala Gly
        195                 200                 205

Asn Phe Ala Gly Asn Trp Val Tyr Trp Val Gly Pro Leu Ile Gly Gly
    210                 215                 220

Gly Leu Ala Gly Leu Val Tyr Gly Asp Val Phe Ile Ala Ser Tyr Gln
225                 230                 235                 240

Pro Val Gly Gln Gln Asp Gln Tyr Pro
                245
```

<210> SEQ ID NO 11
<211> LENGTH: 1160
<212> TYPE: DNA
<213> ORGANISM: Sorghum bicolor

<400> SEQUENCE: 11

```
gcacgaggcg gcgtcggagc ccacgaccgc ttccgcccca gtccccaccg ccctcgaccc     60

cgattccccc aatccctgcc gcgaccgctg aaccctagcc tactccggcc atctgccgct    120

ggccccggcg atcccccgcc atggcctccc ccgagggaac cacgtgggtc ttcgactgtc    180

ccctcatgga cgacctcgcg gtggccgccg acttcgcggc agcccccgcg gggggatttt    240

tctgggcagc gccgccgtcg ctacagccgc aggtggtgca ggcgccggtc cagtctgtcg    300

ttgccgcgtc ggctcccaac ccatgtgtgg aaatcagtag ctctgtggac tgtggtcagg    360

gaaaagaaca gccaacaaat aaacgtccta ggtcagaaag taccgcagaa ccaagcacaa    420

aagcatccag ggagaaaatt agaagggata agctgaacga gagattcctg gaattgggtg    480

ccattttgga gccagggaaa actcctaaaa tggacaagtc agctatatta aatgatgcta    540

ttcgtgtagt aggtgaattg cgtagcgaag caaaagagct caaggattca aatgagagcc    600

tacaagagaa gattaaagag ctaaaggctg agaagaatga gctgcgagac gagaagcaaa    660

ggctgaaggc cgagaaggag agcctggagc agcagatcaa gttcctgaat gcccgcccaa    720

gtctggtacc acaccaccca gtgatctcag cctctgcctt cactgctccc caggggccgg    780

cagtcgccgg gcacaagctg atgatgcctg tgcttggcta ccctggattc ccgatgtggc    840

agttcatgcc gccttctgat gttgacacct ctgatgaccc caagtcttgc ccacctgtgg    900

cgtaagcaag tgaagaggcg atgctgccct ccattgattc aagtctagat cgtgatcagt    960

ctgcagtgtt gttggtgtag ttgactccac tctccagaat ggaagggaag gttatatgtg   1020

tcggatggtg acatggggtg atctgatgac ccctttgtat attatatggt aaatgaataa   1080

attccgtgac cagttgcaaa tgaggattag cagactagct catgtctatt cctgcctttt   1140

tgtcgtataa accacgttgt                                                1160
```

<210> SEQ ID NO 12
<211> LENGTH: 254
<212> TYPE: PRT
<213> ORGANISM: Sorghum bicolor

<400> SEQUENCE: 12

```
Met Ala Ser Pro Glu Gly Thr Thr Trp Val Phe Asp Cys Pro Leu Met
1               5                   10                  15

Asp Asp Leu Ala Val Ala Ala Asp Phe Ala Ala Ala Pro Ala Gly Gly
            20                  25                  30

Phe Phe Trp Ala Ala Pro Pro Ser Leu Gln Pro Gln Val Val Gln Ala
        35                  40                  45

Pro Val Gln Ser Val Val Ala Ala Ser Ala Pro Asn Pro Cys Val Glu
    50                  55                  60

Ile Ser Ser Ser Val Asp Cys Gly Gln Gly Lys Glu Gln Pro Thr Asn
65                  70                  75                  80

Lys Arg Pro Arg Ser Glu Ser Thr Ala Glu Pro Ser Thr Lys Ala Ser
                85                  90                  95

Arg Glu Lys Ile Arg Arg Asp Lys Leu Asn Glu Arg Phe Leu Glu Leu
            100                 105                 110

Gly Ala Ile Leu Glu Pro Gly Lys Thr Pro Lys Met Asp Lys Ser Ala
        115                 120                 125

Ile Leu Asn Asp Ala Ile Arg Val Val Gly Glu Leu Arg Ser Glu Ala
    130                 135                 140

Lys Glu Leu Lys Asp Ser Asn Glu Ser Leu Gln Glu Lys Ile Lys Glu
145                 150                 155                 160

Leu Lys Ala Glu Lys Asn Glu Leu Arg Asp Glu Lys Gln Arg Leu Lys
                165                 170                 175

Ala Glu Lys Glu Ser Leu Glu Gln Gln Ile Lys Phe Leu Asn Ala Arg
            180                 185                 190

Pro Ser Leu Val Pro His His Pro Val Ile Ser Ala Ser Ala Phe Thr
        195                 200                 205

Ala Pro Gln Gly Pro Ala Val Ala Gly His Lys Leu Met Met Pro Val
    210                 215                 220

Leu Gly Tyr Pro Gly Phe Pro Met Trp Gln Phe Met Pro Pro Ser Asp
225                 230                 235                 240

Val Asp Thr Ser Asp Asp Pro Lys Ser Cys Pro Pro Val Ala
                245                 250
```

<210> SEQ ID NO 13
<211> LENGTH: 151
<212> TYPE: PRT
<213> ORGANISM: Zea mays

<400> SEQUENCE: 13

```
Met Gly Arg Met His Ser Arg Gly Lys Gly Ile Ser Ser Ser Ala Leu
1               5                   10                  15

Pro Tyr Lys Arg Thr Pro Pro Thr Trp Leu Lys Thr Ala Ala Ser Asp
            20                  25                  30

Val Glu Glu Met Ile Thr Lys Ala Ala Lys Lys Gly Gln Met Pro Ser
        35                  40                  45

Gln Ile Gly Val Leu Leu Arg Asp Gln His Gly Ile Pro Leu Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr Phe Leu Ile Lys Lys Ala Val
```

```
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Arg Thr Lys Lys Leu Pro Pro Thr Trp Lys Tyr Glu Ser Thr
    130                 135                 140

Thr Ala Ser Thr Leu Val Ala
145                 150


<210> SEQ ID NO 14
<211> LENGTH: 171
<212> TYPE: PRT
<213> ORGANISM: Saccharum officinarum

<400> SEQUENCE: 14

Arg Arg Arg Arg Arg Arg Lys Arg Gln Leu Ala Val Ala Arg Ala Lys
1               5                   10                  15

His Pro Asn Ala Ala Met Gly Arg Met His Ser Arg Gly Lys Gly Ile
            20                  25                  30

Ser Ser Ser Ala Leu Pro Tyr Lys Arg Thr Pro Pro Thr Trp Leu Lys
        35                  40                  45

Thr Ala Ala Ser Asp Val Glu Glu Met Ile Thr Lys Ala Ala Lys Lys
    50                  55                  60

Gly Gln Met Pro Ser Gln Ile Gly Val Leu Leu Arg Asp Gln His Gly
65                  70                  75                  80

Ile Pro Leu Val Lys Ser Val Thr Gly Ser Lys Ile Leu Arg Ile Leu
                85                  90                  95

Lys Ala His Gly Leu Ala Pro Glu Ile Pro Glu Asp Leu Tyr Phe Leu
            100                 105                 110

Ile Lys Lys Ala Val Ala Ile Arg Lys His Leu Glu Arg Asn Arg Lys
        115                 120                 125

Asp Lys Asp Ser Lys Phe Arg Leu Ile Leu Val Glu Ser Arg Ile His
    130                 135                 140

Arg Leu Ala Arg Tyr Tyr Lys Arg Thr Lys Lys Leu Pro Pro Thr Trp
145                 150                 155                 160

Lys Tyr Glu Ser Thr Thr Ala Ser Thr Leu Val
                165                 170


<210> SEQ ID NO 15
<211> LENGTH: 172
<212> TYPE: PRT
<213> ORGANISM: Sorghum bicolor

<400> SEQUENCE: 15

Arg Arg Arg Arg Arg Arg Cys Lys Arg Gln Leu Ala Val Val Arg Ala
1               5                   10                  15

Lys His Pro Asn Ala Ala Met Gly Arg Met His Ser Arg Gly Lys Gly
            20                  25                  30

Ile Ser Ser Ser Ala Leu Pro Tyr Lys Arg Thr Pro Pro Thr Trp Leu
        35                  40                  45

Lys Thr Ala Ala Ser Asp Val Glu Glu Met Ile Thr Lys Ala Ala Lys
    50                  55                  60

Lys Gly Gln Met Pro Ser Gln Ile Gly Val Leu Leu Arg Asp Gln His
65                  70                  75                  80

Gly Ile Pro Leu Val Lys Ser Val Thr Gly Ser Lys Ile Leu Arg Ile
```

```
                85                  90                  95

Leu Lys Ala His Gly Leu Ala Pro Glu Ile Pro Glu Asp Leu Tyr Phe
            100                 105                 110

Leu Ile Lys Lys Ala Val Ala Ile Arg Lys His Leu Glu Arg Asn Arg
        115                 120                 125

Lys Asp Lys Asp Ser Lys Phe Arg Leu Ile Leu Val Glu Ser Arg Ile
    130                 135                 140

His Arg Leu Ala Arg Tyr Tyr Lys Arg Thr Lys Lys Leu Pro Pro Thr
145                 150                 155                 160

Trp Lys Tyr Glu Ser Thr Thr Ala Ser Thr Leu Val
                165                 170


<210> SEQ ID NO 16
<211> LENGTH: 151
<212> TYPE: PRT
<213> ORGANISM: Saccharum officinarum

<400> SEQUENCE: 16

Met Gly Arg Met His Ser Arg Gly Lys Gly Ile Ser Ser Ser Ala Leu
1               5                   10                  15

Pro Tyr Lys Arg Thr Pro Pro Thr Trp Leu Lys Thr Ala Ala Thr Glu
            20                  25                  30

Val Glu Glu Met Ile Thr Lys Ala Ala Lys Lys Gly Gln Met Pro Ser
        35                  40                  45

Gln Ile Gly Val Leu Leu Arg Asp Gln His Gly Ile Pro Leu Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr Phe Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Arg Thr Lys Lys Leu Pro Pro Thr Trp Lys Tyr Glu Ser Thr
    130                 135                 140

Thr Ala Ser Thr Leu Val Ala
145                 150


<210> SEQ ID NO 17
<211> LENGTH: 187
<212> TYPE: PRT
<213> ORGANISM: Sorghum bicolor

<400> SEQUENCE: 17

Met Pro His Ala Pro Pro Leu Ala Leu Ala Pro Pro Pro Pro Pro Gln
1               5                   10                  15

Leu Leu Gln Gln Gln Ala Pro Ala Arg Arg Arg Arg Leu Gly Arg His
            20                  25                  30

Gln Ser Ala Ala Met Gly Arg Met His Ser Arg Gly Lys Gly Ile Ser
        35                  40                  45

Ser Ser Ala Leu Pro Tyr Lys Arg Thr Pro Pro Thr Trp Leu Lys Thr
    50                  55                  60

Ala Ala Thr Glu Val Glu Glu Met Ile Thr Lys Ala Ala Lys Lys Gly
65                  70                  75                  80

Gln Met Pro Ser Gln Ile Gly Val Leu Leu Arg Asp Gln His Gly Ile
```

-continued

```
                85                  90                  95

Pro Leu Val Lys Ser Val Thr Gly Ser Lys Ile Leu Arg Ile Leu Lys
            100                 105                 110

Ala His Gly Leu Ala Pro Glu Ile Pro Glu Asp Leu Tyr Phe Leu Ile
        115                 120                 125

Lys Lys Ala Val Ala Ile Arg Lys His Leu Glu Arg Asn Arg Lys Asp
    130                 135                 140

Lys Asp Ser Lys Phe Arg Leu Ile Leu Val Glu Ser Arg Ile His Arg
145                 150                 155                 160

Leu Ala Arg Tyr Tyr Lys Arg Thr Lys Lys Leu Pro Pro Thr Trp Lys
                165                 170                 175

Tyr Glu Ser Thr Thr Ala Ser Thr Leu Val Ala
            180                 185


<210> SEQ ID NO 18
<211> LENGTH: 184
<212> TYPE: PRT
<213> ORGANISM: Oryza sativa
<220> FEATURE:
<221> NAME/KEY: misc_feature
<222> LOCATION: (1)..(2)
<223> OTHER INFORMATION: Xaa can be any naturally occurring amino acid

<400> SEQUENCE: 18

Xaa Xaa Glu Lys Thr Pro Ser Tyr Arg Arg Ser Arg Pro Ser Arg Pro
1               5                   10                  15

Arg Ala Pro Pro Pro Pro Pro Ala Val Ala Gly Ala Lys Pro Leu Asp
            20                  25                  30

Ala Ala Met Gly Arg Met His Ser Arg Gly Lys Gly Ile Ser Ser Ser
        35                  40                  45

Ala Leu Pro Tyr Lys Arg Thr Pro Pro Ser Trp Leu Lys Thr Ala Ala
    50                  55                  60

Ser Asp Val Glu Glu Met Ile Met Lys Ala Ala Lys Lys Gly Gln Met
65                  70                  75                  80

Pro Ser Gln Ile Gly Val Val Leu Arg Asp Gln His Gly Ile Pro Leu
                85                  90                  95

Val Lys Ser Val Thr Gly Ser Lys Ile Leu Arg Ile Leu Lys Ala His
            100                 105                 110

Gly Leu Ala Pro Glu Ile Pro Glu Asp Leu Tyr Phe Leu Ile Lys Lys
        115                 120                 125

Ala Val Ala Ile Arg Lys His Leu Glu Arg Asn Arg Lys Asp Lys Asp
    130                 135                 140

Ser Lys Phe Arg Leu Ile Leu Val Glu Ser Arg Ile His Arg Leu Ala
145                 150                 155                 160

Arg Tyr Tyr Lys Arg Thr Lys Lys Leu Pro Pro Thr Trp Lys Tyr Glu
                165                 170                 175

Ser Thr Thr Ala Ser Thr Leu Val
            180


<210> SEQ ID NO 19
<211> LENGTH: 151
<212> TYPE: PRT
<213> ORGANISM: Zea mays

<400> SEQUENCE: 19

Met Gly Arg Met His Ser Arg Gly Lys Gly Ile Ser Ser Ser Ala Leu
1               5                   10                  15
```

Pro Tyr Lys Arg Thr Pro Pro Ile Trp Leu Lys Thr Ala Thr Ala Glu
20 25 30

Val Glu Glu Met Ile Thr Lys Ala Ala Lys Lys Gly Gln Met Pro Ser
35 40 45

Gln Ile Gly Val Leu Leu Arg Asp Gln His Gly Ile Pro Leu Val Lys
50 55 60

Ser Val Thr Gly Ser Lys Ile Leu Arg Ile Leu Lys Ala His Gly Leu
65 70 75 80

Ala Pro Glu Ile Pro Glu Asp Leu Tyr Phe Leu Ile Lys Lys Ala Val
85 90 95

Ala Ile Arg Lys His Leu Glu Arg Asn Arg Lys Asp Lys Asp Ser Lys
100 105 110

Phe Arg Leu Ile Leu Val Glu Ser Arg Ile His Arg Leu Ala Arg Tyr
115 120 125

Tyr Lys Arg Thr Lys Lys Leu Pro Pro Thr Trp Lys Tyr Glu Ser Thr
130 135 140

Thr Ala Ser Thr Leu Val Ala
145 150

<210> SEQ ID NO 20
<211> LENGTH: 183
<212> TYPE: PRT
<213> ORGANISM: Hordeum vulgare
<220> FEATURE:
<221> NAME/KEY: misc_feature
<222> LOCATION: (1)..(2)
<223> OTHER INFORMATION: Xaa can be any naturally occurring amino acid

<400> SEQUENCE: 20

Xaa Xaa Pro Leu Phe Tyr Pro Leu Thr Thr Arg Ala Ser Leu Ala Leu
1 5 10 15

Pro Ala Ala Ala Ala Ala Ala Ala Pro Leu Ala Ala Ala Ala Ala Ala
20 25 30

Ala Met Gly Arg Met His Ser Arg Gly Lys Gly Ile Ser Ser Ser Ala
35 40 45

Leu Pro Tyr Lys Arg Thr Pro Pro Ser Trp Val Lys Thr Ala Val Ala
50 55 60

Asp Val Asp Glu Leu Ile Thr Lys Ala Ala Lys Lys Gly Gln Met Pro
65 70 75 80

Ser Gln Ile Gly Val Leu Leu Arg Asp Gln His Gly Ile Pro Leu Val
85 90 95

Lys Ser Val Thr Gly Ser Lys Ile Leu Arg Ile Leu Lys Ala His Gly
100 105 110

Leu Ala Pro Glu Ile Pro Glu Asp Leu Tyr Phe Leu Ile Lys Lys Ala
115 120 125

Val Ala Ile Arg Lys His Leu Glu Arg Asn Arg Lys Asp Lys Asp Ser
130 135 140

Lys Phe Arg Leu Ile Leu Val Glu Ser Arg Ile His Arg Leu Ala Arg
145 150 155 160

Tyr Tyr Lys Arg Thr Lys Lys Leu Pro Pro Thr Trp Lys Tyr Glu Ser
165 170 175

Thr Thr Ala Ser Thr Leu Val
180

<210> SEQ ID NO 21
<211> LENGTH: 178
<212> TYPE: PRT

<213> ORGANISM: Oryza sativa

<400> SEQUENCE: 21

```
Ser Ser Arg Arg Arg Arg Leu Leu Arg Arg Ala Val Ala Asn Arg Arg
1               5                   10                  15

Arg Arg Ser Pro Ser Pro Asn Ser Pro Leu Pro Pro Trp Gly Arg Met
            20                  25                  30

His Ser Arg Gly Lys Gly Ile Ser Ser Ser Ala Ile Pro Tyr Lys Arg
        35                  40                  45

Thr Pro Pro Ser Trp Val Lys Thr Ala Ala Ala Asp Val Glu Glu Met
    50                  55                  60

Ile Met Lys Ala Ala Lys Lys Gly Gln Met Pro Ser Gln Ile Gly Val
65                  70                  75                  80

Val Leu Arg Asp Gln His Gly Ile Pro Leu Val Lys Ser Val Thr Gly
                85                  90                  95

Ser Lys Ile Leu Arg Ile Leu Lys Ala His Gly Leu Ala Pro Glu Ile
            100                 105                 110

Pro Glu Asp Leu Tyr Phe Leu Ile Lys Lys Ala Val Ala Ile Arg Lys
        115                 120                 125

His Leu Glu Arg Asn Arg Lys Asp Lys Asp Ser Lys Phe Arg Leu Ile
    130                 135                 140

Leu Val Glu Ser Arg Ile His Arg Leu Ala Arg Tyr Tyr Lys Arg Thr
145                 150                 155                 160

Lys Lys Leu Pro Pro Thr Trp Lys Tyr Glu Ser Thr Thr Ala Ser Thr
                165                 170                 175

Leu Val
```

<210> SEQ ID NO 22
<211> LENGTH: 170
<212> TYPE: PRT
<213> ORGANISM: Triticum aestivum

<400> SEQUENCE: 22

```
Ala Leu Phe Tyr Pro Leu Thr Thr Arg Ala Ser Leu Ala Leu Pro Ala
1               5                   10                  15

Ala Ala Ala Ala Thr Pro Leu Ala Ala Ala Ala Ala Ala Ala Met Gly
            20                  25                  30

Arg Met His Ser Arg Gly Lys Gly Ile Ser Ser Ser Ala Leu Pro Tyr
        35                  40                  45

Lys Arg Thr Pro Pro Ser Trp Val Lys Thr Ala Val Ala Asp Val Asp
    50                  55                  60

Glu Leu Ile Thr Lys Ala Ala Lys Lys Gly Gln Met Pro Ser Gln Ile
65                  70                  75                  80

Gly Val Leu Leu Arg Asp Gln His Gly Ile Pro Leu Val Lys Ser Val
                85                  90                  95

Thr Gly Ser Lys Ile Leu Arg Ile Leu Lys Ala His Gly Leu Ala Pro
            100                 105                 110

Glu Ile Pro Glu Asp Leu Tyr Phe Leu Ile Lys Lys Ala Val Ala Ile
        115                 120                 125

Arg Lys His Leu Glu Arg Asn Arg Lys Asp Lys Asp Ser Lys Phe Arg
    130                 135                 140

Leu Ile Leu Val Glu Ser Arg Ile His Arg Leu Ala Arg Tyr Tyr Lys
145                 150                 155                 160

Arg Thr Lys Lys Leu Pro Pro Thr Trp Lys
                165                 170
```

<210> SEQ ID NO 23
<211> LENGTH: 177
<212> TYPE: PRT
<213> ORGANISM: Triticum aestivum
<220> FEATURE:
<221> NAME/KEY: misc_feature
<222> LOCATION: (1)..(2)
<223> OTHER INFORMATION: Xaa can be any naturally occurring amino acid

<400> SEQUENCE: 23

```
Xaa Xaa Ala Gly Asn Ser Ala Arg Gly Ser Ser Pro Ser Arg Pro Ser
1               5                   10                  15

Arg Arg Cys Cys Cys Arg Gln Pro Pro Pro Pro Ser Pro Glu Leu Asn
            20                  25                  30

Pro Ser Pro Asp Ala Met Gly Arg Met His Ser Arg Gly Lys Gly Ile
        35                  40                  45

Ser Ser Ser Ala Leu Pro Tyr Lys Arg Thr Pro Pro Ser Trp Val Lys
    50                  55                  60

Thr Ala Val Ala Asp Val Asp Glu Leu Ile Thr Lys Ala Ala Lys Lys
65                  70                  75                  80

Gly Gln Met Pro Ser Gln Ile Gly Val Leu Leu Arg Asp Gln His Gly
                85                  90                  95

Ile Pro Leu Val Lys Ser Val Thr Gly Ser Lys Ile Leu Arg Ile Leu
            100                 105                 110

Lys Ala His Gly Leu Ala Pro Glu Ile Pro Glu Asp Leu Tyr Phe Leu
        115                 120                 125

Ile Lys Lys Ala Val Ala Ile Arg Lys His Leu Glu Arg Asn Arg Lys
    130                 135                 140

Asp Lys Asp Ser Lys Phe Arg Leu Ile Leu Val Glu Ser Arg Ile His
145                 150                 155                 160

Arg Leu Ala Arg Tyr Tyr Lys Arg Thr Lys Lys Leu Pro Pro Thr Trp
                165                 170                 175

Lys
```

<210> SEQ ID NO 24
<211> LENGTH: 171
<212> TYPE: PRT
<213> ORGANISM: Hordeum vulgare

<400> SEQUENCE: 24

```
Arg Arg Arg Ser Cys Pro Ser Ser Pro Ser Arg Arg Cys Cys Cys Arg
1               5                   10                  15

Gln Pro Pro Pro Ser Ser Pro Glu Leu Asn Pro Ser Pro Asp Ala Met
            20                  25                  30

Gly Arg Met His Ser Arg Gly Lys Gly Ile Ser Ser Ser Ala Leu Pro
        35                  40                  45

Tyr Lys Arg Thr Pro Pro Ser Trp Val Lys Thr Ala Val Ala Asp Val
    50                  55                  60

Asp Glu Leu Ile Thr Lys Ala Ala Lys Lys Gly Gln Met Pro Ser Gln
65                  70                  75                  80

Ile Gly Val Leu Leu Arg Asp Gln His Gly Ile Pro Leu Val Lys Ser
                85                  90                  95

Val Thr Gly Ser Lys Ile Leu Arg Ile Leu Lys Ala His Gly Leu Ala
            100                 105                 110

Pro Glu Ile Pro Glu Asp Leu Tyr Phe Leu Ile Lys Lys Ala Val Ala
        115                 120                 125
```

-continued

Ile Arg Lys His Leu Glu Arg Asn Arg Lys Asp Lys Asp Ser Lys Phe
    130                 135                 140

Arg Leu Ile Leu Val Glu Ser Arg Ile His Arg Leu Ala Arg Tyr Tyr
145                 150                 155                 160

Lys Arg Thr Lys Lys Leu Pro Pro Thr Trp Lys
                165                 170

<210> SEQ ID NO 25
<211> LENGTH: 116
<212> TYPE: PRT
<213> ORGANISM: Triticum aestivum

<400> SEQUENCE: 25

Met Ile Thr Lys Ala Ala Lys Lys Gly Gln Met Pro Ser Gln Ile Gly
1               5                   10                  15

Val Leu Leu Arg Asp Gln His Gly Ile Pro Leu Val Lys Ser Val Thr
            20                  25                  30

Gly Ser Lys Ile Leu Arg Ile Leu Lys Ala His Gly Leu Ala Pro Glu
        35                  40                  45

Ile Pro Glu Asp Leu Tyr Phe Leu Ile Lys Lys Ala Val Ala Ile Arg
    50                  55                  60

Lys His Leu Glu Arg Asn Arg Lys Asp Lys Asp Ser Lys Phe Arg Leu
65                  70                  75                  80

Ile Leu Val Glu Ser Arg Ile His Arg Leu Ala Arg Tyr Tyr Lys Arg
                85                  90                  95

Thr Lys Lys Leu Pro Pro Thr Trp Lys Tyr Glu Ser Thr Thr Ala Ser
            100                 105                 110

Thr Leu Val Ala
        115

<210> SEQ ID NO 26
<211> LENGTH: 116
<212> TYPE: PRT
<213> ORGANISM: Zea mays

<400> SEQUENCE: 26

Met Ile Thr Lys Ala Ala Lys Lys Gly Gln Met Pro Ser Gln Ile Gly
1               5                   10                  15

Val Leu Leu Arg Asp Gln His Gly Ile Pro Leu Val Lys Ser Val Thr
            20                  25                  30

Gly Ser Lys Ile Leu Arg Ile Leu Lys Ala His Gly Leu Ala Pro Glu
        35                  40                  45

Ile Pro Glu Asp Leu Tyr Phe Leu Ile Lys Lys Ala Val Ala Ile Arg
    50                  55                  60

Lys His Leu Glu Arg Asn Arg Lys Asp Lys Asp Ser Lys Phe Arg Leu
65                  70                  75                  80

Ile Leu Val Glu Ser Arg Ile His Arg Leu Ala Arg Tyr Tyr Lys Arg
                85                  90                  95

Thr Lys Lys Leu Pro Pro Thr Trp Lys Tyr Glu Ser Thr Thr Ala Ser
            100                 105                 110

Thr Leu Val Ala
        115

<210> SEQ ID NO 27
<211> LENGTH: 122
<212> TYPE: PRT
<213> ORGANISM: Saccharum officinarum

<400> SEQUENCE: 27

Met Ile Thr Asn Ala Ala Lys Lys Gly Gln Met Pro Ser Gln Ile Gly
1 5 10 15

Val Leu Val Arg Asp Gln His Gly Ile Pro Leu Val Lys Ser Val Thr
20 25 30

Gly Ser Met Ile Leu Arg Ile Leu Lys Ala His Gly Leu Ser Leu Glu
35 40 45

Ile Pro Glu Asp Leu Tyr Phe Leu Ile Lys Lys Ala Val Trp Ile Arg
50 55 60

Lys His Leu Glu Arg Asn Arg Lys Asp Lys Asp Phe Lys Phe Thr Leu
65 70 75 80

Ile Leu Val Glu Ser Arg Ile His Arg Leu Ala Arg Tyr Tyr Lys Arg
85 90 95

Thr Lys Lys Leu Pro Pro Thr Cys Lys Tyr Glu Thr Thr Thr Gly Ser
100 105 110

Thr Leu Val Ala Ile Val Val Ser Ser Thr
115 120

<210> SEQ ID NO 28
<211> LENGTH: 210
<212> TYPE: PRT
<213> ORGANISM: Triticum aestivum
<220> FEATURE:
<221> NAME/KEY: misc_feature
<222> LOCATION: (38)..(38)
<223> OTHER INFORMATION: Xaa can be any naturally occurring amino acid

<400> SEQUENCE: 28

Met Pro Ser Gln Ile Gly Val Leu Leu Arg Asp Gln His Gly Ile Pro
1 5 10 15

Leu Val Lys Ser Val Thr Gly Ser Lys Ile Leu Arg Ile Leu Lys Ala
20 25 30

His Gly Leu Ala Pro Xaa Ile Pro Glu Asp Leu Tyr Phe Leu Ile Lys
35 40 45

Lys Ala Val Ala Ile Arg Lys His Leu Glu Arg Asn Arg Arg Asp Lys
50 55 60

Asp Ser Lys Phe Arg Leu Ile Leu Val Glu Ser Arg Ile His Arg Leu
65 70 75 80

Ala Arg Tyr Tyr Lys Arg Thr Lys Lys Leu Pro Pro Thr Trp Lys Trp
85 90 95

Glu Val Lys Ala Val Leu Asp Asp Tyr Pro Lys Leu Cys Leu Thr Lys
100 105 110

Gly Arg Lys Val Leu Glu Ile Arg Pro Ser Ile Glu Trp Asn Lys Gly
115 120 125

His Ala Leu Lys Phe Leu Leu Lys Ser Leu Gly Tyr Ala Gly Arg Ser
130 135 140

Asp Val Phe Pro Ile Tyr Ile Gly Asp Asp Arg Thr Asp Glu Asp Ala
145 150 155 160

Phe Lys Val Leu Gln Asn Met Gly Gln Gly Ile Gly Ile Leu Val Thr
165 170 175

Lys Phe Pro Lys Asp Thr Ser Ala Ser Tyr Ser Leu Arg Glu Pro Ala
180 185 190

Glu Val Lys Glu Phe Met Arg Lys Leu Val Lys Ser Asn Gly Ile Lys
195 200 205

Lys Gly

210

<210> SEQ ID NO 29
<211> LENGTH: 92
<212> TYPE: PRT
<213> ORGANISM: Zea mays

<400> SEQUENCE: 29

Met Pro Leu Val Lys Ser Val Thr Gly Ser Lys Ile Leu Arg Ile Leu
1 5 10 15

Lys Ala His Gly Leu Ala Pro Glu Ile Pro Glu Asp Leu Tyr Phe Leu
20 25 30

Ile Lys Lys Ala Val Ala Ile Arg Lys His Leu Glu Arg Asn Arg Lys
35 40 45

Asp Lys Asp Ser Lys Phe Arg Leu Ile Leu Val Glu Ser Arg Ile His
50 55 60

Arg Leu Ala Arg Tyr Tyr Lys Arg Thr Lys Lys Leu Pro Pro Thr Trp
65 70 75 80

Lys Tyr Glu Ser Thr Thr Ala Ser Thr Leu Val Ala
85 90

<210> SEQ ID NO 30
<211> LENGTH: 96
<212> TYPE: PRT
<213> ORGANISM: Triticum aestivum
<220> FEATURE:
<221> NAME/KEY: misc_feature
<222> LOCATION: (86)..(86)
<223> OTHER INFORMATION: Xaa can be any naturally occurring amino acid

<400> SEQUENCE: 30

Met Gly Arg Met His Ser Arg Gly Lys Gly Ile Ser Ser Ser Ala Leu
1 5 10 15

Pro Tyr Lys Arg Thr Pro Pro Thr Trp Leu Lys Thr Ala Ala Ser Asp
20 25 30

Val Glu Glu Met Ile Thr Lys Ala Ala Lys Lys Gly Gln Met Pro Ser
35 40 45

Gln Ile Gly Val Leu Leu Arg Asp Gln His Gly Ile Pro Leu Val Lys
50 55 60

Ser Val Thr Gly Ser Lys Ile Leu Arg Ile Leu Lys Ala His Gly Trp
65 70 75 80

His Gln Lys Ser Arg Xaa Leu Tyr Phe Ser Ser Arg Arg Arg Trp Arg
85 90 95

<210> SEQ ID NO 31
<211> LENGTH: 327
<212> TYPE: PRT
<213> ORGANISM: Sorghum bicolor
<220> FEATURE:
<221> NAME/KEY: misc_feature
<222> LOCATION: (1)..(2)
<223> OTHER INFORMATION: Xaa can be any naturally occurring amino acid

<400> SEQUENCE: 31

Xaa Xaa Arg Glu Glu Gln Gln Gln Gln Gln Pro Arg His Pro Leu Ala
1 5 10 15

Ser Phe Leu Pro Leu Leu Ser Leu Leu Pro His Arg Arg Arg Arg Leu
20 25 30

Phe Ala Leu Arg Ala Leu Ala Ser His Pro Trp Val Ala Ala Ala Tyr
35 40 45

Leu Pro Thr Cys Val Leu Pro Gly Glu Leu Cys Thr Ser Pro Val Ala
    50              55                  60

Ser Pro Leu Gly Met Asp Ala Gly Gly Glu Lys Phe Ser Asp Ala Ala
65                  70                  75                  80

Ala Ala Glu Gly Gly Glu Gly Gly Gly Asp Leu Tyr Ala Val Leu Gly
                85                  90                  95

Leu Lys Lys Glu Cys Ser Asp Ala Asp Leu Lys Val Ala Tyr Arg Lys
            100                 105                 110

Leu Ala Lys Lys Trp His Pro Asp Lys Cys Ser Ser Ser Ser Ser Val
        115                 120                 125

Lys His Met Glu Glu Ala Lys Glu Lys Phe Gln Glu Ile Gln Gly Ala
    130                 135                 140

Tyr Ser Val Leu Ser Asp Ala Asn Lys Arg Leu Leu Tyr Asp Val Gly
145                 150                 155                 160

Val Tyr Asp Asp Glu Asp Asp Glu Asp Ser Met Gln Gly Met Gly Asp
                165                 170                 175

Phe Ile Gly Glu Met Ala Gln Met Met Ser Gln Val Arg Pro Thr Arg
            180                 185                 190

Gln Glu Ser Phe Glu Glu Leu Gln Gln Leu Phe Val Asp Met Phe Gln
        195                 200                 205

Ser Asp Ile Asp Ser Gly Phe Cys Asn Gly Ser Ala Lys Asp Gln Val
    210                 215                 220

Gln Gly Gln Ala Lys Ser Arg Thr Cys Ser Thr Ser Pro Ser Ser Ser
225                 230                 235                 240

Pro Ser Pro Pro Pro Pro Pro Thr Ile Val Lys Glu Ala Glu Val Ser
                245                 250                 255

Ser Cys Asn Gly Phe Asn Lys Arg Gly Ser Ser Ala Met Asp Ser Gly
            260                 265                 270

Lys Pro Pro Arg Pro Val Glu Gly Gly Ala Gly Gln Ala Gly Phe Cys
        275                 280                 285

Phe Gly Val Ser Asp Thr Lys Gln Thr Pro Lys Pro Arg Gly Pro Asn
    290                 295                 300

Thr Ser Arg Arg Arg Asn Gly Arg Lys Gln Lys Leu Ser Ser Lys His
305                 310                 315                 320

Asp Val Ser Ser Glu Asp Glu
                325

<210> SEQ ID NO 32
<211> LENGTH: 265
<212> TYPE: PRT
<213> ORGANISM: Saccharum officinarum

<400> SEQUENCE: 32

Met Asp Ala Gly Gly Glu Lys Cys Gly Asp Ala Ala Ala Ala Glu Gly
1               5                   10                  15

Gly Glu Gly Gly Gly Asp Leu Tyr Ala Val Leu Gly Leu Lys Lys Glu
            20                  25                  30

Cys Ser Asp Ala Asp Leu Lys Val Ala Tyr Arg Lys Leu Ala Lys Lys
        35                  40                  45

Trp His Pro Asp Lys Cys Ser Ser Ser Ser Ser Val Lys His Met Glu
    50                  55                  60

Glu Ala Lys Glu Lys Phe Gln Glu Ile Gln Gly Ala Tyr Ser Val Leu
65                  70                  75                  80

Ser Asp Ala Asn Lys Arg Leu Leu Tyr Asp Val Gly Val Tyr Asp Asp
                85                  90                  95

Glu Asp Asp Glu Asp Ser Met Gln Gly Met Gly Asp Phe Ile Gly Glu
100 105 110

Met Ala Gln Met Met Ser Gln Val Arg Pro Thr Arg Gln Glu Ser Phe
115 120 125

Glu Glu Leu Gln Gln Leu Phe Val Asp Met Phe Gln Ser Asp Ile Asp
130 135 140

Ser Gly Phe Cys Asn Gly Thr Ala Lys Gly His Gln Val Gln Gly Gln
145 150 155 160

Ala Lys Ser Arg Thr Cys Ser Thr Ser Pro Ser Ser Ser Pro Ser Pro
165 170 175

Pro Pro Pro Thr Ile Val Lys Glu Ala Glu Val Pro Ser Cys Asn Gly
180 185 190

Phe Asn Lys Arg Gly Ser Ser Ala Met Asp Ser Gly Lys Pro Pro Arg
195 200 205

Pro Val Glu Gly Gly Ala Gly Gln Arg Gln Ala Gly Phe Cys Phe Gly
210 215 220

Val Ser Asp Thr Lys Gln Ala Ala Lys Pro Arg Gly Pro Asn Thr Ser
225 230 235 240

Arg Arg Arg Asn Gly Arg Lys Gln Lys Leu Ser Ser Lys His Asp Val
245 250 255

Ser Ser Glu Asp Glu Thr Ala Gly Ser
260 265

<210> SEQ ID NO 33
<211> LENGTH: 320
<212> TYPE: PRT
<213> ORGANISM: Sorghum bicolor

<400> SEQUENCE: 33

Met Asp Ser Leu Trp His Leu Gly Asp Glu Leu Arg Gly Gln Pro Lys
1 5 10 15

Val Val Glu Asp Arg Gln Trp Ser Leu Met Thr Ser Lys Leu Ala Glu
20 25 30

Ile Thr Arg Ser Lys Gly Glu Arg Met Asn Asp Leu Asp Tyr Ala Arg
35 40 45

Met Asn Thr Val Pro Asp Ala Lys Gln Trp Asp Lys Thr Ser Phe Gln
50 55 60

His His Asp Gln Ser Arg Met Asp His Ile Asn Leu Gly Leu Met Asn
65 70 75 80

Leu Asp Leu Lys Met Asn Asp Leu Lys Met Asn Glu Ala Pro Thr Ala
85 90 95

Met Lys Leu Pro Phe His Asn Met Pro Tyr Asn Met Asn Pro Met Tyr
100 105 110

Pro Lys Gly Ser Asn Ala Asn Val Asn Val Asn Ala Phe Lys Met Asn
115 120 125

Val Gly Val Asn Lys Tyr Ser Asn Ser Pro Asn Gly Lys Asp Ala Asn
130 135 140

Gly Lys Asn Asn Gly Gly Ser Asn Asn Asn Gly Gly Asn Ser Asn Gly
145 150 155 160

Ser Ala Asn Gly Asn Ser Ala Val Asp Lys Arg Phe Lys Thr Leu Pro
165 170 175

Thr Ser Glu Met Leu Pro Arg Asn Glu Val Leu Gly Gly Tyr Ile Phe
180 185 190

Val Cys Asn Asn Asp Thr Met Gln Glu Asp Leu Lys Arg Gln Leu Phe

```
        195                 200                 205

Gly Leu Pro Ala Arg Tyr Arg Asp Ser Val Arg Ala Ile Thr Pro Gly
    210                 215                 220

Leu Pro Leu Phe Leu Tyr Asn Tyr Thr Thr His Gln Leu His Gly Val
225                 230                 235                 240

Phe Glu Ala Ala Ser Phe Gly Gly Ser Asn Ile Asp Pro Thr Ala Trp
                245                 250                 255

Glu Asp Lys Lys Cys Lys Gly Glu Ser Arg Phe Pro Ala Gln Val Arg
            260                 265                 270

Ile Arg Ile Arg Lys Leu Cys Lys Pro Leu Glu Glu Asp Ser Phe Arg
        275                 280                 285

Pro Val Leu His His Tyr Asp Gly Pro Lys Phe Arg Leu Glu Leu Ser
    290                 295                 300

Ile Ala Glu Thr Leu Ser Leu Leu Asp Leu Cys Glu Lys Glu Gly Ile
305                 310                 315                 320


<210> SEQ ID NO 34
<211> LENGTH: 265
<212> TYPE: PRT
<213> ORGANISM: Saccharum officinarum

<400> SEQUENCE: 34

Met Asn Thr Asp Pro Asp Ala Lys Gln Trp Asp Lys Thr Ser Tyr Gln
1               5                   10                  15

His His Asn Glu Ser Arg Met Asp His Ile Asn Leu Gly Leu Met Asn
            20                  25                  30

Leu Asp Leu Lys Met Asn Glu Ala Ala Thr Ala Met Lys Leu Pro Phe
        35                  40                  45

His Asn Met Pro Tyr Asn Met Asn Pro Met Tyr Pro Lys Gly Ser Asn
    50                  55                  60

Val Asn Val Asn Ala Phe Lys Met Asn Val Gly Val Asn Lys Tyr Ser
65                  70                  75                  80

Asn Ser Pro Asn Gly Lys Asp Ala Asn Gly Lys Asn Asn Gly Gly Ser
                85                  90                  95

Asn Asn Asn Gly Gly Asn Ser Asn Gly Ser Ala Asn Ser Asn Ser Ala
            100                 105                 110

Val Asp Lys Arg Phe Lys Thr Leu Pro Thr Ser Glu Met Leu Pro Arg
        115                 120                 125

Asn Glu Val Leu Gly Gly Tyr Ile Phe Val Cys Asn Asn Asp Thr Met
    130                 135                 140

Gln Glu Asp Leu Lys Arg Gln Leu Phe Gly Leu Pro Ala Arg Tyr Arg
145                 150                 155                 160

Asp Ser Val Arg Ala Ile Thr Pro Gly Leu Pro Leu Phe Leu Tyr Asn
                165                 170                 175

Tyr Thr Thr His Gln Leu His Gly Val Phe Glu Ala Ala Ser Phe Gly
            180                 185                 190

Gly Ser Asn Ile Asp Pro Thr Ala Trp Glu Asp Lys Lys Cys Lys Gly
        195                 200                 205

Glu Ser Arg Phe Pro Ala Gln Val Arg Ile Arg Ile Arg Lys Leu Cys
    210                 215                 220

Lys Pro Leu Glu Glu Asp Ser Phe Arg Pro Val Leu His His Tyr Asp
225                 230                 235                 240

Gly Pro Lys Phe Arg Leu Glu Leu Ser Ile Ala Glu Thr Leu Ser Leu
                245                 250                 255
```

Leu Asp Leu Cys Glu Lys Glu Gly Ile
260 265

<210> SEQ ID NO 35
<211> LENGTH: 200
<212> TYPE: PRT
<213> ORGANISM: Saccharum officinarum
<220> FEATURE:
<221> NAME/KEY: misc_feature
<222> LOCATION: (1)..(2)
<223> OTHER INFORMATION: Xaa can be any naturally occurring amino acid

<400> SEQUENCE: 35

Xaa Xaa Gln Pro Lys Val Val Glu Asp Arg Gln Trp Ser Leu Met Thr
1 5 10 15

Ser Lys Leu Ala Glu Ile Thr Arg Ser Lys Gly Glu Arg Met Asn Asp
20 25 30

Leu Asp Tyr Ala Arg Met Asn Thr Val Pro Asp Ala Lys Gln Trp Asp
35 40 45

Lys Thr Ser Tyr Gln His His Asp Glu Ser Arg Met Asp His Ile Asn
50 55 60

Leu Gly Leu Met Asn Leu Asp Leu Lys Met Asn Asp Leu Lys Met Asn
65 70 75 80

Glu Ala Ala Thr Ala Met Lys Leu Pro Phe His Asn Met Pro Tyr Asn
85 90 95

Met Asn Pro Met Tyr Pro Lys Gly Ser Asn Val Asn Val Asn Ala Phe
100 105 110

Lys Met Asn Val Gly Val Asn Lys Tyr Ser Ser Ser Pro Asn Gly Lys
115 120 125

Asp Ala Asn Gly Lys Asn Asn Gly Gly Ser Asn Asn Asn Gly Gly Asn
130 135 140

Ser Asn Gly Ser Ala Asn Ser Asn Ser Ala Val Asp Lys Arg Phe Lys
145 150 155 160

Thr Leu Pro Thr Ser Glu Met Leu Pro Arg Asn Glu Val Leu Gly Gly
165 170 175

Tyr Ile Phe Val Cys Asn Asn Asp Thr Met Gln Glu Asp Leu Lys Arg
180 185 190

Gln Leu Phe Gly Leu Pro Ala Arg
195 200

<210> SEQ ID NO 36
<211> LENGTH: 381
<212> TYPE: PRT
<213> ORGANISM: Sorghum bicolor

<400> SEQUENCE: 36

Met Ile Leu Glu Val Ala Ala Val Glu Thr Gln Ser Ile Val His Leu
1 5 10 15

Phe Lys Pro Arg Asp Glu Lys Ile Leu Leu Ala Glu Gly His Lys Arg
20 25 30

Pro Arg Ser Pro Gly Leu Ser Ser Ser Lys Ala Tyr Ser Gly Ser Leu
35 40 45

Val Gly Leu Ser Ile Val Phe Ala Pro Leu Ser Ala Leu Val Ala Ser
50 55 60

Ser Glu Pro Met Ser His Pro Pro Pro Pro Pro Val Asp Gln Asn Ile
65 70 75 80

Ser Leu Arg Phe Cys Glu Ser Phe Ser Leu Gln Gly Thr Glu Thr Pro
85 90 95

-continued

```
Gly Ala Phe Thr Pro Pro Ala Pro Ala Phe Pro Ser Arg Pro Arg Thr
            100                 105                 110

Gly Ala Thr Thr Arg Leu Leu Leu Glu Thr Phe His Ser Ser Met Ala
        115                 120                 125

Lys Leu Val Asn Lys Leu Val Asp Ser Phe Glu Glu Gln Asp Thr Pro
    130                 135                 140

Asp Val Gly Cys Val Arg Ala Val Leu Ala Glu Leu Val Leu Thr Phe
145                 150                 155                 160

Leu Phe Val Phe Thr Gly Val Ser Ala Ala Met Ala Ala Gly Ser Gly
                165                 170                 175

Val Lys Pro Gly Glu Ala Met Pro Met Ala Thr Leu Ala Ala Val Ala
            180                 185                 190

Ile Ala His Ala Leu Ala Ala Gly Val Leu Val Thr Ala Gly Phe His
        195                 200                 205

Val Ser Gly Gly His Leu Asn Pro Ala Val Thr Val Gly Leu Met Val
    210                 215                 220

Arg Gly His Ile Thr Lys Leu Arg Ala Val Leu Tyr Val Ala Ala Gln
225                 230                 235                 240

Val Leu Ala Ser Ser Leu Ala Cys Ile Leu Leu Arg Tyr Leu Ser Gly
                245                 250                 255

Gly Met Val Thr Pro Val His Ala Leu Gly Ala Gly Ile Ser Pro Met
            260                 265                 270

Gln Gly Leu Val Met Glu Val Ile Leu Thr Phe Ser Leu Leu Phe Val
        275                 280                 285

Thr Tyr Ala Met Ile Leu Asp Pro Arg Ser Gln Val Arg Thr Ile Gly
    290                 295                 300

Pro Leu Leu Thr Gly Leu Ile Val Gly Ala Asn Ser Leu Ala Gly Gly
305                 310                 315                 320

Asn Phe Ser Gly Ala Ser Met Asn Pro Ala Arg Ser Phe Gly Pro Ala
                325                 330                 335

Leu Ala Ser Gly Val Trp Thr Asn His Trp Ile Tyr Trp Ile Gly Pro
            340                 345                 350

Leu Leu Gly Gly Pro Leu Ala Gly Phe Ile Tyr Glu Ser Leu Phe Ile
        355                 360                 365

Val Asn Lys Thr His Glu Pro Leu Leu Asn Gly Asp Ile
    370                 375                 380


<210> SEQ ID NO 37
<211> LENGTH: 308
<212> TYPE: PRT
<213> ORGANISM: Saccharum officinarum

<400> SEQUENCE: 37

Pro Thr Arg Pro Pro Pro Pro Val Val Gln Asn Ile Ser Leu Arg Phe
1               5                   10                  15

Ser Glu Ser Phe Ser Leu Gln Gly Thr Gly Thr Thr Gly Ala Phe Thr
            20                  25                  30

Pro Pro Pro Ala Phe Pro Ser Pro Pro Gly Arg Leu Leu Leu Ala Ile
        35                  40                  45

Val His Ser Phe Met Ala Lys Leu Val Asn Lys Leu Val Asp Ser Phe
    50                  55                  60

Asp His Asp Glu Thr Thr Pro Asp Val Gly Cys Val Arg Ala Val Leu
65                  70                  75                  80

Ala Glu Leu Val Leu Thr Phe Leu Phe Val Phe Thr Gly Val Ser Ala
```

-continued 85 90 95

Ala Met Ala Ala Gly Ser Gly Gly Lys Pro Gly Glu Ala Met Pro Met
100 105 110

Ala Thr Leu Ala Ala Val Ala Ile Ala His Ala Leu Ala Ala Gly Val
115 120 125

Leu Val Thr Ala Gly Phe His Val Ser Gly Gly His Leu Asn Pro Ala
130 135 140

Val Thr Val Gly Leu Met Val Cys Gly His Ile Thr Lys Leu Arg Ala
145 150 155 160

Val Leu Tyr Ile Ala Ala Gln Leu Leu Ala Ser Ser Leu Ala Cys Ile
165 170 175

Leu Leu Arg Tyr Leu Ser Gly Gly Met Val Thr Pro Val His Ala Leu
180 185 190

Gly Ala Gly Ile Ser Pro Met Gln Gly Leu Val Met Glu Val Ile Leu
195 200 205

Thr Phe Ser Leu Leu Phe Val Thr Tyr Ala Met Ile Leu Asp Pro Arg
210 215 220

Ser Gln Val Arg Thr Ile Gly Pro Leu Leu Thr Gly Leu Ile Val Gly
225 230 235 240

Ala Asn Ser Leu Ala Gly Gly Asn Phe Thr Gly Ala Ser Met Asn Pro
245 250 255

Ala Arg Ser Phe Gly Pro Ala Leu Ala Thr Gly Val Trp Thr Asn His
260 265 270

Trp Val Tyr Trp Ile Gly Pro Leu Leu Gly Gly Pro Leu Ala Gly Phe
275 280 285

Val Tyr Glu Ser Leu Phe Ile Val Asn Lys Thr His Glu Pro Leu Leu
290 295 300

Asn Gly Asp Ile
305

<210> SEQ ID NO 38
<211> LENGTH: 257
<212> TYPE: PRT
<213> ORGANISM: Zea mays

<400> SEQUENCE: 38

Met Ala Lys Leu Val Asn Lys Leu Val Asp Ser Phe Asp His His Glu
1 5 10 15

Ala Pro Ala Pro Asp Val Gly Cys Val Arg Ala Val Leu Ala Glu Leu
20 25 30

Val Leu Thr Phe Leu Phe Val Phe Thr Gly Val Ser Ala Ser Met Ala
35 40 45

Ala Gly Ala Gly Gly Lys Pro Gly Glu Ala Met Pro Met Ala Thr Leu
50 55 60

Ala Ala Val Ala Ile Ala His Ala Leu Ala Ala Gly Val Leu Val Thr
65 70 75 80

Ala Gly Phe His Val Ser Gly Gly His Leu Asn Pro Ala Val Thr Val
85 90 95

Gly Ile Leu Val Arg Gly His Ile Thr Lys Leu Arg Ala Leu Leu Tyr
100 105 110

Val Ala Ala Gln Leu Leu Ala Ser Ser Leu Ala Cys Ile Leu Leu Arg
115 120 125

Tyr Leu Ser Gly Gly Met Val Thr Pro Val His Ala Leu Gly Ala Gly
130 135 140

```
Ile Ser Pro Met Gln Gly Leu Val Met Glu Val Ile Leu Thr Phe Ser
145                 150                 155                 160

Leu Leu Phe Val Thr Tyr Ala Met Ile Leu Asp Pro Arg Ser Gln Val
                165                 170                 175

Arg Thr Ile Gly Pro Leu Leu Thr Gly Leu Ile Val Gly Ala Asn Ser
            180                 185                 190

Leu Ala Gly Gly Asn Phe Thr Gly Ala Ser Met Asn Pro Ala Arg Ser
        195                 200                 205

Phe Gly Pro Ala Met Ala Thr Gly Val Trp Thr Asn His Trp Val Tyr
    210                 215                 220

Trp Ile Gly Pro Leu Leu Gly Gly Ser Leu Ala Gly Phe Val Tyr Glu
225                 230                 235                 240

Ser Leu Phe Met Val Tyr Lys Thr His Glu Pro Leu Leu Asn Gly Asp
                245                 250                 255

Ile


<210> SEQ ID NO 39
<211> LENGTH: 255
<212> TYPE: PRT
<213> ORGANISM: Zea mays

<400> SEQUENCE: 39

Met Ala Lys Leu Met Asn Lys Leu Val Asp Ser Phe Glu His Asp Glu
1               5                   10                  15

Ile Leu Asp Val Gly Cys Val Arg Ala Val Leu Ala Glu Leu Val Leu
            20                  25                  30

Thr Phe Leu Phe Val Phe Thr Gly Val Ser Ala Ala Met Ala Ala Gly
        35                  40                  45

Ser Asp Gly Lys Pro Gly Asp Ala Met Pro Met Ala Thr Leu Ala Ala
    50                  55                  60

Val Ala Ile Ala His Ala Leu Ala Ala Gly Val Leu Val Thr Ala Gly
65                  70                  75                  80

Phe His Val Ser Gly Gly His Leu Asn Pro Ala Val Thr Val Gly Leu
                85                  90                  95

Met Val Arg Gly His Ile Thr Lys Leu Arg Ala Val Leu Tyr Val Ala
            100                 105                 110

Ala Gln Leu Leu Ala Ser Ser Ala Ala Cys Val Leu Leu Arg Phe Leu
        115                 120                 125

Ser Gly Gly Met Val Thr Pro Val His Ala Leu Gly Arg Gly Ile Ser
    130                 135                 140

Pro Met Gln Gly Leu Val Met Glu Val Ile Leu Thr Phe Ser Leu Leu
145                 150                 155                 160

Phe Val Thr Tyr Ala Met Ile Leu Asp Pro Arg Ser Gln Val Arg Ala
                165                 170                 175

Ile Gly Pro Leu Leu Thr Gly Leu Ile Val Gly Ala Asn Ser Leu Ala
            180                 185                 190

Gly Gly Asn Phe Thr Gly Ala Ser Met Asn Pro Ala Arg Ser Phe Gly
        195                 200                 205

Pro Ala Leu Ala Thr Gly Asp Trp Thr Asn His Trp Val Tyr Trp Ile
    210                 215                 220

Gly Pro Leu Leu Gly Gly Pro Leu Ala Gly Phe Val Tyr Glu Ser Leu
225                 230                 235                 240

Phe Leu Val Gln Lys Met His Glu Pro Leu Leu Asn Gly Glu Val
                245                 250                 255
```

<210> SEQ ID NO 40
<211> LENGTH: 254
<212> TYPE: PRT
<213> ORGANISM: Sorghum bicolor

<400> SEQUENCE: 40

```
Met Ala Ser Pro Glu Gly Thr Thr Trp Val Phe Asp Cys Pro Leu Met
1               5                   10                  15

Asp Asp Leu Ala Val Ala Ala Asp Phe Ala Ala Ala Pro Ala Gly Gly
            20                  25                  30

Phe Phe Trp Ala Ala Pro Pro Ser Leu Gln Pro Gln Val Val Gln Ala
        35                  40                  45

Pro Val Gln Ser Val Val Ala Ala Ser Ala Pro Asn Pro Cys Val Glu
    50                  55                  60

Ile Ser Ser Ser Val Asp Cys Gly Gln Gly Lys Glu Gln Pro Thr Asn
65                  70                  75                  80

Lys Arg Pro Arg Ser Glu Ser Thr Ala Glu Pro Ser Thr Lys Ala Ser
                85                  90                  95

Arg Glu Lys Ile Arg Arg Asp Lys Leu Asn Glu Arg Phe Leu Glu Leu
            100                 105                 110

Gly Ala Ile Leu Glu Pro Gly Lys Thr Pro Lys Met Asp Lys Ser Ala
        115                 120                 125

Ile Leu Asn Asp Ala Ile Arg Val Val Gly Glu Leu Arg Ser Glu Ala
    130                 135                 140

Lys Glu Leu Lys Asp Ser Asn Glu Ser Leu Gln Glu Lys Ile Lys Glu
145                 150                 155                 160

Leu Lys Ala Glu Lys Asn Glu Leu Arg Asp Glu Lys Gln Arg Leu Lys
                165                 170                 175

Ala Glu Lys Glu Ser Leu Glu Gln Gln Ile Lys Phe Leu Asn Ala Arg
            180                 185                 190

Pro Ser Leu Val Pro His His Pro Val Ile Ser Ala Ser Ala Phe Thr
        195                 200                 205

Ala Pro Gln Gly Pro Ala Val Ala Gly His Lys Leu Met Met Pro Val
    210                 215                 220

Leu Gly Tyr Pro Gly Phe Pro Met Trp Gln Phe Met Pro Pro Ser Asp
225                 230                 235                 240

Val Asp Thr Ser Asp Asp Pro Lys Ser Cys Pro Pro Val Ala
                245                 250
```

<210> SEQ ID NO 41
<211> LENGTH: 252
<212> TYPE: PRT
<213> ORGANISM: Zea mays

<400> SEQUENCE: 41

```
Met Ala Ser Pro Glu Gly Thr Thr Trp Val Phe Asp Cys Pro Leu Met
1               5                   10                  15

Asp Asp Leu Ala Val Ala Ala Asp Phe Ala Ala Ala Pro Ala Gly Gly
            20                  25                  30

Phe Phe Trp Ala Ala Pro Pro Ser Leu Gln Pro Gln Ala Pro Val Gln
        35                  40                  45

Ser Val Val Ala Ala Ser Ala Pro Asn Pro Cys Met Glu Ile Ser Ser
    50                  55                  60

Ser Val Asp Cys Gly Gln Glu Lys Glu Gln Pro Thr Asn Lys Arg Pro
65                  70                  75                  80
```

```
Arg Ser Glu Ser Thr Thr Glu Ser Ser Thr Lys Ala Ser Arg Glu Lys
                85                  90                  95

Ile Arg Arg Asp Lys Leu Asn Glu Arg Phe Leu Glu Leu Gly Ala Ile
            100                 105                 110

Leu Glu Pro Gly Lys Thr Pro Lys Met Asp Lys Thr Ala Ile Leu Ser
        115                 120                 125

Asp Ala Ile Arg Val Val Gly Glu Leu Arg Ser Glu Ala Lys Lys Leu
    130                 135                 140

Lys Asp Ser Asn Glu Asn Leu Gln Glu Lys Ile Lys Glu Leu Lys Ala
145                 150                 155                 160

Glu Lys Asn Glu Leu Arg Asp Glu Lys Gln Arg Leu Lys Ala Glu Lys
                165                 170                 175

Glu Ser Leu Glu Gln Gln Ile Lys Phe Leu Asn Ala Arg Pro Ser Leu
            180                 185                 190

Val Pro His His Pro Val Ile Pro Ala Ser Ala Phe Pro Ala Pro Gln
        195                 200                 205

Gly Pro Ala Ala Ala Ala Arg His Lys Leu Met Met Pro Val Ile Gly
    210                 215                 220

Tyr Pro Gly Phe Pro Met Trp Gln Phe Met Pro Pro Ser Asp Val Asp
225                 230                 235                 240

Thr Ser Asp Asp Pro Arg Ser Cys Pro Pro Val Ala
                245                 250


<210> SEQ ID NO 42
<211> LENGTH: 159
<212> TYPE: PRT
<213> ORGANISM: Saccharum officinarum

<400> SEQUENCE: 42

Met Ala Ser Pro Glu Gly Thr Thr Trp Val Phe Asp Cys Pro Leu Met
1               5                   10                  15

Asp Asp Leu Ala Val Ala Ala Asp Phe Ala Ala Ala Pro Ala Gly Gly
            20                  25                  30

Phe Phe Trp Ala Ala Pro Pro Ser Leu Gln Pro Gln Val Val Gln Ala
        35                  40                  45

Pro Val Gln Ser Val Val Ala Ala Ser Ala Pro Asn Pro Pro Cys Val
    50                  55                  60

Glu Ile Ser Ser Ser Val Asp Cys Gly Gln Gly Lys Glu Gln Pro Thr
65                  70                  75                  80

Asn Lys Arg Pro Arg Ser Glu Ser Thr Ala Glu Pro Ser Thr Lys Ala
                85                  90                  95

Ser Arg Glu Lys Ile Arg Arg Asp Lys Leu Asn Lys Arg Phe Leu Glu
            100                 105                 110

Trp Gly Ala Ile Val Glu Pro Gly Glu Thr Pro Lys Met Asp Lys Ser
        115                 120                 125

Ala Ile Leu Asn Asp Ala Ile Arg Ala Val Ser Glu Leu Arg Ser Glu
    130                 135                 140

Thr Lys Lys Leu Lys Asp Ser Asn Glu Ser Leu Gln Gly Glu Asp
145                 150                 155


<210> SEQ ID NO 43
<211> LENGTH: 151
<212> TYPE: PRT
<213> ORGANISM: Brassica napus

<400> SEQUENCE: 43
```

```
Met Gly Arg Met His Ser Arg Gly Lys Gly Ile Ser Ala Ser Ala Leu
1               5                   10                  15

Pro Tyr Lys Arg Ser Pro Pro Thr Trp Leu Lys Thr Thr Ala Leu Asp
            20                  25                  30

Val Asp Glu Ser Ile Cys Lys Phe Ala Lys Lys Gly Leu Thr Pro Ser
        35                  40                  45

Gln Ile Gly Val Ile Leu Arg Asp Ser His Gly Ile Pro Gln Val Lys
    50                  55                  60

Ser Val Thr Gly Asn Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150


<210> SEQ ID NO 44
<211> LENGTH: 151
<212> TYPE: PRT
<213> ORGANISM: Brassica napus

<400> SEQUENCE: 44

Met Gly Arg Met His Ser Arg Gly Lys Gly Ile Ser Ala Ser Ala Leu
1               5                   10                  15

Pro Tyr Lys Arg Ser Pro Pro Thr Trp Leu Lys Thr Thr Ala Leu Asp
            20                  25                  30

Val Asp Glu Ser Ile Cys Lys Phe Ala Lys Lys Gly Leu Thr Pro Ser
        35                  40                  45

Gln Ile Gly Val Ile Leu Arg Asp Ser His Gly Ile Pro Gln Val Lys
    50                  55                  60

Ser Val Thr Gly Asn Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150


<210> SEQ ID NO 45
<211> LENGTH: 151
<212> TYPE: PRT
<213> ORGANISM: Solanum tuberosum

<400> SEQUENCE: 45

Met Gly Arg Met His Ser Arg Gly Lys Gly Ile Ser Ala Ser Ala Leu
1               5                   10                  15
```

-continued

```
Pro Tyr Lys Arg Thr Pro Pro Ser Trp Leu Lys Thr Ser Ala Pro Asp
            20                  25                  30

Val Glu Asp Asn Ile Cys Lys Phe Ala Lys Lys Gly Leu Thr Pro Ser
        35                  40                  45

Gln Ile Gly Val Ile Leu Arg Asp Ser His Gly Ile Ala Gln Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150


<210> SEQ ID NO 46
<211> LENGTH: 151
<212> TYPE: PRT
<213> ORGANISM: Gossypium hirsutum

<400> SEQUENCE: 46

Met Gly Arg Met His Ser Arg Gly Lys Gly Ile Ser Ala Ser Ala Leu
1               5                   10                  15

Pro Tyr Lys Arg Thr Pro Pro Ser Trp Leu Lys Ile Ser Ser Gln Asp
            20                  25                  30

Val Glu Glu Asn Ile Cys Lys Phe Ala Lys Lys Gly Leu Thr Pro Ser
        35                  40                  45

Gln Ile Gly Val Ile Leu Arg Asp Ser His Gly Ile Ala Gln Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150


<210> SEQ ID NO 47
<211> LENGTH: 151
<212> TYPE: PRT
<213> ORGANISM: Gossypium hirsutum

<400> SEQUENCE: 47

Met Gly Arg Met His Ser Arg Gly Lys Gly Ile Ser Ala Ser Ala Leu
1               5                   10                  15

Pro Tyr Lys Arg Thr Pro Pro Ser Trp Leu Lys Ile Ser Ser Gln Asp
            20                  25                  30
```

Val Glu Glu Asn Ile Cys Lys Phe Ala Lys Lys Gly Leu Thr Pro Ser
35 40 45

Gln Ile Gly Val Ile Leu Arg Asp Ser His Gly Ile Ala Gln Val Lys
50 55 60

Ser Val Thr Gly Ser Lys Ile Leu Arg Ile Leu Lys Ala His Gly Leu
65 70 75 80

Ala Pro Glu Ile Pro Glu Asp Leu Tyr His Leu Ile Lys Lys Ala Val
85 90 95

Ala Ile Arg Lys His Leu Glu Arg Asn Arg Lys Asp Lys Asp Ser Lys
100 105 110

Phe Arg Leu Ile Leu Val Glu Ser Arg Ile His Arg Leu Ala Arg Tyr
115 120 125

Tyr Lys Lys Thr Lys Lys Leu Pro Pro Val Trp Lys Tyr Glu Ser Thr
130 135 140

Thr Ala Ser Thr Leu Val Ala
145 150

<210> SEQ ID NO 48
<211> LENGTH: 151
<212> TYPE: PRT
<213> ORGANISM: Lycopersicon esculentum

<400> SEQUENCE: 48

Met Gly Arg Met His Ser Arg Gly Lys Gly Ile Ser Ala Ser Ala Leu
1 5 10 15

Pro Tyr Lys Arg Thr Pro Pro Ser Trp Leu Lys Ile Ser Ala Pro Asp
20 25 30

Val Glu Asp Asn Ile Cys Lys Phe Ala Lys Lys Gly Leu Thr Pro Ser
35 40 45

Gln Ile Gly Val Ile Leu Arg Asp Ser His Gly Ile Ala Gln Val Lys
50 55 60

Ser Val Thr Gly Ser Lys Ile Leu Arg Ile Leu Lys Ala His Gly Leu
65 70 75 80

Ala Pro Glu Ile Pro Glu Asp Leu Tyr His Leu Ile Lys Lys Ala Val
85 90 95

Ala Ile Arg Lys His Leu Glu Arg Asn Arg Lys Asp Lys Asp Ser Lys
100 105 110

Phe Arg Leu Ile Leu Val Glu Ser Arg Ile His Arg Leu Ala Arg Tyr
115 120 125

Tyr Lys Lys Thr Lys Lys Leu Pro Pro Val Trp Lys Tyr Glu Ser Thr
130 135 140

Thr Ala Ser Thr Leu Val Ala
145 150

<210> SEQ ID NO 49
<211> LENGTH: 151
<212> TYPE: PRT
<213> ORGANISM: Lycopersicon esculentum

<400> SEQUENCE: 49

Met Gly Arg Met His Ser Arg Gly Lys Gly Ile Ser Ala Ser Ala Leu
1 5 10 15

Pro Tyr Lys Arg Thr Pro Pro Ser Trp Leu Lys Ile Ser Ala Pro Asp
20 25 30

Val Glu Asp Asn Ile Cys Lys Phe Ala Lys Lys Gly Leu Thr Pro Ser
35 40 45

Gln Ile Gly Val Ile Leu Arg Asp Ser His Gly Ile Ala Gln Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150

<210> SEQ ID NO 50
<211> LENGTH: 151
<212> TYPE: PRT
<213> ORGANISM: Lycopersicon esculentum

<400> SEQUENCE: 50

Met Gly Arg Met His Ser Arg Gly Lys Gly Ile Ser Ala Ser Ala Leu
1               5                   10                  15

Pro Tyr Lys Arg Thr Pro Pro Ser Trp Leu Lys Ile Ser Ala Pro Asp
            20                  25                  30

Val Glu Asp Asn Ile Cys Lys Phe Ala Lys Lys Gly Leu Thr Pro Ser
        35                  40                  45

Gln Ile Gly Val Ile Leu Arg Asp Ser His Gly Ile Ala Gln Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150

<210> SEQ ID NO 51
<211> LENGTH: 151
<212> TYPE: PRT
<213> ORGANISM: Lycopersicon esculentum

<400> SEQUENCE: 51

Met Gly Arg Met His Ser Arg Gly Lys Gly Ile Ser Ala Ser Ala Leu
1               5                   10                  15

Pro Tyr Lys Arg Thr Pro Pro Ser Trp Leu Lys Ile Ser Ala Pro Asp
            20                  25                  30

Val Glu Asp Asn Ile Cys Lys Phe Ala Lys Lys Gly Leu Thr Pro Ser
        35                  40                  45

Gln Ile Gly Val Ile Leu Arg Asp Ser His Gly Ile Ala Gln Val Lys
    50                  55                  60

```
Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150


<210> SEQ ID NO 52
<211> LENGTH: 151
<212> TYPE: PRT
<213> ORGANISM: Solanum tuberosum

<400> SEQUENCE: 52

Met Gly Arg Met His Ser Arg Gly Lys Gly Ile Ser Ala Ser Ala Leu
1               5                   10                  15

Pro Tyr Lys Arg Thr Pro Pro Ser Trp Leu Lys Ile Ser Ala Pro Asp
            20                  25                  30

Val Glu Asp Asn Ile Cys Lys Phe Ala Lys Lys Gly Leu Thr Pro Ser
        35                  40                  45

Gln Ile Gly Val Ile Leu Arg Asp Ser His Gly Ile Ala Gln Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150


<210> SEQ ID NO 53
<211> LENGTH: 151
<212> TYPE: PRT
<213> ORGANISM: Solanum tuberosum

<400> SEQUENCE: 53

Met Gly Arg Met His Ser Arg Gly Lys Gly Ile Ser Ala Ser Ala Leu
1               5                   10                  15

Pro Tyr Lys Arg Thr Pro Pro Ser Trp Leu Lys Ile Ser Ala Pro Asp
            20                  25                  30

Val Glu Asp Asn Ile Cys Lys Phe Ala Lys Lys Gly Leu Thr Pro Ser
        35                  40                  45

Gln Ile Gly Val Ile Leu Arg Asp Ser His Gly Ile Ala Gln Val Lys
    50                  55                  60

Ser Val Thr Gly Ser Lys Ile Leu Arg Ile Leu Lys Ala His Gly Leu
65                  70                  75                  80
```

```
Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150


<210> SEQ ID NO 54
<211> LENGTH: 151
<212> TYPE: PRT
<213> ORGANISM: Solanum tuberosum

<400> SEQUENCE: 54

Met Gly Arg Met His Ser Arg Gly Lys Gly Ile Ser Ala Ser Ala Leu
1               5                   10                  15

Pro Tyr Lys Arg Thr Pro Pro Ser Trp Leu Lys Ile Ser Ala Pro Asp
            20                  25                  30

Val Glu Asp Asn Ile Cys Lys Phe Ala Lys Lys Gly Leu Thr Pro Ser
        35                  40                  45

Gln Ile Gly Val Ile Leu Arg Asp Ser His Gly Ile Ala Gln Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150


<210> SEQ ID NO 55
<211> LENGTH: 151
<212> TYPE: PRT
<213> ORGANISM: Solanum tuberosum

<400> SEQUENCE: 55

Met Gly Arg Met His Ser Arg Gly Lys Gly Ile Ser Ala Ser Ala Leu
1               5                   10                  15

Pro Tyr Lys Arg Thr Pro Pro Ser Trp Leu Lys Ile Ser Ala Pro Asp
            20                  25                  30

Val Glu Asp Asn Ile Cys Lys Phe Ala Lys Lys Gly Leu Thr Pro Ser
        35                  40                  45

Gln Ile Gly Val Ile Leu Arg Asp Ser His Gly Ile Ala Gln Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95
```

-continued

```
Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150


<210> SEQ ID NO 56
<211> LENGTH: 151
<212> TYPE: PRT
<213> ORGANISM: Capsicum annuum

<400> SEQUENCE: 56

Met Gly Arg Met His Ser Arg Gly Lys Gly Ile Ser Ala Ser Ala Leu
1               5                   10                  15

Pro Tyr Lys Arg Thr Pro Pro Ser Trp Leu Lys Ile Ser Ala Pro Asp
            20                  25                  30

Val Glu Asp Asn Ile Cys Lys Phe Ala Lys Lys Gly Leu Thr Pro Ser
        35                  40                  45

Gln Ile Gly Val Ile Leu Arg Asp Ser His Gly Ile Ala Gln Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150


<210> SEQ ID NO 57
<211> LENGTH: 151
<212> TYPE: PRT
<213> ORGANISM: Arabidopsis thaliana

<400> SEQUENCE: 57

Met Gly Arg Met His Ser Arg Gly Lys Gly Ile Ser Ala Ser Ala Leu
1               5                   10                  15

Pro Tyr Lys Arg Ser Ser Pro Ser Trp Leu Lys Thr Thr Ser Gln Asp
            20                  25                  30

Val Asp Glu Ser Ile Cys Lys Phe Ala Lys Lys Gly Leu Thr Pro Ser
        35                  40                  45

Gln Ile Gly Val Ile Leu Arg Asp Ser His Gly Ile Pro Gln Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110
```

```
Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150


<210> SEQ ID NO 58
<211> LENGTH: 151
<212> TYPE: PRT
<213> ORGANISM: Brassica napus

<400> SEQUENCE: 58

Met Gly Arg Leu His Ser Lys Gly Lys Gly Ile Ser Ala Ser Ala Leu
1               5                   10                  15

Pro Tyr Lys Arg Ser Pro Pro Ser Trp Leu Lys Thr Thr Ser Gln Asp
            20                  25                  30

Val Asp Glu Ser Ile Cys Lys Phe Ala Lys Lys Gly Leu Thr Pro Ser
        35                  40                  45

Gln Ile Gly Val Ile Leu Arg Asp Ser His Gly Ile Pro Gln Val Lys
    50                  55                  60

Ser Val Thr Gly Asn Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150


<210> SEQ ID NO 59
<211> LENGTH: 151
<212> TYPE: PRT
<213> ORGANISM: Brassica napus

<400> SEQUENCE: 59

Met Gly Arg Leu His Ser Lys Gly Lys Gly Ile Ser Ala Ser Ala Leu
1               5                   10                  15

Pro Tyr Lys Arg Ser Pro Pro Ser Trp Leu Lys Thr Thr Ser Glu Asp
            20                  25                  30

Val Asp Glu Ser Ile Cys Lys Phe Ala Lys Lys Gly Leu Thr Pro Ser
        35                  40                  45

Gln Ile Gly Val Ile Leu Arg Asp Ser His Gly Ile Pro Gln Val Lys
    50                  55                  60

Ser Val Thr Gly Asn Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125
```

```
Tyr Lys Lys Thr Lys Lys Leu Pro Pro Val Trp Lys Tyr Glu Ser Thr
    130                 135                 140

Thr Ala Ser Thr Leu Val Ala
145                 150


<210> SEQ ID NO 60
<211> LENGTH: 151
<212> TYPE: PRT
<213> ORGANISM: Brassica napus

<400> SEQUENCE: 60

Met Gly Arg Leu His Ser Lys Gly Lys Gly Ile Ser Ala Ser Ala Leu
1               5                   10                  15

Pro Tyr Lys Arg Ser Pro Pro Ser Trp Leu Lys Thr Thr Ser Gln Asp
            20                  25                  30

Val Asp Glu Ser Ile Cys Lys Phe Ala Lys Lys Gly Leu Thr Pro Ser
        35                  40                  45

Gln Ile Gly Val Ile Leu Arg Asp Ser His Gly Ile Pro Gln Val Lys
    50                  55                  60

Ser Val Thr Gly Asn Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150


<210> SEQ ID NO 61
<211> LENGTH: 151
<212> TYPE: PRT
<213> ORGANISM: Gossypium hirsutum

<400> SEQUENCE: 61

Met Gly Arg Met His Ser Arg Gly Lys Gly Ile Ser Ala Ser Ala Leu
1               5                   10                  15

Pro Tyr Arg Arg Thr Pro Pro Ser Trp Leu Lys Ile Ser Ser Gln Asp
            20                  25                  30

Val Glu Glu Asn Ile Cys Lys Phe Ala Lys Lys Gly Leu Thr Pro Ser
        35                  40                  45

Gln Ile Gly Val Ile Leu Arg Asp Ser His Gly Ile Ala Gln Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140
```

Thr Ala Ser Thr Leu Val Ala
145 150

<210> SEQ ID NO 62
<211> LENGTH: 151
<212> TYPE: PRT
<213> ORGANISM: Gossypium hirsutum

<400> SEQUENCE: 62

Met Gly Arg Met His Ser Arg Gly Lys Gly Ile Ser Ala Ser Ala Leu
1 5 10 15

Pro Tyr Lys Arg Thr Pro Pro Ser Trp Leu Lys Ile Ser Ser Gln Asp
20 25 30

Val Glu Asp Asn Ile Cys Lys Phe Ala Lys Lys Gly Leu Thr Pro Ser
35 40 45

Gln Ile Gly Val Ile Leu Arg Asp Ser His Gly Ile Ala Gln Val Lys
50 55 60

Ser Val Thr Gly Ser Lys Ile Leu Arg Ile Leu Lys Ala His Gly Leu
65 70 75 80

Ala Pro Glu Ile Pro Glu Asp Leu Tyr His Leu Ile Lys Lys Ala Val
85 90 95

Ala Ile Arg Lys His Leu Glu Arg Asn Arg Lys Asp Lys Asp Ser Lys
100 105 110

Phe Arg Leu Ile Leu Val Glu Ser Arg Ile His Arg Leu Ala Arg Tyr
115 120 125

Tyr Lys Lys Thr Lys Lys Leu Pro Pro Val Trp Lys Tyr Glu Ser Thr
130 135 140

Thr Ala Ser Thr Leu Val Ala
145 150

<210> SEQ ID NO 63
<211> LENGTH: 151
<212> TYPE: PRT
<213> ORGANISM: Gossypium hirsutum

<400> SEQUENCE: 63

Met Gly Arg Met His Ser Arg Gly Lys Gly Ile Ser Ala Ser Ala Leu
1 5 10 15

Pro Tyr Lys Arg Thr Pro Pro Ser Trp Leu Lys Ile Ser Ser Gln Asp
20 25 30

Val Glu Glu Asn Ile Cys Lys Phe Ala Lys Lys Gly Leu Thr Pro Ser
35 40 45

Gln Ile Gly Val Ile Leu Arg Asp Ser His Gly Ile Ala Gln Val Arg
50 55 60

Ser Val Thr Gly Ser Lys Ile Leu Arg Ile Leu Lys Ala His Gly Leu
65 70 75 80

Ala Pro Glu Ile Pro Glu Asp Leu Tyr His Leu Ile Lys Lys Ala Val
85 90 95

Ala Ile Arg Lys His Leu Glu Arg Asn Arg Lys Asp Lys Asp Ser Lys
100 105 110

Phe Arg Leu Ile Leu Val Glu Ser Arg Ile His Arg Leu Ala Arg Tyr
115 120 125

Tyr Lys Lys Thr Lys Lys Leu Pro Pro Val Trp Lys Tyr Glu Ser Thr
130 135 140

Thr Ala Ser Thr Leu Val Ala
145 150

<210> SEQ ID NO 64
<211> LENGTH: 151
<212> TYPE: PRT
<213> ORGANISM: Arabidopsis thaliana

<400> SEQUENCE: 64

```
Met Gly Arg Met His Ser Arg Gly Lys Gly Ile Ser Ala Ser Ala Leu
1               5                   10                  15

Pro Tyr Lys Arg Ser Ser Pro Ser Trp Leu Lys Thr Thr Pro Gln Asp
            20                  25                  30

Val Asp Glu Ser Ile Cys Lys Phe Ala Lys Lys Gly Leu Thr Pro Ser
        35                  40                  45

Gln Ile Gly Val Ile Leu Arg Asp Ser His Gly Ile Pro Gln Val Lys
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150
```

<210> SEQ ID NO 65
<211> LENGTH: 151
<212> TYPE: PRT
<213> ORGANISM: Glycine max

<400> SEQUENCE: 65

```
Met Gly Arg Met His Ser Arg Gly Lys Gly Ile Ser Ser Ser Ala Leu
1               5                   10                  15

Pro Tyr Lys Arg Thr Pro Pro Ser Trp Leu Lys Ile Ser Ser Gln Asp
            20                  25                  30

Val Glu Glu Asn Ile Cys Lys Phe Ala Lys Lys Gly Leu Thr Pro Ser
        35                  40                  45

Gln Ile Gly Val Ile Leu Arg Asp Ser His Gly Ile Ala Gln Val Asn
    50                  55                  60

Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ser Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150
```

<210> SEQ ID NO 66
<211> LENGTH: 215

<212> TYPE: PRT
<213> ORGANISM: Capsicum annuum
<220> FEATURE:
<221> NAME/KEY: misc_feature
<222> LOCATION: (1)..(3)
<223> OTHER INFORMATION: Xaa can be any naturally occurring amino acid

<400> SEQUENCE: 66

```
Xaa Xaa Xaa Glu Arg Glu Arg Glu Arg Glu Arg Glu Arg Glu Arg Glu
1               5                   10                  15

Arg Glu Arg Glu Arg Glu Arg Glu Arg Glu Arg Glu Arg Glu Arg Glu
            20                  25                  30

Arg Glu Arg Glu Arg Glu Arg Glu Arg Glu Arg Gly Gln Pro Asn Ser
        35                  40                  45

Ser Leu Ser Pro Pro Pro Ser Pro Leu Thr Thr Asn Thr Gln Pro Ala
    50                  55                  60

Ile Met Gly Arg Met His Ser Arg Gly Lys Gly Ile Ser Ala Ser Ala
65                  70                  75                  80

Leu Pro Tyr Lys Arg Thr Pro Pro Ser Trp Leu Lys Ile Ser Ala Pro
                85                  90                  95

Asp Val Glu Asp Asn Ile Cys Lys Phe Ala Lys Lys Gly Leu Ala Pro
            100                 105                 110

Ser Gln Ile Gly Val Ile Leu Arg Asp Ser His Gly Ile Ala Gln Val
        115                 120                 125

Lys Ser Val Thr Gly Ser Lys Ile Leu Arg Ile Leu Lys Ala His Gly
    130                 135                 140

Leu Ala Pro Glu Ile Pro Glu Asp Leu Tyr His Leu Ile Lys Lys Ala
145                 150                 155                 160

Val Ala Ile Arg Lys His Leu Glu Arg Asn Arg Lys Asp Lys Asp Ser
                165                 170                 175

Lys Phe Arg Leu Ile Leu Val Glu Ser Arg Ile His Arg Leu Ala Arg
            180                 185                 190

Tyr Tyr Lys Lys Thr Lys Lys Leu Pro Pro Val Trp Lys Tyr Glu Ser
        195                 200                 205

Thr Thr Ala Ser Thr Leu Val
    210                 215
```

<210> SEQ ID NO 67
<211> LENGTH: 151
<212> TYPE: PRT
<213> ORGANISM: Populus tremula x Populus tremuloides

<400> SEQUENCE: 67

```
Met Gly Arg Met His Ser His Gly Lys Gly Ile Ser Ala Ser Ala Leu
1               5                   10                  15

Pro Tyr Lys Arg Thr Pro Pro Ser Trp Leu Lys Ile Ser Ala Gln Asp
            20                  25                  30

Val Glu Asp Asn Ile Cys Lys Phe Ala Lys Lys Gly Leu Thr Pro Ser
        35                  40                  45

Gln Ile Gly Val Ile Leu Arg Asp Ser His Gly Ile Ala Gln Val Arg
    50                  55                  60

Ser Val Thr Gly Asn Gln Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110
```

Phe Arg Leu Ile Leu Val Glu Ser Arg Ile His Arg Leu Ala Arg Tyr
115 120 125

Tyr Lys Lys Thr Lys Lys Leu Pro Pro Val Trp Lys Tyr Glu Ser Ser
130 135 140

Thr Ala Ser Thr Leu Val Ala
145 150

<210> SEQ ID NO 68
<211> LENGTH: 151
<212> TYPE: PRT
<213> ORGANISM: Medicago truncatula

<400> SEQUENCE: 68

Met Gly Arg Met His Ser Gly Gly Lys Gly Ile Ser Ser Ser Ala Leu
1 5 10 15

Pro Tyr Lys Arg Ser Ala Pro Gly Trp Leu Lys Thr Ser Thr Gln Asp
20 25 30

Val Glu Glu Thr Ile Cys Lys Phe Ala Lys Lys Gly Leu Thr Pro Ser
35 40 45

Gln Ile Gly Val Ile Leu Arg Asp Ser His Gly Ile Ala Gln Val Lys
50 55 60

Phe Ile Thr Gly Ser Lys Ile Leu Arg Ile Leu Lys Ala His Gly Leu
65 70 75 80

Ala Pro Glu Ile Pro Glu Asp Leu Tyr His Leu Ile Lys Lys Ala Val
85 90 95

Ser Ile Arg Lys His Leu Glu Arg Asn Arg Lys Asp Lys Asp Ser Lys
100 105 110

Phe Arg Leu Ile Leu Val Glu Ser Arg Ile His Arg Leu Ala Arg Tyr
115 120 125

Tyr Lys Lys Thr Lys Lys Leu Pro Pro Val Trp Lys Tyr Glu Ser Thr
130 135 140

Thr Ala Ser Thr Leu Val Ala
145 150

<210> SEQ ID NO 69
<211> LENGTH: 151
<212> TYPE: PRT
<213> ORGANISM: Populus tremula x Populus tremuloides

<400> SEQUENCE: 69

Met Gly Arg Met His Ser Arg Gly Lys Gly Ile Ser Ala Ser Ala Leu
1 5 10 15

Pro Tyr Lys Arg Thr Pro Pro Ser Trp Leu Lys Ile Ser Ala Gln Asp
20 25 30

Val Asp Asp Ser Ile Cys Lys Phe Ala Lys Lys Gly Leu Thr Pro Ser
35 40 45

Gln Ile Gly Val Ile Leu Arg Asp Ser His Gly Ile Ala Gln Val Arg
50 55 60

Ser Val Thr Gly Asn Gln Ile Leu Arg Ile Leu Lys Ala His Gly Leu
65 70 75 80

Ala Pro Glu Ile Pro Glu Asp Leu Tyr His Leu Ile Lys Lys Ala Val
85 90 95

Ala Ile Arg Lys His Leu Glu Arg Asn Arg Lys Asp Lys Asp Ser Lys
100 105 110

Phe Arg Leu Ile Leu Val Glu Ser Arg Ile His Arg Leu Ala Arg Tyr
115 120 125

Tyr Lys Lys Thr Lys Lys Leu Ala Pro Val Trp Lys Tyr Glu Ser Ser
    130                 135                 140

Thr Ala Ser Thr Leu Val Ala
145                 150

<210> SEQ ID NO 70
<211> LENGTH: 151
<212> TYPE: PRT
<213> ORGANISM: Medicago truncatula

<400> SEQUENCE: 70

Met Gly Arg Met His Ser Gly Gly Lys Gly Ile Ser Ser Ser Ala Leu
1               5                   10                  15

Pro Tyr Lys Arg Thr Pro Ala Ser Trp Leu Lys Ile Ser Thr Gln Asp
            20                  25                  30

Val Asp Glu Thr Ile Cys Lys Phe Ala Lys Lys Gly Leu Thr Pro Ser
        35                  40                  45

Gln Ile Gly Val Ile Leu Arg Asp Ser His Gly Ile Ala Gln Val Lys
    50                  55                  60

Ala Val Thr Gly Asn Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ser Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Thr
    130                 135                 140

Thr Ala Ser Thr Leu Val Ala
145                 150

<210> SEQ ID NO 71
<211> LENGTH: 151
<212> TYPE: PRT
<213> ORGANISM: Populus tremula x Populus tremuloides

<400> SEQUENCE: 71

Met Gly Arg Met His Ser Lys Gly Lys Gly Ile Ser Ala Ser Ala Leu
1               5                   10                  15

Pro Tyr Lys Arg Thr Pro Pro Ser Trp Leu Lys Ile Ser Pro Gln Asp
            20                  25                  30

Val Asp Asp Asn Ile Cys Lys Phe Ala Lys Lys Gly Leu Thr Pro Ser
        35                  40                  45

Gln Ile Gly Val Ile Leu Arg Asp Ser His Gly Ile Ala Gln Val Lys
    50                  55                  60

Ala Val Thr Gly Asn Gln Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asn Arg Lys Asp Lys Asp Ser Lys
            100                 105                 110

Phe Arg Leu Ile Leu Val Glu Ser Arg Ile His Arg Leu Ala Arg Tyr
        115                 120                 125

Tyr Lys Lys Thr Lys Lys Leu Pro Pro Val Trp Lys Tyr Glu Ser Ser
    130                 135                 140

Thr Ala Ser Thr Leu Val Ala
145 150

<210> SEQ ID NO 72
<211> LENGTH: 148
<212> TYPE: PRT
<213> ORGANISM: Medicago truncatula

<400> SEQUENCE: 72

Met His Ser Lys Gly Lys Gly Ile Ser Ser Ser Ala Leu Pro Tyr Lys
1 5 10 15

Arg Thr Ser Pro Ser Trp Leu Lys Ile Ser Ser Pro Glu Val Asp Glu
20 25 30

Thr Ile Cys Lys Phe Ala Lys Lys Gly Leu Thr Pro Ser Gln Ile Gly
35 40 45

Val Ile Leu Arg Asp Ser His Gly Ile Ala Gln Val Lys Ser Val Thr
50 55 60

Gly Ser Lys Ile Leu Arg Ile Leu Lys Ala His Gly Leu Ala Pro Glu
65 70 75 80

Ile Pro Glu Asp Leu Tyr His Leu Ile Lys Lys Ala Val Ser Ile Arg
85 90 95

Lys His Leu Glu Arg Asn Arg Lys Asp Lys Asp Ser Lys Phe Arg Leu
100 105 110

Ile Leu Val Glu Ser Arg Ile His Arg Leu Ala Arg Tyr Tyr Lys Lys
115 120 125

Thr Lys Lys Leu Pro Pro Val Trp Lys Tyr Glu Ser Thr Thr Ala Ser
130 135 140

Thr Leu Val Ala
145

<210> SEQ ID NO 73
<211> LENGTH: 151
<212> TYPE: PRT
<213> ORGANISM: Oryza sativa

<400> SEQUENCE: 73

Met Gly Arg Leu His Ser Lys Gly Lys Gly Ile Ala Ser Ser Thr Leu
1 5 10 15

Pro Tyr Ser Arg Thr Pro Pro Ala Trp Leu Lys Thr Thr Pro Asp Gln
20 25 30

Val Val Asp His Ile Cys Lys Leu Ala Lys Lys Gly Ala Thr Pro Ser
35 40 45

Gln Ile Gly Val Val Leu Arg Asp Ser His Gly Val Ala Gln Val Lys
50 55 60

Ile Val Thr Gly Asn Lys Ile Leu Arg Ile Leu Lys Ser Asn Gly Leu
65 70 75 80

Ala Pro Glu Leu Pro Glu Asp Leu Tyr Phe Leu Ile Lys Lys Ala Val
85 90 95

Ala Val Arg Lys His Leu Glu Arg Asn Arg Lys Asp Lys Asp Ser Lys
100 105 110

Phe Arg Leu Ile Leu Ile Glu Ser Arg Ile His Arg Leu Ser Arg Tyr
115 120 125

Tyr Lys Thr Val Gly Val Leu Pro Pro Thr Trp Arg Tyr Glu Ser Ala
130 135 140

Thr Ala Ser Thr Leu Val Ala
145 150

<210> SEQ ID NO 74
<211> LENGTH: 151
<212> TYPE: PRT
<213> ORGANISM: Oryza sativa

<400> SEQUENCE: 74

```
Met Gly Arg Met His Ser Ser Gly Lys Gly Met Ser Cys Ser Val Leu
1               5                   10                  15

Pro Tyr Arg Arg Ala Ala Pro Ala Trp Val Lys Thr Ser Ala Ser Glu
            20                  25                  30

Val Glu Glu Met Ile Val Arg Val Ala Lys Lys Gly Gln Leu Pro Ser
        35                  40                  45

Gln Ile Gly Ala Ile Leu Arg Asp Ala His Ala Val Pro Leu Ala Gln
    50                  55                  60

Gly Val Thr Gly Gly Lys Ile Leu Arg Val Leu Lys Ser Arg Gly Leu
65                  70                  75                  80

Ala Pro Glu Val Pro Glu Asp Leu Tyr Phe Leu Ile Lys Lys Ala Val
                85                  90                  95

Ala Met Arg Lys His Leu Glu Arg Asn Arg Lys Asp Lys Asp Thr Lys
            100                 105                 110

Phe Arg Leu Ile Leu Val Glu Ser Arg Val His Arg Leu Thr Arg Tyr
        115                 120                 125

Tyr Arg Leu Ala Lys Lys Ile Pro Ala Phe Phe Lys Tyr Asp Ser Thr
    130                 135                 140

Thr Ala Ser Thr Leu Val Ala
145                 150
```

<210> SEQ ID NO 75
<211> LENGTH: 151
<212> TYPE: PRT
<213> ORGANISM: Triticum aestivum

<400> SEQUENCE: 75

```
Met Gly Arg Leu His Ser Lys Gly Lys Gly Ile Ser Ala Ser Ala Leu
1               5                   10                  15

Pro Tyr Ser Arg Ser Ser Pro Ala Trp Leu Lys Thr Thr Pro Glu Gln
            20                  25                  30

Val Val Glu Gln Ile Ser Lys Leu Ala Arg Lys Gly Ala Thr Pro Ser
        35                  40                  45

Gln Ile Gly Val Ile Leu Arg Asp Ser His Gly Ile Ala Gln Val Lys
    50                  55                  60

His Val Thr Gly Asn Arg Ile Leu Arg Ile Leu Lys Ser Ser Gly Leu
65                  70                  75                  80

Ala Pro Glu Leu Pro Glu Asp Leu Tyr Met Leu Ile Lys Lys Ala Val
                85                  90                  95

Ala Val Arg Lys His Leu Glu Arg Asn Arg Lys Asp Lys Asp Ser Lys
            100                 105                 110

Phe Arg Leu Ile Leu Ile Glu Ser Arg Ile His Arg Leu Ala Arg Tyr
        115                 120                 125

Tyr Lys Thr Val Gly Val Leu Pro Pro Thr Trp Lys Tyr Glu Ser Ala
    130                 135                 140

Thr Ala Ser Thr Ile Val Ala
145                 150
```

<210> SEQ ID NO 76

<211> LENGTH: 151
<212> TYPE: PRT
<213> ORGANISM: Hordeum vulgare

<400> SEQUENCE: 76

Met Gly Arg Leu His Ser Lys Gly Lys Gly Ile Ser Ala Ser Ala Leu
1 5 10 15

Pro Tyr Ser Arg Ser Ser Pro Ala Trp Leu Lys Thr Thr Pro Glu Gln
20 25 30

Val Val Glu Gln Ile Ser Lys Leu Ala Arg Lys Gly Ala Thr Pro Ser
35 40 45

Gln Ile Gly Val Ile Leu Arg Asp Ser His Gly Ile Ala Gln Val Lys
50 55 60

His Val Thr Gly Asn Arg Ile Leu Arg Ile Leu Lys Ser Ser Gly Leu
65 70 75 80

Ala Pro Glu Leu Pro Glu Asp Leu Tyr Met Leu Ile Lys Lys Ala Val
85 90 95

Ala Val Arg Lys His Leu Glu Arg Asn Arg Lys Asp Lys Asp Ser Lys
100 105 110

Phe Arg Leu Ile Leu Ile Glu Ser Arg Ile His Arg Leu Ala Arg Tyr
115 120 125

Tyr Lys Thr Val Gly Val Leu Pro Pro Thr Trp Lys Tyr Glu Ser Ala
130 135 140

Thr Ala Ser Thr Ile Val Ala
145 150

<210> SEQ ID NO 77
<211> LENGTH: 151
<212> TYPE: PRT
<213> ORGANISM: Arabidopsis thaliana

<400> SEQUENCE: 77

Met Gly Arg Leu His Ser Lys Gly Lys Gly Ile Ser Ala Ser Ala Leu
1 5 10 15

Pro Tyr Ser Arg Ser Ser Pro Ala Trp Leu Lys Thr Thr Pro Glu Gln
20 25 30

Val Val Glu Gln Ile Ser Lys Leu Ala Arg Lys Gly Ala Thr Pro Ser
35 40 45

Gln Ile Gly Val Ile Leu Arg Asp Ser His Gly Ile Ala Gln Val Lys
50 55 60

His Val Thr Gly Asn Arg Ile Leu Arg Ile Leu Lys Ser Ser Gly Leu
65 70 75 80

Ala Pro Glu Leu Pro Glu Asp Leu Tyr Met Leu Ile Lys Lys Ala Val
85 90 95

Ala Val Arg Lys His Leu Glu Arg Asn Arg Lys Asp Lys Asp Ser Lys
100 105 110

Phe Arg Leu Ile Leu Ile Glu Ser Arg Ile His Arg Leu Ala Arg Tyr
115 120 125

Tyr Lys Thr Val Gly Val Leu Pro Pro Thr Trp Lys Tyr Glu Ser Ala
130 135 140

Thr Ala Ser Thr Ile Val Ala
145 150

<210> SEQ ID NO 78
<211> LENGTH: 151
<212> TYPE: PRT
<213> ORGANISM: Hordeum vulgare

<400> SEQUENCE: 78

Met Gly Arg Met His Ser Gly Gly Lys Gly Ile Ala Lys Ser Ser Leu
1 5 10 15

Pro Tyr Arg Arg Ser Pro Pro Ser Trp Leu Lys Val Thr Ala Ser Gln
20 25 30

Val Glu Asp His Val Asn Lys Leu Ala Lys Arg Gly Leu Thr Pro Ser
35 40 45

Gln Ile Gly Val Ile Leu Arg Asp Ser Asn Gly Ile Ala Gln Val Lys
50 55 60

Ser Val Thr Gly Asn Lys Ile Leu Arg Ile Leu Lys Lys Ser Gly Leu
65 70 75 80

Ala Pro Ala Ile Pro Glu Asp Leu Tyr Met Leu Ile Lys Lys Ala Val
85 90 95

Ala Val Arg Lys His Leu Glu Arg Asn Lys Lys Asp Lys Asp Ser Lys
100 105 110

Phe Arg Leu Ile Leu Ile Glu Ser Arg Ile His Arg Leu Ala Arg Tyr
115 120 125

Tyr Arg Ala Ser Arg Lys Leu Asp Ala Asn Trp Lys Tyr Glu Ser Ala
130 135 140

Thr Ala Ser Ala Leu Val Ala
145 150

<210> SEQ ID NO 79
<211> LENGTH: 175
<212> TYPE: PRT
<213> ORGANISM: Saccharum officinarum

<400> SEQUENCE: 79

Leu Ala Thr Ala Ala Asn Leu Ser Leu Ala Leu Pro Pro Ala Arg Arg
1 5 10 15

Arg Pro Pro Leu Ala Ala Thr Ala Ala Met Gly Arg Met Tyr Gly Pro
20 25 30

Gly Lys Gly Met Ser Ser Ser Val Leu Pro Tyr Ala Arg Val Ala Pro
35 40 45

Gly Trp Val Arg Ser Thr Ala Gly Glu Val Glu Glu Met Ile Val Arg
50 55 60

Ala Ala Lys Lys Gly His Leu Pro Ser Gln Ile Gly Ala Leu Leu Arg
65 70 75 80

Asp Thr His Gly Val Pro Leu Val His Gly Val Thr Gly Gly Lys Ile
85 90 95

Leu Arg Met Leu Lys Ala Arg Gly Leu Ala Pro Glu Val Pro Glu Asp
100 105 110

Leu Tyr Phe Leu Ile Lys Lys Ala Val Ala Ile Arg Lys His Leu Asp
115 120 125

Arg Asn Arg Thr Asp Val Asp Ala Lys Phe Arg Leu Ile Leu Val Glu
130 135 140

Ser Arg Val His Arg Leu Ile Arg Tyr Tyr Arg Arg Thr Lys Lys Ile
145 150 155 160

Ala Pro Asn Leu Lys Tyr Glu Ser Thr Thr Ala Ser Ala Leu Val
165 170 175

<210> SEQ ID NO 80
<211> LENGTH: 131
<212> TYPE: PRT
<213> ORGANISM: Hordeum vulgare

<400> SEQUENCE: 80

Ile Ser Ala Ser Ala Leu Pro Tyr Lys Arg Thr Pro Pro Ser Trp Leu
1 5 10 15

Lys Ile Ser Ser Gln Asp Val Glu Asp Asn Ile Cys Lys Phe Ala Lys
20 25 30

Lys Gly Leu Thr Pro Ser Gln Ile Gly Val Ile Leu Arg Asp Ser His
35 40 45

Gly Ile Ala His Val Lys Ser Val Thr Gly Ser Lys Ile Leu Arg Ile
50 55 60

Leu Lys Ala His Gly Leu Ala Pro Glu Ile Pro Glu Asp Leu Tyr His
65 70 75 80

Leu Ile Lys Lys Ala Val Ala Ile Arg Lys His Leu Glu Arg Asn Arg
85 90 95

Lys Asp Lys Asp Ser Lys Phe Arg Leu Ile Leu Val Glu Ser Arg Ile
100 105 110

His Arg Leu Ala Arg Tyr Tyr Lys Lys Thr Lys Lys Leu Pro Pro Val
115 120 125

Trp Lys Tyr
130

<210> SEQ ID NO 81
<211> LENGTH: 151
<212> TYPE: PRT
<213> ORGANISM: Populus tremula x Populus tremuloides

<400> SEQUENCE: 81

Met Gly Arg Met His Asn Pro His Lys Gly Ile Ala Gly Ser Ala Leu
1 5 10 15

Pro Tyr Lys Arg Thr Pro Pro Arg Trp Leu Lys Val Thr Pro Glu Glu
20 25 30

Val Ser Glu Gln Ile Phe Lys Leu Ala Arg Lys Gly Met Thr Pro Ser
35 40 45

Gln Ile Gly Val Val Leu Arg Asp Ser His Gly Ile Ala Gln Val Lys
50 55 60

Ser Val Thr Gly Ala Lys Ile Leu Arg Ile Leu Lys Gly Asn Gly Leu
65 70 75 80

Ala Pro Glu Leu Pro Glu Asp Leu Tyr His Leu Ile Lys Lys Ala Val
85 90 95

Ser Val Arg Lys His Leu Glu Arg Asn Arg Lys Asp Lys Asp Ser Lys
100 105 110

Phe Arg Leu Ile Leu Ile Glu Ser Arg Ile His Arg Leu Val Arg Tyr
115 120 125

Tyr Lys Thr Lys Ser Gln Leu Ser Pro Ser Phe Lys Tyr Glu Ser Ala
130 135 140

Thr Ala Ser Thr Ile Val Ser
145 150

<210> SEQ ID NO 82
<211> LENGTH: 151
<212> TYPE: PRT
<213> ORGANISM: Hordeum vulgare

<400> SEQUENCE: 82

Met Gly Arg Met His Thr Pro Gly Lys Gly Ile Ser Lys Ser Ala Leu
1 5 10 15

-continued

Pro Tyr Arg Arg Ser Val Ala Thr Trp Leu Lys Ser Ser Ser Glu Asp
20 25 30

Val Lys Asp His Ile Phe Lys Leu Ala Lys Lys Gly Leu Thr Pro Ser
35 40 45

Lys Ile Gly Val Ile Leu Arg Asp Ser His Gly Val Ala Gln Val Arg
50 55 60

Phe Val Thr Gly Asn Lys Ile Leu Arg Ile Met Lys Ala Met Gly Leu
65 70 75 80

Ala Pro Gly Leu Pro Glu Asp Leu Tyr His Leu Ile Lys Lys Ala Val
85 90 95

Ala Ile Arg Lys His Leu Glu Arg Asn Arg Lys Asp Arg Asp Ser Lys
100 105 110

Phe Arg Leu Ile Leu Val Glu Ser Arg Ile His Arg Leu Ala Arg Tyr
115 120 125

Tyr Lys Arg Lys Ser Lys Ile Ala Pro Asn Trp Arg Tyr Glu Ser Ser
130 135 140

Thr Ala Ser Ala Leu Val Ala
145 150

<210> SEQ ID NO 83
<211> LENGTH: 164
<212> TYPE: PRT
<213> ORGANISM: Oryza sativa
<220> FEATURE:
<221> NAME/KEY: misc_feature
<222> LOCATION: (1)..(2)
<223> OTHER INFORMATION: Xaa can be any naturally occurring amino acid

<400> SEQUENCE: 83

Xaa Xaa Glu Lys Gly Ile Ser Ser Ser Ala Leu Pro Cys Lys Arg Ile
1 5 10 15

Pro Pro Ser Leu Leu Lys Asn Ala Ala Ser Asn Val Glu Glu Met Ile
20 25 30

Met Lys Ala Ala Lys Met Gly Gln Met Ser Ser Gln Ile Gly Val Val
35 40 45

Leu Arg His Gln His Gly Ile Pro Leu Val Lys Ser Ile Ala Ser Ser
50 55 60

Lys Ile Leu His Ile Leu Lys Ala His Gly Leu Ala Pro Lys Ile Leu
65 70 75 80

Glu Asp Leu Tyr Phe Leu Ile Lys Lys Ala Val Ala Ile Arg Lys His
85 90 95

Leu Glu Arg Asn Arg Lys Asp Lys Asp Ser Ser Phe Arg Leu Ile Leu
100 105 110

Val Glu Ser Arg Ile His Arg Leu Val Arg Tyr Tyr Lys Arg Thr Lys
115 120 125

Lys Leu Pro Pro Thr Leu Arg Phe Lys Trp Ile Leu Phe Lys Val Gly
130 135 140

Leu Met Leu Ser Ser Leu Leu Leu Thr Cys Val Leu Ser Asn Leu Arg
145 150 155 160

Asn Gly Leu Leu

<210> SEQ ID NO 84
<211> LENGTH: 118
<212> TYPE: PRT
<213> ORGANISM: Glycine max

<400> SEQUENCE: 84

```
Glu Glu Asn Ile Cys Lys Phe Ala Lys Lys Gly Leu Thr Pro Ser Gln
1               5                   10                  15

Ile Gly Val Ile Leu Arg Asp Ser His Gly Ile Ala Gln Val Asn Ser
            20                  25                  30

Val Thr Gly Ser Lys Ile Leu Arg Ile Leu Lys Ala His Gly Leu Ala
        35                  40                  45

Pro Glu Ile Pro Glu Asp Leu Tyr His Leu Ile Lys Lys Ala Val Ser
    50                  55                  60

Ile Arg Lys His Leu Glu Arg Asn Arg Lys Asp Lys Asp Ser Lys Phe
65                  70                  75                  80

Arg Leu Ile Leu Val Glu Ser Arg Ile His Arg Leu Ala Arg Tyr Tyr
                85                  90                  95

Lys Lys Thr Lys Lys Leu Pro Pro Val Trp Lys Tyr Glu Ser Thr Thr
            100                 105                 110

Ala Ser Thr Leu Val Ala
        115


<210> SEQ ID NO 85
<211> LENGTH: 135
<212> TYPE: PRT
<213> ORGANISM: Populus tremula x Populus tremuloides

<400> SEQUENCE: 85

Ser Ala Leu Pro Tyr Lys Arg Thr Pro Pro Ser Trp Leu Lys Thr Ser
1               5                   10                  15

Ala Asn Glu Val Cys Asp His Val Cys Arg Leu Ala Lys Lys Gly Leu
            20                  25                  30

Thr Pro Ser Gln Ile Gly Val Val Leu Arg Asp Ser His Gly Ile Pro
        35                  40                  45

Gln Val Lys Ser Val Thr Asn Asn Lys Ile Leu Arg Ile Leu Lys Ala
    50                  55                  60

Asn Gly Phe Ala Pro Glu Leu Pro Glu Asp Leu Tyr His Leu Ile Lys
65                  70                  75                  80

Lys Ala Ala Ser Ile Arg Lys His Leu Lys Arg Ser Arg Gln Asp Lys
                85                  90                  95

Asp Ala Lys Phe His Leu Ile Leu Val Glu Ala Arg Ile His Arg Val
            100                 105                 110

Ser Arg Tyr Tyr Lys Glu Ser Lys His Leu Pro Ala Asn Trp Arg Tyr
        115                 120                 125

Glu Ser Pro Thr Ala Ala Thr
    130                 135


<210> SEQ ID NO 86
<211> LENGTH: 116
<212> TYPE: PRT
<213> ORGANISM: Nicotiana tabacum

<400> SEQUENCE: 86

Met Gly Arg Met His Ser Arg Gly Lys Gly Ile Ser Ala Ser Ala Leu
1               5                   10                  15

Pro Tyr Lys Arg Thr Pro Pro Ser Trp Leu Lys Ile Ser Ala Pro Asp
            20                  25                  30

Val Glu Asp Asn Ile Cys Lys Phe Ala Lys Lys Gly Leu Thr Pro Ser
        35                  40                  45

Gln Ile Gly Val Ile Leu Arg Asp Ser His Gly Ile Ala Gln Val Lys
    50                  55                  60
```

```
Ser Val Thr Gly Ser Lys Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Ala Ile Arg Lys His Leu Glu Arg Asp Arg Lys Asp Lys Asp Ser Lys
            100                 105                 110

Phe Arg Leu Ile
        115


<210> SEQ ID NO 87
<211> LENGTH: 152
<212> TYPE: PRT
<213> ORGANISM: Triticum aestivum
<220> FEATURE:
<221> NAME/KEY: misc_feature
<222> LOCATION: (129)..(130)
<223> OTHER INFORMATION: Xaa can be any naturally occurring amino acid

<400> SEQUENCE: 87

Met Gly Gly Ile Asp Ser Arg Arg Glu Gly Tyr Met Val Val Gly Val
1               5                   10                  15

Ala Val Gln Glu Asp Ser Ser Glu Val Gly Ser Arg Pro Thr Val Ala
            20                  25                  30

Asp Val Asp Glu Leu Ile Thr Lys Ala Ala Lys Lys Gly Gln Met Pro
        35                  40                  45

Ser Gln Ile Gly Val Leu Leu Arg Asp Gln His Gly Ile Pro Leu Val
    50                  55                  60

Lys Ser Val Thr Gly Ser Lys Ile Leu Arg Ile Ile Lys Ala His Gly
65                  70                  75                  80

Leu Ala Pro Glu Ile Pro Glu Asp Leu Tyr Phe Leu Ile Lys Lys Ala
                85                  90                  95

Val Ala Ile Arg Lys His Leu Glu Arg Asn Arg Lys Asp Lys Asp Ser
            100                 105                 110

Lys Phe Arg Leu Ile Leu Val Glu Ser Arg Ile His Arg Pro Pro Arg
        115                 120                 125

Xaa Xaa Lys Gly Arg Lys Lys Phe Pro Asp Lys Trp Lys Pro Pro Pro
    130                 135                 140

Pro Pro Gly Ser Ile Leu Val Ala
145                 150


<210> SEQ ID NO 88
<211> LENGTH: 112
<212> TYPE: PRT
<213> ORGANISM: Brassica napus

<400> SEQUENCE: 88

Leu Gln Val Cys Glu Glu Gly Leu Thr Pro Ser Gln Ile Gly Val Ile
1               5                   10                  15

Leu Arg Asp Ser His Gly Ile Pro Gln Val Lys Ser Val Thr Gly Asn
            20                  25                  30

Lys Ile Leu Arg Ile Leu Lys Ala His Gly Leu Ala Pro Glu Ile Pro
        35                  40                  45

Asp Asp Leu Tyr His Leu Ile Lys Lys Ala Val Ala Ile Arg Lys His
    50                  55                  60

Leu Glu Arg Asn Arg Lys Asp Lys Asp Ser Lys Phe Arg Leu Ile Leu
65                  70                  75                  80

Ala Glu Ser Arg Ile His Arg Leu Ala Arg Tyr Tyr Lys Lys Thr Lys
                85                  90                  95
```

```
Lys Leu Pro Pro Val Trp Lys Tyr Glu Ser Thr Thr Ala Ser Thr Leu
            100                 105                 110


<210> SEQ ID NO 89
<211> LENGTH: 121
<212> TYPE: PRT
<213> ORGANISM: Triticum aestivum
<220> FEATURE:
<221> NAME/KEY: misc_feature
<222> LOCATION: (113)..(113)
<223> OTHER INFORMATION: Xaa can be any naturally occurring amino acid
<220> FEATURE:
<221> NAME/KEY: misc_feature
<222> LOCATION: (116)..(116)
<223> OTHER INFORMATION: Xaa can be any naturally occurring amino acid

<400> SEQUENCE: 89

Ala Ala Met Gly Arg Met His Ser Arg Gly Lys Gly Ile Ser Ser Ser
1               5                   10                  15

Ala Leu Pro Tyr Lys Arg Thr Pro Pro Thr Trp Leu Lys Thr Ala Ala
            20                  25                  30

Ser Asp Val Glu Glu Met Ile Thr Lys Ala Ala Lys Lys Gly Gln Met
        35                  40                  45

Pro Ser Gln Ile Gly Val Leu Leu Arg Asp Gln His Gly Ile Pro Leu
    50                  55                  60

Val Lys Ser Val Thr Gly Ser Lys Ile Leu Arg Ile Leu Lys Ala Met
65                  70                  75                  80

Gly Trp Asn Arg Asn Pro Gly Gly Leu Tyr Ser His Gln Glu Ala Val
                85                  90                  95

Ala Ile Arg Asn Thr Leu Glu Glu Gln Glu Gly Gln Arg Ser Lys Ser
            100                 105                 110

Xaa Ser Ser Xaa Gln Asn Arg Phe Asn
        115                 120


<210> SEQ ID NO 90
<211> LENGTH: 102
<212> TYPE: PRT
<213> ORGANISM: Populus tremula x Populus tremuloides

<400> SEQUENCE: 90

Met Gly Arg Met His Ser Lys Gly Lys Gly Ile Ser Ala Ser Ala Leu
1               5                   10                  15

Pro Tyr Lys Arg Thr Ser Pro Ser Trp Leu Lys Ile Ser Pro Gln Asp
            20                  25                  30

Val Asp Asp Asn Ile Cys Lys Phe Ala Lys Lys Gly Leu Thr Pro Ser
        35                  40                  45

Gln Ile Gly Val Ile Leu Arg Asp Ser His Gly Ile Ala Gln Val Lys
    50                  55                  60

Thr Val Thr Gly Asn Gln Ile Leu Arg Ile Leu Lys Ala His Gly Leu
65                  70                  75                  80

Ala Pro Glu Ile Pro Glu Asp Leu Tyr His Leu Ile Lys Lys Ala Val
                85                  90                  95

Cys Tyr Leu Gly Ser Ile
            100


<210> SEQ ID NO 91
<211> LENGTH: 142
<212> TYPE: PRT
<213> ORGANISM: Oryza sativa
```

<400> SEQUENCE: 91

Glu Asp Gly Ser Asp Val Val Ala Asp Trp Arg Cys Ala Pro Ser Gln
1               5                   10                  15

His Gly Ile Pro Leu Val Lys Ser Ile Ala Ser Ser Lys Ile Leu His
            20                  25                  30

Ile Leu Asn Ala His Gly Leu Ala Pro Lys Ile Leu Glu Asp Leu Tyr
        35                  40                  45

Phe Leu Ile Lys Lys Ala Val Ala Ile Arg Lys His Leu Glu Arg Asn
    50                  55                  60

Arg Lys Asp Lys Asp Ser Ser Phe Arg Leu Ile Leu Val Glu Ser Arg
65                  70                  75                  80

Ile His Arg Leu Val Arg Tyr Tyr Lys Arg Thr Lys Lys Leu Pro Pro
                85                  90                  95

Thr Leu Arg Ser Trp Ile Ile Phe Leu Glu Phe Ser Thr Val Phe Ser
            100                 105                 110

Cys Ser Arg Met Leu Gln Met Asp Thr Leu Gln Ser Arg Leu Asp Val
        115                 120                 125

Glu Phe Leu Val Ala His Met Cys Ser Val Lys Phe Lys Glu
    130                 135                 140

<210> SEQ ID NO 92
<211> LENGTH: 163
<212> TYPE: PRT
<213> ORGANISM: Triticum aestivum

<400> SEQUENCE: 92

Phe Pro Ser Pro Pro Pro Gln Gln Leu Leu Pro Ile Ser Leu Leu Ala
1               5                   10                  15

Ala Ala Leu Arg Ser Pro Leu Ala Ala Met Gly Arg Met His Ser Asn
            20                  25                  30

Gly Lys Gly Met Ser Ser Ser Val Ile Pro Tyr Lys Arg Glu Ala Pro
        35                  40                  45

Thr Trp Val Lys Thr Ser Ala Pro Asp Val Glu Glu Ile Ile Val Arg
    50                  55                  60

Ala Ala Lys Lys Gly Gln Leu Pro Ser Gln Ile Gly Ala Leu Leu Arg
65                  70                  75                  80

Asp Gly Tyr Gly Ile Pro Leu Ser Lys Ala Val Thr Gly Ala Lys Ile
                85                  90                  95

Val Arg Leu Leu Lys Ala Arg Gly Leu Ala Pro Glu Met Pro Arg Gly
            100                 105                 110

Pro Leu Leu Pro His Gln Glu Gly Arg Cys Asp Ser Glu Ala Pro Gly
        115                 120                 125

Arg Gly Thr Ser Arg Thr Trp Thr Pro Ser Ser Ala Ser Ser Ser Ser
    130                 135                 140

Arg Thr Arg Ser Asn Ala Ser Thr Ala Thr Thr Ala Ser Thr Arg Arg
145                 150                 155                 160

Cys Arg Arg

<210> SEQ ID NO 93
<211> LENGTH: 333
<212> TYPE: PRT
<213> ORGANISM: Oryza sativa
<220> FEATURE:
<221> NAME/KEY: misc_feature
<222> LOCATION: (1)..(2)
<223> OTHER INFORMATION: Xaa can be any naturally occurring amino acid

<400> SEQUENCE: 93

Xaa Xaa Val Glu Thr Ser Asp Leu Arg Glu Arg Glu Arg Glu Gly Lys
1               5                   10                  15

Gly Arg Arg Arg Arg Arg Gly Thr Lys Arg Thr Arg Arg Ala Arg Ala
            20                  25                  30

Ile Phe Ala Leu Leu Pro Leu Ser Ser Leu Ser Ser Pro Leu Leu Arg
        35                  40                  45

Ser Ser Ala Ser Pro Ala Gly Arg Arg Leu Pro Val Leu Glu Ala Ala
    50                  55                  60

Ala Ala Asp Thr Gly Gly Asp Asp Met Ala Asp Gly Gly Glu Lys Cys
65                  70                  75                  80

Arg Asp Ala Ala Gly Glu Gly Gly Gly Gly Gly Asp Leu Tyr Ala Val
                85                  90                  95

Leu Gly Leu Lys Lys Glu Cys Ser Asp Ala Asp Leu Lys Leu Ala Tyr
            100                 105                 110

Arg Lys Leu Ala Met Arg Trp His Pro Asp Lys Cys Ser Ser Ser Ser
        115                 120                 125

Ser Ala Lys His Met Glu Glu Ala Lys Glu Lys Phe Gln Glu Ile Gln
    130                 135                 140

Gly Ala Tyr Ser Val Leu Ser Asp Ser Asn Lys Arg Phe Leu Tyr Asp
145                 150                 155                 160

Val Gly Val Tyr Asp Asp Asp Asp Asn Asp Asp Asp Asn Leu Gln Gly
                165                 170                 175

Met Gly Asp Phe Ile Gly Glu Met Ala Gln Met Met Ser Gln Ala Arg
            180                 185                 190

Pro Thr Arg Gln Glu Ser Phe Lys Glu Leu Gln Gln Leu Phe Val Asp
        195                 200                 205

Met Phe Gln Ala Asp Leu Asp Ser Gly Phe Cys Asn Gly Pro Ser Lys
    210                 215                 220

Cys Tyr His Thr Gln Ala Gln Ser Gln Thr Arg Thr Ser Ser Thr Ser
225                 230                 235                 240

Pro Ser Met Ser Pro Ser Pro Pro Pro Pro Val Ala Thr Glu Ala Glu
                245                 250                 255

Ser Pro Ser Cys Asn Gly Ile Asn Lys Arg Gly Ser Ser Ala Met Asp
            260                 265                 270

Ser Gly Lys Pro Pro Arg Ala Ser Glu Val Ser Ala Gly Gln Ser Gln
        275                 280                 285

Ser Gly Phe Cys Phe Gly Lys Ser Asp Ala Lys Gln Ala Ala Lys Thr
    290                 295                 300

Arg Ser Gly Asn Thr Ala Ser Arg Arg Arg Asn Gly Arg Lys Gln Lys
305                 310                 315                 320

Val Ser Ser Lys His Asp Val Ser Ser Glu Asp Glu Met
                325                 330

<210> SEQ ID NO 94
<211> LENGTH: 294
<212> TYPE: PRT
<213> ORGANISM: Hordeum vulgare

<400> SEQUENCE: 94

Trp Arg Gly Ala Gln Thr Ala Glu Glu Arg Glu Arg Gly Lys Leu Gln
1               5                   10                  15

Glu Pro Pro Pro Pro Pro Pro Ala His Pro Pro Ala Gly Asp Ala Arg
            20                  25                  30

```
Gly Met Ala Thr Gly Gly Asp Gly Asp Pro Ala Ala Pro Gly Gly Gly
        35                  40                  45

Asp Leu Tyr Ala Val Leu Gly Leu Ser Lys Glu Cys Ser Asp Ala Asp
    50                  55                  60

Leu Lys Val Ala Tyr Arg Lys Leu Ala Met Arg Trp His Pro Asp Arg
65                  70                  75                  80

Cys Ser Ser Ser Ser Gly Thr Lys His Met Glu Glu Ala Lys Glu Lys
                85                  90                  95

Phe Gln Glu Ile Gln Gly Ala Tyr Ser Val Leu Ser Asp Ala Asn Lys
            100                 105                 110

Arg Phe Leu Tyr Asp Val Gly Val Tyr Gln Glu Glu Glu Asp Ser Asp
        115                 120                 125

Asp Ser Met Gln Gly Met Gly Asp Phe Leu Gly Glu Met Ala His Met
    130                 135                 140

Met Ser Gln Thr Arg Pro Ala Arg Gln Glu Ser Phe Glu Glu Leu Gln
145                 150                 155                 160

Gln Leu Phe Val Asp Met Phe Gln Ser Asp Ile Asp Ser Gly Phe Cys
                165                 170                 175

Asn Gly Pro Ala Lys Gly His His Asp Pro Phe Gln Arg Gln Thr Gln
            180                 185                 190

Thr Phe Ser Thr Ser Pro Ser Ser Pro Pro Ser Pro Pro Pro Pro Leu
        195                 200                 205

Ala Thr Glu Ala Glu Ala Ala Ser Cys Asn Gly Ile Asn Lys Arg Gly
    210                 215                 220

Ser Ser Ala Met Gly Ser Gly Lys Pro Pro Arg Ala Ala Glu Ala Gly
225                 230                 235                 240

Ala Gly Tyr Gly Gln Ser Glu Phe Cys Phe Gly Thr Ser Asp Ala Lys
                245                 250                 255

Gln Ala Pro Arg Ala Arg Gly Gly Asn Thr Ser Arg Arg Arg Asn Gly
            260                 265                 270

Gln Lys Gln Lys Leu Ser Ser Lys His Asp Val Ser Ser Glu Asp Glu
        275                 280                 285

Met Leu Ser Pro Gln Gln
    290
```

<210> SEQ ID NO 95
<211> LENGTH: 301
<212> TYPE: PRT
<213> ORGANISM: Triticum aestivum

<400> SEQUENCE: 95

```
Arg Glu Arg Glu Arg Glu Gly Arg Lys Arg Gln Glu Pro Pro Pro Pro
1               5                   10                  15

Ser Ser Pro Leu Ser Ser Ser Ser Ser Pro Ala His Pro Arg Ala Pro
            20                  25                  30

Gln Ala Gly Gly Ala Gly Arg Gly Met Ala Thr Gly Gly Asp Gly Cys
        35                  40                  45

Gly Gly Gly Glu Pro Ala Ala Pro Gly Gly Gly Asp Leu Tyr Ala Val
    50                  55                  60

Leu Gly Leu Ser Lys Glu Cys Ser Asp Ala Asp Leu Lys Leu Ala Tyr
65                  70                  75                  80

Arg Lys Leu Ala Met Arg Trp His Pro Asp Arg Cys Ser Ser Ser Ser
                85                  90                  95

Gly Thr Lys Arg Met Glu Glu Ala Lys Glu Lys Phe Gln Glu Ile Gln
            100                 105                 110
```

```
Gly Ala Tyr Ser Val Leu Ser Asp Ala Asn Lys Arg Phe Leu Tyr Asp
        115                 120                 125

Val Gly Val Tyr Gln Glu Glu Glu Asp Ser Asp Asp Ser Met Gln Gly
    130                 135                 140

Met Gly Asp Phe Leu Gly Glu Met Ala His Met Met Ser Gln Thr Arg
145                 150                 155                 160

Pro Ala Arg Gln Glu Ser Phe Glu Glu Leu Gln Gln Leu Phe Val Asp
                165                 170                 175

Met Phe Gln Ser Asp Ile Asp Ser Gly Phe Cys Asn Arg Pro Ala Lys
            180                 185                 190

Gly His His Asp Pro Phe Gln Thr Phe Ser Thr Ser Pro Ser Ser Ser
        195                 200                 205

Pro Ser Pro Pro Pro Pro Val Ala Thr Glu Ala Glu Ala Ala Ser Cys
    210                 215                 220

Asn Gly Ile Asn Lys Arg Gly Ser Ser Ala Met Gly Ser Gly Lys Pro
225                 230                 235                 240

Pro Arg Ala Gly Glu Ala Gly Ala Gly Tyr Gly Gln Pro Glu Phe Cys
                245                 250                 255

Phe Gly Thr Ser Asp Ala Lys Gln Ala Pro Lys Ala Arg Gly Arg Asn
            260                 265                 270

Thr Ser Arg Arg Arg Asn Gly Gln Lys Gln Lys Leu Ser Ser Lys His
        275                 280                 285

Asp Val Ser Ser Glu Asp Glu Met Leu Ser Pro Gln Gln
    290                 295                 300


<210> SEQ ID NO 96
<211> LENGTH: 203
<212> TYPE: PRT
<213> ORGANISM: Zea mays

<400> SEQUENCE: 96

Met Glu Glu Ala Lys Glu Lys Phe Gln Glu Ile Gln Gly Ala Tyr Ser
1               5                   10                  15

Val Leu Ser Asp Ala Asn Lys Arg Leu Leu Tyr Asp Val Gly Val Tyr
            20                  25                  30

Asp Asp Glu Asp Asp Glu Glu Ser Met Gln Gly Met Gly Asp Phe Ile
        35                  40                  45

Gly Glu Met Ala Gln Met Met Ser Gln Ala Gln Pro Thr Arg Gln Glu
    50                  55                  60

Ser Phe Glu Glu Leu Gln Gln Leu Phe Val Asp Met Phe Gln Ser Asp
65                  70                  75                  80

Ile Asp Ser Gly Phe Cys Asn Arg Thr Ala Lys Ala His Gln Phe Gln
                85                  90                  95

Gly Pro Ala Lys Ser Arg Thr Cys Ser Thr Ser Pro Ser Ser Ser Pro
            100                 105                 110

Ser Pro Pro Pro Thr Thr Ala Lys Asp Ala Glu Val Pro Ser Cys Asn
        115                 120                 125

Gly Phe Asn Lys Arg Gly Ser Ser Ala Leu Asp Ser Gly Lys Pro Pro
    130                 135                 140

Lys Pro Val Glu Gly Gly Ala Gly Gln Asn Gln Ala Gly Phe Cys Phe
145                 150                 155                 160

Gly Val Ser Asp Thr Lys Glu Thr Pro Lys Leu Pro Gly Gln Asn Ala
                165                 170                 175

Ser Arg Arg Arg Asn Gly Arg Lys Gln Lys Leu Ser Ser Lys His Asp
```

```
            180                 185                 190

Val Ser Ser Glu Asp Glu Thr Ala Ala Gly Ser
        195                 200


<210> SEQ ID NO 97
<211> LENGTH: 164
<212> TYPE: PRT
<213> ORGANISM: Triticum aestivum

<400> SEQUENCE: 97

Met Gln Gly Met Gly Asp Phe Leu Gly Glu Met Ala His Met Met Ser
1               5                   10                  15

Gln Thr Arg Pro Ala Arg Gln Glu Ser Phe Glu Glu Leu Gln Gln Leu
            20                  25                  30

Phe Val Asp Met Phe Gln Ser Asp Ile Asp Ser Gly Phe Cys Asn Gly
        35                  40                  45

Pro Ala Lys Gly His His Asp Pro Phe Gln Thr Phe Ser Thr Phe Pro
    50                  55                  60

Ser Ser Ser Pro Ser Pro Pro Pro Pro Leu Ala Thr Glu Ala Glu Ala
65                  70                  75                  80

Ala Ser Cys Asn Gly Ile Asn Lys Arg Gly Ser Ser Ala Met Gly Ser
                85                  90                  95

Gly Lys Pro Pro Arg Thr Gly Glu Ala Gly Ala Gly Tyr Gly Gln Pro
            100                 105                 110

Glu Phe Cys Phe Gly Arg Ser Asp Ala Lys Gln Ala Pro Lys Ala Arg
        115                 120                 125

Gly Gly Asn Thr Ser Arg Arg Arg Asn Gly Gln Lys Gln Lys Pro Ser
    130                 135                 140

Ser Lys His Asp Val Ser Ser Glu Asp Glu Met Leu Ser Pro Gln Gln
145                 150                 155                 160

Pro Arg Val Val


<210> SEQ ID NO 98
<211> LENGTH: 134
<212> TYPE: PRT
<213> ORGANISM: Zea mays

<400> SEQUENCE: 98

Met Arg Gln Glu Ser Phe Glu Glu Leu Gln Gln Leu Phe Val Asp Met
1               5                   10                  15

Phe Gln Ser Asp Ile Asp Ser Gly Phe Cys Asn Gly Thr Ala Lys Gly
            20                  25                  30

His Gln Val Gln Gly Gln Ala Lys Ser Arg Thr Cys Ser Pro Arg Ser
        35                  40                  45

Pro Pro Thr Thr Ile Val Lys Glu Ala Glu Val Ser Ser Cys Asn Gly
    50                  55                  60

Phe Asn Lys Arg Gly Ser Ser Ala Met Asp Ser Gly Lys Pro Pro Arg
65                  70                  75                  80

Pro Val Glu Cys Gly Ala Gly Gln Ser Gln Ala Gly Phe Cys Phe Gly
                85                  90                  95

Val Ser Asp Thr Pro Lys Pro Arg Gly Pro Asn Ala Asn Arg Lys Arg
            100                 105                 110

Asn Gly Arg Lys Gln Lys Leu Phe Pro Lys His Tyr Val Thr Ser Glu
        115                 120                 125

Asp Asp Thr Ala Gly Ser
    130
```

<210> SEQ ID NO 99
<211> LENGTH: 143
<212> TYPE: PRT
<213> ORGANISM: Triticum aestivum
<220> FEATURE:
<221> NAME/KEY: misc_feature
<222> LOCATION: (132)..(132)
<223> OTHER INFORMATION: Xaa can be any naturally occurring amino acid
<220> FEATURE:
<221> NAME/KEY: misc_feature
<222> LOCATION: (141)..(142)
<223> OTHER INFORMATION: Xaa can be any naturally occurring amino acid

<400> SEQUENCE: 99

```
Gly Ala Leu Val Leu Pro Ser Arg Cys Cys Ser Cys Ala Val Leu Ser
1               5                   10                  15

Asp Ala Asn Lys Arg Phe Leu Tyr Asp Val Gly Val Tyr Gln Glu Glu
            20                  25                  30

Glu Asp Ser Asp Asp Ser Met Gln Gly Met Gly Asp Phe Leu Gly Glu
        35                  40                  45

Met Ala His Met Met Ser Gln Ala Arg Pro Ala Arg Gln Glu Ser Phe
    50                  55                  60

Glu Glu Leu Gln Gln Leu Phe Val Asp Met Phe Gln Ser Asp Ile Asp
65                  70                  75                  80

Ser Gly Phe Cys Asn Gly Pro Ala Lys Gly His His Asp Pro Phe Gln
                85                  90                  95

Thr Phe Ser Thr Ser Pro Ser Ser Ser Pro Ser Pro Pro Pro Pro Leu
            100                 105                 110

Ala Thr Glu Ala Glu Ala Ala Ser Cys Asn Gly Ile Asn Lys Arg Gly
        115                 120                 125

Ser Ser Ala Xaa Gly Leu Trp Gly Lys Pro Pro Arg Xaa Xaa Gly
    130                 135                 140
```

<210> SEQ ID NO 100
<211> LENGTH: 322
<212> TYPE: PRT
<213> ORGANISM: Zea mays

<400> SEQUENCE: 100

```
Met Asp Gly Leu Trp His Leu Gly Asp Glu Leu Arg Gly Gln Pro Lys
1               5                   10                  15

Val Val Glu Asp Arg Gln Trp Ser Leu Met Thr Ser Lys Leu Ala Glu
            20                  25                  30

Ile Thr Arg Ser Arg Gly Glu Arg Thr Asn Asp Leu Asp Tyr Ala Arg
        35                  40                  45

Met Asn Ala Ala Pro Asp Ala Lys Arg Trp Gly Lys Ala Ala Ser Tyr
    50                  55                  60

Gln His His Asp Glu Gly Arg Met Asp His His Val Gly Leu Ser Leu
65                  70                  75                  80

Lys Met Asn Asp Leu Lys Met Asn Glu Ala Ala Ala Ala Ala Val Met
                85                  90                  95

Lys Leu Pro Phe Arg Gly Val Pro Tyr Asn Val Asn Pro Met Tyr Pro
            100                 105                 110

Lys Gly Ser Asn Ala Asn Ala Asn Val Asn Ala Phe Lys Met Asn Val
        115                 120                 125

Gly Val Asn Lys Tyr Ser Ser Ser Ala Asn Gly Lys Asp Ser Gly Gly
    130                 135                 140
```

```
Lys Ser Ser Gly Gly Ser Asn Asn Asn Ser Gly Gly Gly Gly Asn Gly
145                 150                 155                 160

Asn Gly Thr Ala Asn Gly Ser Ser Ala Val Asp Lys Arg Phe Lys Thr
                165                 170                 175

Leu Pro Thr Ser Glu Met Leu Pro Lys Asn Glu Val Leu Gly Gly Tyr
            180                 185                 190

Ile Phe Val Cys Asn Asn Asp Thr Met Gln Glu Asp Leu Lys Arg Gln
        195                 200                 205

Leu Phe Gly Leu Pro Ala Arg Tyr Arg Asp Ser Val Arg Ala Ile Thr
    210                 215                 220

Pro Gly Leu Pro Leu Phe Leu Tyr Asn Tyr Thr Thr His Gln Leu His
225                 230                 235                 240

Gly Val Phe Glu Ala Ala Ser Phe Gly Gly Ser Asn Ile Asp Pro Thr
                245                 250                 255

Ala Trp Glu Asp Lys Lys Cys Lys Gly Glu Ser Arg Phe Pro Ala Gln
            260                 265                 270

Val Arg Ile Arg Val Arg Lys Leu Cys Lys Pro Leu Glu Glu Asp Ser
        275                 280                 285

Phe Arg Pro Val Leu His His Tyr Asp Gly Pro Lys Phe Arg Leu Glu
    290                 295                 300

Leu Ser Ile Ala Glu Thr Leu Ser Leu Leu Asp Leu Cys Glu Lys Glu
305                 310                 315                 320

Gly Ile


<210> SEQ ID NO 101
<211> LENGTH: 310
<212> TYPE: PRT
<213> ORGANISM: Triticum aestivum

<400> SEQUENCE: 101

Met Asp Asn Leu Trp His Leu Gly Asp Glu Phe Arg Gly Gln Ser Lys
1               5                   10                  15

Val Val Glu Asp Arg Gln Trp Ser Leu Met Thr Ser Lys Leu Ala Glu
            20                  25                  30

Ile Thr Lys Ser Lys Ala Glu Arg Met Asn Asp Phe Glu Tyr Ala Arg
        35                  40                  45

Met Asn Thr Val Pro Asp Val Lys Gln Trp Asp Lys Leu Ser Tyr His
    50                  55                  60

Gln Glu Asp Asn Lys Met Asp His Leu Asn Leu Gly Leu Met Asn Leu
65                  70                  75                  80

Asp Leu Lys Met Asn Asp Leu Lys Met Asn Glu Ala Ala Met Lys Tyr
                85                  90                  95

Pro Phe Arg Asn Met Ala Tyr Asn Met Asn Pro Met Tyr Pro Lys Gly
            100                 105                 110

Asn Asn Gly Asn Val Asn Ser Phe Lys Met Asn Val Gly Val Asn Lys
        115                 120                 125

Tyr Pro Asn Asn Gln Asn Gly Lys Glu Ala Asn Gly Lys His Asn Gly
    130                 135                 140

Gly Asn Asn Asn Asn Gly Gly Asn Ser Asn Asn Asn Ser Val Asp Lys
145                 150                 155                 160

Arg Phe Lys Thr Leu Pro Thr Ser Glu Met Leu Pro Arg Asn Glu Val
                165                 170                 175

Leu Gly Gly Tyr Ile Phe Val Cys Asn Asn Asp Thr Met Gln Glu Asp
            180                 185                 190
```

```
Leu Lys Arg Gln Leu Phe Gly Leu Pro Ala Arg Tyr Arg Asp Ser Val
        195                 200                 205

Arg Ala Ile Thr Pro Gly Leu Pro Leu Phe Leu Tyr Asn Tyr Thr Thr
    210                 215                 220

His Gln Leu His Gly Val Phe Glu Ala Ala Ser Phe Gly Gly Ser Asn
225                 230                 235                 240

Ile Asp Pro Thr Ala Trp Glu Asp Lys Lys Cys Lys Gly Glu Ser Arg
                245                 250                 255

Phe Pro Ala Gln Val Arg Ile Arg Ile Arg Arg Leu Cys Lys Ala Leu
            260                 265                 270

Glu Glu Asp Ala Phe Arg Pro Val Leu His His Tyr Asp Gly Pro Lys
        275                 280                 285

Phe Arg Leu Glu Leu Ser Ile Ala Glu Thr Leu Ser Leu Leu Asp Leu
    290                 295                 300

Cys Lys Thr Glu Asp Ala
305                 310


<210> SEQ ID NO 102
<211> LENGTH: 309
<212> TYPE: PRT
<213> ORGANISM: Hordeum vulgare

<400> SEQUENCE: 102

Met Asp Asn Leu Trp His Leu Gly Asp Glu Phe Arg Gly Gln Ser Lys
1               5                   10                  15

Val Val Glu Asp Arg Gln Trp Ser Leu Met Thr Ser Lys Leu Ala Glu
            20                  25                  30

Ile Thr Lys Ser Lys Ala Glu Arg Met Asn Asp Phe Glu Tyr Ala Arg
        35                  40                  45

Met Asn Thr Val Pro Asp Val Lys Gln Trp Asp Lys Leu Ser Tyr His
    50                  55                  60

Gln Glu Asp Asn Lys Met Asp His Leu Asn Leu Gly Leu Met Asn Leu
65                  70                  75                  80

Asp Leu Lys Met Asn Asp Leu Lys Met Asn Glu Ala Ala Met Lys Tyr
                85                  90                  95

Pro Phe Arg Asn Met Ala Tyr Asn Met Asn Pro Met Tyr Pro Lys Gly
            100                 105                 110

Asn Asn Gly Asn Val Asn Ser Phe Lys Met Asn Val Gly Val Asn Lys
        115                 120                 125

Tyr Pro Asn Asn Gln Asn Gly Lys Glu Ala Asn Gly Lys His Asn Gly
    130                 135                 140

Gly Asn Asn Asn Asn Gly Gly Asn Ser Asn Asn Ser Val Asp Lys Arg
145                 150                 155                 160

Phe Lys Thr Leu Pro Thr Ser Glu Met Leu Pro Arg Asn Glu Val Leu
                165                 170                 175

Gly Gly Tyr Ile Phe Val Cys Asn Asn Asp Thr Met Gln Glu Asp Leu
            180                 185                 190

Lys Arg Gln Leu Phe Gly Leu Pro Ala Arg Tyr Arg Asp Ser Val Arg
        195                 200                 205

Ala Ile Thr Pro Gly Leu Pro Leu Phe Leu Tyr Asn Tyr Thr Thr His
    210                 215                 220

Gln Leu His Gly Val Phe Glu Ala Ala Ser Phe Gly Gly Ser Asn Ile
225                 230                 235                 240

Asp Pro Thr Ala Trp Glu Asp Lys Lys Cys Lys Gly Glu Ser Arg Phe
                245                 250                 255
```

```
Pro Ala Gln Val Arg Ile Arg Ile Arg Arg Leu Cys Lys Ala Leu Glu
            260                 265                 270

Glu Asp Ala Phe Arg Pro Val Leu His His Tyr Asp Gly Pro Lys Phe
        275                 280                 285

Arg Leu Glu Leu Ser Ile Ala Glu Thr Leu Ser Leu Leu Asp Leu Cys
    290                 295                 300

Lys Ser Glu Asp Ala
305


<210> SEQ ID NO 103
<211> LENGTH: 314
<212> TYPE: PRT
<213> ORGANISM: Oryza sativa

<400> SEQUENCE: 103

Met Asp Asn Leu Trp His Leu Gly Asp Glu Phe Arg Gly Gln Ser Lys
1               5                   10                  15

Val Val Glu Asp Arg Gln Trp Ser Leu Met Thr Ser Lys Leu Ala Glu
            20                  25                  30

Ile Asn Lys Ser Lys Ala Glu Arg Thr Asn Glu Leu Asp Tyr Ala Arg
        35                  40                  45

Met Asn Thr Ile Pro Asp Val Lys Gln Trp Asp Lys Val Ser Tyr His
    50                  55                  60

Gln Asp Glu Ser Lys Met Asp His Leu Asn Leu Gly Leu Met Asn Leu
65                  70                  75                  80

Asp Leu Lys Met Asn Asp Ile Arg Met Asn Asp Ala Ala Met Lys Asn
                85                  90                  95

Pro Phe Arg Gly Met Ala Tyr Asn Met Asn Gln Leu Tyr Pro Lys Gly
            100                 105                 110

Gly Asn Gly Asn Val Asn Ser Phe Lys Met Asn Val Gly Val Asn Lys
        115                 120                 125

Tyr Leu His Ser Pro Asn Gly Lys Asp Val Asn Gly Lys Asn Ser Gly
    130                 135                 140

Ala Asn Ser Asn Gly Ser Asn Ser Ser Gly Asn Asn Ser Ser Asn Ser
145                 150                 155                 160

Ala Val Asp Lys Arg Phe Lys Thr Leu Pro Thr Ser Glu Met Leu Pro
                165                 170                 175

Arg Asn Glu Val Leu Gly Gly Tyr Ile Phe Val Cys Asn Asn Asp Thr
            180                 185                 190

Met Gln Glu Asp Leu Lys Arg Gln Leu Phe Gly Leu Pro Ala Arg Tyr
        195                 200                 205

Arg Asp Ser Val Arg Ala Ile Ile Pro Gly Leu Pro Leu Phe Leu Tyr
    210                 215                 220

Asn Tyr Thr Thr His Gln Leu His Gly Val Phe Glu Ala Ser Ser Phe
225                 230                 235                 240

Gly Gly Ser Asn Ile Asp Pro Thr Ala Trp Glu Asp Lys Lys Cys Lys
                245                 250                 255

Gly Glu Ser Arg Phe Pro Ala Gln Val Arg Ile Arg Ile Arg Lys Leu
            260                 265                 270

Cys Lys Pro Leu Glu Glu Asp Ala Phe Arg Pro Val Leu His His Tyr
        275                 280                 285

Asp Gly Pro Lys Phe Arg Leu Glu Leu Ser Ile Ala Glu Thr Leu Ser
    290                 295                 300

Leu Leu Asp Leu Cys Glu Lys Glu Gly Val
```

305 310

<210> SEQ ID NO 104
<211> LENGTH: 356
<212> TYPE: PRT
<213> ORGANISM: Zea mays
<220> FEATURE:
<221> NAME/KEY: misc_feature
<222> LOCATION: (1)..(2)
<223> OTHER INFORMATION: Xaa can be any naturally occurring amino acid

<400> SEQUENCE: 104

Xaa Xaa Ala Thr Cys Leu Leu Ser Phe Leu Pro Ser Ile Pro Pro Cys
1 5 10 15

Leu Arg Pro Leu Leu Thr Pro Val Gly Arg Gly Ala Ala Ala Asp Cys
20 25 30

Trp Asp Cys Pro Thr Pro Ser Ala Gln Val Ile Phe Gly Pro Phe Ala
35 40 45

Gly Asp Glu His His Gln Val Cys Gln Val Asp Arg Ala Met Asp Ser
50 55 60

Leu Trp His Leu Gly Asp Glu Leu Arg Gly Gln Pro Lys Val Val Glu
65 70 75 80

Asp Arg Gln Trp Ser Leu Met Thr Ser Lys Leu Ala Glu Ile Thr Arg
85 90 95

Ser Lys Gly Glu Arg Met Asn Thr Val Pro Asp Ala Lys Gln Trp Asp
100 105 110

Lys Thr Ser Tyr Gln Leu His Asp Asp Ser Arg Met Gly His Ile Asn
115 120 125

Leu Gly Leu Met Asn Leu Asp Leu Lys Met Asn Glu Ala Ala Ala Met
130 135 140

Lys Leu Pro Phe Arg Gly Met Pro Tyr Asn Met Asn Gln Met Tyr Leu
145 150 155 160

Lys Gly Ser Asn Ala Asn Ser Asn Val Asn Ala Phe Lys Met Asn Val
165 170 175

Gly Val Asn Lys Tyr Ser Asn Ser Pro Asn Gly Lys Asp Ala Asn Gly
180 185 190

Lys Asn Asn Gly Gly Ser Gly Gly Asn Asn Asn Asn Gly Ser Ala Asn
195 200 205

Gly Thr Ser Val Ala Asp Lys Arg Phe Lys Thr Leu Pro Thr Ser Glu
210 215 220

Met Leu Pro Arg Asn Glu Val Leu Gly Gly Tyr Ile Phe Val Cys Asn
225 230 235 240

Asn Asp Thr Met Gln Glu Asp Leu Lys Arg Gln Leu Phe Gly Leu Pro
245 250 255

Ala Arg Tyr Arg Asp Ser Val Arg Ala Ile Thr Pro Gly Leu Pro Leu
260 265 270

Phe Leu Tyr Asn Tyr Thr Thr His Gln Leu His Gly Val Phe Glu Ala
275 280 285

Ala Ser Phe Gly Gly Ser Asn Ile Asp Pro Thr Ala Trp Glu Asp Lys
290 295 300

Lys Cys Lys Gly Glu Ser Arg Phe Pro Ala Gln Val Arg Ile Cys Ile
305 310 315 320

Arg Lys Leu Cys Lys Pro Leu Glu Glu Asp Ser Phe Arg Pro Val Leu
325 330 335

His His Tyr Asp Gly Pro Lys Phe Arg Leu Glu Leu Ser Ile Ala Glu
340 345 350

Thr Leu Ser Leu
        355

<210> SEQ ID NO 105
<211> LENGTH: 340
<212> TYPE: PRT
<213> ORGANISM: Triticum aestivum
<220> FEATURE:
<221> NAME/KEY: misc_feature
<222> LOCATION: (338)..(340)
<223> OTHER INFORMATION: Xaa can be any naturally occurring amino acid

<400> SEQUENCE: 105

```
Val Gly Gly Ala Lys Trp Glu Pro Thr Pro Ser Gln Pro Ser Gly Leu
1               5                   10                  15

Leu Ser Ser Ser Gln Gln Phe Ala Ile Arg Pro Gln Ile Gln Arg Pro
            20                  25                  30

Pro Arg Arg Asn Pro Ala Pro Asn Leu Ala Glu Ser Leu Asn Arg Ala
        35                  40                  45

Met Asp Asn Leu Trp His Leu Gly Asp Glu Phe Arg Gly Gln Ser Lys
    50                  55                  60

Val Val Glu Asp Arg Gln Trp Ser Leu Met Thr Ser Lys Leu Ala Glu
65                  70                  75                  80

Ile Thr Lys Ser Lys Ala Glu Arg Met Asn Asp Phe Glu Tyr Ala Arg
                85                  90                  95

Met Asn Thr Val Pro Asp Val Lys Gln Trp Asp Lys Leu Ser Tyr His
            100                 105                 110

Gln Glu Asp Asn Lys Met Asp His Leu Asn Leu Gly Leu Met Asn Leu
        115                 120                 125

Asp Leu Lys Met Asn Asp Leu Lys Met Asn Glu Ala Ala Met Lys Tyr
    130                 135                 140

Pro Phe Arg Asn Met Ala Tyr Asn Met Asn Pro Met Tyr Pro Lys Gly
145                 150                 155                 160

Asn Asn Gly Asn Val Asn Ser Phe Lys Met Asn Val Gly Val Asn Lys
                165                 170                 175

Tyr Pro Asn Asn Gln Asn Gly Lys Glu Ala Asn Gly Lys His Asn Gly
            180                 185                 190

Gly Asn Asn Asn Asn Gly Gly Asn Ser Asn Asn Asn Ser Val Asp Lys
        195                 200                 205

Arg Phe Lys Thr Leu Pro Thr Ser Glu Met Leu Pro Arg Asn Glu Val
    210                 215                 220

Leu Gly Gly Tyr Ile Phe Val Cys Asn Asn Asp Thr Met Gln Glu Asp
225                 230                 235                 240

Leu Lys Arg Gln Leu Phe Gly Leu Pro Ala Arg Tyr Arg Asp Ser Val
                245                 250                 255

Arg Ala Ile Thr Pro Gly Leu Pro Leu Phe Leu Tyr Asn Tyr Thr Thr
            260                 265                 270

His Gln Leu His Gly Val Phe Glu Ala Ala Ser Phe Gly Gly Ser Asn
        275                 280                 285

Ile Asp Pro Thr Ala Trp Glu Asp Lys Lys Cys Lys Gly Glu Ser Arg
    290                 295                 300

Phe Pro Ala Gln Val Arg Ile Arg Ile Arg Arg Leu Cys Lys Ala Leu
305                 310                 315                 320

Glu Glu Asp Ala Phe Arg Pro Val Leu His His Tyr Asp Gly Pro Lys
                325                 330                 335
```

Phe Xaa Xaa Xaa
340

<210> SEQ ID NO 106
<211> LENGTH: 314
<212> TYPE: PRT
<213> ORGANISM: Oryza sativa

<400> SEQUENCE: 106

Met Asp Asn Leu Trp His Leu Gly Asp Glu Phe Arg Gly Gln Ser Lys
1 5 10 15

Val Val Glu Asp Arg Gln Trp Ser Leu Met Thr Ser Lys Leu Ala Glu
20 25 30

Ile Asn Lys Ser Lys Ala Glu Arg Thr Asn Glu Leu Asp Tyr Ala Arg
35 40 45

Met Asn Thr Ile Pro Asp Val Lys Gln Trp Asp Lys Val Ser Tyr His
50 55 60

Gln Asp Glu Ser Lys Met Asp His Leu Asn Leu Gly Leu Met Asn Leu
65 70 75 80

Asp Leu Lys Met Asn Asp Ile Arg Met Asn Asp Ala Ala Met Lys Asn
85 90 95

Pro Phe Arg Gly Met Ala Tyr Asn Met Asn Gln Leu Tyr Pro Lys Gly
100 105 110

Gly Asn Gly Asn Val Asn Ser Phe Lys Met Asn Val Gly Val Asn Lys
115 120 125

Tyr Leu His Ser Pro Asn Gly Lys Asp Val Asn Gly Lys Asn Ser Gly
130 135 140

Ala Asn Ser Asn Gly Ser Asn Ser Ser Gly Asn Asn Ser Ser Asn Ser
145 150 155 160

Ala Val Asp Lys Arg Phe Lys Thr Leu Pro Thr Ser Glu Met Leu Pro
165 170 175

Arg Asn Glu Val Leu Gly Gly Tyr Ile Phe Val Cys Asn Asn Asp Thr
180 185 190

Met Gln Glu Asp Leu Lys Arg Gln Leu Phe Gly Leu Pro Ala Arg Tyr
195 200 205

Arg Asp Ser Val Arg Ala Ile Ile Pro Gly Leu Pro Leu Phe Leu Tyr
210 215 220

Asn Tyr Thr Thr His Gln Leu His Gly Val Ser Glu Ala Ser Ser Phe
225 230 235 240

Gly Gly Ser Asn Leu Asp Pro Thr Glu Trp Asp Asp Thr Thr Cys Asn
245 250 255

Gly Glu Ser Arg Phe Pro Ala Gln Val Thr Leu Arg Leu Pro Lys Leu
260 265 270

Cys Lys Pro Leu Glu Asp Ala Ala Ser Thr Pro Val Leu His His Tyr
275 280 285

Asp Gly Pro Gln Ser Arg Leu Asp Leu Ser Ile Ala Asp Asn Leu Ser
290 295 300

Leu Leu His Leu Cys Ala Gln Gln Arg Val
305 310

<210> SEQ ID NO 107
<211> LENGTH: 184
<212> TYPE: PRT
<213> ORGANISM: Oryza sativa

<400> SEQUENCE: 107

-continued

```
Met Asp Asn Leu Trp His Leu Gly Asp Glu Phe Arg Gly Gln Ser Lys
1               5                   10                  15

Val Val Glu Asp Arg Gln Trp Ser Leu Met Thr Ser Lys Leu Ala Glu
            20                  25                  30

Ile Asn Lys Ser Lys Ala Glu Arg Thr Asn Glu Leu Asp Tyr Ala Arg
        35                  40                  45

Met Asn Thr Ile Pro Asp Val Lys Gln Trp Asp Lys Val Ser Tyr His
    50                  55                  60

Gln Asp Glu Ser Lys Met Asp His Leu Asn Leu Gly Leu Met Asn Leu
65                  70                  75                  80

Asp Leu Lys Met Asn Asp Ile Arg Met Asn Asp Ala Ala Met Lys Asn
                85                  90                  95

Pro Phe Arg Gly Met Ala Tyr Asn Met Asn Gln Leu Tyr Pro Lys Gly
            100                 105                 110

Gly Asn Gly Asn Val Asn Ser Phe Lys Met Asn Val Gly Val Asn Lys
        115                 120                 125

Tyr Leu His Ser Pro Asn Gly Lys Asp Val Asn Gly Lys Arg Phe Lys
    130                 135                 140

Thr Leu Pro Thr Ser Glu Met Leu Pro Arg Asn Glu Val Leu Gly Gly
145                 150                 155                 160

Tyr Ile Phe Val Cys Asn Asn Asp Thr Met Gln Glu Asp Leu Lys Arg
                165                 170                 175

Gln Leu Phe Gly Leu Pro Ala Arg
            180


<210> SEQ ID NO 108
<211> LENGTH: 197
<212> TYPE: PRT
<213> ORGANISM: Gossypium hirsutum

<400> SEQUENCE: 108

Met Gly Thr Arg Ala Lys Glu Lys Asn Ile Met Glu Pro Arg Val Gly
1               5                   10                  15

Arg Arg Thr Ala Thr Arg Lys Asn Asn Asn Asn Asn Asp Asn Asn Asn
            20                  25                  30

Glu Asn Lys Asp Gly Lys Ser Ala Ala Asp Lys Arg Phe Lys Thr Leu
        35                  40                  45

Pro Pro Ser Glu Ser Leu Pro Arg Asn Glu Thr Val Gly Gly Tyr Ile
    50                  55                  60

Phe Val Cys Asn Asn Asp Thr Met Glu Glu Asn Leu Arg Arg Gln Leu
65                  70                  75                  80

Phe Gly Leu Pro Pro Arg Tyr Arg Asp Ser Val Arg Ala Ile Thr Pro
                85                  90                  95

Gly Leu Pro Leu Phe Leu Tyr Asn Tyr Ser Thr His Gln Leu His Gly
            100                 105                 110

Val Phe Glu Ala Ala Ser Phe Gly Gly Thr Asn Ile Asp Pro Thr Ala
        115                 120                 125

Trp Glu Asp Lys Lys Cys Pro Gly Glu Ser Arg Phe Pro Ala Gln Val
    130                 135                 140

Arg Val Ile Thr Arg Lys Ile Cys Glu Pro Leu Glu Glu Asp Ser Phe
145                 150                 155                 160

Arg Pro Ile Leu His His Tyr Asp Gly Pro Lys Phe Arg Leu Glu Leu
                165                 170                 175

Asn Ile Pro Glu Ala Leu Ser Leu Leu Asp Ile Phe Ala Asp Gln Gln
            180                 185                 190
```

```
Asp Thr Cys Ile Ser
        195


<210> SEQ ID NO 109
<211> LENGTH: 188
<212> TYPE: PRT
<213> ORGANISM: Solanum tuberosum

<400> SEQUENCE: 109

Lys Phe Gly Lys Gly Phe Phe Glu Asp Glu His Lys Ser Val Lys Lys
1               5                   10                  15

Asn Asn Lys Ser Val Lys Glu Ser Asn Lys Asp Val Asn Ser Glu Lys
            20                  25                  30

Gln Asn Gly Val Asp Lys Arg Phe Lys Thr Leu Pro Pro Ala Glu Ser
        35                  40                  45

Leu Pro Arg Asn Glu Thr Val Gly Gly Tyr Ile Phe Val Cys Asn Asn
    50                  55                  60

Asp Thr Met Ala Glu Asn Leu Lys Arg Glu Leu Phe Gly Leu Pro Pro
65                  70                  75                  80

Arg Tyr Arg Asp Ser Val Arg Gln Ile Thr Pro Gly Leu Pro Leu Phe
                85                  90                  95

Leu Tyr Asn Tyr Ser Thr His Gln Leu His Gly Val Phe Glu Ala Ala
            100                 105                 110

Ser Phe Gly Gly Ser Asn Ile Asp Pro Ser Ala Trp Glu Asp Lys Lys
        115                 120                 125

Asn Pro Gly Glu Ser Arg Phe Pro Ala Gln Val Leu Val Val Thr Arg
    130                 135                 140

Lys Val Cys Glu Pro Leu Glu Glu Asp Ser Phe Arg Pro Ile Leu His
145                 150                 155                 160

His Tyr Asp Gly Pro Lys Phe Arg Leu Glu Leu Asn Val Pro Glu Ala
                165                 170                 175

Ile Ser Leu Leu Asp Ile Phe Glu Glu Asn Lys Asn
            180                 185


<210> SEQ ID NO 110
<211> LENGTH: 255
<212> TYPE: PRT
<213> ORGANISM: Triticum aestivum

<400> SEQUENCE: 110

Met Asp Thr Lys His Ala Asp Ser Phe Asp Glu Arg Asp Val Val Val
1               5                   10                  15

Asp Ala Gly Cys Val Arg Ala Val Leu Gly Glu Leu Val Leu Thr Phe
            20                  25                  30

Leu Phe Val Phe Thr Gly Val Ala Ala Ala Met Ala Ala Gly Val Pro
        35                  40                  45

Glu Leu Gln Gly Ala Ala Met Pro Met Ala Thr Leu Ala Gly Val Ala
    50                  55                  60

Leu Ala Gln Ala Leu Ala Ala Gly Val Leu Val Thr Ala Gly Phe His
65                  70                  75                  80

Val Ser Gly Gly His Leu Asn Pro Ala Val Thr Val Ala Leu Leu Ala
                85                  90                  95

Arg Gly His Ile Thr Ala Phe Arg Ala Val Leu Tyr Val Ala Ala Gln
            100                 105                 110

Leu Leu Ala Ser Ser Leu Ala Cys Ile Leu Leu Arg Tyr Leu Ser Gly
        115                 120                 125
```

```
Gly Gln Ala Thr Pro Val Pro Val His Thr Leu Gly Ala Gly Ile Gly
    130                 135                 140

Pro Met Gln Gly Leu Val Met Glu Val Ile Leu Thr Phe Ser Leu Leu
145                 150                 155                 160

Phe Val Val Tyr Ala Thr Ile Ile Asp Pro Arg Thr Thr Val Pro Gly
                165                 170                 175

Tyr Gly Pro Met Leu Thr Gly Leu Ile Val Gly Ala Asn Thr Ile Ala
            180                 185                 190

Gly Gly Asn Phe Ser Gly Ala Ser Met Asn Pro Ala Arg Ser Phe Gly
        195                 200                 205

Pro Ala Leu Ala Thr Gly Val Trp Thr Asn His Trp Val Tyr Trp Val
    210                 215                 220

Gly Pro Leu Val Gly Gly Pro Leu Ala Gly Phe Val Tyr Glu Thr Val
225                 230                 235                 240

Phe Met Val Thr Lys Thr His Glu Pro Leu Leu Gly Trp Asp Phe
                245                 250                 255


<210> SEQ ID NO 111
<211> LENGTH: 256
<212> TYPE: PRT
<213> ORGANISM: Triticum aestivum

<400> SEQUENCE: 111

Met Asp Thr Lys His Ala Asp Ser Leu Asp Glu Arg Asp Val Val Val
1               5                   10                  15

Val Asp Ala Gly Cys Val Arg Ala Val Leu Gly Glu Leu Val Leu Thr
            20                  25                  30

Phe Leu Phe Val Phe Thr Gly Val Ala Ala Ala Met Ala Ala Gly Val
        35                  40                  45

Pro Glu Leu Gln Gly Ala Ala Met Pro Met Ala Thr Leu Ala Gly Val
    50                  55                  60

Ala Leu Ala Gln Ala Leu Ala Ala Gly Val Leu Val Thr Ala Gly Phe
65                  70                  75                  80

His Val Ser Gly Gly His Leu Asn Pro Ala Val Thr Val Ala Leu Leu
                85                  90                  95

Ala Arg Gly His Ile Thr Ala Phe Arg Ala Val Leu Tyr Val Ala Ala
            100                 105                 110

Gln Leu Leu Ala Ser Ser Leu Ala Cys Ile Leu Leu Arg Tyr Leu Ser
        115                 120                 125

Gly Gly Gln Ala Thr Pro Val Pro Val His Thr Leu Gly Thr Gly Ile
    130                 135                 140

Gly Pro Met Gln Gly Leu Val Met Glu Ile Ile Leu Thr Phe Ser Leu
145                 150                 155                 160

Leu Phe Val Val Tyr Ala Thr Ile Leu Asp Pro Arg Thr Thr Val Pro
                165                 170                 175

Gly Tyr Gly Pro Met Leu Thr Gly Leu Ile Val Gly Ala Asn Thr Ile
            180                 185                 190

Ala Gly Gly Asn Phe Ser Gly Ala Ser Met Asn Pro Ala Arg Ser Phe
        195                 200                 205

Gly Pro Ala Leu Ala Thr Gly Val Trp Thr Asn His Trp Val Tyr Trp
    210                 215                 220

Val Gly Pro Leu Val Gly Gly Pro Leu Ala Gly Phe Val Tyr Glu Thr
225                 230                 235                 240

Val Phe Met Val Thr Lys Thr His Glu Pro Leu Leu Gly Trp Asp Phe
```

245 250 255

<210> SEQ ID NO 112
<211> LENGTH: 257
<212> TYPE: PRT
<213> ORGANISM: Hordeum vulgare

<400> SEQUENCE: 112

Met Ala Ala Thr Lys His Ala Asp Ser Phe Asp Glu Arg Glu Val Ala
1 5 10 15

Val Val Asp Thr Gly Cys Val Arg Ala Val Leu Gly Glu Leu Val Leu
20 25 30

Thr Phe Leu Phe Val Phe Thr Gly Val Ala Ala Ala Met Ala Ala Gly
35 40 45

Val Pro Glu Leu Pro Gly Ala Ala Met Pro Met Ala Thr Leu Ala Gly
50 55 60

Val Ala Leu Ala Gln Ala Leu Ala Ala Gly Val Leu Val Thr Ala Gly
65 70 75 80

Phe His Val Ser Gly Gly His Leu Asn Pro Ala Val Thr Val Ala Leu
85 90 95

Leu Ala Arg Gly His Ile Thr Ala Phe Arg Ala Val Leu Tyr Val Val
100 105 110

Ala Gln Leu Leu Ala Ser Ser Leu Ala Cys Ile Leu Leu Arg Cys Leu
115 120 125

Thr Gly Gly Gln Pro Thr Pro Val Pro Val His Thr Leu Gly Ala Gly
130 135 140

Ile Gly Pro Met Gln Gly Leu Val Met Glu Ile Ile Leu Thr Phe Ser
145 150 155 160

Leu Leu Phe Val Val Tyr Ala Thr Ile Leu Asp Pro Arg Thr Thr Val
165 170 175

Pro Gly Tyr Gly Pro Met Leu Thr Gly Leu Ile Val Gly Ala Asn Thr
180 185 190

Ile Ala Gly Gly Asn Phe Ser Gly Ala Ser Met Asn Pro Ala Arg Ser
195 200 205

Phe Gly Pro Ala Leu Ala Thr Gly Val Trp Thr Asn His Trp Ile Tyr
210 215 220

Trp Val Gly Pro Leu Val Gly Gly Pro Leu Ala Gly Phe Val Tyr Glu
225 230 235 240

Met Val Phe Met Val Lys Lys Thr His Glu Pro Leu Leu Gly Trp Asp
245 250 255

Phe

<210> SEQ ID NO 113
<211> LENGTH: 336
<212> TYPE: PRT
<213> ORGANISM: Triticum aestivum

<400> SEQUENCE: 113

Met Gly Pro Val Phe Leu Leu Gly Leu Ser Gln His Gly Ser Ala Pro
1 5 10 15

Gly Leu Phe Arg Ala Leu Phe Leu Pro Arg Ser His Thr Asp Tyr Ser
20 25 30

His His Ile Pro Arg Ser Arg Ala Thr Ser Leu Val Ser Met Asp Thr
35 40 45

Lys His Ala Asp Ser Phe Glu Glu Arg Asp Val Val Val Asp Ala Gly
50 55 60

```
Cys Val Arg Ala Val Leu Gly Glu Leu Val Leu Thr Phe Leu Phe Val
65                  70                  75                  80

Phe Thr Gly Val Ala Ala Ala Met Ala Ala Gly Val Pro Glu Leu Pro
                85                  90                  95

Gly Ala Ala Met Pro Met Ala Thr Leu Ala Gly Val Ala Leu Ala Gln
            100                 105                 110

Ala Leu Ala Ala Gly Val Leu Val Thr Ala Gly Phe His Val Ser Gly
        115                 120                 125

Gly His Leu Asn Pro Ala Val Thr Val Ala Leu Leu Ala Arg Gly His
    130                 135                 140

Ile Thr Ala Phe Arg Ala Val Leu Tyr Val Ala Ala Gln Leu Leu Ala
145                 150                 155                 160

Ser Ser Leu Ala Cys Ile Leu Leu Arg Tyr Leu Ser Gly Gly Gln Ala
                165                 170                 175

Thr Pro Val Pro Val His Thr Leu Gly Ala Gly Ile Gly Pro Met Gln
            180                 185                 190

Gly Leu Val Met Glu Val Ile Leu Thr Phe Ser Leu Leu Phe Val Val
        195                 200                 205

Tyr Ala Thr Ile Ile Asp Pro Arg Thr Thr Val Pro Gly Tyr Gly Pro
    210                 215                 220

Met Leu Thr Gly Leu Ile Val Gly Ala Asn Thr Ile Ala Gly Gly Asn
225                 230                 235                 240

Phe Ser Gly Ala Ser Met Asn Pro Ala Arg Ser Phe Gly Pro Ala Leu
                245                 250                 255

Ala Met Gly Val Trp Thr Asn His Trp Val Tyr Trp Val Gly Pro Leu
            260                 265                 270

Val Gly Gly Pro Leu Ala Gly Phe Val Tyr Glu Met Val Phe Met Val
        275                 280                 285

Lys Lys Asp Ala Arg Ala Ser Ala Trp Leu Gly Leu Leu Glu Asn Arg
    290                 295                 300

Leu Leu Pro Tyr Leu His Leu His Phe Ala Met Tyr Thr Ser Val Tyr
305                 310                 315                 320

Lys Ala Ile Asp Val Ala Gly Arg Phe Phe Arg Pro Ser Asp Ser Ser
                325                 330                 335
```

<210> SEQ ID NO 114
<211> LENGTH: 251
<212> TYPE: PRT
<213> ORGANISM: Oryza sativa

<400> SEQUENCE: 114

```
Met Ala Lys Glu Val Asp Pro Cys Asp His Gly Glu Val Val Asp Ala
1               5                   10                  15

Gly Cys Val Arg Ala Val Leu Ala Glu Leu Val Leu Thr Phe Val Phe
            20                  25                  30

Val Phe Thr Gly Val Ala Ala Thr Met Ala Ala Gly Val Pro Glu Val
        35                  40                  45

Ala Gly Ala Ala Met Pro Met Ala Ala Leu Ala Gly Val Ala Ile Ala
    50                  55                  60

Thr Ala Leu Ala Ala Gly Val Leu Val Thr Ala Gly Phe His Val Ser
65                  70                  75                  80

Gly Gly His Leu Asn Pro Ala Val Thr Val Ala Leu Leu Ala Arg Gly
                85                  90                  95

His Ile Thr Ala Phe Arg Ser Ala Leu Tyr Val Ala Ala Gln Leu Leu
```

```
            100                 105                 110

Ala Ser Ser Leu Ala Cys Ile Leu Leu Arg Tyr Leu Thr Gly Gly Met
        115                 120                 125

Ala Thr Pro Val His Thr Leu Gly Ser Gly Ile Gly Pro Met Gln Gly
    130                 135                 140

Leu Val Met Glu Ile Ile Leu Thr Phe Ser Leu Leu Phe Val Val Tyr
145                 150                 155                 160

Ala Thr Ile Leu Asp Pro Arg Ser Ser Val Pro Gly Phe Gly Pro Leu
                165                 170                 175

Leu Thr Gly Leu Ile Val Gly Ala Asn Thr Ile Ala Gly Gly Asn Phe
            180                 185                 190

Ser Gly Ala Ser Met Asn Pro Ala Arg Ser Phe Gly Pro Ala Leu Ala
        195                 200                 205

Thr Gly Val Trp Thr His His Trp Ile Tyr Trp Leu Gly Pro Leu Ile
    210                 215                 220

Gly Gly Pro Leu Ala Gly Leu Val Tyr Glu Ser Leu Phe Leu Val Lys
225                 230                 235                 240

Arg Thr His Glu Pro Leu Leu Asp Asn Ser Phe
                245                 250


<210> SEQ ID NO 115
<211> LENGTH: 202
<212> TYPE: PRT
<213> ORGANISM: Saccharum officinarum
<220> FEATURE:
<221> NAME/KEY: misc_feature
<222> LOCATION: (198)..(198)
<223> OTHER INFORMATION: Xaa can be any naturally occurring amino acid

<400> SEQUENCE: 115

Pro Pro Pro Pro Pro Pro Pro Pro Val Val Gln Asn Ile Ser Leu Arg
1               5                   10                  15

Phe Ser Glu Ser Phe Ser Leu Gln Gly Thr Gly Thr Thr Gly Ala Phe
            20                  25                  30

Thr Pro Pro Pro Ala Phe Pro Ser Pro Pro Gly Thr Gly Ala Thr Arg
        35                  40                  45

Leu Leu Leu Ala Ile Val His Ser Phe Met Ala Lys Leu Val Asn Lys
    50                  55                  60

Leu Leu Asp Ser Phe Asp His Asp Asp Thr Thr Pro Asp Val Gly Cys
65                  70                  75                  80

Val Arg Ala Val Leu Ala Glu Leu Val Leu Thr Phe Leu Phe Val Phe
                85                  90                  95

Thr Gly Val Ser Ala Ala Met Ala Ala Gly Ser Gly Gly Lys Pro Gly
            100                 105                 110

Glu Ala Met Pro Met Ala Thr Leu Ala Ala Val Ala Ile Ala Asn Ala
        115                 120                 125

Leu Ala Ala Gly Val Leu Val Thr Ala Gly Phe His Val Ser Gly Gly
    130                 135                 140

His Leu Asn Pro Ala Val Thr Val Gly Leu Met Val Cys Arg His Ile
145                 150                 155                 160

Thr Lys Leu Arg Ala Val Leu Tyr Ile Ala Ala Gln Leu Leu Ala Ser
                165                 170                 175

Ser Leu Ala Cys Ile Leu Leu Arg Tyr Leu Ser Gly Gly Met Val Thr
            180                 185                 190

Pro Val His Ala Leu Xaa Ala Gly Ile Lys
        195                 200
```

<210> SEQ ID NO 116
<211> LENGTH: 256
<212> TYPE: PRT
<213> ORGANISM: Oryza sativa

<400> SEQUENCE: 116

```
Met Ala Ser Pro Glu Gly Ser Thr Trp Val Phe Asp Cys Pro Leu Met
1               5                   10                  15

Asp Asp Leu Ala Ala Ala Ala Gly Phe Asp Ala Ala Pro Ala Gly Gly
            20                  25                  30

Phe Tyr Trp Thr Thr Pro Ala Pro Pro Gln Ala Ala Leu Gln Pro Pro
        35                  40                  45

Pro Pro Gln Gln Gln Pro Val Ala Pro Ala Thr Ala Ala Pro Asn Ala
    50                  55                  60

Cys Ala Glu Ile Asn Gly Ser Val Asp Cys Glu His Gly Lys Glu Gln
65                  70                  75                  80

Pro Thr Asn Lys Arg Pro Arg Ser Glu Ser Gly Thr Arg Pro Ser Ser
                85                  90                  95

Lys Ala Cys Arg Glu Lys Val Arg Arg Asp Lys Leu Asn Glu Arg Phe
            100                 105                 110

Leu Glu Leu Gly Ala Val Leu Glu Pro Gly Lys Thr Pro Lys Met Asp
        115                 120                 125

Lys Ser Ser Ile Leu Asn Asp Ala Ile Arg Val Met Ala Glu Leu Arg
    130                 135                 140

Ser Glu Ala Gln Lys Leu Lys Glu Ser Asn Glu Ser Leu Gln Glu Lys
145                 150                 155                 160

Ile Lys Glu Leu Lys Ala Glu Lys Asn Glu Leu Arg Asp Glu Lys Gln
                165                 170                 175

Lys Leu Lys Ala Glu Lys Glu Ser Leu Glu Gln Gln Ile Lys Phe Leu
            180                 185                 190

Asn Ala Arg Pro Ser Phe Val Pro His Pro Pro Val Ile Pro Ala Ser
        195                 200                 205

Ala Phe Thr Ala Pro Gln Gly Gln Ala Ala Gly Gln Lys Leu Met Met
    210                 215                 220

Pro Val Ile Gly Tyr Pro Gly Phe Pro Met Trp Gln Phe Met Pro Pro
225                 230                 235                 240

Ser Asp Val Asp Thr Thr Asp Asp Thr Lys Ser Cys Pro Pro Val Ala
                245                 250                 255
```

<210> SEQ ID NO 117
<211> LENGTH: 251
<212> TYPE: PRT
<213> ORGANISM: Triticum aestivum

<400> SEQUENCE: 117

```
Met Ala Ser Pro Glu Gly Ser Asn Trp Val Phe Asp Cys Pro Leu Met
1               5                   10                  15

Asp Asp Leu Ala Ala Ala Asp Phe Ala Ala Ala Ser Ala Gly Gly Phe
            20                  25                  30

Tyr Trp Thr Pro Pro Met Gln Pro Gln Met His Thr Leu Ala Gln Ala
        35                  40                  45

Val Ser Ala Thr Pro Ala Pro Asn Pro Cys Ala Glu Ile Asn Ser Ser
    50                  55                  60

Val Ser Val Asp Trp Asp His Ala Lys Gly Gln Pro Lys Asn Lys Arg
65                  70                  75                  80
```

```
Pro Arg Ser Glu Thr Gly Ala Gln Pro Ser Ser Lys Ala Cys Arg Glu
                85                  90                  95

Lys Val Arg Arg Asp Lys Leu Asn Glu Arg Phe Leu Glu Leu Gly Ala
            100                 105                 110

Val Leu Asp Pro Gly Lys Thr Pro Lys Ile Asp Lys Cys Ala Ile Leu
        115                 120                 125

Asn Asp Ala Ile Arg Ala Val Thr Glu Leu Arg Ser Glu Ala Glu Lys
    130                 135                 140

Leu Lys Asp Ser Asn Glu Ser Leu Gln Glu Lys Ile Arg Glu Leu Lys
145                 150                 155                 160

Ala Glu Lys Asn Glu Leu Arg Asp Glu Lys Gln Lys Leu Lys Ala Glu
                165                 170                 175

Lys Glu Ser Leu Glu Gln Gln Ile Lys Phe Met Asn Ala Arg Gln Ser
            180                 185                 190

Leu Val Pro His Pro Ser Val Ile Pro Ala Ala Ala Phe Ala Ala Ala
        195                 200                 205

Gln Gly Gln Ala Ala Gly His Lys Leu Met Met Pro Val Met Ser Tyr
    210                 215                 220

Pro Gly Phe Pro Met Trp Gln Phe Met Pro Pro Ser Asp Val Asp Thr
225                 230                 235                 240

Ser Asp Asp Pro Lys Ser Cys Pro Pro Val Ala
                245                 250


<210> SEQ ID NO 118
<211> LENGTH: 251
<212> TYPE: PRT
<213> ORGANISM: Hordeum vulgare

<400> SEQUENCE: 118

Met Ala Ser Pro Glu Gly Ser Asn Trp Val Phe Asp Cys Pro Leu Met
1               5                   10                  15

Asp Asp Leu Ala Ala Ala Asp Phe Ala Ala Val Pro Ala Gly Gly Phe
            20                  25                  30

Tyr Trp Asn Pro Pro Met Pro Pro Gln Met His Thr Leu Ala Gln Ala
        35                  40                  45

Val Ser Ala Thr Pro Ala Pro Asn Pro Cys Ala Glu Ile Asn Ser Ser
    50                  55                  60

Val Ser Val Asp Trp Asp His Ala Lys Gly Gln Pro Lys Asn Lys Arg
65                  70                  75                  80

Pro Arg Ser Glu Thr Gly Ala Gln Pro Ser Ser Lys Ala Cys Arg Glu
                85                  90                  95

Lys Val Arg Arg Asp Lys Leu Asn Glu Arg Phe Leu Glu Leu Gly Ala
            100                 105                 110

Val Leu Asp Pro Gly Lys Thr Pro Lys Ile Asp Lys Cys Ala Ile Leu
        115                 120                 125

Asn Asp Ala Ile Arg Ala Val Thr Glu Leu Arg Ser Glu Ala Glu Lys
    130                 135                 140

Leu Lys Asp Ser Asn Glu Ser Leu Gln Glu Lys Ile Arg Glu Leu Lys
145                 150                 155                 160

Ala Glu Lys Asn Glu Leu Arg Asp Glu Lys Gln Lys Leu Lys Ala Glu
                165                 170                 175

Lys Glu Ser Leu Glu Gln Gln Ile Lys Phe Met Asn Ala Arg Gln Arg
            180                 185                 190

Leu Val Pro His Pro Ser Val Ile Pro Ala Thr Ala Phe Ala Ala Ala
```

```
        195                 200                 205

Gln Gly Gln Ala Ala Gly His Lys Leu Met Met Pro Val Met Ser Tyr
    210                 215                 220

Pro Gly Phe Pro Met Trp Gln Phe Met Pro Pro Ser Asp Val Asp Thr
225                 230                 235                 240

Ser Asp Asp Pro Lys Ser Cys Pro Pro Val Ala
                245                 250


<210> SEQ ID NO 119
<211> LENGTH: 214
<212> TYPE: PRT
<213> ORGANISM: Oryza sativa

<400> SEQUENCE: 119

Met Tyr Leu Leu Leu Tyr Ile Ile Val Thr Tyr Gly Ile Leu Lys Tyr
1               5                   10                  15

Lys Phe Ile Phe Phe Thr Ser Ala Glu Ile Asn Gly Ser Val Asp Cys
            20                  25                  30

Glu His Gly Lys Glu Gln Pro Thr Asn Lys Arg Pro Arg Ser Glu Ser
        35                  40                  45

Gly Thr Arg Pro Ser Ser Lys Ala Cys Arg Glu Lys Val Arg Arg Asp
    50                  55                  60

Lys Leu Asn Glu Arg Phe Leu Glu Leu Gly Ala Val Leu Glu Pro Gly
65                  70                  75                  80

Lys Thr Pro Lys Met Asp Lys Ser Ser Ile Leu Asn Asp Ala Ile Arg
                85                  90                  95

Val Met Ala Glu Leu Arg Ser Glu Ala Gln Lys Leu Lys Glu Ser Asn
            100                 105                 110

Glu Ser Leu Gln Glu Lys Ile Lys Glu Leu Lys Ala Glu Lys Asn Glu
        115                 120                 125

Leu Arg Asp Glu Lys Gln Lys Leu Lys Ala Glu Lys Glu Ser Leu Glu
    130                 135                 140

Gln Gln Ile Lys Phe Leu Asn Ala Arg Pro Ser Phe Val Pro His Pro
145                 150                 155                 160

Pro Val Ile Pro Ala Ser Ala Phe Thr Ala Pro Gln Gly Gln Ala Ala
                165                 170                 175

Gly Gln Lys Leu Met Met Pro Val Ile Gly Tyr Pro Gly Phe Pro Met
            180                 185                 190

Trp Gln Phe Met Pro Pro Ser Asp Val Asp Thr Thr Asp Asp Thr Lys
        195                 200                 205

Ser Cys Pro Pro Val Ala
    210


<210> SEQ ID NO 120
<211> LENGTH: 877
<212> TYPE: DNA
<213> ORGANISM: Cauliflower mosaic virus

<400> SEQUENCE: 120

aagcttgcat gcctgcaggt ccccagatta gccttttcaa tttcagaaag aatgctaacc      60

cacagatggt tagagaggct tacgcagcag gtctcatcaa gacgatctac ccgagcaata     120

atctccagga aatcaaatac cttcccaaga aggttaaaga tgcagtcaaa agattcagga     180

ctaactgcat caagaacaca gagaaagata tatttctcaa gatcagaagt actattccag     240

tatggacgat tcaaggcttg cttcacaaac caaggcaagt aatagagatt ggagtctcta     300
```

-continued aaaaggtagt tcccactgaa tcaaaggcca tggagtcaaa gattcaaata gaggacctaa 360
cagaactcgc cgtaaagact ggcgaacagt tcatacagag tctcttacga ctcaatgaca 420
agaagaaaat cttcgtcaac atggtggagc acgacacact tgtctactcc aaaaatatca 480
aagatacagt ctcagaagac caaagggcaa ttgagacttt tcaacaaagg gtaatatccg 540
gaaacctcct cggattccat tgcccagcta tctgtcactt tattgtgaag atagtggaaa 600
aggaaggtgg ctcctacaaa tgccatcatt gcgataaagg aaaggccatc gttgaagatg 660
cctctgccga cagtggtccc aaagatggac ccccacccac gaggagcatc gtggaaaaag 720
aagacgttcc aaccacgtct tcaaagcaag tggattgatg tgatatctcc actgacgtaa 780
gggatgacgc acaatcccac tatccttcgc aagacccttc ctctatataa ggaagttcat 840
ttcatttgga gagaacacgg gggactctag aggatcc 877

<210> SEQ ID NO 121
<211> LENGTH: 2322
<212> TYPE: DNA
<213> ORGANISM: Arabidopsis thaliana

<400> SEQUENCE: 121
aagctttaag ctccaagccc acatctatgc acttcaacat atctttttct agatgagttg 60
gtaaaagtag aaaaagatat gatgatttta aatttgtttc tatttatatg tgttcatcga 120
aacttcattt tttttagttt taatagagag tttatatgac ttttaaaaat tgatttaaaa 180
ctgtgtcaaa aattaaaagg acaataaaaa atttgcatac aaccgaaaat acttatattt 240
agacaagaaa aaataatact tgtgatgctg attttatttt attatatatc atgaatcatg 300
atcatccaat tttccggata agccaaagtc aaaatgatgg gttcccccta atcttttatg 360
ctgagaaata gatgtatatt cttagatagt aatataaaat tgggttaaag aatgatgatt 420
cgattatagc ctcaactaga agatacgtgt agtgcaggtg tgtagttaac tggtggtagt 480
ggcagacaac cagattagga gttaaataaa gcctttagat ttgagagatt gaaatattcg 540
attggaacct ttctagattt ttacagccat ctaaaattag atgcagatca cctactacca 600
ttcaaaaatg aacaaaataa tttcatttac attttcctag cataagatat aataataaaa 660
tagtgctcat tttaattact ttttctaaat attttcgtta ttttaaattt tgcttgtcta 720
tactctacag ctcatttaat aacggaaaca aaaataattg cagggatacg gatgggtagc 780
tttcaaaact tacatcatct tctgtttctt gagatcaact atttttggag ctttgtctca 840
atcgtaccaa aggataatgg tcctacctcc ttttgcattc ttaactttat cttctctact 900
tatttctttt ttgggatttt tgggggtatt attttatctt ttgtagatat acacattgat 960
ttactacaaa cgtatactac tatccatctt caactcttcg gaatatgatt tcgaaaaaac 1020
tatgaagatt aacgggtatc ttaaacatgt taagatacac cggacaattt tcatttagaa 1080
gaattgatat gcaattaaca ataaatagtt gatgatcttt tagttttgaa gatgtgcgtt 1140
aagacttaag cgtgtggtaa caaggtggga ctcgggcaac gcaaagcctt gtagagtcca 1200
cttgctcaac ttgtctttct tttatctctt ttccaagtct caagattcaa tgaactccgt 1260
gtaacacaaa cacgcccata gatgagctca tttttggtat ttccaatatt gccactccat 1320
gataatatca tctagggatg ggttcattt attttgaaat ctcaacaaat ctcgtcgatt 1380
ctaacacaca tgattgattt gtttacttac ttgaaagttg gcaactatct gggattaaaa 1440
tttatctttt tctactgcta gctagaagca tctatatatg ttagcctaat acgtggaaga 1500
tgtcattgct aataatggct aaagatgtgt attaattttt cttctttttt ccttgaattt 1560

```
ttgttctttg acataaacta tgctgtcaaa atgtgtagaa tctttttaca taaatcattc   1620

cctgttacac actaaaaggt tcacaacgga cgattgtatt ggacttccag atcataaacc   1680

atgcaaaact gaaaaccaca agaataatta gttctaactt tagaacgttc gtacgtgttt   1740

catgttcaaa aagcgtcaat tataaaagtt gggaaattac ttttgagttt tgacatttct   1800

aaggacagtc aaatatgaca acattgggat gcaacttacc ttgtattaac ttattttgtt   1860

ataaaaccat atattacata ttttaaaggg ttgataaata atcaaatata ccaaaacata   1920

gcttttcaat atatttgtaa aacacgtttg gtctactagc taattatgag aacatttgtt   1980

caatgcatga ttatctagta tctactagtg gattatgaaa attagatatt ttcattgcat   2040

gattatcttc catatatagt gataacatca aaagaatcta caccaattat tgcatttttt   2100

cattatataa taagcactaa actgtaaaat tatattcagc cacccaaacc atgacaaatc   2160

accttaaagg cttaaacaca taacagccat tacgagtcac aggtaagggt ataatagtaa   2220

agaatcaatc tatataatat acgacccacc ctttctcatt ctttctggag agtaacatcg   2280

agacaaagaa gaaaaactaa aaaagagaac cccaaaggat cc                      2322
```

<210> SEQ ID NO 122
<211> LENGTH: 456
<212> TYPE: DNA
<213> ORGANISM: Lycopersicon esculentum

<400> SEQUENCE: 122

```
atgggtcgta tgcacagtcg tggtaagggt atttcagctt ctgctctccc ttacaagaga     60

actcctccta gttggctcaa gatctctgct ccagatgttg aggacaacat ctgcaagttc    120

gctaagaaag gattgacccc ttcacagatt ggtgtgattc ttcgtgattc tcatggaatt    180

gcacaagtga agagtgttac tggtagcaag atcttgcgta tcctcaaggc acatgggctt    240

gcacctgaga ttccagagga tttgtaccac ctgattaaga aggctgttgc cattaggaag    300

catttggaga ggaacaggaa ggataaggat tctaagttcc gtttgatttt ggtggagagc    360

aggattcatc gccttgctcg ttattacaag aaaacaaaaa agctcccacc tgtctggaaa    420

tacgaatcta ccactgctag cacacttgtg gcatag                              456
```

<210> SEQ ID NO 123
<211> LENGTH: 657
<212> TYPE: DNA
<213> ORGANISM: Lycopersicon esculentum

<400> SEQUENCE: 123

```
atggaagaca aaagcaatga ttattatgca gttttggggt tgaagaagga atgcactgac     60

acagaactta ggaatgccta taagaagctt gcactgaaat ggcacccaga tcgctgttca    120

gcatcgggga atttgaagtt tgtagatgaa gcaaagaagc aatttcaggc aattcaagaa    180

gcatattctg tgttatcgga tgcaaacaaa aagtttttgt acgatgtagg agtttatgac    240

tctggtgatg atgacgacga aaatggcatg ggtgatttcc tgaatgaaat ggcagctatg    300

atgagccaaa ataagtccaa tgaaaatcag ggagaagaaa cctttgagga attgcaggat    360

atgtttaatg aaatgttcaa cagtgataat ggaacgtttt cttcttcttc ttcttcttct    420

tcttcttgga ctggaactcc ttcaatgtgc tctactacat catctacatc ttcaagtgag    480

actttttttaa cctttcccaa caagagaagt tcaggtgaaa tgaagtcggg tagtagtgta    540

agaggcgatt cttgccaatt ccaaggattt tgtgtagggg caggtggaac ttctggaaaa    600
```

-continued tgcaatgaaa gagaacgaag ttggaggaaa aattccaaga gtggacggaa gcattag 657

<210> SEQ ID NO 124
<211> LENGTH: 897
<212> TYPE: DNA
<213> ORGANISM: Lycopersicon esculentum

<400> SEQUENCE: 124
atggagaata tgcagagcta ttggcaattt ggcgacgagc ttcgaggaca atcaaaagcc 60
tcagaggatc ataaatggtc aacagctgct ataaaattat ctgaacagat gaagtacaaa 120
ggtgaacgta ggaataacct tgacctttca aagagctctg ctgaaattag gcccaggggt 180
aatcatatgt ttcaggaaga taacaagtgg gaaagcctta acttcaatat gttaaatttg 240
gaaagcaaga tgactgaaaa tatgagcaag aatcgcatta tggatagcat tttcaatgca 300
aatccagttt atcttaagcc caattttaac agcttgggaa attcatcttt aagcaagttc 360
aatgctagca actataccaa ggaacctagc aagaataaca ataacaacgt tgagagcaca 420
aatggaaata actccgttga caaaaggttt aagactctgc ctgctgctga aacactgccg 480
aagaatgagg ttcttggtgg atatatattt gtttgtaaca atgacacaat gcaggaagac 540
ctaaagcgcc tgctctttgg ccttcctcct agatacagag attccgtgag ggcaataaca 600
ccagggttgc ccttgttcct atataattac actactcacc agttgcatgg tatctttgag 660
gcatcgagtt ttggaggttc caacattgat ccaactgcct gggaggataa aaagtgtaaa 720
ggagagtcaa ggttccctgc tcaggtgagg atccgtgtcc ggaaagtctg taatcctttg 780
gaggaagatg ctttcagacc agttttacat cattatgatg gccccaagtt ccgtctggag 840
ctctccattc ctgagacttt ggacttacta gatctctgtg aaaaagccgg tgtgtag 897

<210> SEQ ID NO 125
<211> LENGTH: 750
<212> TYPE: DNA
<213> ORGANISM: Lycopersicon esculentum

<400> SEQUENCE: 125
atggctggcg gcgtagctat tggaagtttt agtgattcat tcagcgttgt ctctcttaag 60
tcctatcttg ccgaattcat ctccacactc atctttgtct tcgccggagt tggttccgcc 120
attgcttacg gcaagttgac aacaaatgct gcacttgatc cggctgggct tgtagctatt 180
gcagtttgcc atggatttgc tctattcgta gccgtttcga tttccgctaa catctccggt 240
ggtcatgtta accctgcggt cacctgtgga ttaaccttcg gcggacatat taccttttatc 300 actggctcct tctacatgct tgctcaactt accggcgccg ctgtagcttg cttcctcctc 360
aaattcgtca ccggaggatg tgctattcca acccatggag tgggagctgg tgtgagcata 420
ctagaaggac tcgtgatgga aataataatc acatttggtt tagtttatac tgtgttcgca 480
accgccgctg acccgaagaa gggttcattg ggcacaattg caccgattgc aattggtctc 540
attgttggag ctaatatttt ggctgccgga ccattctccg gtggatcaat gaacccagct 600
cgttcatttg gacctgcaat ggttagtggt aactttgagg gtttctggat ctactggatt 660
ggtccattag ttggtggtag tttggctggt cttatttaca caaatgtgtt catgacacaa 720
gaacatgctc ctttatccaa tgagttctaa 750

<210> SEQ ID NO 126
<211> LENGTH: 735
<212> TYPE: DNA
<213> ORGANISM: Lycopersicon esculentum

<400> SEQUENCE: 126
atggaggtcg attctagtgg gaatcctaat tggttatttg attatgagtt gatgacggat 60
attacttctg ctgcatctgt taccgtcgct gagtttcagt ctccggctac tattgatttc 120
agctggcctg ctcaaacgat ctatgcttct tctaatctca ttactgaaac agattacaca 180
tttgcggatt cagaagttag caaggaggca agctcacgaa agcggttaaa aagtgaatgt 240
tgcagctctc cgagatctaa ggcatgcaga gagaaattgc ggagggacag actgaatgag 300
aggttcctcg cattgagctc tgtccttgat cctggaaggc caccaaaaac tgagaaagtt 360
gcaattctaa gtgatgctca aaggatgctg attgagctgc gaactgaaac ccagaagctg 420
aaggagtcaa atgaggagct gcaagagaag ataaaagaac ttaaggcaga gaagaatgag 480
ctccgagatg aaaagcaaag gctaaaggaa gaaaaggata atttggagca gcaggttaaa 540
agcttagctt ctaaagcagg atttctctcc catccttctg ccatgggagc tgcatttact 600
gcacaaggac aagttgctgc aggcaacaaa ttgatgcctt tcattggtta tcccagygty 660
gcgatgtggc rattcatgca acctgctgtt gttgacacat ctcaagatca tgtgctccgt 720
cctccagttg cttaa 735

<210> SEQ ID NO 127
<211> LENGTH: 151
<212> TYPE: PRT
<213> ORGANISM: Lycopersicon esculentum

<400> SEQUENCE: 127

Met Gly Arg Met His Ser Arg Gly Lys Gly Ile Ser Ala Ser Ala Leu
1 5 10 15

Pro Tyr Lys Arg Thr Pro Pro Ser Trp Leu Lys Ile Ser Ala Pro Asp
20 25 30

Val Glu Asp Asn Ile Cys Lys Phe Ala Lys Lys Gly Leu Thr Pro Ser
35 40 45

Gln Ile Gly Val Ile Leu Arg Asp Ser His Gly Ile Ala Gln Val Lys
50 55 60

Ser Val Thr Gly Ser Lys Ile Leu Arg Ile Leu Lys Ala His Gly Leu
65 70 75 80

Ala Pro Glu Ile Pro Glu Asp Leu Tyr His Leu Ile Lys Lys Ala Val
85 90 95

Ala Ile Arg Lys His Leu Glu Arg Asn Arg Lys Asp Lys Asp Ser Lys
100 105 110

Phe Arg Leu Ile Leu Val Glu Ser Arg Ile His Arg Leu Ala Arg Tyr
115 120 125

Tyr Lys Lys Thr Lys Lys Leu Pro Pro Val Trp Lys Tyr Glu Ser Thr
130 135 140

Thr Ala Ser Thr Leu Val Ala
145 150

<210> SEQ ID NO 128
<211> LENGTH: 219
<212> TYPE: PRT
<213> ORGANISM: Lycopersicon esculentum

<400> SEQUENCE: 128

Met Glu Asp Lys Ser Asn Asp Tyr Tyr Ala Val Leu Gly Leu Lys Lys
1 5 10 15

Glu Cys Thr Asp Thr Glu Leu Arg Asn Ala Tyr Lys Lys Leu Ala Leu

```
            20                  25                  30

Lys Trp His Pro Asp Arg Cys Ser Ala Ser Gly Asn Leu Lys Phe Val
        35                  40                  45

Asp Glu Ala Lys Lys Gln Phe Gln Ala Ile Gln Glu Ala Tyr Ser Val
    50                  55                  60

Leu Ser Asp Ala Asn Lys Lys Phe Leu Tyr Asp Val Gly Val Tyr Asp
65                  70                  75                  80

Ser Gly Asp Asp Asp Asp Glu Asn Gly Met Gly Asp Phe Leu Asn Glu
                85                  90                  95

Met Ala Ala Met Met Ser Gln Asn Lys Ser Asn Glu Asn Gln Gly Glu
            100                 105                 110

Glu Thr Phe Glu Glu Leu Gln Asp Met Phe Asn Glu Met Phe Asn Ser
        115                 120                 125

Asp Asn Gly Thr Phe Ser Ser Ser Ser Ser Ser Ser Ser Ser Ser Trp
    130                 135                 140

Thr Gly Thr Pro Ser Met Cys Ser Thr Thr Ser Ser Thr Ser Ser Ser
145                 150                 155                 160

Glu Thr Phe Leu Thr Phe Pro Asn Lys Arg Ser Ser Gly Glu Met Lys
                165                 170                 175

Ser Gly Ser Ser Val Arg Gly Asp Ser Cys Gln Phe Gln Gly Phe Cys
            180                 185                 190

Val Gly Ala Gly Gly Thr Ser Gly Lys Cys Asn Glu Arg Glu Arg Ser
        195                 200                 205

Trp Arg Lys Asn Ser Lys Ser Gly Arg Lys His
    210                 215


<210> SEQ ID NO 129
<211> LENGTH: 298
<212> TYPE: PRT
<213> ORGANISM: Lycopersicon esculentum

<400> SEQUENCE: 129

Met Glu Asn Met Gln Ser Tyr Trp Gln Phe Gly Asp Glu Leu Arg Gly
1               5                   10                  15

Gln Ser Lys Ala Ser Glu Asp His Lys Trp Ser Thr Ala Ala Ile Lys
            20                  25                  30

Leu Ser Glu Gln Met Lys Tyr Lys Gly Glu Arg Arg Asn Asn Leu Asp
        35                  40                  45

Leu Ser Lys Ser Ser Ala Glu Ile Arg Pro Arg Gly Asn His Met Phe
    50                  55                  60

Gln Glu Asp Asn Lys Trp Glu Ser Leu Asn Phe Asn Met Leu Asn Leu
65                  70                  75                  80

Glu Ser Lys Met Thr Glu Asn Met Ser Lys Asn Arg Ile Met Asp Ser
                85                  90                  95

Ile Phe Asn Ala Asn Pro Val Tyr Leu Lys Pro Asn Phe Asn Ser Leu
            100                 105                 110

Gly Asn Ser Ser Leu Ser Lys Phe Asn Ala Ser Asn Tyr Thr Lys Glu
        115                 120                 125

Pro Ser Lys Asn Asn Asn Asn Asn Val Glu Ser Thr Asn Gly Asn Asn
    130                 135                 140

Ser Val Asp Lys Arg Phe Lys Thr Leu Pro Ala Ala Glu Thr Leu Pro
145                 150                 155                 160

Lys Asn Glu Val Leu Gly Gly Tyr Ile Phe Val Cys Asn Asn Asp Thr
                165                 170                 175
```

```
Met Gln Glu Asp Leu Lys Arg Leu Leu Phe Gly Leu Pro Pro Arg Tyr
            180                 185                 190

Arg Asp Ser Val Arg Ala Ile Thr Pro Gly Leu Pro Leu Phe Leu Tyr
        195                 200                 205

Asn Tyr Thr Thr His Gln Leu His Gly Ile Phe Glu Ala Ser Ser Phe
    210                 215                 220

Gly Gly Ser Asn Ile Asp Pro Thr Ala Trp Glu Asp Lys Lys Cys Lys
225                 230                 235                 240

Gly Glu Ser Arg Phe Pro Ala Gln Val Arg Ile Arg Val Arg Lys Val
                245                 250                 255

Cys Asn Pro Leu Glu Glu Asp Ala Phe Arg Pro Val Leu His His Tyr
            260                 265                 270

Asp Gly Pro Lys Phe Arg Leu Glu Leu Ser Ile Pro Glu Thr Leu Asp
        275                 280                 285

Leu Leu Asp Leu Cys Glu Lys Ala Gly Val
    290                 295


<210> SEQ ID NO 130
<211> LENGTH: 249
<212> TYPE: PRT
<213> ORGANISM: Lycopersicon esculentum

<400> SEQUENCE: 130

Met Ala Gly Gly Val Ala Ile Gly Ser Phe Ser Asp Ser Phe Ser Val
1               5                   10                  15

Val Ser Leu Lys Ser Tyr Leu Ala Glu Phe Ile Ser Thr Leu Ile Phe
            20                  25                  30

Val Phe Ala Gly Val Gly Ser Ala Ile Ala Tyr Gly Lys Leu Thr Thr
        35                  40                  45

Asn Ala Ala Leu Asp Pro Ala Gly Leu Val Ala Ile Ala Val Cys His
    50                  55                  60

Gly Phe Ala Leu Phe Val Ala Val Ser Ile Ser Ala Asn Ile Ser Gly
65                  70                  75                  80

Gly His Val Asn Pro Ala Val Thr Cys Gly Leu Thr Phe Gly Gly His
                85                  90                  95

Ile Thr Phe Ile Thr Gly Ser Phe Tyr Met Leu Ala Gln Leu Thr Gly
            100                 105                 110

Ala Ala Val Ala Cys Phe Leu Leu Lys Phe Val Thr Gly Gly Cys Ala
        115                 120                 125

Ile Pro Thr His Gly Val Gly Ala Gly Val Ser Ile Leu Glu Gly Leu
    130                 135                 140

Val Met Glu Ile Ile Ile Thr Phe Gly Leu Val Tyr Thr Val Phe Ala
145                 150                 155                 160

Thr Ala Ala Asp Pro Lys Lys Gly Ser Leu Gly Thr Ile Ala Pro Ile
                165                 170                 175

Ala Ile Gly Leu Ile Val Gly Ala Asn Ile Leu Ala Ala Gly Pro Phe
            180                 185                 190

Ser Gly Gly Ser Met Asn Pro Ala Arg Ser Phe Gly Pro Ala Met Val
        195                 200                 205

Ser Gly Asn Phe Glu Gly Phe Trp Ile Tyr Trp Ile Gly Pro Leu Val
    210                 215                 220

Gly Gly Ser Leu Ala Gly Leu Ile Tyr Thr Asn Val Phe Met Thr Gln
225                 230                 235                 240

Glu His Ala Pro Leu Ser Asn Glu Phe
                245
```

<210> SEQ ID NO 131
<211> LENGTH: 244
<212> TYPE: PRT
<213> ORGANISM: Lycopersicon esculentum

<400> SEQUENCE: 131

Met Glu Val Asp Ser Ser Gly Asn Pro Asn Trp Leu Phe Asp Tyr Glu
1               5                   10                  15

Leu Met Thr Asp Ile Thr Ser Ala Ala Ser Val Thr Val Ala Glu Phe
            20                  25                  30

Gln Ser Pro Ala Thr Ile Asp Phe Ser Trp Pro Ala Gln Thr Ile Tyr
        35                  40                  45

Ala Ser Ser Asn Leu Ile Thr Glu Thr Asp Tyr Thr Phe Ala Asp Ser
    50                  55                  60

Glu Val Ser Lys Glu Ala Ser Ser Arg Lys Arg Leu Lys Ser Glu Cys
65                  70                  75                  80

Cys Ser Ser Pro Arg Ser Lys Ala Cys Arg Glu Lys Leu Arg Arg Asp
                85                  90                  95

Arg Leu Asn Glu Arg Phe Leu Ala Leu Ser Ser Val Leu Asp Pro Gly
            100                 105                 110

Arg Pro Pro Lys Thr Glu Lys Val Ala Ile Leu Ser Asp Ala Gln Arg
        115                 120                 125

Met Leu Ile Glu Leu Arg Thr Glu Thr Gln Lys Leu Lys Glu Ser Asn
    130                 135                 140

Glu Glu Leu Gln Glu Lys Ile Lys Glu Leu Lys Ala Glu Lys Asn Glu
145                 150                 155                 160

Leu Arg Asp Glu Lys Gln Arg Leu Lys Glu Glu Lys Asp Asn Leu Glu
                165                 170                 175

Gln Gln Val Lys Ser Leu Ala Ser Lys Ala Gly Phe Leu Ser His Pro
            180                 185                 190

Ser Ala Met Gly Ala Ala Phe Thr Ala Gln Gly Gln Val Ala Ala Ser
        195                 200                 205

Asn Lys Leu Met Pro Phe Ile Gly Tyr Pro Ser Val Ala Met Trp Arg
    210                 215                 220

Phe Met Gln Pro Ala Val Val Asp Thr Ser Gln Asp His Val Leu Arg
225                 230                 235                 240

Pro Pro Val Ala

<210> SEQ ID NO 132
<211> LENGTH: 20
<212> TYPE: DNA
<213> ORGANISM: Artificial sequence
<220> FEATURE:
<223> OTHER INFORMATION: Single strand DNA oligonulcotide

<400> SEQUENCE: 132
aggcgattaa gttgggtaac                                                  20

<210> SEQ ID NO 133
<211> LENGTH: 23
<212> TYPE: DNA
<213> ORGANISM: Artificial sequence
<220> FEATURE:
<223> OTHER INFORMATION: Single strand DNA oligonulcotide

<400> SEQUENCE: 133
gcgggactct aatcataaaa acc                                              23

<210> SEQ ID NO 134
<211> LENGTH: 22
<212> TYPE: DNA
<213> ORGANISM: Artificial sequence
<220> FEATURE:
<223> OTHER INFORMATION: Single strand DNA oligonulcotide

<400> SEQUENCE: 134
tagtttggtc agatgggaaa cg 22

<210> SEQ ID NO 135
<211> LENGTH: 25
<212> TYPE: DNA
<213> ORGANISM: Artificial sequence
<220> FEATURE:
<223> OTHER INFORMATION: Single strand DNA oligonulcotide

<400> SEQUENCE: 135
aaatattgga tcctttgggg ttctc 25

<210> SEQ ID NO 136
<211> LENGTH: 3207
<212> TYPE: DNA
<213> ORGANISM: Artificial sequence
<220> FEATURE:
<223> OTHER INFORMATION: Plasmid vector

<400> SEQUENCE: 136
taaattatcg cgcgcggtgt catctatgtt actagatcgg gaattcaatg cggccgccac 60
cgcggtggcc agcttttgtt ccctttagtg agggttaatt gcgcgcttgg cgtaatcatg 120
gtcatagctg tttcctgtgt gaaattgtta tccgctcaca attccacaca acatacgagc 180
cggaagcata aagtgtaaag cctggggtgc ctaatgagtg agctaactca cattaattgc 240
gttgcgctca ctgcccgctt tccagtcggg aaacctgtcg tgccagctgc attaatgaat 300
cggccaacgc gcggggagag gcggtttgcg tattgggcgc tcttccgctt cctcgctcac 360
tgactcgctg cgctcggtcg ttcggctgcg gcgagcggta tcagctcact caaaggcggt 420
aatacggtta tccacagaat caggggataa cgcaggaaag aacatgtgag caaaaggcca 480
gcaaaaggcc aggaaccgta aaaaggccgc gttgctggcg tttttccata ggctccgccc 540
ccctgacgag catcacaaaa atcgacgctc aagtcagagg tggcgaaacc cgacaggact 600
ataaagatac caggcgtttc cccctggaag ctccctcgtg cgctctcctg ttccgaccct 660
gccgcttacc ggatacctgt ccgcctttct cccttcggga agcgtggcgc tttctcatag 720
ctcacgctgt aggtatctca gttcggtgta ggtcgttcgc tccaagctgg gctgtgtgca 780
cgaacccccc gttcagcccg accgctgcgc cttatccggt aactatcgtc ttgagtccaa 840
cccggtaaga cacgacttat cgccactggc agcagccact ggtaacagga ttagcagagc 900
gaggtatgta ggcggtgcta cagagttctt gaagtggtgg cctaactacg gctacactag 960
aaggacagta tttggtatct gcgctctgct gaagccagtt accttcggaa aaagagttgg 1020
tagctcttga tccggcaaac aaaccaccgc tggtagcggt ggtttttttg tttgcaagca 1080
gcagattacg cgcagaaaaa aaggatctca agaagatcct ttgatctttt ctacggggtc 1140
tgacgctcag tggaacgaaa actcacgtta agggattttg gtcatgagat tatcaaaaag 1200
gatcttcacc tagatccttt taaattaaaa atgaagtttt aaatcaatct aaagtatata 1260
tgagtaaact tggtctgaca gttaccaatg cttaatcagt gaggcaccta tctcagcgat 1320

```
ctgtctattt cgttcatcca tagttgcctg actccccgtc gtgtagataa ctacgatacg   1380

ggagggctta ccatctggcc ccagtgctgc aatgataccg cgagacccac gctcaccggc   1440

tccagattta tcagcaataa accagccagc cggaagggcc gagcgcagaa gtggtcctgc   1500

aactttatcc gcctccatcc agtctattaa ttgttgccgg gaagctagag taagtagttc   1560

gccagttaat agtttgcgca acgttgttgc cattgctaca ggcatcgtgg tgtcacgctc   1620

gtcgtttggt atggcttcat tcagctccgg ttcccaacga tcaaggcgag ttacatgatc   1680

ccccatgttg tgcaaaaaag cggttagctc cttcggtcct ccgatcgttg tcagaagtaa   1740

gttggccgca gtgttatcac tcatggttat ggcagcactg cataattctc ttactgtcat   1800

gccatccgta agatgctttt ctgtgactgg tgagtactca accaagtcat tctgagaata   1860

gtgtatgcgg cgaccgagtt gctcttgccc ggcgtcaata cgggataata ccgcgccaca   1920

tagcagaact ttaaaagtgc tcatcattgg aaaacgttct tcggggcgaa aactctcaag   1980

gatcttaccg ctgttgagat ccagttcgat gtaacccact cgtgcaccca actgatcttc   2040

agcatctttt actttcacca gcgtttctgg gtgagcaaaa acaggaaggc aaaatgccgc   2100

aaaaaaggga ataagggcga cacggaaatg ttgaatactc atactcttcc tttttcaata   2160

ttattgaagc atttatcagg gttattgtct catgagcgga tacatatttg aatgtattta   2220

gaaaaataaa caaatagggg ttccgcgcac atttccccga aaagtgccac ctaaattgta   2280

agcgttaata ttttgttaaa attcgcgtta aatttttgtt aaatcagctc atttttttaac  2340

caataggccg aaatcggcaa aatcccttat aaatcaaaag aatagaccga gatagggttg   2400

agtgttgttc cagtttggaa caagagtcca ctattaaaga acgtggactc caacgtcaaa   2460

gggcgaaaaa ccgtctatca gggcgatggc ccactacgtg aaccatcacc ctaatcaagt   2520

tttttggggt cgaggtgccg taaagcacta aatcggaacc ctaaagggag cccccgattt   2580

agagcttgac ggggaaagcc ggcgaacgtg gcgagaaagg aagggaagaa agcgaaagga   2640

gcgggcgcta gggcgctggc aagtgtagcg gtcacgctgc gcgtaaccac cacacccgcc   2700

gcgcttaatg cgccgctaca gggcgcgtcc cattcgccat tcaggctgcg caactgttgg   2760

gaagggcgat cggtgcgggc ctcttcgcta ttacgccagc tggcgaaagg gggatgtgct   2820

gcaaggcgat taagttgggt aacgccaggg ttttcccagt cacgacgttg taaaacgacg   2880

gccagtgagc gcgcgtaata cgactcacta tagggcgaat tgggtaccgc ggccgctatt   2940

gataagctta atatgtcgac gatttctcta gaatacgagc tcgaatttcc ccgatcgttc   3000

aaacatttgg caataaagtt tcttaagatt gaatcctgtt gccggtcttg cgatgattat   3060

catataattt ctgttgaatt acgttaagca tgtaataatt aacatgtaat gcatgacgtt   3120

atttatgaga tgggttttta tgattagagt cccgcaatta tacatttaat acgcgataga   3180

aaacaaaata tagcgcgcaa actagga                                     3207
```

<210> SEQ ID NO 137
<211> LENGTH: 3868
<212> TYPE: DNA
<213> ORGANISM: Artificial sequence
<220> FEATURE:
<223> OTHER INFORMATION: Plasmid vector

<400> SEQUENCE: 137

```
gtaggtatct cagttcggtg taggtcgttc gctccaagct gggctgtgtg cacgaacccc     60

ccgttcagcc cgaccgctgc gccttatccg gtaactatcg tcttgagtcc aacccggtaa    120

gacacgactt atcgccactg gcagcagcca ctggtaacag gattagcaga gcgaggtatg    180
```

```
taggcggtgc tacagagttc ttgaagtggt ggcctaacta cggctacact agaaggacag    240
tatttggtat ctgcgctctg ctgaagccag ttaccttcgg aaaaagagtt ggtagctctt    300
gatccggcaa acaaaccacc gctggtagcg gtggtttttt tgtttgcaag cagcagatta    360
cgcgcagaaa aaaaggatct caagaagatc ctttgatctt ttctacgggg tctgacgctc    420
agtggaacga aaactcacgt taagggattt tggtcatgag attatcaaaa aggatcttca    480
cctagatcct tttaaattaa aaatgaagtt ttaaatcaat ctaaagtata tatgagtaaa    540
cttggtctga cagttaccaa tgcttaatca gtgaggcacc tatctcagcg atctgtctat    600
ttcgttcatc catagttgcc tgactccccg tcgtgtagat aactacgata cgggagggct    660
taccatctgg ccccagtgct gcaatgatac cgcgagaccc acgctcaccg gctccagatt    720
tatcagcaat aaaccagcca gccggaaggg ccgagcgcag aagtggtcct gcaactttat    780
ccgcctccat ccagtctatt aattgttgcc gggaagctag agtaagtagt tcgccagtta    840
atagtttgcg caacgttgtt gccattgcta caggcatcgt ggtgtcacgc tcgtcgtttg    900
gtatggcttc attcagctcc ggttcccaac gatcaaggcg agttacatga tcccccatgt    960
tgtgcaaaaa agcggttagc tccttcggtc ctccgatcgt tgtcagaagt aagttggccg   1020
cagtgttatc actcatggtt atggcagcac tgcataattc tcttactgtc atgccatccg   1080
taagatgctt ttctgtgact ggtgagtact caaccaagtc attctgagaa tagtgtatgc   1140
ggcgaccgag ttgctcttgc ccggcgtcaa tacgggataa taccgcgcca catagcagaa   1200
ctttaaaagt gctcatcatt ggaaaacgtt cttcggggcg aaaactctca aggatcttac   1260
cgctgttgag atccagttcg atgtaaccca ctcgtgcacc caactgatct tcagcatctt   1320
ttactttcac cagcgtttct gggtgagcaa aaacaggaag gcaaaatgcc gcaaaaaagg   1380
gaataagggc gacacggaaa tgttgaatac tcatactctt cctttttcaa tattattgaa   1440
gcatttatca gggttattgt ctcatgagcg gatacatatt tgaatgtatt tagaaaaata   1500
aacaaatagg ggttccgcgc acatttcccc gaaaagtgcc acctaaattg taagcgttaa   1560
tattttgtta aaattcgcgt taaatttttg ttaaatcagc tcatttttta accaataggc   1620
cgaaatcggc aaaatccctt ataaatcaaa agaatagacc gagatagggt tgagtgttgt   1680
tccagtttgg aacaagagtc cactattaaa gaacgtggac tccaacgtca aagggcgaaa   1740
aaccgtctat cagggcgatg gcccactacg tgaaccatca ccctaatcaa gttttttggg   1800
gtcgaggtgc cgtaaagcac taaatcggaa ccctaaaggg agcccccgat ttagagcttg   1860
acggggaaag ccggcgaacg tggcgagaaa ggaagggaag aaagcgaaag gagcgggcgc   1920
tagggcgctg gcaagtgtag cggtcacgct gcgcgtaacc accacacccg ccgcgcttaa   1980
tgcgccgcta cagggcgcgt cccattcgcc attcaggctg cgcaactgtt gggaagggcg   2040
atcggtgcgg gcctcttcgc tattacgcca gctggcgaaa gggggatgtg ctgcaaggcg   2100
attaagttgg gtaacgccag ggttttccca gtcacgacgt tgtaaaacga cggccagtga   2160
gcgcgcgtaa tacgactcac tatagggcga attgggtacc gcggccgcta ttgataagct   2220
tgcatgcctg caggtcaatt ctcatgtttg acagcttatc atcggtgcga tgccccccat   2280
cgtaggtgaa ggtggaaatt aatgatccat cttgagacca caggcccaca acagctacca   2340
gtttcctcaa gggtccacca aaaacgtaag cgcttacgta catggtcgat aagaaaaggc   2400
aatttgtaga tgttaacatc caacgtcgct ttcagggatc ccccctcaga agaccagagg   2460
gctattgaga cttttcaaca aagggtaata tcgggaaacc tcctcggatt ccattgccca   2520
```

gctatctgtc acttcatcga aaggacagta gaaaaggaag gtggctccta caaatgccat 2580
cattgcgata aaggaaaggc tatcgttcaa gatgcctcta ccgacagtgg tcccaaagat 2640
ggacccccac ccacgaggaa catcgtggaa aaagaagacg ttccaaccac gtcttcaaag 2700
caagtggatt gatgtgatat ctccactgac gtaagggatg acgcacaatc ccactatcct 2760
tcgcaagacc cttcctctat ataaggaagt tcatttcatt tggagaggac aggcttcttg 2820
agatccttca acaattacca acaacaacaa acaacaaaca acattacaat tactatttac 2880
aattacagtc gacgatttct ctagaatacg agctcgaatt tccccgatcg ttcaaacatt 2940
tggcaataaa gtttcttaag attgaatcct gttgccggtc ttgcgatgat tatcatataa 3000
tttctgttga attacgttaa gcatgtaata attaacatgt aatgcatgac gttatttatg 3060
agatgggttt ttatgattag agtcccgcaa ttatacattt aatacgcgat agaaaacaaa 3120
atatagcgcg caaactagga taaattatcg cgcgcggtgt catctatgtt actagatcgg 3180
gaattcaatg cggccgccac cgcggtggcc agcttttgtt ccctttagtg agggttaatt 3240
gcgcgcttgg cgtaatcatg gtcatagctg tttcctgtgt gaaattgtta tccgctcaca 3300
attccacaca acatacgagc cggaagcata aagtgtaaag cctggggtgc ctaatgagtg 3360
agctaactca cattaattgc gttgcgctca ctgcccgctt tccagtcggg aaacctgtcg 3420
tgccagctgc attaatgaat cggccaacgc gcggggagag gcggtttgcg tattgggcgc 3480
tcttccgctt cctcgctcac tgactcgctg cgctcggtcg ttcggctgcg gcgagcggta 3540
tcagctcact caaaggcggt aatacggtta tccacagaat caggggataa cgcaggaaag 3600
aacatgtgag caaaaggcca gcaaaaggcc aggaaccgta aaaaggccgc gttgctggcg 3660
tttttccata ggctccgccc ccctgacgag catcacaaaa atcgacgctc aagtcagagg 3720
tggcgaaacc cgacaggact ataaagatac caggcgtttc cccctggaag ctccctcgtg 3780
cgctctcctg ttccgaccct gccgcttacc ggatacctgt ccgcctttct cccttcggga 3840
agcgtggcgc tttctcatag ctcacgct 3868

<210> SEQ ID NO 138
<211> LENGTH: 20
<212> TYPE: DNA
<213> ORGANISM: Artificial sequence
<220> FEATURE:
<223> OTHER INFORMATION: Single strand DNA oligonulcotide

<400> SEQUENCE: 138
tcagccaccc aaaccatgac 20

<210> SEQ ID NO 139
<211> LENGTH: 882
<212> TYPE: PRT
<213> ORGANISM: Oryza sativa

<400> SEQUENCE: 139

Met Val Lys Leu Ala Phe Gly Ser Cys Gly Asp Ser Phe Ser Ala Ser
1 5 10 15

Ser Ile Lys Ala Tyr Val Ala Glu Phe Ile Ala Thr Leu Leu Phe Val
20 25 30

Phe Ala Gly Val Gly Ser Ala Ile Ala Tyr Gly Gln Leu Thr Lys Gly
35 40 45

Gly Ala Leu Asp Pro Ala Gly Leu Val Ala Ile Ala Ile Ala His Ala
50 55 60

Phe Ala Leu Phe Val Gly Val Ser Met Ala Ala Asn Ile Ser Gly Gly

-continued 65 70 75 80

His Leu Asn Pro Val Val Thr Phe Gly Leu Ala Val Gly Gly His Ile
85 90 95

Thr Ile Leu Thr Gly Ile Phe Tyr Trp Val Ala Gln Leu Leu Gly Ala
100 105 110

Ser Val Ala Cys Leu Leu Cys Ser Ser Pro Pro Thr Asp Arg Leu Ala
115 120 125

Ile Pro Thr His Ala Ile Ala Gly Ile Ser Glu Ile Glu Gly Met Val
130 135 140

Met Glu Ile Val Ile Thr Phe Ala Leu Val Tyr Thr Gly Tyr Ala Thr
145 150 155 160

Ala Ala Asp Pro Lys Lys Gly Ser Leu Gly Thr Val Ala Pro Met Asp
165 170 175

Ile Gly Phe Ile Val Gly Ala Asn Ile Leu Ala Ala Gly Pro Phe Ser
180 185 190

Gly Ser Ser Met Asn Pro Ala Arg Ser Phe Gly Pro Ala Val Ala Ala
195 200 205

Gly Asn Phe Ala Gly Asn Trp Val Tyr Trp Val Gly Pro Leu Ile Gly
210 215 220

Gly Gly Leu Ala Gly Leu Val Tyr Asp Asp Val Phe Ile Ala Ser Tyr
225 230 235 240

Gln Pro Val Met Ile Gly Phe Thr Val Ile Leu Cys Asp Arg Ser Asp
245 250 255

Gln Ala Val Tyr Ala Gly Gln Thr Ser Gly Asp Arg Ala Val Thr Pro
260 265 270

Cys Leu Gly Arg Val Phe Ala Val Met Asp Arg Glu Ser Ala Trp Cys
275 280 285

Arg Met Gln Ser Tyr Ile Met Ala Glu Asn Tyr Asp Ile Trp Arg Lys
290 295 300

Val Ser His Pro Tyr Val Ile Pro Glu Ala Ile Asn Thr Ala Ala Glu
305 310 315 320

Lys Thr Ala Phe Glu Gln Asn Cys Lys Ala Arg Asn Ile Leu Leu Ser
325 330 335

Gly Ile Ser Arg Ser Asp Tyr Asp Arg Val Ala His Leu Gln Thr Ala
340 345 350

His Glu Ile Trp Ile Ala Leu Ser Asn Phe His Gln Gly Thr Asn Asn
355 360 365

Ile Lys Glu Leu Arg Arg Asp Leu Phe Lys Lys Glu Tyr Ile Lys Phe
370 375 380

Glu Met Lys Pro Gly Glu Ala Leu Asp Asp Tyr Leu Ser Arg Phe Asn
385 390 395 400

Lys Ile Leu Ser Asp Leu Arg Ser Val Asp Ser Ser Tyr Asp Ala Asn
405 410 415

Tyr Pro Gln Ser Glu Ile Ser Arg His Phe Leu Asn Gly Leu Asp Met
420 425 430

Ser Ile Trp Glu Met Lys Val Thr Ser Ile Gln Glu Ser Val Asn Met
435 440 445

Ser Thr Leu Thr Leu Asp Ser Leu Tyr Thr Lys Leu Lys Thr His Glu
450 455 460

Met Asn Ile Leu Ala Arg Lys Val Asp Ser Lys Ser Ser Ala Leu Val
465 470 475 480

Ser Ser Ser Thr Ser Leu Asp Val Gly Ala Ser Ser Ser Lys Ser Ser
485 490 495

```
Val Leu Ala Leu Phe Asn Ala Met Ser Asp Asp Gln Leu Glu Gln Phe
            500                 505                 510

Glu Glu Glu Asp Leu Val Leu Leu Ser Asn Lys Phe Ser Arg Ala Met
        515                 520                 525

Lys Asn Val Arg Asn Arg Lys Arg Gly Glu Pro Asn Arg Cys Phe Glu
    530                 535                 540

Cys Gly Ala Leu Asp His Leu Arg Ser His Cys Pro Lys Leu Gly Arg
545                 550                 555                 560

Gly Lys Lys Glu Asp Asp Gly Arg Val Lys Glu Asp Asp Val Asn Lys
                565                 570                 575

Lys Lys Asn Met Lys Glu Lys Glu Lys Lys Lys His Cys Met Gln Trp
            580                 585                 590

Leu Ile Gln Glu Leu Ile Lys Val Phe Asp Glu Ser Glu Asp Glu Asp
        595                 600                 605

Glu Gly Lys Gly Lys Gln Val Val Asp Leu Ala Phe Ile Ala Arg Asn
    610                 615                 620

Ala Ser Ser Asp Val Asp Glu Ser Asp Asp Asp Asn Glu Glu Lys Leu
625                 630                 635                 640

Ser Tyr Asp Gln Leu Glu Tyr Ala Ala Tyr Lys Phe Ala Lys Lys Leu
                645                 650                 655

Gln Thr Cys Ser Ile Val Leu Asp Glu Lys Asp His Thr Ile Glu Ile
            660                 665                 670

Leu Asn Ala Glu Ile Ala Arg Leu Lys Ser Leu Ile Pro Asn Asp Asp
        675                 680                 685

Asn Cys Gln Ser Cys Glu Val Leu Phe Ser Glu Ile Asn Ala Leu Arg
    690                 695                 700

Asp Val Asn Ser Val Asn Cys Lys Lys Leu Glu Phe Glu Ile Glu Lys
705                 710                 715                 720

Ser Lys Lys Leu Glu Ser Ser Phe Ala Leu Gly Phe Ala Leu His Ala
                725                 730                 735

Arg Val Val Asp Glu Leu Ile Leu Thr Lys Asn Val Leu Lys Lys Ile
            740                 745                 750

Gln Ser Cys Phe Leu Cys Lys Phe Phe Gly Gln Cys Phe Met Cys Asn
        755                 760                 765

Lys Ala Lys Gln Asn Asn Gly Val Leu Ile Ser Gln Asp Cys Ser Lys
    770                 775                 780

Cys Val Leu Asn Glu Leu Lys Leu Lys Asp Ala Leu Glu Arg Val Lys
785                 790                 795                 800

His Met Glu Glu Ile Ile Lys Gln Asp Glu Val Phe Ser Cys Ser Thr
                805                 810                 815

Cys Arg Lys Gln Lys Gly Leu Leu Asp Ala Cys Lys Asn Cys Ala Ile
            820                 825                 830

Leu Thr Gln Glu Val Ser Tyr Leu Lys Ser Ser Leu Gln Arg Phe Ser
        835                 840                 845

Asp Gly Lys Lys Asn Leu Asn Met Ile Leu Asp Gln Ser Asn Val Ser
    850                 855                 860

Thr His Asn Arg Gly Leu Gly Phe Asp Ser Tyr Ser Lys Asp Leu Asp
865                 870                 875                 880

Val Ala
```

<210> SEQ ID NO 140
<211> LENGTH: 249
<212> TYPE: PRT

<213> ORGANISM: Glycine max

<400> SEQUENCE: 140

```
Met Val Lys Ile Ala Leu Gly Thr Leu Asp Asp Ser Phe Ser Ala Ala
1               5                   10                  15

Ser Leu Lys Ala Tyr Phe Ala Glu Phe His Ala Thr Leu Ile Phe Val
            20                  25                  30

Phe Ala Gly Val Gly Ser Ala Ile Ala Tyr Asn Glu Leu Thr Lys Asp
        35                  40                  45

Ala Ala Leu Asp Pro Thr Gly Leu Val Ala Val Ala Val Ala His Ala
    50                  55                  60

Phe Ala Leu Phe Val Gly Val Ser Val Ala Ala Asn Ile Ser Gly Gly
65                  70                  75                  80

His Leu Asn Pro Ala Val Thr Phe Gly Leu Ala Ile Gly Gly Asn Ile
                85                  90                  95

Thr Leu Ile Thr Gly Phe Leu Tyr Trp Ile Ala Gln Leu Leu Gly Ser
            100                 105                 110

Ile Val Ala Cys Leu Leu Leu Asn Leu Ile Thr Ala Lys Ser Ile Pro
        115                 120                 125

Ser His Ser Pro Ala Asn Gly Val Asn Asp Leu Gln Ala Val Val Phe
    130                 135                 140

Glu Ile Val Ile Thr Phe Gly Leu Val Tyr Thr Val Tyr Ala Thr Ala
145                 150                 155                 160

Val Asp Pro Lys Lys Gly Ser Leu Gly Ile Ile Ala Pro Ile Ala Ile
                165                 170                 175

Gly Phe Val Val Gly Ala Asn Ile Leu Ala Ala Gly Pro Phe Ser Gly
            180                 185                 190

Gly Ser Met Asn Pro Ala Arg Ser Phe Gly Pro Ala Val Val Ser Gly
        195                 200                 205

Asp Leu Ala Ala Asn Trp Ile Tyr Trp Val Gly Pro Leu Ile Gly Gly
    210                 215                 220

Gly Leu Ala Gly Leu Ile Tyr Gly Asp Val Phe Ile Gly Ser Tyr Ala
225                 230                 235                 240

Pro Val Pro Ala Ser Glu Thr Tyr Pro
                245
```

<210> SEQ ID NO 141
<211> LENGTH: 248
<212> TYPE: PRT
<213> ORGANISM: Triticum aestivum

<400> SEQUENCE: 141

```
Met Pro Ala Ser Ile Ala Phe Gly Arg Phe Asp Asp Ser Phe Ser Leu
1               5                   10                  15

Ala Ser Phe Lys Ala Tyr Ile Ala Glu Phe Ile Ser Thr Leu Ile Phe
            20                  25                  30

Val Phe Ala Gly Val Gly Ser Ala Ile Ala Tyr Ser Lys Val Ser Gly
        35                  40                  45

Gly Ala Pro Leu Asp Pro Ser Gly Leu Ile Ala Val Ala Ile Cys His
    50                  55                  60

Gly Phe Gly Leu Phe Val Ala Val Ala Val Gly Ala Asn Ile Ser Gly
65                  70                  75                  80

Gly His Val Asn Pro Ala Val Thr Phe Gly Leu Ala Leu Gly Gly Gln
                85                  90                  95

Ile Thr Ile Leu Thr Gly Ile Phe Tyr Trp Val Ala Gln Leu Leu Gly
```

-continued

```
            100                 105                 110

Ala Ile Val Gly Ala Phe Leu Val Gln Phe Cys Thr Gly Val Ala Thr
        115                 120                 125

Pro Thr His Gly Leu Ser Gly Val Gly Ala Phe Glu Gly Val Val Met
    130                 135                 140

Glu Ile Ile Val Thr Phe Gly Leu Val Tyr Thr Val Tyr Ala Thr Ala
145                 150                 155                 160

Ala Asp Pro Lys Lys Gly Ser Leu Gly Thr Ile Ala Pro Ile Ala Ile
                165                 170                 175

Gly Phe Ile Val Gly Ala Asn Ile Leu Val Ala Gly Pro Phe Ser Gly
            180                 185                 190

Gly Ser Met Asn Pro Ala Arg Ser Phe Gly Pro Ala Val Ala Ser Gly
        195                 200                 205

Asp Phe Thr Asn Ile Trp Ile Tyr Trp Ala Gly Pro Leu Ile Gly Gly
    210                 215                 220

Gly Leu Ala Gly Val Val Tyr Arg Tyr Leu Tyr Met Cys Asp Asp His
225                 230                 235                 240

Thr Ala Val Ala Gly Asn Asp Tyr
                245


<210> SEQ ID NO 142
<211> LENGTH: 248
<212> TYPE: PRT
<213> ORGANISM: Triticum aestivum

<400> SEQUENCE: 142

Met Pro Gly Ser Ile Ala Phe Gly Arg Phe Asp Asp Ser Phe Ser Leu
1               5                   10                  15

Ala Ser Phe Lys Ala Tyr Ile Ala Glu Phe Ile Ser Thr Leu Ile Phe
            20                  25                  30

Val Phe Ala Gly Val Gly Ser Ala Ile Ala Tyr Thr Lys Val Ser Gly
        35                  40                  45

Gly Ala Pro Leu Asp Pro Ser Gly Leu Ile Ala Val Ala Ile Cys His
    50                  55                  60

Gly Phe Gly Leu Phe Val Ala Val Ala Ile Gly Ala Asn Ile Ser Gly
65                  70                  75                  80

Gly His Val Asn Pro Ala Val Thr Phe Gly Leu Ala Leu Gly Gly Gln
                85                  90                  95

Ile Thr Ile Leu Thr Gly Ile Phe Tyr Trp Val Ala Gln Leu Leu Gly
            100                 105                 110

Ala Ile Val Gly Ala Phe Leu Val Gln Phe Cys Thr Gly Val Ala Thr
        115                 120                 125

Pro Thr His Gly Leu Ser Gly Val Gly Ala Phe Glu Gly Val Val Met
    130                 135                 140

Glu Ile Ile Val Thr Phe Gly Leu Val Tyr Thr Val Tyr Ala Thr Ala
145                 150                 155                 160

Ala Asp Pro Lys Lys Gly Ser Leu Gly Thr Ile Ala Pro Ile Ala Ile
                165                 170                 175

Gly Phe Ile Val Gly Ala Asn Ile Leu Val Ala Gly Pro Phe Ser Gly
            180                 185                 190

Gly Ser Met Asn Pro Ala Arg Ser Phe Gly Pro Ala Val Ala Ser Gly
        195                 200                 205

Asp Phe Thr Asn Ile Trp Ile Tyr Trp Ala Gly Pro Leu Ile Gly Gly
    210                 215                 220
```

```
Gly Leu Ala Gly Val Val Tyr Arg Tyr Val Tyr Met Cys Asp Asp His
225                 230                 235                 240

Ser Ser Val Ala Gly Asn Asp Tyr
                245


<210> SEQ ID NO 143
<211> LENGTH: 207
<212> TYPE: PRT
<213> ORGANISM: Solanum tuberosum

<400> SEQUENCE: 143

Met Val Lys Ile Ala Phe Gly Ser Ile Gly Asp Ser Leu Ser Val Gly
1               5                   10                  15

Ser Leu Lys Ala Tyr Leu Ala Glu Phe Ile Ala Thr Leu Leu Phe Val
            20                  25                  30

Phe Ala Gly Val Gly Ser Ala Ile Ala Tyr Asn Lys Leu Thr Ser Asp
        35                  40                  45

Ala Ala Leu Asp Pro Ala Gly Leu Val Ala Ile Ala Val Ala His Ala
    50                  55                  60

Phe Ala Leu Phe Val Gly Val Ser Met Ala Ala Asn Ile Ser Gly Gly
65                  70                  75                  80

His Leu Asn Pro Ala Val Thr Leu Gly Leu Ala Val Gly Gly Asn Ile
                85                  90                  95

Thr Ile Leu Thr Gly Leu Phe Tyr Trp Val Ala Gln Leu Leu Gly Ser
            100                 105                 110

Thr Val Ala Cys Leu Leu Leu Lys Tyr Val Thr Asn Gly Leu Ala Val
        115                 120                 125

Pro Thr His Gly Val Ala Ala Gly Met Asn Gly Ala Glu Gly Val Val
    130                 135                 140

Met Glu Ile Val Ile Thr Phe Ala Leu Val Tyr Thr Val Tyr Ala Thr
145                 150                 155                 160

Ala Ala Val Val Ala Gly Asp Phe Ser Gln Asn Trp Ile Tyr Trp Val
                165                 170                 175

Gly Pro Leu Ile Gly Gly Gly Leu Ala Gly Phe Ile Tyr Gly Asp Val
            180                 185                 190

Phe Ile Gly Ser His Thr Pro Leu Pro Thr Ser Glu Asp Tyr Ala
        195                 200                 205


<210> SEQ ID NO 144
<211> LENGTH: 224
<212> TYPE: PRT
<213> ORGANISM: Saccharum officinarum
<220> FEATURE:
<221> NAME/KEY: misc_feature
<222> LOCATION: (172)..(172)
<223> OTHER INFORMATION: Xaa can be any naturally occurring amino acid
<220> FEATURE:
<221> NAME/KEY: misc_feature
<222> LOCATION: (215)..(215)
<223> OTHER INFORMATION: Xaa can be any naturally occurring amino acid

<400> SEQUENCE: 144

Phe Gln Pro Arg Arg Ala Lys Arg Glu Ser Lys Met Val Lys Leu Ala
1               5                   10                  15

Phe Gly Ser Val Gly Asp Ser Phe Ser Ala Thr Ser Ile Lys Ala Tyr
            20                  25                  30

Val Ser Glu Phe Ile Ala Thr Leu Leu Phe Val Phe Ala Gly Val Gly
        35                  40                  45

Ser Ala Ile Ala Tyr Gly Gln Leu Thr Asn Asp Gly Ala Leu Asp Pro
```

```
    50                  55                  60

Ala Gly Leu Val Ala Ile Ala Ile Ala His Ala Leu Ala Leu Phe Val
65                  70                  75                  80

Gly Val Ser Ile Ala Ala Asn Ile Ser Gly Gly His Leu Asn Pro Ala
                85                  90                  95

Val Thr Phe Gly Leu Ala Val Gly Gly His Ile Thr Ile Leu Thr Gly
            100                 105                 110

Leu Phe Tyr Trp Val Ala Gln Leu Leu Gly Ala Ser Val Ala Cys Leu
        115                 120                 125

Leu Leu Lys Phe Val Thr His Gly Lys Ala Ile Pro Thr His Gly Val
    130                 135                 140

Ser Gly Ile Ser Glu Leu Glu Gly Val Val Phe Glu Ile Val Ile Thr
145                 150                 155                 160

Phe Ala Leu Val Tyr Thr Val Tyr Ala Thr Ala Xaa Arg Pro Gln Glu
                165                 170                 175

Gly Leu Pro Arg His His Arg Ala His Arg His Arg Leu His Arg Arg
            180                 185                 190

Arg Gln His Pro Arg Arg Gly Ala Leu Gln Pro Arg Leu His Glu Pro
        195                 200                 205

Gly Pro Ser Phe Gly Pro Xaa Val Ala Arg Gly Asn Phe Ala Gly Asn
    210                 215                 220


<210> SEQ ID NO 145
<211> LENGTH: 128
<212> TYPE: PRT
<213> ORGANISM: Populus tremula x Populus tremuloides

<400> SEQUENCE: 145

Met Ile Thr Trp Phe Gln Gln Ala Val Pro Ile His Ser Val Ala Ala
1               5                   10                  15

Gly Val Gly Ala Ile Glu Gly Val Val Met Glu Ile Ile Ile Thr Phe
            20                  25                  30

Ala Leu Val Tyr Thr Val Tyr Ala Thr Ala Ala Asp Pro Lys Lys Gly
        35                  40                  45

Ser Leu Gly Thr Ile Ala Pro Ile Ala Ile Gly Phe Ile Val Gly Ala
    50                  55                  60

Asn Ile Leu Ala Ala Gly Pro Phe Ser Gly Gly Ser Met Asn Pro Ala
65                  70                  75                  80

Arg Ser Phe Gly Pro Ala Val Ala Ser Gly Asp Phe His Asp Asn Trp
                85                  90                  95

Ile Tyr Trp Ala Gly Pro Leu Val Gly Gly Ile Ala Gly Leu Ile
            100                 105                 110

Tyr Gly Asn Val Phe Ile Thr Asp His Thr Pro Leu Ser Gly Asp Phe
        115                 120                 125


<210> SEQ ID NO 146
<211> LENGTH: 114
<212> TYPE: PRT
<213> ORGANISM: Solanum tuberosum

<400> SEQUENCE: 146

Met Ser Gly Ala Glu Gly Val Val Met Glu Ile Val Ile Thr Phe Ala
1               5                   10                  15

Leu Val Tyr Thr Val Tyr Ala Thr Ala Ala Asp Pro Lys Lys Gly Ser
            20                  25                  30

Leu Gly Thr Ile Ala Pro Met Ala Ile Gly Phe Ile Val Gly Ala Asn
```

```
        35                  40                  45

Ile Leu Ala Ala Gly Pro Phe Ser Gly Gly Ser Met Asn Pro Ala Arg
    50                  55                  60

Ser Phe Gly Pro Ala Val Val Ala Gly Asp Phe Phe Gln Asn Trp Ile
65                  70                  75                  80

Tyr Trp Val Gly Pro Leu Ile Gly Gly Gly Leu Ala Gly Phe Ile Tyr
                85                  90                  95

Gly Asp Val Phe Ile Gly Ser Pro Pro Pro Leu Pro Thr Ser Glu Asp
            100                 105                 110

Tyr Ala


<210> SEQ ID NO 147
<211> LENGTH: 128
<212> TYPE: PRT
<213> ORGANISM: Glycine max
<220> FEATURE:
<221> NAME/KEY: misc_feature
<222> LOCATION: (13)..(15)
<223> OTHER INFORMATION: Xaa can be any naturally occurring amino acid

<400> SEQUENCE: 147

Met Ser Gln Glu Ala Phe Gln Leu Gln Ser Thr Val Xaa Xaa Xaa Gly
1               5                   10                  15

Val Gly Ala Val Glu Gly Val Val Thr Glu Ile Ile Ile Thr Phe Gly
            20                  25                  30

Leu Val Tyr Thr Val Tyr Ala Thr Ala Ala Asp Pro Lys Lys Gly Ser
        35                  40                  45

Leu Gly Thr Ile Ala Pro Ile Ala Ile Gly Phe Ile Val Gly Ala Asn
    50                  55                  60

Ile Leu Ala Ala Gly Pro Phe Ser Gly Gly Ser Met Asn Pro Ala Arg
65                  70                  75                  80

Ser Phe Gly Pro Ala Val Val Ser Gly Asp Phe His Asp Asn Trp Ile
                85                  90                  95

Tyr Trp Val Gly Pro Leu Ile Gly Gly Gly Leu Ala Gly Leu Ile Tyr
            100                 105                 110

Gly Asn Val Phe Ile Arg Ser Asp His Ala Pro Leu Ser Ser Glu Phe
        115                 120                 125


<210> SEQ ID NO 148
<211> LENGTH: 104
<212> TYPE: PRT
<213> ORGANISM: Solanum tuberosum

<400> SEQUENCE: 148

Met Glu Ile Ile Ile Thr Phe Gly Leu Val Tyr Thr Val Phe Ala Thr
1               5                   10                  15

Ala Ala Asp Pro Lys Lys Gly Ser Leu Gly Thr Ile Ala Pro Ile Ala
            20                  25                  30

Ile Gly Phe Ile Val Gly Ala Asn Ile Leu Ala Ala Gly Pro Phe Ser
        35                  40                  45

Gly Gly Ser Met Asn Pro Ala Arg Ser Phe Gly Pro Ala Met Ala Thr
    50                  55                  60

Gly Asn Phe Glu Gly Phe Trp Ile Tyr Trp Ile Gly Pro Leu Val Gly
65                  70                  75                  80

Gly Ser Leu Ala Gly Leu Ile Tyr Thr Asn Val Phe Met Gln Gln Glu
                85                  90                  95

His Ala Pro Leu Ser Asn Glu Phe
```

100

<210> SEQ ID NO 149
<211> LENGTH: 149
<212> TYPE: PRT
<213> ORGANISM: Zea mays

<400> SEQUENCE: 149

```
Met Val Lys Leu Ala Phe Gly Ser Phe Arg Asp Ser Leu Ser Ala Ala
1               5                   10                  15

Ser Leu Lys Ala Tyr Val Ala Glu Phe Ile Ala Thr Leu Leu Phe Val
            20                  25                  30

Phe Ala Gly Val Gly Ser Ala Ile Ala Tyr Ser Gln Leu Thr Lys Gly
        35                  40                  45

Gly Ala Leu Asp Pro Ala Gly Leu Val Ala Ile Ala Ile Ala His Ala
    50                  55                  60

Phe Ala Leu Phe Val Gly Val Ser Met Ala Ala Asn Ile Ser Gly Gly
65                  70                  75                  80

His Leu Asn Pro Ala Val Thr Phe Gly Pro Phe Asp Gly Ala Ser Met
                85                  90                  95

Asn Pro Ala Arg Ser Phe Gly Pro Ala Val Ala Ala Gly Asn Phe Ala
            100                 105                 110

Gly Asn Trp Val Tyr Trp Val Gly Pro Leu Val Gly Gly Gly Leu Ala
        115                 120                 125

Gly Leu Val Tyr Gly Asp Val Phe Ile Ala Ser Tyr Gln Pro Val Gly
    130                 135                 140

Gln Gln Glu Tyr Pro
145
```

<210> SEQ ID NO 150
<211> LENGTH: 149
<212> TYPE: PRT
<213> ORGANISM: Zea mays

<400> SEQUENCE: 150

```
Met Val Lys Leu Ala Phe Gly Ser Phe Arg Asp Ser Leu Ser Ala Ala
1               5                   10                  15

Ser Leu Lys Ala Tyr Val Ala Glu Phe Ile Ala Thr Leu Leu Phe Val
            20                  25                  30

Phe Ala Gly Val Gly Ser Ala Ile Ala Tyr Ser Gln Leu Thr Lys Gly
        35                  40                  45

Gly Ala Leu Asp Pro Ala Gly Leu Val Ala Ile Ala Ile Ala His Ala
    50                  55                  60

Phe Ala Leu Phe Val Gly Val Ser Met Ala Ala Asn Ile Ser Gly Gly
65                  70                  75                  80

His Leu Asn Pro Ala Val Thr Phe Gly Pro Phe Asp Gly Ala Ser Met
                85                  90                  95

Asn Pro Ala Arg Ser Phe Gly Pro Ala Val Ala Ala Gly Asn Phe Ala
            100                 105                 110

Gly Asn Trp Val Tyr Trp Val Gly Pro Leu Val Gly Gly Gly Leu Ala
        115                 120                 125

Gly Leu Val Tyr Gly Asp Val Phe Ile Ala Ser Tyr Gln Pro Val Gly
    130                 135                 140

Gln Gln Glu Tyr Pro
145
```

<210> SEQ ID NO 151
<211> LENGTH: 105
<212> TYPE: PRT
<213> ORGANISM: Oryza sativa

<400> SEQUENCE: 151

```
Met Glu Ile Ile Val Thr Phe Gly Leu Val Tyr Thr Val Tyr Ala Thr
1               5                   10                  15

Ala Ala Asp Pro Lys Lys Gly Ser Leu Gly Thr Ile Ala Pro Ile Ala
            20                  25                  30

Ile Gly Phe Ile Val Gly Ala Asn Ile Leu Val Ala Gly Pro Phe Ser
        35                  40                  45

Gly Gly Ser Met Asn Pro Ala Arg Ser Phe Gly Pro Ala Val Ala Ser
    50                  55                  60

Gly Asp Tyr Thr Asn Ile Trp Ile Tyr Trp Val Gly Pro Leu Val Gly
65                  70                  75                  80

Gly Gly Leu Ala Gly Leu Val Tyr Arg Tyr Val Tyr Met Cys Gly Asp
                85                  90                  95

His Ala Pro Val Ala Ser Ser Glu Phe
            100                 105
```

<210> SEQ ID NO 152
<211> LENGTH: 104
<212> TYPE: PRT
<213> ORGANISM: Lycopersicon esculentum

<400> SEQUENCE: 152

```
Met Glu Ile Ile Ile Thr Phe Gly Leu Val Tyr Thr Val Phe Ala Thr
1               5                   10                  15

Ala Ala Asp Pro Lys Lys Gly Ser Leu Gly Thr Ile Ala Pro Ile Ala
            20                  25                  30

Ile Gly Leu Ile Val Gly Ala Asn Ile Leu Ala Ala Gly Pro Phe Ser
        35                  40                  45

Gly Gly Ser Met Asn Pro Ala Arg Ser Phe Gly Pro Ala Met Val Ser
    50                  55                  60

Gly Asn Phe Glu Gly Phe Trp Ile Tyr Trp Ile Gly Pro Leu Val Gly
65                  70                  75                  80

Gly Ser Leu Ala Gly Leu Ile Tyr Thr Asn Val Phe Met Thr Gln Glu
                85                  90                  95

His Ala Pro Leu Ser Asn Glu Phe
            100
```

<210> SEQ ID NO 153
<211> LENGTH: 140
<212> TYPE: PRT
<213> ORGANISM: Capsicum annuum

<400> SEQUENCE: 153

```
Met Ala Gly Ile Ala Phe Gly Arg Val Asp Asp Ser Phe Ser Ala Gly
1               5                   10                  15

Ser Leu Lys Ala Tyr Leu Ala Glu Phe Ile Ser Thr Leu Leu Phe Val
            20                  25                  30

Phe Ala Gly Val Gly Ser Ala Ile Ala Tyr Asn Lys Leu Thr Val Asn
        35                  40                  45

Ala Ala Leu Asp Pro Ala Gly Leu Val Ala Ile Ala Val Cys His Gly
    50                  55                  60

Phe Gly Leu Phe Val Ala Val Ser Ile Ala Ala Asn Ile Ser Gly Gly
65                  70                  75                  80
```

```
His Val Asn Pro Ala Val Thr Phe Gly Leu Ala Leu Gly Gly Gln Ile
                85                  90                  95

Thr Leu Leu Thr Gly Leu Phe Leu His His Cys Ser Thr Phe Gly Leu
            100                 105                 110

His Cys Ser Leu His Pro Pro Gln Ile Arg His Arg Arg Ile Gly Tyr
        115                 120                 125

Ser Asn Ser Trp Ser Gly Ser Trp Cys Gly Cys His
    130                 135                 140


<210> SEQ ID NO 154
<211> LENGTH: 101
<212> TYPE: PRT
<213> ORGANISM: Hordeum vulgare

<400> SEQUENCE: 154

Met Thr Phe Gly Leu Val Tyr Thr Val Tyr Ala Thr Ala Val Asp Pro
1               5                   10                  15

Lys Lys Gly Ser Leu Gly Thr Ile Ala Pro Ile Ala Ile Gly Phe Ile
            20                  25                  30

Val Gly Ala Asn Ile Leu Val Gly Gly Ala Phe Ser Gly Ala Ser Met
        35                  40                  45

Asn Pro Ala Val Ser Phe Gly Pro Ala Leu Val Ser Trp Glu Trp Gly
    50                  55                  60

Tyr Gln Trp Val Tyr Trp Val Gly Pro Leu Ile Gly Gly Gly Leu Ala
65                  70                  75                  80

Gly Val Ile Tyr Glu Leu Leu Phe Ile Ser Arg Thr His Glu Gln Leu
                85                  90                  95

Pro Thr Thr Asp Tyr
            100


<210> SEQ ID NO 155
<211> LENGTH: 154
<212> TYPE: PRT
<213> ORGANISM: Gossypium hirsutum

<400> SEQUENCE: 155

Met Val Met Pro Phe Gly Leu Val Tyr Pro Val Tyr Ala Pro Ala Val
1               5                   10                  15

Asp Pro Lys Lys Gly Ser Leu Gly Thr Ile Ala Pro Leu Ala Ile Gly
            20                  25                  30

Phe Ile Val Gly Ala Asn Ile Leu Ala Gly Gly Ala Phe Asp Gly Ala
        35                  40                  45

Ser Met Asn Pro Ala Val Ser Phe Gly Pro Pro Leu Val Ser Trp Thr
    50                  55                  60

Trp Asp Asn Pro Trp Ile Tyr Trp Val Gly Pro Leu Ile Gly Gly Gly
65                  70                  75                  80

Leu Ala Gly Phe Phe Arg Ser Ser Phe Ser Ser Ala Thr Pro Arg Ser
                85                  90                  95

Ser Ser Gln Pro Pro Ile Ile Lys Pro Asn Gln Gly Leu Ile Asp Leu
            100                 105                 110

Phe Val Pro Leu Lys Pro Asp Phe Phe Arg Phe His Leu Ser Phe Leu
        115                 120                 125

Phe Leu Ser Leu Phe Phe Val Phe Asn Leu Gly Pro Val Asp Phe Val
    130                 135                 140

Tyr Phe Phe Phe Ile Pro His Pro Phe Ser
145                 150
```

<210> SEQ ID NO 156
<211> LENGTH: 488
<212> TYPE: DNA
<213> ORGANISM: Artificial sequence
<220> FEATURE:
<223> OTHER INFORMATION: Artificially optimized ABSTgene

<400> SEQUENCE: 156
gtcgactcta gaggatcccc gggatgggaa gaatgcattc tagggggaag ggaatctctt 60
cttctgcttt gccatacaag agaactccac caacttggct taagaccgca gcttctgatg 120
ttgaggaaat gattaccaag gctgctaaaa agggtcaaat gccatctcag attggagtgc 180
ttcttaggga tcagcatgga atcccacttg tgaagtctgt gaccggatct aaaatcctca 240
ggatcttgaa ggctcatgga cttgctccag agattccaga ggatctctac ttcttgatta 300
agaaggctgt tgctatcaga aagcacctcg agagaaatag aaaggataag gattcaaagt 360
tcaggcttat cctcgttgag tctaggattc ataggctcgc taggtactat aagaggacca 420
agaagttgcc accaacttgg aagtacgaga gtactactgc ttctactctc gtggcttgat 480
gagagctc 488

<210> SEQ ID NO 157
<211> LENGTH: 830
<212> TYPE: DNA
<213> ORGANISM: Artificial sequence
<220> FEATURE:
<223> OTHER INFORMATION: Artificially optimized ABSTgene

<400> SEQUENCE: 157
ggtaccgtcg actctagagg atccccggga tggatgctgg aggagagaag ttctctgatg 60
ctgctgctgc tgaaggagga gagggaggag gagatcttta cgctgtgctc ggacttaaga 120
aagaatgctc tgatgctgat ctcaaggtgg cataccgtaa gttggctaag aagtggcatc 180
cagataagtg ctcttcatct tcttcagtta agcacatgga agaggctaag gaaaagtttc 240
aggagattca gggagcttac tctgtgcttt ctgatgctaa caagaggctc ttgtacgatg 300
ttggggtgta cgatgatgag gatgatgaag attctatgca aggaatggga gatttcattg 360
gggaaatggc tcaaatgatg tctcaagtga ggccaactag acaagagtct ttcgaggagc 420
ttcaacagct cttcgttgat atgttccagt ctgatattga tagtggtttc tgcaacggat 480
ctgctaagga tcaagttcag gggcaagcta agtctaggac ttgctctacc tctccatctt 540
cttctccatc tccaccacca ccaccaacta tcgttaagga ggctgaggtt tcatcttgca 600
acgggttcaa caagcgtgga tcttctgcta tggattctgg aaagccacca agaccagttg 660
aaggaggagc tggacaagct ggtttctgct tcggagtgtc tgatacaaag cagactccaa 720
agccaagagg accaaacact tctaggagaa ggaacggaag gaagcaaaag ctctctagta 780
agcacgatgt gtctagtgag gatgagactg ctgggtcttg atgagagctc 830

<210> SEQ ID NO 158
<211> LENGTH: 1127
<212> TYPE: DNA
<213> ORGANISM: Artificial sequence
<220> FEATURE:
<223> OTHER INFORMATION: Artificially optimized ABSTgene

<400> SEQUENCE: 158
ggtaccgtcg actctagagg atccccggga tggaaggata cgatagagag ttctggcagt 60

```
tctctgatac tcttaggctt cagaccgctg ctttctctgg actttctctc ggagattcta    120

tctggtctcc agctactgga ggagctgctg ctgctgatag aaggaacaac tctaacgatc    180

tcttcgctgc ttctgcttct ccagctgata caaccgctgc taagaacaat ggaggagtgg    240

gacttaggct taaccttaac gatggaggac caggacttat tggatctggg aagttggctt    300

tcggaggatc taaggctgat aggtacaaca accttccagc tactactgag aaggctgctt    360

cagcttacaa taacaacatc aacgtgaacg ctggatacgc taagaataac aataacaatg    420

ctctcgcttt caacaagatg ggaatctatg gatacaacac taacaactca aacatctcta    480

acaactcttc atctggggag gtgaagtctt acttcaataa gagtgctgga agggctgctt    540

ctaacaactc tcatggacat ggacatgctg gaggaaagaa gggaggagag tacggaaata    600

agaagaagca cgggaagaac gaaggaaata acggaggagg aggagctgga gctactgata    660

agaggttcaa gacccttcca gcttctgaag ctcttccaag aggacaagct atcggaggtt    720

acattttcgt gtgtaataac gatacaatgg atgagaactt gagaagagag cttttcggac    780

tcccatcaag ataccgtgat tcagtgaggg ctattagacc aggacttcca ctcttcttgt    840

acaattactc tacccatcag ttgcatggga ttttcgaggc tgtttctttc ggaggaacta    900

acatcgatcc aaccgcttgg gaagataaga agtgtccagg ggagtcaaga ttcccagctc    960

aagtgagagt tgctaccaga aagatctatg atccactcga ggaggatgct ttcagaccaa   1020

tcctccatca ttacgatgga ccaaagttca ggcttgagct ttctgttact gaggctcttg   1080

ctcttctcga tatctttgct gataaggatg atgcttgatg agagctc                 1127
```

<210> SEQ ID NO 159
<211> LENGTH: 803
<212> TYPE: DNA
<213> ORGANISM: Artificial sequence
<220> FEATURE:
<223> OTHER INFORMATION: Artificially optimized ABSTgene

<400> SEQUENCE: 159

```
ggtaccgtcg actctagagg atccccggga tggcttctcc agaaggaact acctgggttt     60

tcgattgccc actcatggat gatcttgctg tggctgctga ttttgctgct gctccagctg    120

gaggattctt ttgggctgct ccaccatctc ttcagccaca agttgttcaa gctccagttc    180

agtcagttgt tgctgcttct gctccaaatc catgcgtgga gatctcttca tctgttgatt    240

gcggacaagg aaaggagcag ccaactaaca agagaccaag gagtgagtct actgctgagc    300

catctactaa ggcttctagg gagaagatca ggagggataa gctcaacgaa agatttctcg    360

agcttggagc tattcttgag cctggaaaga ccccaaagat ggataagtct gctatcctca    420

acgatgctat cagagttgtt ggggagctta gatctgaggc taaggagctt aaggattcta    480

acgagtcact ccaggagaag atcaaggaac tcaaggctga aaagaacgag cttagggatg    540

agaagcagag actcaaggca gaaaaggagt ctcttgagca acagattaag tttctcaacg    600

ctaggccatc tcttgttcca catcaccctg tgatttctgc ttcagctttc actgctccac    660

aaggaccagc tgttgctgga cataagctca tgatgccagt tcttggatac ccagggtttc    720

caatgtggca attcatgcca ccatctgatg tggataccag tgatgatcca aagtcttgcc    780

caccagttgc ttgatgagag ctc                                            803
```

<210> SEQ ID NO 160
<211> LENGTH: 775
<212> TYPE: DNA
<213> ORGANISM: Zea mays

<400> SEQUENCE: 160
gacgcgcttc ctctcgccct cgctcctccg ccgccgccgc cgccgcatca agccccc gcc 60 ccgccgtcgc ctgaggtaga caccaatccg ccgccatggg gcgtatgcac agccgcggga 120
agggtatctc atcgtcggcg cttccctaca agaggacgcc tcctacctgg ctcaagaccg 180
ctgcctccga cgtggaggag atgatcacaa aggcagcgaa gaagggacag atgccgtcgc 240
agatcggcgt cctgctccgt gaccagcacg gtatccccct tgtcaagagc gtcaccggca 300
gcaagatcct ccgcatcctc aaggcccatg ggctggcacc agaaatcccc gaggacctgt 360
acttcctcat caagaaggcg gtggcgataa ggaagcacct tgagaggaac aggaaggaca 420
aagactctaa attcaggctc attcttgtgg agagcaggat ccaccgcctt gcccgctact 480
acaagcgcac aaagaagctt ccacccacct ggaagtatga gtcaaccaca gcgagcactc 540
tggtggccta agtgtggtat cctccgacag cttgttctag atatgaattt gtgtaatgct 600
tcttatgtct cgatccggtt aaatggacaa cggacctcat ctttttttat gtttaccttg 660
agaatcccgt aaaccatttt ggggttttga attgtctgtt aaacgtaaca tgcatatgtt 720
ttgaagccta gggtgagctt ttacttcacc atcacttatt attgttggct tgttc 775

<210> SEQ ID NO 161
<211> LENGTH: 877
<212> TYPE: DNA
<213> ORGANISM: Saccharum officinarum

<400> SEQUENCE: 161
agatagcgga cgccgctgca gcagtttcgt ccgctatcca cgcgcagcgg acgcggatag 60
cggacgcggt gcggacagtc taatccgtcc ccctcttctc gcactcgcgc ctctttccca 120
ttcgcgccgc cgccgccgcc gcaagcgcca gctcgccgtc gcccgagcca aacaccccaa 180
cgccgccatg gggcgtatgc acagccgcgg gaagggtatc tcgtcgtcgg cgctgccgta 240
caagaggacg ccgccgacct ggctcaagac cgccgcctcc gacgtggagg agatgatcac 300
taaggcggcg aagaagggtc agatgccgtc gcagatcggc gtcctgctcc gtgaccagca 360
cggtatcccc cttgtcaaga gcgtcaccgg cagcaagatc ctccgcatcc tcaaggcaca 420
tgggctggca ccagaaatcc cagaggacct gtacttcctc atcaagaagg cggtggcgat 480
aaggaagcac cttgagagga acaggaagga caaagactcc aaattcaggc tcattcttgt 540
tgagagcagg atccaccgcc ttgcccgcta ctacaagcgc acaaagaagc ttccacccac 600
ctggaagtat gagtcaacca ccgcaagcac tctggtggcc taagtgggga gctcaacatg 660
aggtgcttga agctggggct attcttggaa tcaattttat gtaccgtttt atgagtttgg 720
agtgaactag agatcgtgaa tgtcctgtgg aggatgccat aaacccttttt ggttacatag 780 aactgtctgt tgttaacttt tgctactcgg catccagatt ttgtcagtta taatgatcat 840
ttatattaca tggtttgtcc attcctgcct gcggtcc 877

<210> SEQ ID NO 162
<211> LENGTH: 1037
<212> TYPE: DNA
<213> ORGANISM: Sorghum bicolor

<400> SEQUENCE: 162
acggtaacag agcaatttca gatcagtaga tgcgaacaaa aaccttgctc actcttctct 60
catttcatag cggaaagtaa ccaaagcgga cagtaacatc atcgaacacg gggtaccaa 120

-continued

```
cacctaatcc aaaggttcaa cggacactaa cacatgggta actcagaatc caacggaacg    180
gtaacacgat actatagata gatagatagc taggataact tggccgaagc cagggtgggc    240
ccacacaatc agttctcgca ctcgcgcgcc tttcccattc gcgccgccgc cgccgccgct    300
gcaagcgcca gctcgccgtc gtccgagcca aacaccccaa cgccgccatg ggcgtatgc     360
acagccgcgg gaagggtatc tcgtcgtcgg cgctgccgta caagaggacg ccgccgacct    420
ggctcaagac cgccgcctcc gacgtggagg agatgatcac taaggcggcg aagaagggtc    480
agatgccgtc gcagatcggc gtcctgctcc gtgaccagca cggtatcccc cttgtcaaga    540
gcgtcacggg cagcaagatc ctccgcatcc tcaaggccca tgggctggcg ccagaaatcc    600
cggaggacct ctacttcctc atcaagaagg cggtggcgat aaggaagcac cttgagagga    660
acaggaagga caaagactcc aaattcaggc tcattcttgt tgagagcagg atccaccgcc    720
ttgcccgcta ctacaagcgc acaaagaagc ttccacccac ctggaagtat gagtcaacca    780
ccgcaagcac tctggtggcc taagtgagga gctcaacatt aggtgcttga agctgggcta    840
ttcttggaat catttttatg taccgtttta tgagtttgga gtgaactaga gatcttgaat    900
gtcctgtgga ggatgccata aacccttttg gttacataga actgcctgtt gttaactttt    960
gctactcggc atccagattt tgtcagctat aatatgatca tttacattac atggtttgcc   1020
cctaccttcc tgcagtc                                                  1037
```

```
<210> SEQ ID NO 163
<211> LENGTH: 947
<212> TYPE: DNA
<213> ORGANISM: Saccharum officinarum
<220> FEATURE:
<221> NAME/KEY: misc_feature
<222> LOCATION: (799)..(799)
<223> OTHER INFORMATION: n is a, c, g, or t
<220> FEATURE:
<221> NAME/KEY: misc_feature
<222> LOCATION: (874)..(874)
<223> OTHER INFORMATION: n is a, c, g, or t
<220> FEATURE:
<221> NAME/KEY: misc_feature
<222> LOCATION: (876)..(876)
<223> OTHER INFORMATION: n is a, c, g, or t

<400> SEQUENCE: 163

cggacgcgtg ggcggacgcg tgggcgcgcc gcagccgccg ccgccgccgc tgcagcagca     60
agcccccgcc ccgccgtcgc ctgaggtaga caccaatccg ccgccatggg gcgtatgcac    120
agccgcggga agggtatctc gtcgtcggcg ctgccgtaca agaggactcc tccgacctgg    180
ctcaagacgg ccgccaccga ggtggaggag atgattacca aggctgcgaa gaagggccag    240
atgccgtcgc agattggcgt cctgctccgt gaccagcacg gtatcccgct cgtcaagagc    300
gtcactggta gcaagatcct ccgcatcctt aaggcccatg ggctggcgcc ggagatccct    360
gaggatctct acttcctgat taagaaggct gtggcgatta ggaagcatct ggagaggaac    420
aggaaggaca aggactccaa attcaggctt attcttgttg agagcaggat ccaccgcctt    480
gcccgctact acaagcgcac caagaagctc ccgcccacct ggaagtatga atcaaccacg    540
gccagcactc tggtggccta agtgatatcc tccgatggcg tggtctgtag cacctttgag    600
cttgttctag atatggattt atgtaatggt tattatgtct ggagcgggtt agatggacaa    660
ggaacctcaa ccgttttatg tttacttgtt tactgagaat cccataaacc atttttggtt    720
ttgcaattct gtctgttaaa acgtaacatg catccatgtt ttgtcgccta cagtgagcgt    780
tcactgagcc atcatttang atcggtgctt ggccccctgt atcccggttt ctatgactat    840
```

taatattaaa aattggccac ttaaaccctc atantnaaaa accaacctca actaccctac 900
aatccgagct ctcttttttt tatatttctt ccccacttct attcact 947

<210> SEQ ID NO 164
<211> LENGTH: 889
<212> TYPE: DNA
<213> ORGANISM: Sorghum bicolor

<400> SEQUENCE: 164
ctactggctc tcctatgccg cacgcgcctc ctctcgccct cgcgccgccg ccgccgccgc 60
agctgctgca gcagcaagct cccgcccgcc gtcgtcgcct gaggtagaca ccaatccgcc 120
gccatggggc gtatgcacag ccgcgggaag ggtatctcgt cgtcggccct gccgtacaag 180
aggactcctc cgacctggct caagacggcc gccaccgagg tggaggagat gattaccaag 240
gctgcgaaga agggtcagat gccgtcgcag attggcgtcc tgctccgtga ccagcacggc 300
atccctctcg tcaagagcgt tactggtagc aagatcctcc gcatccttaa ggcccatggg 360
ctggcgccgg agatcccgga ggacctgtac ttcctgatta agaaggctgt ggcaattagg 420
aagcatttgg agaggaacag gaaggataag gactccaaat tcaggctcat tcttgttgag 480
agcaggatcc accgccttgc ccgctactac aagcgcacca agaagctccc gcccacctgg 540
aagtatgaat caaccacggc cagcactctg gtggcctaag tgatatcctc cgatggcgtg 600
gtcttgagca cctttgaact tgttctagat atgaatttat gtaatgctta atatgtctgg 660
agcgggttag atggacaagg aacctcaact tttttatgtt attacttgga gaatctataa 720
accatttttg gttttgcaat tctgtctgtt aaacgtaaca tggatccatg ttttgtcgcc 780
ttcagtgagc gtttactgtg ccaccattta gattgttgct tgccccccctg tagcccggtt 840 ttctatttgg ttatatgact attaattaat atgaaaattg tccacttat 889

<210> SEQ ID NO 165
<211> LENGTH: 940
<212> TYPE: DNA
<213> ORGANISM: Oryza sativa

<400> SEQUENCE: 165
aagaaaaaac tccatcctac cgccgctcgc gcccctctcg ccctcgcgcg ccgccgccgc 60
cgcccgccgt cgccggagct aaacccctcg acgccgccat ggggcgcatg cacagccgcg 120
ggaagggtat ctcgtcgtcg gcgctgccgt acaagaggac tcccccgagc tggctcaaga 180
ccgccgcctc cgatgtggag gagatgatca tgaaggccgc gaagaagggt cagatgccgt 240
cgcagatcgg cgtggtgctc cgtgaccagc acggaatccc cctcgtcaag agcgtcaccg 300
gcagcaagat cctccgcatc ctcaaggccc acgggcttgc cccggagatc ccggaggacc 360
tctacttctt gatcaagaag gctgttgcta ttaggaagca cttggagagg aacaggaagg 420
acaaggactc caagttcagg cttattcttg ttgagagcag gatccaccgc ctcgcccgct 480
actataagcg cacaaagaag ctcccaccca cctggaagta tgagtcaacc acggccagca 540
ctctggtggc ctaagagaac actggcgtgc tcttagatgc ttcgatatgg acctggttct 600
agaaatcaat ttatgtactg ctttgagttt ggagcgagtt agacgtggac aagaaactgc 660
aagtttttct atgtttactc gggggatcct ataaaccatt tttggtttca caattctgtc 720
tgttaaacat gcatcggtat tttgttattt acaattagct gttaccttac cataatgttc 780
ggcatcgttt gcatccagct ctatcccgta ctttggtatt gtgtttgaac tcatcgtacg 840

-continued atgttagttc ataattctgg ttgatcgagg ctaatttgct cacaagcgct tctcatagaa 900
cttttcacaa tatttgtgag agaaatccgg tgctatgaat 940

<210> SEQ ID NO 166
<211> LENGTH: 810
<212> TYPE: DNA
<213> ORGANISM: Zea mays

<400> SEQUENCE: 166
cgccgctcgc gcatcctatt gccctcgcgc caccgtcgcc gccgccgctg cagcgagcca 60
ccgccctgcc gtcgcctgag gtagacacca atccaccgcc atggggcgta tgcacagccg 120
cgggaagggt atctcttcat cggcgctgcc gtacaagagg actcctccga tctggctcaa 180
gacagctacc gccgaggtgg aggagatgat taccaaggct gcgaagaagg gccagatgcc 240
gtcgcagatt ggtgttctgc tccgtgacca gcacggcatc ccgcttgtca agagcgtgac 300
tggtagcaag atcctccgca tcctcaaggc ccatgggttg gcgccggaga tcccggagga 360
tctctacttc ctcattaaga aggccgtggc gattaggaag catttggaga ggaacaggaa 420
ggacaaggac tccaaattca gactcattct tgttgagagc aggatccacc gccttgcccg 480
ctactacaag cgtaccaaga agctcccacc cacctggaag tacgagtcaa ccacggcgag 540
cactctggtg gcctaagtga tatcctctga tggcttggtc tttagcacct atgagcttgt 600
tctagatatg aatttatgta attcttgtta tgtctggagc tggttagatg gacaaggaac 660
ctcaactttt tctatgttta cttggagaat cccataaacc atttttggtt tcgcaattct 720
gtctgttaaa cgtaacatgc atccatgttt tgtcgagcgt ttcctccacc atcataaatt 780
cctgtagatt atatttttct tctagttatc 810

<210> SEQ ID NO 167
<211> LENGTH: 820
<212> TYPE: DNA
<213> ORGANISM: Hordeum vulgare

<400> SEQUENCE: 167
cctcttttct atcctctcac cactcgcgcc tctctcgccc ttcccgccgc cgccgccgcc 60
gccgctcccc tcgccgcagc agcagccgca gccatggggc gcatgcacag tcgcgggaag 120
ggcatctcgt cgtcggcgct gccgtacaag aggactccac cgagctgggt caagaccgcc 180
gtcgccgatg tggacgagtt aatcaccaag gccgcgaaga agggccagat gccgtcgcag 240
atcggcgtcc tgctccgtga ccagcacggc atccccctcg tcaagagcgt caccgggagc 300
aagatccttc gcatcctcaa ggcccatggg ctggcaccag agatcccgga ggacctctac 360
tttctgatca agaaggcggt ggcgataagg aagcacctgg agaggaacag gaaggacaag 420
gactctaagt tcagactcat ccttgtggag agcaggatcc accgcctcgc tcgctactac 480
aagcgcacca agaagctccc acccacctgg aagtacgagt ctaccaccgc cagcactctg 540
gtggcctaag ggagatatgc atctggtgtg ctcttagctg attaaagctt gattgttcca 600
gaaaccattc ttatgtaacg ctttatgaga gtttggagcc aagtcgatgc tgcaaatttt 660
ctatgtttga ctggaggatg ctgtaaaacc tttgttgttt cactgttctg tctgttaaac 720
gactgttata atgtacccag attttgtcag ttacagttag cagttacctt atgtgttttc 780
agatagctca tgttgctctt tggctaaaga tcatatagtt 820

<210> SEQ ID NO 168
<211> LENGTH: 867

<212> TYPE: DNA
<213> ORGANISM: Oryza sativa

<400> SEQUENCE: 168
ctcactactc gctcttcccg ccgccgccgc ctcctccgcc gcgcagtcgc caaccgccgt 60
cgccggtcgc cgtcgccaaa ttccccactg ccaccatggg ggcgtatgca cagccgcggg 120
aagggcatct cgtcgtcggc gattccgtac aagaggactc ccccaagctg ggtcaagacc 180
gccgccgccg atgtggagga gatgatcatg aaggccgcga agaagggcca gatgccgtcg 240
cagatcggcg tggtgctccg tgaccagcac ggaatccccc tcgtcaagag cgtcaccggc 300
agcaagatcc tccgcatcct caaggcccat ggtcttgcgc cggagatccc ggaggacctg 360
tacttcctga tcaagaaggc tgttgctatt aggaagcatt tggagaggaa caggaaggac 420
aaggactcca agtttaggct catccttgtt gagagcagga tccaccgcct cgctcgctac 480
tacaagcgca ccaagaagct cccgcccacc tggaagtatg agtcgaccac agccagcact 540
ctggtggcct agagagagag ctctgcttct gctgtgctcc ttgctgcttc aagcttagct 600
tgttctagga atggatttta tttatgtagc gcattatgag tcttgagaca agcaggagct 660
gctaattttc ctttgtctgg agaatgccat aaaaccctta tgcattcaat attctgaacg 720
ttaaacttct agtaatgtgc atcgagacta tgtaaatcaa taacaatctg gagcaaaaac 780
aatcaatcac atgcagaaaa aatttttgac aggcttgaca agttacactt gaacaaggaa 840
ggtataataa tgggcaaaat caacttg 867

<210> SEQ ID NO 169
<211> LENGTH: 817
<212> TYPE: DNA
<213> ORGANISM: Triticum aestivum

<400> SEQUENCE: 169
ccaggctctt ttctatcctc tcaccactcg cgcctctctc gcccttcccg ccgccgccgc 60
cgccactccc ctcgccgccg cagcagccgc agccatgggg cgcatgcaca gccgcgggaa 120
gggcatctcg tcgtcggcgc tgccgtacaa gaggactcca ccgagctggg tcaagaccgc 180
cgtcgccgat gtggacgagt taatcaccaa ggccgcgaag aagggccaga tgccgtcgca 240
gatcggcgtc ctgctccgtg accagcacgg catccccctc gtcaagagcg tcaccgggag 300
caagatcctc cgcatcctca aggcccatgg gctggcacca gagatcccgg aggacctcta 360
ctttctgatc aagaaggcgg tggcgataag gaagcacctg gagaggaaca ggaaggacaa 420
ggactctaag ttcaggctca tccttgtgga gagcaggatc caccgcctcg ctcgctacta 480
caagcgcacc aagaagctcc cgcccacctg gaagtacgag tctaccaccg ccagcactct 540
ggtggcttaa gggagatcca gatctggtgt gctcttagct gattaaagct tgattgttct 600
ggaaaccatt cttatgtaat gctttatgag agtttggagc caagcagatg ctgcaaattt 660
tctatgtttg cctggaggat gctgtaaaac ctttatggtt tcactgttct gtctgttaaa 720
cgactgttat aatgtaccca gattttgtca gttacagtta gcagttaccg tatgtttttt 780
ccaatagtac atgttgctct tcggctgaag atcgtat 817

<210> SEQ ID NO 170
<211> LENGTH: 912
<212> TYPE: DNA
<213> ORGANISM: Triticum aestivum
<220> FEATURE:
<221> NAME/KEY: misc_feature
<222> LOCATION: (7)..(7)

-continued

<223> OTHER INFORMATION: n is a, c, g, or t
<220> FEATURE:
<221> NAME/KEY: misc_feature
<222> LOCATION: (905)..(905)
<223> OTHER INFORMATION: n is a, c, g, or t

<400> SEQUENCE: 170

```
tgcaggnaat tcggcacgag gctcgagccc ctctcgccct tcgcgccgct gctgctgcag     60

gcaaccgccg ccgccgtcgc cggagctaaa cccctcgcct gacgccatgg ggcgtatgca    120

cagccgcggg aagggtatct cgtcgtcggc gctgccgtac aagaggactc ccccgagctg    180

ggtcaagacc gccgtcgctg atgtcgacga gttgatcacg aaggctgcga agaagggtca    240

gatgccctcg cagatcggtg ttctgctccg tgaccagcac ggtatccccc tcgtcaagag    300

cgttaccgga agcaagatcc tccgcatcct caaggctcat ggcctggcgc cggaaatccc    360

agaggatctg tactttttga ttaagaaggc tgtggccatt aggaagcatc ttgagaggaa    420

caggaaggac aaggactcca aattcaggct cattcttgtt gagagcagga tccaccgtct    480

tgcccgttac tacaagcgca ccaagaagct cccgcccacc tggaagtacg agtctaccac    540

tgccagcact ctggtggctt aggagggctc ttcatctggt gtgctcttac cggcttcagg    600

atggtcttgt tctacatatt atcaatttca tgtaacgctt ttgagtttgg agcgatttag    660

atgaacaaga gaccaaattt tctatgttta cttggagaat cccataaacc atttttggtt    720

ttgcaattct gtctggttct gtttagcgtc tatctacaat tcatcagtta aaattagaca    780

ttgtgatatt cgtgttgtct gatctgagtg agtgtaatcg ctgctttcag tgcactcaag    840

cttggacagt ttgactatat ggttatcctg aaatctaaaa agtggccgca cactttttgg    900

tcaanaaaaa aa                                                        912
```

<210> SEQ ID NO 171
<211> LENGTH: 863
<212> TYPE: DNA
<213> ORGANISM: Hordeum vulgare

<400> SEQUENCE: 171

```
cacgaggcaa tcgcgccgcc gctcgtgccc ctctagccct tcgcgccgct gctgctgcag     60

gcaaccgccg ccgtcgtcgc cggagctaaa cccctcgcct gacgccatgg ggcgcatgca    120

cagccgcggg aagggtatct cgtcgtcggc gctgccgtac aagaggactc ccccgagctg    180

ggtcaagacc gccgtcgctg atgtggatga gttgatcacg aaggctgcga agaagggtca    240

gatgccctcg cagatcggtg ttctgctccg cgaccagcac ggtatccccc tcgtgaagag    300

tgttaccgga agcaagatcc tccgcatcct caaggctcat ggcctggcgc cggaaatccc    360

cgaggatctg tactttttga ttaagaaggc cgtggccatt aggaagcatc ttgagaggaa    420

caggaaggac aaggactcca aattcaggct cattcttgtt gagagcagga tccaccgtct    480

tgcccgttac tacaagcgca ccaagaagct cccgcccacc tggaagtacg agtctaccac    540

agccagcact ctggtggctt aggagggctc ttcatctggt gtgctcttac cagcctcagg    600

atggtcttgt tctacatatc atcaatttta tgtaacgctt ttgagtttgg agcgatttag    660

atgaacaaga gaccaaattt tctatgttta ctcggagaat cccataaacc atttttggtt    720

ttgcagttct gtctggttac ttttggcatg catccacatt tcattcagtt aaacttttga    780

cgtcatgata tttgtgttgt gattgtagcg agtgcctcgc tagtttcagt gcatcttctc    840

gtgcccgaat ggtttgactg act                                            863
```

<210> SEQ ID NO 172
<211> LENGTH: 568
<212> TYPE: DNA
<213> ORGANISM: Triticum aestivum

<400> SEQUENCE: 172

| | | | | | |
|---|---|---|---|---|---|
| gcaaaaccaa | aaatggttta | tagattctcc | aagtaataac | ataaaaaagt | tgaggttcct | 60 |
| tgtccatcta | acccgctcca | gacatattaa | gcattacata | aattcatatc | tagaacaagt | 120 |
| tcaaaggtgc | tcaagaccac | gccatcggag | gatatcactt | aggccaccag | agtgctggcc | 180 |
| gtggttgatt | catacttcca | ggtgggcggg | agcttcttgg | tgcgcttgta | gtagcgggca | 240 |
| aggcggtgga | tcctgctctc | aacaagaatg | agcctgaatt | tggagtcctt | atccttcctg | 300 |
| ttcctctcca | aatgcttcct | aattgccaca | gccttcttaa | tcaggaagta | caggtcctcc | 360 |
| gggatctccg | gcgccagccc | atgggcctta | aggatgcgga | ggatcttgct | accagtaacg | 420 |
| ctcttgacga | gagggatgcc | gtgctggtca | cggagcagga | cgccaatctg | cgacggcatc | 480 |
| tgacccttct | tcgcagcctt | ggtaatcatc | tcctccacct | cggtggcggc | cgtcttgagc | 540 |
| caggtcggag | gagtcctctt | gtacggcc | | | | 568 |

<210> SEQ ID NO 173
<211> LENGTH: 778
<212> TYPE: DNA
<213> ORGANISM: Zea mays

<400> SEQUENCE: 173

| | | | | | |
|---|---|---|---|---|---|
| actcgcgtct | ctttccctat | ttcgcgccgc | cgccgctgct | gcaagcgcca | gctcgccgtc | 60 |
| gtccgaatag | tacactctaa | cgccgccatg | gggcgtatgc | acagccgcgg | gaagggtatc | 120 |
| tcgtcgggtc | ggcgctgccg | tacaagagga | cgcctcctac | ctggctgaag | accgccgcct | 180 |
| ccgacgtgga | ggagatgatc | acaaaggcag | cgaagaaggg | acagatgccg | tcgcagatcg | 240 |
| gcgtcctgct | ccgtgaccag | cacggtatcc | cccttgtcaa | gagtgtcacc | ggcagcaaaa | 300 |
| tcctccgcat | cctcaaggcc | catgggctgg | cacccgaaat | cccggaggac | ctgtacttcc | 360 |
| tcatcaagaa | ggcggtggcg | ataaggaagc | accttgagag | gaacaggaag | acaaagact | 420 |
| ctaaattcag | gctcattctt | gtcgagagca | ggatccaccg | ccttgcccgc | tactacaagc | 480 |
| gcacaaagaa | gcttccaccc | acgtggaagt | acgagtcaac | cactgcaagc | actctggtgg | 540 |
| cctaagcgag | gagctcagcg | tacggcgctt | gaagccgagg | gcattgttgg | aaatcatttt | 600 |
| tatgtaccgt | tttaagagtt | tggagtgaac | tagagatggt | gaatgtccct | cctctggagg | 660 |
| atgccatgga | cccttttgt | ttacatagaa | ctgccctgct | gttaaacttt | tgctacttgg | 720 |
| cgaaggcagt | tgattgcttg | cctccattaa | cacctgctat | gcgagaagct | tttagcct | 778 |

<210> SEQ ID NO 174
<211> LENGTH: 697
<212> TYPE: DNA
<213> ORGANISM: Saccharum officinarum

<400> SEQUENCE: 174

| | | | | | |
|---|---|---|---|---|---|
| ctcaagcgcc | agctcgccgt | gtgccgagcc | aaacacccga | acgccggcat | ggggcgtatg | 60 |
| cacagctcgc | gggaagggta | tctcgacgtc | ggagctgccg | tacaagagga | cgccggcgac | 120 |
| ctggctcaag | accgccgtct | tcgacgtgga | ggagatgatc | actaacgcgg | cgaagaaggg | 180 |
| tcagatgccg | tcgcagatcg | gcgtcctggt | tcgtgaccag | cacggtatcc | cccttgtcaa | 240 |
| gagcgtaacc | ggcagcatga | tcctccgcat | cctcaaggca | catgggctgt | cactagaaat | 300 |

```
cccagaggac ctgtacttcc tcataaagaa agcggtgtgg ataaggaagc accttgagag    360

gaacaggaag gacaaagact tcaaattcac gctcattctt gttgagagca ggatccaccg    420

tcttgcccgt tactacaagc gcacaaagaa gcttccaccc acctgcaaat atgagacaac    480

caccggaagc actctggtgg ccatagtggt gagctcaaca tgacgggctt tgatgctggc    540

gctattcttg gaatcaattt tatgtaccgg ttaatgagtt tggagtgaac taaagatcgt    600

gaatggcctg tggaggatgc cataaaccct tttggctaca tagaactggc tgtggtaact    660

tgtgctactc gccatcagat tttgtcagta taatgat                             697
```

```
<210> SEQ ID NO 175
<211> LENGTH: 1050
<212> TYPE: DNA
<213> ORGANISM: Triticum aestivum
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (199)..(199)
<223> OTHER INFORMATION: n is a, c, g, or t

<400> SEQUENCE: 175

gggnagagga ctccaccaag cgtgggtcaa gaccgccgtc gccgatgtgg acgagttaat     60

caccaaggcc gcgaagaagg gccagatgcc gtcgcagatc ggcgtcctgc tccgtgacca    120

gcacggcatc cccctcgtca agagcgtcac cgggagcaag atcctccgca tcctcaaggc    180

ccatgggctg gcgccagana tcccggagga tctctacttt ctgatcaaga aggcggtggc    240

gataaggaag cacctggaga ggaacaggag ggacaaggac tctaagttca ggctcatcct    300

tgtggagagc aggatccacc gcctcgctcg ctactacaag cgcaccaaga agctcccgcc    360

cacctggaag tgggaggtga aggcagttct ggacgactac ccgaaactct gcctcaccaa    420

ggggagaaag gtcctcgaga tccggccctc catcgagtgg aacaagggac acgctctcaa    480

gttcttgctc aagtctctcg gctatgcggg gcgcagcgac gttttcccga tatacatcgg    540

ggatgaccgt acagacgagg atgcattcaa ggtgctgcag aacatgggac aaggcatcgg    600

gatccttgtg accaagtttc caaaggacac cagcgcatcc tactctctgc gtgagcctgc    660

tgaggtaaag gagttcatgc gcaagctagt gaagagcaac gggataaaga agggttaatt    720

catcaatcaa cagccttcta gctctaactc gcatgaagat cgagcaggct atatagctag    780

tacatcaagt ctagcttgtt tcctttttgg acttggtgtt gtctctcctt tcatctagta    840

gaacaatgca tgcatgcgtg tcagggtcga tatagaagat ccagatcgat cagtgaccca    900

tgccaggcct tggctctgaa ggtttctatt actgtatcct tctctcaagg tcttgtaatt    960

agccttccct tagctatgac agaaatggta ttgacaaagt agccctcctt tttctcgccc   1020

tgcactataa aattgttcta ttgcttgctt                                    1050
```

```
<210> SEQ ID NO 176
<211> LENGTH: 375
<212> TYPE: DNA
<213> ORGANISM: Zea mays

<400> SEQUENCE: 176

acataaaaat gatttccaac aatgccctcg gcttcaagcg ccgtacgctg agctcctcgc     60

ttaggccacc agagtgcttg cagtggttga ctcgtacttc cacgtgggtg gaagcttctt    120

tgtgcgcttg tagtagcggg caaggcggtg gatcctgctc tcaacaagaa tgagtctgaa    180
```

```
tttggagtcc ttgtccttcc tgttcctctc caaatgcttc ctaatcgcca ccgccttctt    240

aatgaggaag tagagatcct ccgggatctc cggcgccaac ccatgggcct tgaggatgcg    300

gaggatcttg ctaccagtca cgctcttgac aagcggcatg ccgtgctggt cacggagcag    360

aacaccaatc tgcga                                                     375
```

```
<210> SEQ ID NO 177
<211> LENGTH: 528
<212> TYPE: DNA
<213> ORGANISM: Triticum aestivum
<220> FEATURE:
<221> NAME/KEY: misc_feature
<222> LOCATION: (305)..(305)
<223> OTHER INFORMATION: n is a, c, g, or t
<220> FEATURE:
<221> NAME/KEY: misc_feature
<222> LOCATION: (355)..(355)
<223> OTHER INFORMATION: n is a, c, g, or t
<220> FEATURE:
<221> NAME/KEY: misc_feature
<222> LOCATION: (365)..(365)
<223> OTHER INFORMATION: n is a, c, g, or t
<220> FEATURE:
<221> NAME/KEY: misc_feature
<222> LOCATION: (385)..(385)
<223> OTHER INFORMATION: n is a, c, g, or t
<220> FEATURE:
<221> NAME/KEY: misc_feature
<222> LOCATION: (387)..(387)
<223> OTHER INFORMATION: n is a, c, g, or t
<220> FEATURE:
<221> NAME/KEY: misc_feature
<222> LOCATION: (398)..(398)
<223> OTHER INFORMATION: n is a, c, g, or t
<220> FEATURE:
<221> NAME/KEY: misc_feature
<222> LOCATION: (450)..(450)
<223> OTHER INFORMATION: n is a, c, g, or t
<220> FEATURE:
<221> NAME/KEY: misc_feature
<222> LOCATION: (470)..(470)
<223> OTHER INFORMATION: n is a, c, g, or t
<220> FEATURE:
<221> NAME/KEY: misc_feature
<222> LOCATION: (480)..(480)
<223> OTHER INFORMATION: n is a, c, g, or t
<220> FEATURE:
<221> NAME/KEY: misc_feature
<222> LOCATION: (508)..(508)
<223> OTHER INFORMATION: n is a, c, g, or t

<400> SEQUENCE: 177

atcaagcccc cgccccgccg tcgcctgagg tagacaccaa tccgccgcca tggggcgtat     60

gcacagccgc gggaagggta tctcatcgtc ggcgcttccc tacaagagga cgcctcctac    120

ctggctcaag accgctgcct ccgacgtgga ggagatgatc acaaaggcag cgaagaaggg    180

acagatgccg tcgcagatcg gcgtcctgct ccgtgaccag cacggtatcc cccttgtcaa    240

gagcgtcacc ggcagcaaga tcctccgcat tctcaaggcc catggctggc accagaaatc    300

ccgangactg tacttctcat caagaaggcg gtggcgataa ggaagcactt gagangaaca    360

ggaangacaa agactctaaa ttcangntca ttcttgtnga gaacaggatt caccgcttgc    420

ccgctactac aagcgcacaa gaagtttcan ccacttgaag tatgagtaan cacagcgagn    480

atctggtggc taagtttgta tcttcganag ttgttctaga tatgattt                 528
```

```
<210> SEQ ID NO 178
<211> LENGTH: 1346
<212> TYPE: DNA
```

<213> ORGANISM: Sorghum bicolor

<400> SEQUENCE: 178

```
aagagaagag cagcagcagc aacagccgcg ccatccgctt gcttccttcc ttcctcttct      60
ctccctccta ccccaccgcc ggcgtcgcct cttcgcgttg cgcgccctcg cgtcgcaccc     120
gtgggtagca gccgcgtacc taccaacctg cgtgctgccg ggggagctct gcacgtctcc     180
tgtcgcctcg cctctcggca tggacgccgg gggagagaag ttcagcgacg cggcggcggc     240
ggagggcggt gagggcggcg gcgacctcta cgccgtcctc gggctcaaga aggagtgctc     300
cgacgccgac ctcaaggtcg cttaccggaa gctcgccaag aaatggcacc cggacaaatg     360
ctcctcctcc agcagcgtga aacacatgga ggaagccaag gagaagttcc aagagatcca     420
gggcgcctat tccgtactct ctgacgccaa taaacggctc ctctacgatg ttggagtata     480
cgacgatgag gacgacgagg atagcatgca ggggatgggt gacttcattg gtgagatggc     540
ccagatgatg agccaggtgc ggccgacgag gcaggaaagc tttgaggagc tgcagcagct     600
ttttgtggac atgttccagt ctgatattga ttcaggattc tgcaacgggt ctgctaagga     660
tcaagttcag gggcaagcca aaagtagaac atgctcgacc tcaccttcat catcaccgtc     720
cccacctcct cctcctacta tagtaaagga ggcagaggtg tcatcatgta atggcttcaa     780
taagcggggt tcatcagcaa tggactcagg gaagcctcca aggcctgttg aaggcggtgc     840
tggtcaggct ggattttgtt ttggggtgag cgatacgaag caaacgccga agccgagagg     900
tccgaacacc agccggagga ggaacggccg gaaacagaag ctgtcatcca agcacgatgt     960
ttcatctgaa gatgaaacgg ccggttccta gcaccagcag ctacggtagc agtttgacct    1020
gtggctttgg tgatatcatt cgttggtcct tggcggtgcc gagggcccta gtagccagca    1080
gcggcaggga ggcacagcat gtcgcttctg ctagctgctg tgatctgaag aggcgtttag    1140
ctcatcatat gccttacctt aggcctgtga gggacttcca ttgaaactcg tcgaggatac    1200
tgcatttttc tttctccatc tgtgtcggtt gtgttgtaca atacattgag tgacttctaa    1260
tcgattcttt tttttacca ttaattaaca tctggtatat ccgattgatc gatccctagc    1320
cactgattac atgcatgagt tctttg                                         1346
```

<210> SEQ ID NO 179
<211> LENGTH: 1209
<212> TYPE: DNA
<213> ORGANISM: Saccharum officinarum

<400> SEQUENCE: 179

```
cgtaccatgg acgccggggg agagaagtgt ggcgacgcgg cggcggcgga gggcggtgag      60
ggcggcggcg acctctacgc cgtcctcggg ctcaagaagg agtgctccga cgccgacctc     120
aaggtcgctt accggaagct cgccaagaaa tggcacccgg acaaatgctc ctcctccagc     180
agcgtgaagc acatggagga agcgaaggag aagttccaag agatccaggg cgcctattct     240
gtactctctg acgccaataa acggctcctc tacgacgtgg gagtatatga tgatgaggac     300
gacgaggata gtatgcaggg gatgggggac ttcattggtg agatggccca gatgatgagc     360
caggtgcggc cgacgaggca ggaaagcttt gaggagctgc agcagctttt tgtggacatg     420
ttccagtctg atattgattc aggattctgc aatgggactg ctaagggcca tcaagttcag     480
gggcaagcca aaagtagaac atgctcgacc tcaccttcat catcaccgtc ccctcctcct     540
cctactatag taaaggaggc agaggtgcca tcatgtaatg gcttcaacaa gcggggttca     600
tcagcaatgg actcagggaa gcctccaagg cctgttgaag gtggtgcggg tcagaggcag     660
```

-continued gctggatttt gttttggggt gagcgacacg aaacaagcgg caaagccgcg aggtccaaac 720
accagccgga ggaggaacgg ccggaaacag aagctgtcat ccaagcacga tgtttcatct 780
gaagatgaaa ctgccggttc ctagcaccag cagctatggt agcagtttga cccttggctt 840
tggtgatatc attcgttggc ccttggatgt gccgaaggcc ctagtagcca gcagcagcag 900
ggagggcaca gcatgtcgcc tctgctagct gctgtgatct gaagaggcgt ttagctcatc 960
atatgcctta cctttaggcc cgtgagggac ttacattgaa actcgtcgat gatactgcat 1020
ttttctttct ccatctgtgt cagttgtgtt gtaccaatac attgagtgac ttctaatcga 1080
ttagcctttt atcattaatt aacttctggt atatatacgt tgctgcctgt tgttgacagg 1140
ctacggtagc ctgttggtaa gatcttaatc tcgaagggag aaaaataaat aacattgtgg 1200
acgtagctc 1209

<210> SEQ ID NO 180
<211> LENGTH: 1623
<212> TYPE: DNA
<213> ORGANISM: Sorghum bicolor

<400> SEQUENCE: 180
gcacgaggcc ctcttccgcc tcctctctct ctctctctct ctctcggctc tcgctctcag 60
acgactgctg ggcagccgcc gccctaggcc aggtgctgag gctttccctg gtctcttcgc 120
cgtcgacgag cacccaccag taggtacttg attggacgag ccatggacag cctgtggcat 180
ctgggggacg agctccgtgg gcaaccgaag gtggtggagg accgccagtg gtcgctcatg 240
acgtccaagc tggcggagat caccaggtcc aagggcgaga ggatgaacga cctcgactac 300
gccaggatga acaccgtccc tgacgccaag cagtgggaca agacgtcctt ccagcatcat 360
gaccagagca ggatggacca catcaatctc ggcctcatga acctggatct caagatgaac 420
gatctcaaga tgaacgaggc ccccaccgcc atgaagctcc ccttccacaa catgccctat 480
aacatgaacc caatgtaccc caaggggagc aatgccaatg tcaatgtcaa tgcgttcaag 540
atgaatgttg ggtgaacaa gtactccaat agtcctaacg ggaaagacgc caatgggaaa 600
aacaatggcg gcagcaacaa caatggagga aacagcaatg ggagcgcaaa cggcaattct 660
gcagttgaca agcgcttcaa gacattgcca acaagtgaga tgctaccgag gaatgaagtc 720
cttggtggat acatctttgt ctgcaacaac gataccatgc aggaggatct caagaggcag 780
ctttttggat tgccagcaag atatcgtgat tcagtccgag caattactcc tggcctgcct 840
cttttcctct ataactacac aacccaccag cttcatgggg tatttgaggc tgccagcttt 900
ggtgggtcta atatcgatcc cactgcatgg gaggataaga agtgtaaagg tgaatctaga 960
ttcccagctc aggtgaggat ccgcattagg aagctttgca agccgttgga agaggattcc 1020
ttcaggccag ttttgcacca ttatgatggc ccaaagtttc gccttgagct ctctatcgcg 1080
gagaccttgt cgctgctaga cctatgtgag aaggaaggta tctgagctgt tggggaggtg 1140
gttgccttgt gagcttctag taaatatcaa tcatccttgt atgttttgtg gatggtggtt 1200
ggttggcaat gttgtttatt ttagcgaaag ctgctgctgg ttttgttttc cctaccctgg 1260
atgaaagcaa ggacctggta cttggaaggc cccctcaaac aagctgtgag cctgtcagtg 1320
tactgcgttg tgtctgtcgt cgtcaagaac caaaccaatc ttggaccgac tgagagttgg 1380
agtgtgtatg ttttgctgtc tatctacatg tgttagtaga gtgggtatac ctgggcagaa 1440
tgggtcctca aaagatgggg ggcctatctg tatactatgt gtaatggtta agatgcatgc 1500
ggccctaagt aagggctggt gatgtcgatg ctggtgctcc tggtgtgtat tttgtactct 1560
gttgtacctt gaacctcctt tgcatttgcc ttaatgctgc tgctttttgc actgtcaaaa 1620
aaa 1623

<210> SEQ ID NO 181
<211> LENGTH: 1336
<212> TYPE: DNA
<213> ORGANISM: Saccharum officinarum

<400> SEQUENCE: 181
agatcaccag gtccaaaggc gagaggataa acgatctcga ctacgcaacg atgaacaccg 60
accctgacgc caagcagtgg gacaagacgt cctaccagca tcacaacgag agcaggatgg 120
accacatcaa cctcggcctc atgaacctgg atctcaagat gaacgaggcc gccaccgcca 180
tgaagctccc cttccacaac atgccctata acatgaaccc aatgtacccc aaggggagca 240
atgtcaatgt caatgcgttc aagatgaatg ttggggtgaa caagtactcc aatagtccta 300
acgggaaaga cgccaatggg aaaaacaatg gtggcagcaa caacaatgga ggaaacagca 360
atgggagcgc caacagcaat tctgcagttg acaagcgctt caagacattg ccaacgagtg 420
agatgctacc gaggaatgaa gtccttggtg gatacatctt tgtctgcaac aatgatacca 480
tgcaggagga tctcaaaagg cagcttttttg gattgccagc aagatatcgt gattcagtcc 540
gagcaattac tcctggcctg ccacttttcc tctataacta cacgactcac cagcttcatg 600
gggtatttga ggctgccagt ttcggtgggt ctaatatcga tcccactgca tgggaggata 660
agaagtgtaa aggtgaatct agattcccag cgcaggtgag gatccgcatt aggaagcttt 720
gcaagccgtt ggaagaggat tccttcaggc cagttttgca ccattatgat ggcccaaagt 780
ttcgccttga gctctccatt gcggagacct tgtcgctgct agacctatgc gagaaggaag 840
gcatctgagc tgttggggag gtggttgcct tgtgagcttc tagtaaatat caatcatcct 900
tgtatgtttt gtggatggtg gttggcaatg ttgtttattt aagcgcaagc tgctactggt 960
tccgttttcc ctaccctgga tggaaggaat gacctggtac ttggaaggcc ccctcaaaca 1020
agctgtgagc ctgtcagtgt actgcgttgt gtctgtcgtc gtcaagaacc aaaccaatct 1080
tggaccgact gagagttgga gtgtgtatgt tttgctatct atctacatgt cttagtagag 1140
tgggtatacc ttggcagaat gggtccccaa aagatggggg cctgtctgta tactatgtgt 1200
aatggttaag atgcatgtag ggccggtgat gtcgatgccg gtgctccggg tgtttatttt 1260
gtcctctgtt gtaccttgaa cctcctttgc atttgcctta atgctgctgc tttgcactgt 1320
aacggagtgt tggctt 1336

<210> SEQ ID NO 182
<211> LENGTH: 674
<212> TYPE: DNA
<213> ORGANISM: Saccharum officinarum

<400> SEQUENCE: 182
ggcagccgaa ggtggtggag gaccgccagt ggtctctcat gacgtccaag ctggcggaga 60
tcaccaggtc caagggcgag aggatgaacg acctcgacta cgcgaggatg aacaccgtcc 120
ctgacgccaa gcagtgggac aagacgtcct accagcatca cgacgagagc aggatggacc 180
acatcaacct cggcctcatg aacctggatc tcaagatgaa cgatctcaag atgaacgagg 240
ccgccaccgc catgaagctc cccttccaca acatgcccta taacatgaac ccaatgtacc 300
ccaaggggag caatgtcaat gtcaatgcgt tcaagatgaa tgttggggtg aacaagtact 360

```
ccagtagtcc taacgggaaa gacgccaatg ggaaaaacaa tggtggcagc aacaacaatg    420

gaggaaacag caatgggagc gccaacagca attctgcagt tgacaagcgc ttcaagacat    480

tgccaacgag tgagatgcta ccgaggaatg aagtccttgg tggatacatc tttgtctgca    540

acaatgatac catgcaggag gatctcaaaa ggcagctttt tggattgcca gcaagatatc    600

gtgattcagt ccgagcaatt actcctggcc tgcctctttt cctctataac tacacgactc    660

accagcttca tggg                                                      674
```

<210> SEQ ID NO 183
<211> LENGTH: 1726
<212> TYPE: DNA
<213> ORGANISM: Sorghum bicolor

<400> SEQUENCE: 183

```
aaaaattccc tgcactttat ttcatttaca tcggtggttg tatcttgcac acggttcatt     60

taccatacat acatccaaac tttcctcatc aatttttcgt cgtcaggtac ttctaataaa    120

taccaaaaac ctcgggggca gctcctcttc actgccatga ttttggaagt cgccgcagta    180

gaaactcaaa gtattgtgca cctgttcaag ccaagagacg agaagatcct cctcgcagaa    240

ggccacaagc ggccaagaag cccaggcctc tcttcctcga aggcgtactc tggttctctg    300

gtcggactat ccattgtatt tgcacctcta tcagcacttg ttgcctcatc agagcccatg    360

tcccaccctc ctcctcctcc tgttgatcaa aatatctcgc tgcgcttttg cgagtccttt    420

tccctccaag gaacagaaac acccggcgct tttaccccac ccgcacccgc tttcccctcc    480

cggccaagaa caggagcaac aacaaggctc ctcctcgaga cattccattc atccatggcg    540

aagctcgtga acaagctggt cgattcgttc gaggagcaag acaccccgga cgtcggctgc    600

gtgcgcgccg tgctggccga gctcgtcctc accttcctct tcgtcttcac cggcgtctcc    660

gccgccatgg ccgccgggtc cggcgtgaag cccggcgagg ctatgccgat ggcgacgctg    720

gcggcggtgg caatcgcgca cgcgctggca gccggcgtac tggtgacggc cgggttccac    780

gtctccggcg gccacctcaa ccccgccgtg acggtggggc tcatggtgcg cggccacatc    840

accaagctcc gggcggtgct ctacgtcgcc gcgcaggtgc tggcgtcctc cctcgcctgc    900

atcctgctcc gctacctcag cggcggcatg gtgaccccgg tgcacgccct tggcgcgggc    960

atcagcccga tgcagggcct ggtgatggag gtgatcctca ccttctccct gctcttcgtc   1020

acctacgcca tgatcctgga cccacggagc caggtccgca ccatcggccc gctgctgacc   1080

ggcctcatcg ttggtgccaa cagcctcgcc ggtggcaact tcagcggcgc gtccatgaac   1140

ccggcacggt ccttcgggcc agccctggcc agcggggtct ggacaaacca ctggatctac   1200

tggatcggcc cgctgcttgg cgggcccctg gccgggttca tctacgagtc tttgttcatt   1260

gtgaacaaga cgcacgagcc gctgctcaat ggagacatct gacgaaccat cggcctgccc   1320

tgtggctgtg ggcagggcag tcagcatggt tggttcatgc ttgtttctgt aaaatagttc   1380

attgtctaca agcatgatgg atacatatat tggtcaaggt aattagagag ggttgctgta   1440

aaatagttac cctggtatag gattgttgga tgtagaaatt gttgatgggc tttgtatttt   1500

tttccccctt ttcatgccaa ggaattcttt ttttttaga gggcggggtt ctgtcaagga    1560

tttgttaagg ctattagtag ttagccatgt agtagaaaac tagagaatgg tatacgtggg   1620

agtgggacct gaagtttttt caggtacact gtagtactat tgtaattttg tcttgaagat   1680

ggaattggat gtacagagta aaaacttctc tttcaagcag taaaaa                  1726
```

<210> SEQ ID NO 184
<211> LENGTH: 1290
<212> TYPE: DNA
<213> ORGANISM: Saccharum officinarum
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (11)..(12)
<223> OTHER INFORMATION: n is a, c, g, or t

<400> SEQUENCE: 184
nacctcccgg nncgacccac gcgtccgcct cctcctgtcg ttcaaaatat ctcgctgcgc 60
ttttccgagt ccttttccct ccaaggaaca ggaacaaccg gcgcttttac cccaccaccc 120
gctttcccct ccccgccagg aaggctcctc ctcgcaatag ttcattcatt catggcgaag 180
ctcgtgaaca agctggtcga ttcgttcgac cacgacgaga ctacgccgga cgtcggctgc 240
gtgcgcgccg tgctggccga gctcgtcctc accttcctct tcgtcttcac cggcgtctcc 300
gccgccatgg ccgccgggtc cggcgggaag cccggcgagg ctatgccgat ggcgacgctg 360
gcggcggtgg caatcgcgca cgccctggcc gccggcgtcc tggtgacggc cgggttccac 420
gtctccggcg gccacctcaa ccccgccgtg acggtggggc tcatggtgtg cggccacatc 480
accaagctcc gggcggtgct ctacatcgcc gcgcagctgc tggcctcctc cctcgcctgc 540
atcctcctcc gctacctcag cggcggcatg gtgaccccgg tgcacgccct gggcgctggc 600
atcagcccga tgcagggcct ggtgatggag gtgatcctca ccttctccct gctgttcgtc 660
acctacgcca tgatcctgga cccgcggagc caggtccgca ccatcggccc gctgctcacg 720
ggcctcatcg tgggcgccaa cagcctcgcc ggcggcaact tcaccggcgc gtccatgaac 780
ccggcgcggt cctttgggcc ggccctggcc accggggtct ggacaaacca ctgggtctac 840
tggatcggcc cactgctcgg cgggcccctg gctggcttcg tgtacgagtc gctgttcatt 900
gtgaacaaga cgcacgagcc gctgctcaat ggagacatct gacgaactat cggcctgccc 960
tgtgggcagt cagcatggtc catgcatgct tgtttctgta aaatagttca ttgtctacaa 1020
gcatgataca tacatatatt ggccaaggta attagagagg gttgctgtaa aatagctacc 1080
ctggtaggat tgttggctgt agaaattgtg gatgggcctt gtgttttttt ttccttttcc 1140
tgccatggaa ttcttttttt agagggctgg gttttgtcaa ggatttgtta aggtactttg 1200
tagaactatg ttatttttgc cttccagatg aaattggatg tacagaattg cagtattttt 1260
ggcttccaga tgaaattcga tgtgcagagt 1290

<210> SEQ ID NO 185
<211> LENGTH: 1243
<212> TYPE: DNA
<213> ORGANISM: Zea mays

<400> SEQUENCE: 185
caaaatatct ccctgcgctt ttccgagtcc ttttccctcc aaggaacaga aacaaccgga 60
gcttttaccc cacccgcttt cccctccccg ccaggaacaa cagggctcct cgcaataatt 120
cgtccatcca tggcgaagct cgtcaacaag ctggtcgatt cgttcgacca ccacgaggcg 180
ccggcgccgg acgtcggctg cgtgcgcgcc gtgctggccg agctcgtcct caccttcctc 240
ttcgtcttca ccggcgtctc cgcctccatg gccgccgggg ccggcgggaa gcccggggag 300
gctatgccga tggcgacgct ggcggcggtg gctatcgcgc acgcgctggc cgctggcgtc 360

-continued

```
ctggtgacgg ccggcttcca cgtctccggc ggccacctca accccgcggt gacggtgggg    420

atcttggttc gcggccacat caccaagctc cgggcgctgc tgtacgtcgc cgcccagctg    480

ctggcgtcct ccctcgcctg catcctcctc cgctacctca gcggcggcat ggtgaccccg    540

gtgcacgccc tgggcgctgg catcagcccg atgcagggcc tggtgatgga ggtgatcctc    600

accttctcgc tgctcttcgt cacctacgcc atgatcctgg acccgcggag ccaggtccgc    660

accatcggcc cgctgctgac ggggctcata gtcggcgcca acagcctcgc cggcggcaac    720

ttcaccggcg cgtccatgaa cccggcgcgg tccttcggtc ccgccatggc caccggggtc    780

tggaccaacc actgggtcta ctggatcggc ccgctgctcg gcgggtccct ggccggcttc    840

gtgtacgagt cgctgttcat ggtgtacaag acgcacgagc cgctgctcaa tggagacatc    900

tgacgaccgt cgggccccca gggcagtgag cacggttcat gcttgttttc tgtaaaatag    960

ttcgttacct acaagcatga tgcatatatt gaccaaggta attaatagga gagggttgct   1020

gttataccct ggtgggattg tgggatgtag aaattgttgc tgggctttgc tttttttttt   1080

acttttcctc ccaaggaatt ttttaagagg gctgggttct gtaaaggatt tgtttaggct   1140

attagttagc tatgtagtag aaaactagag aatgctatac gttggacgtg attttttttc   1200

acgtatattg ttgtacgata tggtattttt tatcttccgg atg                     1243
```

<210> SEQ ID NO 186
<211> LENGTH: 1274
<212> TYPE: DNA
<213> ORGANISM: Zea mays

<400> SEQUENCE: 186

```
aatatctccc tgcgcttttc ctagcccttt gtcatccaag gatacaataa acaaccggcg     60

cttttacacc cccgccaaga acaggagcaa caacaataag gctcctcgca acaatccatt    120

ctcatccatg gcgaagctca tgaacaagtt ggtcgattcg tttgagcacg acgagatact    180

ggacgtcggc tgcgtgcgcg ccgtgctggc cgagctcgtc ctcaccttcc tcttcgtctt    240

caccggcgtc tccgccgcca tggccgccgg atccgacggg aagcccggcg acgctatgcc    300

gatggcgacg ctggcggcgg tggcaatcgc gcacgcgctg gccgctggcg tcctggtgac    360

ggccgggttc cacgtctccg gcggccacct gaaccccgcg gtgacggtgg ggctcatggt    420

gcgcggccac atcaccaagc tccgggcggt gctgtacgtc gccgcccagc tgctggcctc    480

ctccgccgcc tgcgtcctcc tccgcttcct cagcggcggc atggtgaccc cggtgcacgc    540

cctgggcagg ggcatcagcc cgatgcaggg cctggtgatg gaggtcatcc tcaccttctc    600

cctgctcttc gtcacctacg ccatgatcct ggacccgcgg agccaggtcc gcgccatcgg    660

cccgctgctg acgggcctca tcgtcggcgc caacagcctc gccggcggca acttcaccgg    720

cgcgtccatg aacccggcac gctccttcgg cccggccctg gccaccgggg actggacaaa    780

ccactgggtc tactggatcg gcccgctgct cggcgggccc ctggcaggct tcgtgtacga    840

gtcgctgttc ctggtgcaga agatgcacga gccgctgctc aatggggaag tctgacgacc    900

atcagcccct gtgttgtggc gcatgcttca tgcttgtttc tgtaaaacag gtcattctct    960

gcaagcatgg tacatacatt ggccaaggta attagagagg cttgctgtaa agcagtagga   1020

ttgctggctg tagaaattgt tgatgggctt tttttggggg tttcctgcca aggaattctt   1080

tcttttatat aatctcaaaa aagttttttt ttttttggta tgggctgggt tctatcaagg   1140

gtttgttaag gctattagtt taccatgtag cagaaaaact agtgggacgt gaagtttttt   1200
```

```
cacgtacatt gtaatacttt ggtatttttg tctaccagat gaaactggaa gtacagagca   1260

aaaacttctc tatc                                                     1274


<210> SEQ ID NO 187
<211> LENGTH: 1160
<212> TYPE: DNA
<213> ORGANISM: Sorghum bicolor

<400> SEQUENCE: 187

gcacgaggcg gcgtcggagc ccacgaccgc ttccgcccca gtccccaccg ccctcgaccc     60

cgattccccc aatccctgcc gcgaccgctg aaccctagcc tactccggcc atctgccgct    120

ggccccggcg atcccccgcc atggcctccc ccgagggaac cacgtgggtc ttcgactgtc    180

ccctcatgga cgacctcgcg gtggccgccg acttcgcggc agcccccgcg gggggatttt    240

tctgggcagc gccgccgtcg ctacagccgc aggtggtgca ggcgccggtc cagtctgtcg    300

ttgccgcgtc ggctcccaac ccatgtgtgg aaatcagtag ctctgtggac tgtggtcagg    360

gaaaagaaca gccaacaaat aaacgtccta ggtcagaaag taccgcagaa ccaagcacaa    420

aagcatccag ggagaaaatt agaagggata agctgaacga gagattcctg gaattgggtg    480

ccattttgga gccagggaaa actcctaaaa tggacaagtc agctatatta aatgatgcta    540

ttcgtgtagt aggtgaattg cgtagcgaag caaaagagct caaggattca aatgagagcc    600

tacaagagaa gattaaagag ctaaaggctg agaagaatga gctgcgagac gagaagcaaa    660

ggctgaaggc cgagaaggag agcctggagc agcagatcaa gttcctgaat gcccgcccaa    720

gtctggtacc acaccaccca gtgatctcag cctctgcctt cactgctccc caggggccgg    780

cagtcgccgg gcacaagctg atgatgcctg tgcttggcta ccctggattc ccgatgtggc    840

agttcatgcc gccttctgat gttgacacct ctgatgaccc caagtcttgc ccacctgtgg    900

cgtaagcaag tgaagaggcg atgctgccct ccattgattc aagtctagat cgtgatcagt    960

ctgcagtgtt gttggtgtag ttgactccac tctccagaat ggaagggaag gttatatgtg   1020

tcggatggtg acatggggtg atctgatgac ccctttgtat attatatggt aaatgaataa   1080

attccgtgac cagttgcaaa tgaggattag cagactagct catgtctatt cctgcctttt   1140

tgtcgtataa accacgttgt                                               1160


<210> SEQ ID NO 188
<211> LENGTH: 1242
<212> TYPE: DNA
<213> ORGANISM: Zea mays

<400> SEQUENCE: 188

ccacgcgtcc gggctacacg gcctatattc cgtactcgtg aacctcgtgc tgacgtgctc     60

acacagtcac tccgtttagc tcaaatcctt atcggcgact cggcgtcgga gctcacgacc    120

acgaccgctt ccacgccctc gaccccgaac ccccaatccc ggacgcgacc gctgaaccct    180

agcatactcc ggccatctgc tgccggcccc ggcgatcccc cgccatggcc tcccccgagg    240

gcacaacgtg ggtcttcgac tgtcccctta tggacgacct cgcggtcgcc gccgacttcg    300

cggcagcccc cgcgggagga tttttctggg cagcgccgcc gtcgctgcag ccgcaggcgc    360

cagtgcagtc tgtcgttgcc gcgtcggctc ccaacccatg tatggaaatc agtagctctg    420

tggactgtgg tcaggaaaaa gaacagccaa caaataaacg tccaaggtca gaaagtacta    480

cagaatcaag cacaaaagca tccagggaga aaattagaag ggacaagctg aacgagagat    540

tcttggaatt gggtgccatt ttggagccag ggaaaactcc taaaatggac aaaacagcta    600
```

tattgagtga tgctattcgt gtagtaggtg aattgcgtag tgaagcaaaa aagctcaagg 660
attcaaatga gaatctccaa gagaagatta aagagctgaa ggccgagaag aatgagctgc 720
gagacgagaa gcaaaggctg aaggccgaga aggagagcct ggagcagcag atcaagttcc 780
tgaatgcccg gccaagcctc gtaccacacc acccagtgat cccagcctct gcgttccctg 840
ctccccaggg gccagcagcc gccgccaggc acaagctgat gatgcctgtg attggctacc 900
ctggattccc gatgtggcag ttcatgccgc cttcagatgt tgacacctct gatgacccta 960
ggtcttgtcc tcctgtggcg tagaagccgt gcgaaatcct gttggaaaga ggcgatgctg 1020
ccttccattg attcaaatct tgatcggtcc gcagtgttgt tggtgtagtt gattccagaa 1080
ctgaagggga tgttacatgt gtcggacggt gacatggggt gatctgatga ccccttttgta 1140 tattatatat ggtatggtat aaataaattc cgcgaccaga agctaatgtg gatcggtgga 1200
ttaacttatg ttctattctt gcctgtttgt cctataaccc ac 1242

<210> SEQ ID NO 189
<211> LENGTH: 706
<212> TYPE: DNA
<213> ORGANISM: Saccharum officinarum

<400> SEQUENCE: 189
cgtagtgacc gggtcgaccc acgcgtccgc cgccctcgac cccgaatccc ccaatccctg 60
acgcgaccgc tgaaccctag cctactccgg ccatctgccg ctggccccgg cgatcccccg 120
ccatggcctc ccccgaggga accacgtggg tcttcgactg tccccttatg gacgacctcg 180
cggtggccgc cgacttcgcg gcagcccccg cggggggatt tttctgggcg gcgccgccgt 240
cgctgcagcc gcaggtggtg caggcgccgg tgcagtctgt cgttgccgcg tcggctccta 300
accccccatg tgtggaaatt agtagctctg tggattgtgg tcagggaaaa gaacaaccaa 360
caaataaacg tcctaggtca gaaagtactg cagaaccaag cacaaaagca tccagggaga 420
aaattagaag ggacaagctg aacaagagat tcctggaatg gggtgccatt gtggagccag 480
gggaaactcc taaaatggac aaatcagcta tattgaatga tgctattcgt gcagtaagtg 540
aattgcgtag cgaaacaaaa aagctgaagg actcaaatga gagtttgcag ggagaagatt 600
aaagagctga aggctgagaa gaatgagtcg cgagacgaga agcaaaggct gaaagccgag 660
aacgagagcc tggagcagca gatcaagttc ctgaatgccc gcccaa 706

<210> SEQ ID NO 190
<211> LENGTH: 658
<212> TYPE: DNA
<213> ORGANISM: Brassica napus

<400> SEQUENCE: 190
gaactcatct catcgagaca gggaaacaaa ccctagttcg tcaagatggg gcgtatgcat 60
tcgagaggaa agggtatctc cgcatctgcg ttgccgtaca agcgctcacc tccgacatgg 120
ctcaagacca cggcccttga tgttgatgag tcgatctgca agtttgcgaa gaagggtttg 180
acaccatctc agattggtgt gattcttcgt gactctcacg gtatccctca ggtgaagagt 240
gtcaccggaa acaagatctt gcgtattctc aaagctcacg gtcttgcacc tgagattcct 300
gaggatctgt accatttgat caagaaggca gttgctatcc gcaagcactt ggagaggaac 360
aggaaggaca aggattccaa gtttaggttg attcttgttg agagcaggat ccaccgtctt 420
gcccgttact acaagaagac caagaagctt cctcctgtct ggaagtacga gtctactact 480
gcttctaccc ttgtggctta gatcatggtc aagagcacta ctgtttcttt tggctgtctt 540
attatgaact tagtttctat gcttctcagt acttggtttg gtcaagtgac aatgacgttt 600
ggatgatttc aaggaaccaa tgtgtttcaa tctatggtca gaattgctta tgccgggt 658

<210> SEQ ID NO 191
<211> LENGTH: 671
<212> TYPE: DNA
<213> ORGANISM: Brassica napus

<400> SEQUENCE: 191
gctcttcacg cgcagctgct acgagctcat cgagacagtg aagaaactct tagttgttca 60
agatggggcg tatgcactca agaggaaagg gaatctccgc atctgctttg ccgtacaaac 120
gttcacctcc gacatggctc aagaccaccg cactcgatgt tgatgagtcg atttgcaagt 180
ttgcaaagaa gggtttgaca ccatctcaga ttggtgtcat tctccgggac tctcacggta 240
tccctcaggt caagagcgtt accggaaaca agatcttgcg tattctcaaa gcacacggtc 300
ttgctcctga gattcctgag gatctgtacc atttgatcaa gaaagcagtt gctatccgca 360
agcacttgga gaggaacagg aaagacaagg attccaagtt caggttgatt cttgtcgaga 420
gcaggatcca ccgccttgct cgctattaca agaagaccaa gaagcttcct ccagtctgga 480
agtacgagtc tactactgcc tccacgcttg ttgcttagag agcatgaagt gcatggattg 540
aagtggagtt gttggtcgtt tctattcgta tcaactagag ttgttttttt ttctcatttt 600
cgttttattg tttgtttttt caagttacaa ttgtggtttt gatgatttca aggaaaaaaa 660
ctttttaact t 671

<210> SEQ ID NO 192
<211> LENGTH: 713
<212> TYPE: DNA
<213> ORGANISM: Solanum tuberosum
<220> FEATURE:
<221> NAME/KEY: misc_feature
<222> LOCATION: (13)..(13)
<223> OTHER INFORMATION: n is a, c, g, or t

<400> SEQUENCE: 192
gttgctgtac cgncgcacat cggagcacgc cgtcagccac catgggtcgt atgcacagtc 60
gaggtaaggg tatttcagct tcagcacttc cgtataagag gactccaccg agttggttga 120
aaacatctgc tcccgatgtt gaggataata tatgcaagtt tgccaagaag ggtttgacac 180
cttctcaaat tggtgttata cttcgtgatt ctcatgggat tgctcaggtg aagagtgtaa 240
ctggtagcaa gattctcaga attttgaagg ctcacggact tgctcctgag attccggagg 300
atctctatca ccttatcaag aaggccgttg caatccggaa gcatcttgag agaaacagga 360
aagacaaaga ttccaagttt aggttgattc ttgttgagag caggattcac cgacttgctc 420
gttactataa gaaaaccaag aagcttcccc cagtctggaa gtatgaatct accaccgcca 480
gtactctcgt ggcatagaga agactctgct tttgcggtca aattttgcct ccaaagttca 540
atattaagtc ggaactgcca ggatgcttaa ttgagaaata aaactgttaa gatattggtg 600
atgatttagt tgtttttga gttggtattt aattcccttt tctttcttta gatgttgtga 660
tatattcaaa tcttggctgc ttatgtttaa tagttgatct taccaaaaaa aag 713

<210> SEQ ID NO 193
<211> LENGTH: 694
<212> TYPE: DNA
<213> ORGANISM: Gossypium hirsutum

<400> SEQUENCE: 193
aagcaagaaa ggagcagagg ttaattaaac cgagagagaa gcagccgtaa agctcgaaac 60
tctgtcgcca tgggtcgtat gcatagccga ggtaagggta tttccgcatc tgctcttccg 120
tacaaaagaa ctccacctag ttggctcaag atctcctctc aagatgtgga ggagaacatt 180
tgcaagtttg cgaagaaggg tttgacccca tctcaaattg gtgtcattct ccgtgattca 240
catgggattg ctcaggtgaa gagtgttacg ggcagcaaga ttttgcggat actgaaagcc 300
catggtctcg ctcctgaaat tcccgaagat ttgtaccacc tgattaagaa agctgttgcc 360
atcagaaagc atcttgagag gaaccgcaaa gacaaggatt ccaagttccg gttgatcctg 420
gttgagagca gaatccatcg ccttgcccgc tattataaga agacaaagaa gcttccaccc 480
gtctggaaat acgagtcgac tactgccagc acacttgtgg cctaagggaa gacactgctg 540
gaaccagctt cttgggcttt gattgatgga cgcctggata tgggttggag tagtaaagtt 600
ttaattacat gctatattta tgcttttaaa gaaccagttc acattatggt tggaaattga 660
tatacttagg agggataata ttatgtttag tgat 694

<210> SEQ ID NO 194
<211> LENGTH: 757
<212> TYPE: DNA
<213> ORGANISM: Gossypium hirsutum

<400> SEQUENCE: 194
tgagccagcc agccagccag ccaagcaatc gagctcggaa ctccgcaacc atgggtcgta 60
tgcacagccg aggtaagggt atttccgcat ctgctctgcc ctacaagagg actccaccaa 120
gttggttgaa gatctcttct caagatgtgg aggagaacat ttgtaagttt gcaaagaaag 180
gtttgacccc atcacaaatt ggtgtcattc tccgtgattc tcacgggatt gctcaggtga 240
agagtgttac aggcagcaag attttgcgga tactgaaagc ccacggactt gctcctgaaa 300
tccccgagga tctgtaccac ttgatcaaga aagccgttgc catcagaaag catcttgaga 360
ggaacaggaa agacaaggat tccaaattca ggttgatctt ggtcgagagc agaatccatc 420
gtcttgcccg ctattacaag aaaacaaaga agctcccacc cgtgtggaaa tatgagtcaa 480
ccaccgccag tactcttgtg gcttagggca gccacatttt tgaaccagtt tcctggtgct 540
tcaatagcga ttcgcctttg acttttagct aatggtggtt tgaaattgag aggggaaata 600
ttatgtttag tgtattagaa taattgatat ttttttcgtt tgaaatgttt ttgaatctta 660
atggttacat ggaattgttt tcttaatatt tttggcttac aaattttaat gtagtatgaa 720
attaaattaa aataattcga aggagaatat taatact 757

<210> SEQ ID NO 195
<211> LENGTH: 767
<212> TYPE: DNA
<213> ORGANISM: Lycopersicon esculentum

<400> SEQUENCE: 195
aaaccctaga agaagaaaga gccttttaag gtttgtcaac ttccatcaac caaacgaagc 60
tacaatttga gcaacacagt tcagtgagct cactctaatc ttcgccatgg gtcgtatgca 120
cagtcgcggt aagggtatct cagcgtcggc tcttccttac aagagaactc ctccaagttg 180
gcttaagatc tctgctccag atgtggagga caatatctgc aagtttgcga aaaaaggact 240
gacaccttca caaattggtg tgattcttcg tgattctcat ggaattgctc aagtcaagag 300

```
tgtcaccggg agcaagattt tgcgtatcct caaagctcac ggacttgctc ctgagattcc    360

ggaggatcta taccacctta ttaagaaggc agttgccatc aggaagcatt tggagaggaa    420

cagaaaggac aaggattcca agttccgctt gattttggtg gagagtagga ttcaccgcct    480

tgctcgttat tacaagaaaa ctaagaagct accacctgtc tggaaatatg agtctaccac    540

agcaagtaca ctagtagctt aaactgagac atggatggat tattagcttt gagaagaaag    600

attgatcagc tgaagtcttt tcttctctat gtattcgaat agttctcagg tccatttttt    660

tgaattctga tacttataga tgctttaatt tgggtattga tgtcaatttc tttcgactac    720

ctcgatgaat atcaagcctc tactcagcct ttttcttgtt caccctc                  767


<210> SEQ ID NO 196
<211> LENGTH: 717
<212> TYPE: DNA
<213> ORGANISM: Lycopersicon esculentum

<400> SEQUENCE: 196

cggccggggg tcattttaga gatttcgctg ctacttatag ccaatcggag cgcggcagcc     60

accgtcacac caccaaccag ccaccatggg tcgtatgcac agtcgaggta agggtatttc    120

agcttcagct cttccataca agaggactcc accaagttgg ctgaaaatct ctgctcctga    180

tgttgaggat aacatatgca agttcgccaa aaaaggtttg acaccttctc aaattggtgt    240

tattcttcgt gattctcatg ggattgctca ggtgaagagt gttactggta gcaagattct    300

cagaattttg aaggctcatg gacttgctcc cgagattccc gaggatctct accaccttat    360

caagaaagca gtggcaatca ggaagcatct tgagaggaac agaaaagaca aggactccaa    420

gtttagattg attcttgttg agagcaggat tcatcgactt gctcgctact ataagaaaac    480

aaagaagctt ccaccagtct ggaagtacga gtctaccacc gcgagtactc ttgtggctta    540

gagaaggtca tggattggga ttacaagttt gttggtcaag tcccatcttc ataattacag    600

acttaagttg tttttgtatg agagaccagg ttgtttgaaa ctttgaatgg aacaaatttt    660

gttttatgag agatgataag gggaacgttt cctactttaa atttgcatcc aattctt       717


<210> SEQ ID NO 197
<211> LENGTH: 767
<212> TYPE: DNA
<213> ORGANISM: Lycopersicon esculentum

<400> SEQUENCE: 197

gtccattcta gggtttcctt cttcagagct aaccggacag cagccccaga aacacaccgg     60

cagcgaagat gggtcgtatg cacagtcgag gtaagggtat ttctgcttca gcactcccat    120

acaagaggac tccaccaagt tggctcaaaa tatctgcacc agatgttgaa gataacatct    180

gcaagtttgc caaaaaaggt ttaacaccct ctcaaattgg tgttattctt cgtgattccc    240

atggcattgc tcaggtgaag agtgtaactg gtagcaagat tctcagaatt ttgaaggctc    300

atggacttgc tcctgagatt cccgaggatc tctaccacct tatcaaaaaa gcagttgcaa    360

tccggaagca tcttgagaga aacaggaaag acaaggattc caagtttagg ttgattcttg    420

ttgagagcag gattcaccga cttgctcgct actacaagaa aacaaaaaag cttccaccag    480

tctggaagta tgaatctacc actgccagta ctcttgtggc ataagagatg acaaaaggag    540

cattcagagt gctactttct ttgccaagtc atatcttaga aattctacat taagctgttt    600

tggcatggcc aggatacttg atttggtgaa caaattatgt actcgaggag atgataggg    660

gcttcacgta atttcttgtt tgagattttg acattgagac ttgttatctg tggtatactt    720
```

```
attttagttt agctatgttt taattatcat cttgtgaaaa tctcgat                767

<210> SEQ ID NO 198
<211> LENGTH: 820
<212> TYPE: DNA
<213> ORGANISM: Lycopersicon esculentum

<400> SEQUENCE: 198

aaatccttcc gcacaaccaa aggtaagcct ccattgcaga ccaccagtag cctccgccat     60

catgggtcgt atgcacagtc gtggtaaggg tatttcagct tctgctctcc cttacaagag    120

aactcctcct agttggctca agatctctgc tccagatgtt gaggacaaca tctgcaagtt    180

cgctaagaaa ggattgaccc cttcacagat tggtgtgatt cttcgtgatt ctcatggaat    240

tgcacaagtg aagagtgtta ctggtagcaa gatcttgcgt atcctcaagg cacatgggct    300

tgcacctgag attccagagg atttgtacca cctgattaag aaggctgttg ccattaggaa    360

gcatttggag aggaacagga aggataagga ttctaagttc cgtttgattt tggtggagag    420

caggattcat cgccttgctc gttattacaa gaaaacaaaa aagctcccac ctgtctggaa    480

atacgaatct accactgcta gcacacttgt ggcataggct gagacgtgag ctggagtagc    540

tttggctgat cgcaatatgt agttttcttg tgtcatgaac tgtttgctat atccaatttt    600

gtttgattta atcatgctac tcaatggaaa atagttttct ggatagtatt tgctcctatt    660

tttaccaagt gttaagcata gatgctttta tttagatatt caaatgaatg acttgtttct    720

caagctcatg gtggtaatct gtaatttgga ttgctgaaaa ttgtggttta atgcctcatc    780

attctatgtt catggcagtg aagtaccact tttaaagcag                          820

<210> SEQ ID NO 199
<211> LENGTH: 834
<212> TYPE: DNA
<213> ORGANISM: Solanum tuberosum

<400> SEQUENCE: 199

ccgaccgaag ctacgctttg agcaacacag ttcagtgagc tcactctaat cttcgccatg     60

ggtcgtatgc acagtcgcgg taaaggtatc tcagcgtcgg ctcttcctta caagagaact    120

cctcccagtt ggcttaagat ctccgctcca gatgttgagg acaatatctg caagtttgcg    180

aaaaaaggat tgacaccttc acaaattggt gtgattcttc gtgattctca tggaattgct    240

caagttaaga gtgtcactgg gagcaagatt ttgcgtatcc tcaaagctca cggacttgct    300

cctgagatcc cggaggatct ataccacctt attaagaagg cagttgccat caggaagcat    360

ttggagagga acagaaagga caaggattcc aagttccgct tgattttggt ggagagtagg    420

attcaccgcc ttgctcgtta ttacaagaaa actaagaagc ttccacctgt ctggaaatat    480

gagtctacca cagcaagtac acttgtagct taaactgaga catggatgga ttattagctt    540

tgagaagatt gatcagctga agtcttcttc tctatgtatt cgaatagttc tcaggtccat    600

ttttttgaat tttgatactt aatggtgata gtttctggat actttctcca acttttacta    660

aatgttatgc atagatgctt taatttgggt attgatgtca atttctttcg actactcgat    720

aaatatccag ctctactcaa ccttttctgg ttcaccccaa caaaaaaaaa aaaaaaaatg    780

cccaacttta cccgtggcaa tgcccgcgca gacttaaaca agatgaagtg ttta          834

<210> SEQ ID NO 200
<211> LENGTH: 815
<212> TYPE: DNA
```

<213> ORGANISM: Solanum tuberosum
<220> FEATURE:
<221> NAME/KEY: misc_feature
<222> LOCATION: (28)..(28)
<223> OTHER INFORMATION: n is a, c, g, or t

<400> SEQUENCE: 200
attcttcata gcgaaccggg acagcagncc caggaaacac acctgcagcc aagatgggtc 60
gtatgcacag tcgaggtaag ggtatttctg cttcagcact cccatacaag aggactccac 120
caagttggct caaaatatct gcaccagatg ttgaagataa catctgcaag tttgccaaaa 180
aaggtttaac accctctcaa attggtgtta ttcttcgtga ttcccatggc attgctcagg 240
tgaagagtgt aactggtagc aagattctca gaattttgaa ggctcatgga cttgctcccg 300
agattcccga ggatctctac caccttatca aaaaagcagt tgcaattcgg aagcatcttg 360
agagaaacag gaaagacaag gattccaagt ttaggttgat tcttgttgag agcaggattc 420
accgacttgc tcgctactac aagaaaacaa aaaagcttcc accagtctgg aagtatgaat 480
ctaccactgc cagtactctt gtggcatgag agaagacaac gggagcattc agattgctac 540
tttcttcgcc aagtcatatc ttagatattc tatattaagc tgttttggca tgtccaggat 600
acttgaaatc gtaaacaaaa ttatgtactc gaggagatga tagggcctcc ttttagtttc 660
ttgtttgaga ttttgacatt gagactttgt tatctgtggt atacttcttt tggtttagct 720
atgttttaat tatcatgttg cgaaattctc ggtaaagcta gaaatgctgg gatatggtta 780
tactcgccgc tctggtctgt ggacctgtgc ccagc 815

<210> SEQ ID NO 201
<211> LENGTH: 959
<212> TYPE: DNA
<213> ORGANISM: Solanum tuberosum

<400> SEQUENCE: 201
ctttcaagaa aaatccttcc gcacaaccca aggtaagcct ccattgcaga ccaccagtcg 60
ccaaccctaa ctccgccatc atgggtcgca tgcacagtcg tggtaagggt atttcagctt 120
ctgctctccc ttacaagaga actcctccta gttggctcaa gatctccgct ccagatgttg 180
aggacaacat ttgcaagttc gctaagaaag gattgacccc ttcacagatt ggtgtgattc 240
ttcgtgattc tcatggaatt gcacaagtga agagtgttac tggtagcaag atcttgcgta 300
tcctcaaggc acacgggctt gcacctgaga ttccagagga tttgtaccac ctgattaaga 360
aggctgttgc catcaggaag catttggaga ggaacaggaa ggataaggat tccaagttcc 420
gtttgatttt ggtggagagc aggatccatc gccttgctcg ctattacaag aaaacaaaaa 480
agctcccacc tgtctggaaa tacgaatcta ccactgccag cacacttgtg gcatagggtg 540
agacttgagc tggagtagct ttggctgatc gcaatatgta gttttcttgt gtcatgaatt 600
gtttgctaaa tccaattttg tttgatttaa tcatgctact caatggaaga tagttttctg 660
gatagtattt gctcctattt ttaccaagtg ttaagcatag atgcttttat ttagatattc 720
gaatgaatga cttgtttctc aagctcatag tggtaacatg aaagccaata tccaactggt 780
ctggctgctc tgtaatttgg attgctgaaa attatggttt aatgctcttc actttatgtg 840
catggcagtg aagtaccatt tttaagccta aaggggtcgt tattctgtga ttatattctt 900
gggattgtaa tccttcgact aagcttgagt tatttcatga ttaagcttgg attaaattt 959

<210> SEQ ID NO 202
<211> LENGTH: 940

<212> TYPE: DNA
<213> ORGANISM: Solanum tuberosum

<400> SEQUENCE: 202
agccaaccgg agcgcggcag ccaccgtcac accgccaaac agccaccatg ggtcgtatgc 60
acagtcgagg taagggtatt tcagcttcag ctcttccata caagaggact ccaccaagtt 120
ggctgaaaat ctctgctcct gatgttgagg ataacatctg caagtttgcc aaaaaaggtt 180
tgacaccttc tcaaattggt gttattcttc gtgattctca tgggattgct caggtgaaga 240
gtgtcactgg tagcaagatt ctcagaattt tgaaggctca tggacttgct cccgagattc 300
ccgaggatct ctaccacctt atcaagaaag cagtggcaat caggaagcat cttgagagga 360
acaggaaaga caaggactcc aagtttagat tgattcttgt tgagagcagg attcatcgac 420
ttgctcgcta ctataagaaa acaaagaagc ttccaccagt ctggaagtac gagtctacca 480
ccgcgagtac tcttgtggct tagagaagat catggattgg gattacaagt ttcttggtca 540
agtcccatct tcaaaattac agacttgagt tgtttttgta tggccgggtt gtttgaaact 600
atgaatggaa caaattttgt tttatgagag atgataaggg ttacatttcc taaaaaaaaa 660
aacctcgtgc cgaattcggc acgaggatga aaactgccac tcaactcgat cctctcaaag 720
ttgaatttat caatgatgta cattaacaaa atccaatatc aaagtatgta ttcctaaatt 780
attgtaatgc tttcataata cttaattcac tttcttttcc aaaatattcg ggtccaatat 840
ttttgcagtg attgtggcat gtacacatgt atattcgatg aatgtatacg caatgacgtt 900
ttttatatgg gtcacattga cattgatgtc aaatatcctc 940

<210> SEQ ID NO 203
<211> LENGTH: 765
<212> TYPE: DNA
<213> ORGANISM: Capsicum annuum

<400> SEQUENCE: 203
gctttgagaa aaaaatcctt gcgaacaacc aaaggtaagg cagaccaccc caaagtaagg 60
catcatgggt cgcatgcaca gtcgtggtaa gggtatttca gcttcggctc tcccttacaa 120
gagaactcct cctagttggc tcaagatctc cgctcctgat gttgaggaca acatttgcaa 180
gttcgctaag aaaggattga caccttcaca gattggtgtg attcttcgtg attcacacgg 240
aattgctcaa gttaagagtg tcactggtag caagatcttg cgtatcctca aggcccacgg 300
gctcgcacct gagattccag aggatctgta ccacctgatt aagaaagctg ttgccattag 360
gaagcatttg gagaggaaca ggaaggacaa ggattccaag ttccgattga ttttggtcga 420
gagcaggatc catcgccttg ctcgctatta caagaaaact aaaaaactcc cacctgtctg 480
gaaatacgaa tctaccactg ccagcacact ggtggcatag ggtgaaacgc gagctggagt 540
agctttggct gatggcgata tgtagttttc tcgtgtcatt gcttacttgc taaatccaat 600
tttgtttgat tcgatcgtgc tactcaatgg aagagagtct tgctgtgttt acccaagtat 660
tgaggataga tgctttcatt cacatattca tatgaatgac tttgtttctc aagctcaaaa 720
aaccaatgtc catctggtat ggctgctccc taatttggcc tgcag 765

<210> SEQ ID NO 204
<211> LENGTH: 723
<212> TYPE: DNA
<213> ORGANISM: Arabidopsis thaliana

<400> SEQUENCE: 204

```
gagccagaat tagggtttct ctttgtcttc agcagtcagt gcgcatccgt aggagaaaag     60

tgtgagaatc tgccaccatg ggtcgtatgc acagtcgagg aaagggtatt tcagcctctg    120

cgttgcctta caagagatcg tctccgagct ggctcaagac cacctctcag gatgttgatg    180

aatcaatctg caaatttgcc aaaaagggat tgaccccttc ccagattggt gtgattctcc    240

gtgactctca cggtatccct caggtcaaga gtgttactgg aagcaagatc ttgaggatac    300

tcaaagctca tggccttgct cctgagatcc ctgaggatct gtaccatcta attaagaagg    360

ctgttgccat ccgtaaacat ctcgagagga acaggaagga caaggattcc aagttcaggc    420

tcatcttggt tgagagcagg attcaccgcc tcgctcgcta ttacaagaag accaagaagc    480

tccctcccgt ctggaagtac gaatccacta ccgcgagcac ccttgtggct taagctggag    540

tctggaggag gattctacta gtctgttgct tcccttttgt tttgatgaat tctcaacttt    600

agtcttaatg tgtcagcagg atttttgtgt ttgcctctct ttttttccg gaatcttatg    660

ctcccttgtt taagagaatc gtatgatctt gaatttacta ttgaatatgc ttttgcatca    720

aaa                                                                  723

<210> SEQ ID NO 205
<211> LENGTH: 669
<212> TYPE: DNA
<213> ORGANISM: Brassica napus

<400> SEQUENCE: 205

gacacagtcg ccgccggaaa aaaaccgagg aagaaccatc ttcagagaaa gtacactccg     60

tccaccgccg tcgtcatggg ccgactccac tctaaaggta agggaatctc agcttctgct    120

ttgccgtaca agcgatcacc tccaagttgg ctcaagacaa cctctcagga tgttgatgag    180

tcaatctgca agtttgcgaa gaagggtttg actccatctc agattggtgt cattcttcgt    240

gactctcacg gtatcccaca agtgaagagt gtaaccggaa acaagatttt gagaatcttg    300

aaagctcatg gtcttgctcc tgagatccca gaggatttgt atcacctgat caagaaagca    360

gttgctatcc gcaagcacct tgagaggaac aggaaagaca aggattccaa gttcaggttg    420

attctcgtgg agagcagaat ccaccgtctt gctcgttact acaagaagac caagaagctc    480

ccacctgtct ggaagtatga gtccaccacg gcaagcactc ttgtggctta aggaaaagca    540

tagagtaggt caaagtcatt catgagcgac tatgtcatta caagggactt ggtatctcat    600

ttctctagtt ttgatgtgtt acaacttaca aggcgatttg gaatttaatg aaaactcttt    660

gttcttgtc                                                            669

<210> SEQ ID NO 206
<211> LENGTH: 675
<212> TYPE: DNA
<213> ORGANISM: Brassica napus

<400> SEQUENCE: 206

gaagcgcagt cgcagccgga cgaagaacag acagcaacaa acgtcggcat ggggcgactc     60

cactccaaag gtaagggaat ctcagcatct gctttgccgt acaagcgttc acccccgagc    120

tggctcaaga caacctccga ggatgttgat gaatccattt gcaagtttgc gaagaagggt    180

ttgactccgt ctcagattgg tgtgattctt cgtgactctc acggtatccc tcaggtgaag    240

agtgttaccg ggaacaagat tctgagaatc ttgaaagctc atggtcttgc tcctgagatc    300

cctgaggatc tgtaccacct gatcaagaaa gcagttgcta tccgcaagca ccttgagagg    360

aacaggaagg acaaggactc caagttcagg ttgattcttg ttgagagcag aatccaccgt    420
```

```
cttgctcgtt actacaagaa gaccaagaag ctccctcccg tctggaagta cgagtcaact    480

accgcaagca ctcttgtggc ttgagtaatc atagagcttg tcaaagtcct tcatgaacta    540

caatttgatt gctgcatttg caactctatt tctatgacga tggattttgt atctgttttt    600

tttatggttt ttgtggggtt tacaacttaa caatgcgaat tttgaattga atgaatactt    660

ttgataaaaa aaaat                                                     675


<210> SEQ ID NO 207
<211> LENGTH: 713
<212> TYPE: DNA
<213> ORGANISM: Brassica napus
<220> FEATURE:
<221> NAME/KEY: misc_feature
<222> LOCATION: (700)..(700)
<223> OTHER INFORMATION: n is a, c, g, or t
<220> FEATURE:
<221> NAME/KEY: misc_feature
<222> LOCATION: (710)..(710)
<223> OTHER INFORMATION: n is a, c, g, or t

<400> SEQUENCE: 207

ctctttagcg cagtcgcagc ccgaccaaac cgaagaagaa ccttctcaga gtaaagcaat     60

ctccgttaac ttacgtcagc atggggaggc tccactctaa aggtaaggga atctcagcat    120

ctgctttgcc gtacaagcgc tcacccccga gctggctcaa gacaacctcc caggatgttg    180

atgagtccat ttgcaagttt gcgaagaagg gtttgacacc atctcagatt ggtgtcattc    240

ttcgtgactc tcacggtatc cctcaggtga agagtgttac cggaaacaag attttgagaa    300

tcttgaaagc tcatggtctt gctcctgaga tccctgagga tctctaccac ctgattaaga    360

aagcagtggc tatccgcaag caccttgaga ggaacaggaa agacaaggac tccaagttca    420

ggttgattct tgtcgagagc agaatccacc gtcttgctcg ttactacaag aagaccaaga    480

agctccctcc cgtttggaaa tacgagtcta ccacagcaag cactcttgtg gcttaaggaa    540

tcatagagct ggtcaaagtc tttcatgaac atccatttca tttccattgc aactcaaaag    600

ttctatgaca atagactttg tatctgtttt tgatagtttt gattattttg aatttaatga    660

aaactctcgt tgatgttttg tttcatttat cttaacgagn ctacaattgn gcc           713


<210> SEQ ID NO 208
<211> LENGTH: 618
<212> TYPE: DNA
<213> ORGANISM: Gossypium hirsutum

<400> SEQUENCE: 208

aatcagccga gctcgaaact ctgccaccat gggtcgtatg cacagccgag gtaagggtat     60

ttccgcatcc gctttgcctt acaggagaac tcctcctagt tggttgaaga tctcttctca    120

agatgttgag gagaacattt gcaagtttgc aaagaagggt ttgactccat ctcaaattgg    180

tgtcattctc cgtgattctc atggcattgc tcaggtgaag agtgttactg gcagcaagat    240

tttgcgaata ttgaaagccc atggtcttgc tccagaaatc cctgaggatc tgtaccacct    300

gattaagaaa gcggtagcca tcagaaagca cctcgagcgg aacaggaaag acaaggattc    360

caagtttagg ttaatcttgg ttgagagcag aattcaccgt cttgcccgtt attacaaaaa    420

gacaaagaag ctaccaccag tgtggaaata tgaatctacc actgccagca ctcttgtggc    480

ttagaggtgg cacagtttga accatcttcc aagcgctgca gttgacattc tccttgatgc    540

agggctaaac ttttggtatt tatgctttta aaatttaaag aactagttca tttgtggttt    600
```

gaaaatgaga tacttggg 618

<210> SEQ ID NO 209
<211> LENGTH: 727
<212> TYPE: DNA
<213> ORGANISM: Gossypium hirsutum

<400> SEQUENCE: 209
gtttcttttc tcttagcaat tagcaggcaa tacagaatca gagtgaagca gctaagcttg 60
gaattcttcc atcatgggtc gtatgcacag ccgaggtaag gggatttctg catctgccct 120
gccttacaag aggactccac ctagttggtt gaagatctcc tctcaagatg ttgaggataa 180
catttgcaag tttgctaaga agggtttgac cccatctcaa attggtgtca ttctccgaga 240
ttctcatggg attgctcagg tgaagagtgt tactggcagc aagattctgc gcatactgaa 300
agcccatggt cttgctcctg aaatacccga ggatctgtac cacctgatta agaaagccgt 360
tgccatcaga aagcatcttg agaggaaccg aaaagacaag gattccaagt ttaggttgat 420
cttggttgag agcaggatcc accgactcgc ccgctattat aagaagacaa agaagctgcc 480
accagtgtgg aaatatgagt ctactactgc cagcactctt gtggcctaga taaatcaaat 540
tttgaactgt cttcctgtgc ttcgattgat attcttctgg atcggctagg aggagttgga 600
ctttttgtat tacgttctat taatgccgta aaagaactag tccacttaat ttgaagttga 660
gatacttaat gtgttaaatc ttatgtttag tatattggaa taattcatct ttcatttcat 720
ttttcat 727

<210> SEQ ID NO 210
<211> LENGTH: 1125
<212> TYPE: DNA
<213> ORGANISM: Gossypium hirsutum
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(46)
<223> OTHER INFORMATION: n is a, c, g, or t
<220> FEATURE:
<221> NAME/KEY: misc_feature
<222> LOCATION: (49)..(49)
<223> OTHER INFORMATION: n is a, c, g, or t
<220> FEATURE:
<221> NAME/KEY: misc_feature
<222> LOCATION: (61)..(61)
<223> OTHER INFORMATION: n is a, c, g, or t
<220> FEATURE:
<221> NAME/KEY: misc_feature
<222> LOCATION: (63)..(63)
<223> OTHER INFORMATION: n is a, c, g, or t
<220> FEATURE:
<221> NAME/KEY: misc_feature
<222> LOCATION: (67)..(67)
<223> OTHER INFORMATION: n is a, c, g, or t

<400> SEQUENCE: 210
atcacacatt ctatatatcg aatgttcaaa ctattaattc nntnnnttna aaatagaaca 60
ntngtangaa acaattggag ctcccgcgca cggctgtcca cactagtgca tccaaataat 120
tcggcccgag gtacttcgtc acaatctcgg gaaagagaga agcctcacca ccgctgccgc 180
agccaccatg ggtcgtatgc acagtcgcgg taagggtatt tcagcctcag ctctgcctta 240
caagaggacc ccgccaagct ggctcaagat ctcttctcaa gatgttgagg aaaacatttg 300
caagttcgca aagaaaggct tgaccccatc tcagattggt gtcattctcc gtgattctca 360

```
tggtattgct caagttagga gcgttactgg cagcaagatc ttgcgtatcc tcaaggctca    420

tggtctggcc cctgaaattc ctgaggattt gtatcacctt atcaagaagg cagttgccat    480

ccgcaagcat ttggagagaa acaggaagga caaggattcc aagttcaggt tgatccttgt    540

tgagagccgg attcacaggc ttgctcgcta ctacaagaaa acaaagaagc ttcccccggt    600

ctggaaatac gaatctacaa cagccagcac tctcgttgct taagttaggc atgtggggtg    660

gtgcaatttt gtgggaatcc gggtttgatg ttgatgctac ggtggaagct agattgtgtt    720

ttgttgttct agtgagatgt cctgatataa gactttaatt atagctgtta aaatttttgt    780

tatgcttgga aaagaaagtc gaaaacttgt tttacttatg agattgtact tgttttcttt    840

tcgtccattt gaaattttaa gcaagaaatc tttgaatttt gaaaccctag tacacccttt    900

tcctataagg gttctcgaaa tggaaagggt tggtgtttga agaggcattt ttgtgttcaa    960

catcggtttt gttcaaaacc ttcacatgga ctttggtttt aaaacaattt ctccttcatc   1020

tccttcaagg tgctgacatg ctatgttgaa cgtataaatt atttgttgta aactagcgta   1080

gtttgtacaa tttatggtat taatttatta acataatttt agtgt                   1125
```

<210> SEQ ID NO 211
<211> LENGTH: 784
<212> TYPE: DNA
<213> ORGANISM: Arabidopsis thaliana

<400> SEQUENCE: 211

```
gcacgagatt ctctgaagcg cagcagcagc cgtaagaaag aaaccgagga agaacgatct     60

cagtgagagg acgatcactt cgccgtcgca gtcatgggtc gaatgcatag tagaggtaag    120

ggtatctcgg catctgcttt gccgtacaag cgttcatctc cgagctggct caagacaacc    180

cctcaagatg ttgatgagtc catctgcaaa tttgcgaaga agggtttgac cccatcgcag    240

attggtgtca ttcttcgtga ctctcacgga attccacagg tgaaaagtgt tactggaagc    300

aagattctca gaattttgaa agctcatggt cttgcacctg agatccctga ggatctgtat    360

cacttgatca agaaagctgt tgctatccgc aagcatcttg agaggaacag gaaagataag    420

gattccaaat tcaggctgat tcttgtagag agcagaatcc atcgtcttgc tcgttactac    480

aagaagacca agaagctccc acccgtctgg aagtacgagt ctacaactgc aagcactctt    540

gtggcttgag aagaatagag ttgatcatgt ccttcaagaa ggaccatttc attgtctgca    600

ttgcaactca aagctcttct tcttttgaac ctatgtatct gttttcgcta gttttgatgg    660

gttacaactt gctatgagat tttgatttta gggaacgaat ttgtttatgc gaatctttcc    720

attatcgtta cagcttatct ttcaattaac gttaattatc gttctcagag aatttttaca    780

gact                                                                 784
```

<210> SEQ ID NO 212
<211> LENGTH: 1016
<212> TYPE: DNA
<213> ORGANISM: Glycine max
<220> FEATURE:
<221> NAME/KEY: misc_feature
<222> LOCATION: (6)..(6)
<223> OTHER INFORMATION: n is a, c, g, or t

<400> SEQUENCE: 212

```
ccgggnaatt cggccttacg gccgggggtt tcagagtggt ggagtgtgca gaagagcgtc     60

gcagtcgcaa ccctaatcag aagaagcgca gcttcaagcg agtgacagcc accagccatg    120
```

-continued ggtcgtatgc acagccgcgg taagggtata tcctcttctg ctttgcccta caaaaggaca 180
cctcctagct ggctcaagat ctcttcgcaa gatgtcgaag aaaatatctg caagtttgcg 240
aagaaaggtt tgaccccgtc tcagattggt gtcattctca gagattctca cggtattgct 300
caggtcaata gcgtcactgg cagcaaaatc cttcgcatcc tcaaagctca cggacttgcg 360
cctgaaattc cagaggacct gtaccatttg attaagaagg cagtttcaat taggaagcat 420
cttgagagga acaggaagga caaggactcc aagttcaggt tgattcttgt tgagagcaga 480
atccaccgac ttgctcgcta ttacaagaag actaagaagc tcccaccagt ctggaagtac 540
gaatcaacaa ctgctagcac tctggttgct tagagaatgt atcaactttc atgggttttg 600
ctaccgtgca gtcgccgttg agctagcaat ttgcgatatc attttgatgt ttatttgaag 660
gctggatagg ttatgtggct taattttgtt aagaacctat ggtttgactg ggaaagataa 720
tttaactagt taagtcaatt tatcaatgtg gtgttctttt tcttttagcc gttggaggtt 780
gtcttttaaa gagatgacta tggtttttgg ctttatttc aagtaatata tatgcttaga 840
agatttgaag gatcgtattc tttattgctt atgcattcaa ttggtttcca aaggaaaact 900
attacttgta actgaacttg agttcataaa gtcaagttca atcaaattcc acttcttaaa 960
atgtaatcca tacagacact aaggttttca cgtcatttcc ttatttaagc gtttct 1016

<210> SEQ ID NO 213
<211> LENGTH: 760
<212> TYPE: DNA
<213> ORGANISM: Capsicum annuum

<400> SEQUENCE: 213
gagagagaga gagagagaga gagagagaga gagagagaga gagagagaga gagagagaga 60
gagagagaga gagagagaga gagagagaga gagagagaga gagagagaga gagagagaga 120
gaggccaacc gaacagcagc ctctcccccc ctccttcccc actcaccaca aacacacagc 180
cagccatcat gggtcgtatg cacagtcgag gtaagggtat ttctgcttca gcactgccat 240
acaagagaac tccaccaagt tggctgaaaa tatctgcacc agatgtcgaa gataacatct 300
gcaagtttgc caaaaaaggt ttagcacctt ctcaaattgg tgttattctt cgtgattcac 360
atggtattgc tcaggtgaag agtgtaactg gtagcaagat tctcagaatt ttgaaggctc 420
atggacttgc tcctgagatt cctgaggatc tctaccacct tatcaaaaaa gcagttgcaa 480
ttcggaagca tcttgagaga aacaggaagg acaaggattc caagtttagg ttgattcttg 540
tcgagagcag gattcaccga cttgctcgct actacaagaa aacgaaaaag cttccaccag 600
tctggaagta tgaatctacc actgccagta ctctcgtggc atagagagga tggaggcatt 660
tggggtgcta ctttctttgt cgagtcatct ttgaaattct atattaagct gttttggcat 720
gcccaggata gtttggaatc gtatcaaatt atgtactcga 760

<210> SEQ ID NO 214
<211> LENGTH: 955
<212> TYPE: DNA
<213> ORGANISM: Populus tremula x Populus tremuloides

<400> SEQUENCE: 214
cataaaaaag caattattgt tatcacttat gtataaagtg caaaccctag aaatggcgat 60
aataagtaag ctctagggtt gcggctagtc gcagaggaag cgaatcacaa acacacacac 120
agagcgccgg cttcatcacc gtcaccatgg gtcgtatgca cagtcacggt aagggtattt 180
cagcttcagc tttgccttac aagagaaccc caccaagctg gcttaagatt tctgctcaag 240
atgttgagga taacatctgc aaatttgcaa agaagggttt gaccccatct cagattggtg 300
tcattcttcg tgactcgcac ggtattgctc aggtcaggag tgttactgga aaccagatct 360
tgcgtatcct taaggctcat ggtcttgccc ctgaaattcc tgaggatctg taccacctca 420
tcaagaaagc tgttgccatc agaaagcatt tggaaaggaa caggaaggat aaggattcca 480
agttcaggtt gatccttgtc gagagcagaa ttcacaggct tgctcgctac tacaagaaga 540
caaagaagct tcctcctgtc tggaaatacg agtcatccac tgccagcacg ctggtggctt 600
agacatagtt atgtatgtgg cacggtttgg tacatcctgc atggatgatg gtcttcgcgt 660
gtgggactcc gtcatagttc ataagcatta ttatgatatc atgttagctg ggacaaaaga 720
tggagtggat cctagaacat aaattttgct ttaaatgttt gttttggcgt ttgagattct 780
gtactccgtg tatcctttaa gtatattttg tgttttgagc tattaaatta tcttttaaac 840
ataattgatt tgcctcaaac tgcctattcg ggagacggtg gttgtctccc aagtctcatc 900
tcgttgaaac ctgttaccaa ttttataaga taatgtacat cagtacatgg cccgc 955

<210> SEQ ID NO 215
<211> LENGTH: 825
<212> TYPE: DNA
<213> ORGANISM: Medicago truncatula

<400> SEQUENCE: 215
ggcacgaggc aaaaatcgtc atttcggcag agcaaaaccc taatcacaaa gctcgcagct 60
caaagcttca gcaatcatgg ggcgtatgca cagtggcggt aagggtattt catcttctgc 120
tttaccatac aagaggtctg caccaggatg gctcaagacc tctacacaag atgtggaaga 180
gactatttgc aagtttgcaa agaagggttt gactccatct cagatcggtg ttattcttag 240
ggattctcat ggaattgccc aggttaagtt tatcactggc agcaaaatcc ttaggatcct 300
caaggctcat ggacttgcac ctgaaattcc tgaggatctg taccatttga tcaagaaggc 360
agtttcaatt aggaagcatt tggagaggaa cagaaaggat aaggactcca agttcaggtt 420
gattcttgtg gagagcagaa tccaccgtct tgctcgctat tacaagaaga ccaagaagct 480
cccaccagtc tggaagtatg aatcaacaac tgccagcact ttggttgctt agagaagtcc 540
ttgattttga cttgttattc tgttctgcag tcgcatttgg actagaaatt tgctcgtatt 600
tagttttttt tggtgtcatg atcagtcctg gaagacttga actagttaat ttacttatca 660
atgtcttatt ccttcttttt tatcagttgt agaactagct gttgtcattc gaagatgtga 720
gctgacttca gtttttggtt ttaattttaa gttatataca tgctagaaat cttggaaaaa 780
cccattttac tgcatttgaa tgatacattg tttggttctt gaagg 825

<210> SEQ ID NO 216
<211> LENGTH: 794
<212> TYPE: DNA
<213> ORGANISM: Populus tremula x Populus tremuloides

<400> SEQUENCE: 216
ggccccccct gagaggtcga ccccacgggt cccggcaagt tgcagaggaa gctagacaca 60
aacacacaca gagagctcca ccttcatcac cgtcaccatg ggtcgtatgc acagtcgagg 120
taagggtatt tcagcttcag ccctgcctta caagagaacc ccaccaagct ggctgaaaat 180
ttctgcacaa gatgttgatg atagcatttg caagtttgcg aagaagggtt tgactccatc 240
tcagattggt gtcattcttc gtgattctca tggtattgct caggtcagga gtgttactgg 300

```
aaaccagatc ttgcgtatcc ttaaggctca tggtcttgcc cctgaaattc ctgaggattt    360

gtaccacctc atcaagaagg ctgttgccat caggaaacat ttggaaagga acaggaagga    420

caaggattcc aagttcaggt tgatccttgt tgagagcagg attcacaggc ttgctcgcta    480

ctacaagaag acaaagaagc ttgctcctgt ctggaaatac gaatcaagca ctgccagcac    540

tctggtggct taggctagtt atgttatgcg gcacagtttt gggacatcct gcatagttgt    600

tcttcacgtg tggaactctg gcatggtttc ataagcatta ggagatcatg ttaactggga    660

aaaaggatgt agtggatcct agatttcaat tttttcttta aatttttgtt ttggccttga    720

gcttttgtac tccattctaa cttttttctt atactgtttg ttttgagcta taaaatttgc    780

aactttagac ctct                                                      794
```

<210> SEQ ID NO 217
<211> LENGTH: 744
<212> TYPE: DNA
<213> ORGANISM: Medicago truncatula

<400> SEQUENCE: 217

```
attatggccg gggggcacaa gctcaagcag cagcgaagcg tagtagttag agcctttgtt     60

cttcttcctc atctcaatca ttcaccatgg gtcgtatgca cagtggcgga aagggtattt    120

caagttcagc tcttccttac aagagaacac cagcaagctg gctcaagatc tctacccagg    180

atgttgacga gaccatctgc aagtttgcca agaaaggtct aactccatct caaattggtg    240

ttattcttcg tgactcccat ggaattgctc aggttaaggc tgtaaccgga aacaagattt    300

tgcgcatatt gaaggcgcat ggacttgctc ctgaaattcc tgaagatctg tatcacctga    360

tcaagaaggc tgtctctatt aggaagcatt tggagaggaa caggaaggac aaggattcca    420

agttcaggct aattttggtc gagagcagga tccatcgcct tgctcgttac tataagaaga    480

caaagaagct tccaccagta tggaaatacg aatcaacaac tgccagcact cttgttgctt    540

gaagagatga tcggcgatat tattgtagtt gtgctttctg tgtactttat ttttgtatgc    600

aaatgaattg ctttcatgtg attttgaaat tttggaacat ttgaaattca tgtttagact    660

cgtttgatgt tagttttgat gatggacctt gttcctttaa ttgatatact ctctttcaat    720

cgcattagtt ttaaatttgc tatt                                           744
```

<210> SEQ ID NO 218
<211> LENGTH: 799
<212> TYPE: DNA
<213> ORGANISM: Populus tremula x Populus tremuloides

<400> SEQUENCE: 218

```
cgcccaacgc gtccggagcc accaaaggag ctgcgctaaa gtgactgcaa tagaagcagc     60

aaatctccaa agtccgtcac catgggtcgt atgcacagta aaggtaaggg tatttcagcg    120

tctgctttgc catacaagag aaccccacct agttggctca agatttctcc tcaagatgtt    180

gacgacaaca tctgtaagtt tgccaagaaa ggtttgacac catctcaaat tggtgttatt    240

cttcgtgatt ctcacggtat tgctcaggtg aaagctgtca ctggcaacca gattttgagg    300

atattgaagg cacatggcct tgcccctgaa attcctgagg atttgtacca cctcatcaag    360

aaagcagttg ctattaggaa gcatctagag aggaacagga aggataaaga ttccaagttt    420

aggttgattt tggttgagag caggattcac cgccttgctc gctattacaa gaagaccaag    480

aagcttccac ctgtctggaa atatgaatcc tccaccgcca gcactcttgt ggcttaggca    540

agatatgttt ggttttagtt gtcggaactt ccttgaactt aatcttggat gaactgatct    600
```

cagctttttg atatttgtta ttctcatttt ttcagaactt attcatgaat attacctttt 660
atttttcgta atctcagctt ctggtttgat gtttttgatg ctacaagtaa tgtcgggatt 720
ctgaatttga atagatgctg aattaagttg atccttgtca acatttgcag aatttgaaac 780
ctggttgtta atgcctagc 799

<210> SEQ ID NO 219
<211> LENGTH: 681
<212> TYPE: DNA
<213> ORGANISM: Medicago truncatula

<400> SEQUENCE: 219
agacaccatg ggccgtatg catagtaaag gcaagggtat ttcttcctct gctttaccct 60
acaaaagaac ttctcctagc tggcttaaga tctcctcacc agaggttgat gagactattt 120
gcaagtttgc taagaagggt ttgactcctt ctcagatcgg tgttattctt cgtgattctc 180
acggcattgc tcaggtcaag agcgttaccg gcagcaaaat ccttcgtatc ctcaaagctc 240
acggacttgc acctgagatt cctgaggatc tgtaccattt gataaagaag gcggtttcaa 300
tccgcaagca tttggagagg aacagaaagg acaaggactc caagttcaga ctcatccttg 360
ttgagagcag aatccaccgt cttgctcgtt attacaagaa aaccaagaag cttcctcctg 420
tgtggaaata cgaatcaaca actgccagca ctttggttgc ttagagattg tatgggctca 480
ttcttcatgc tttccgtttc cggtaacaga gggttgctgc actggcaatc tgcgaggtca 540
ttttgaggtt tatctagaga cttgatgggc catgcaattt cttattttgt taagaacctt 600
tgataaagta gaaagatatt aattatttta cgttgactgc attgtattct ttttaagtaa 660
actgttcgaa agttgtttca a 681

<210> SEQ ID NO 220
<211> LENGTH: 775
<212> TYPE: DNA
<213> ORGANISM: Hordeum vulgare

<400> SEQUENCE: 220
aggtttccct ctccgccgcc acagccgctt ctccccccac ctccctcctc gccgccatgg 60
gacgcatgca cagcaacggg aaggggatgt cgtcctcggt gatcccctac aagcgggagg 120
ccccggcctg ggtcaagaca gccgcgccgg acgtggagga gatgatcgtg cgcgccgcca 180
agaagggcca gctgccgtct cagatcggcg ccctgctccg cgacggccac ggcatcccgc 240
tgtccaaggc cgtcaccggc gccaagatcg tgcgcctgct caaggcgcgc gggctcgcgc 300
cggagatgcc cgaggacctc tacttcctca tcaagaaggc cgttgcgatc aggaagcacc 360
tggagaggaa caggtcggac gtcgacgcca agttccgcct catcctcgtc gagagcaggg 420
tccaccgcct cacccgctac taccgcctca ccaagaagat gcccgccgcc tggaagtacg 480
agtccaccac cgcgagcacc ctcgtcgcct gattcggtta atcttcggtt cttcgacgta 540
attctctgca gttttggact tcggttttgt gttaagtact gtagtaagca atgcttttgg 600
caatgtaagc ttttaaacct atcgattacc tctcgtgtgc ctggatagga gtatttcgag 660
agttcagtgg gagtggatta gattttgatc cttggaagtt gagactattt acaatgtgtt 720
gctttggtaa gaggtctttt aatgttagcc gagtggtaaa tcagttgttc atagc 775

<210> SEQ ID NO 221
<211> LENGTH: 889
<212> TYPE: DNA

<213> ORGANISM: Triticum aestivum

<400> SEQUENCE: 221
ggcacgagca tttttgctag gtttccctct ccgccgccac agcagcttct ccccatctcc 60
ctcctcgccg ccgccctccg ctcgccgctc gccgccatgg gacgcatgca cagcaacggg 120
aagggcatgt cgtcctcggt gatcccctac aagcgggagg ccccggcctg ggtcaagacg 180
tccgcgccgg acgtggagga gatcatcgtc cgcgccgcca agaagggcca gctgccgtcg 240
cagatcggcg ccctgctccg cgacggctac ggcatcccgc tgtccaaggc cgtcaccggc 300
gccaagatcg tgcgcctgct caaggcgcgc gggctggcgc cggagatgcc cgaggacctc 360
tacttcctca tcaagaaggc cgttgcgatc cggaagcacc tggagaggaa caggtcggac 420
gtggacgcca agttccgcct catcctcgtc gagagcaggg tccaccgcct cacccgctac 480
taccgcctca ccaagaagat gcccgccgcc tggaagtacg agtccaccac cgcgagcact 540
ctcgtcgcct gattcggtta agcttcggtt ctttgacgta attctctgca gcttggactt 600 cggtttttttg ttaagtactc cagtaagcaa tgctttttgg gatgtaagct gttaaaccta 660
tcagctaccg ctcgtgtgcc tgcacagaag tatttcgaga gtttagtggg actggatcag 720
gttttgatcc ttggaagttg agactattta caatgtgttg gtttcctaac ttcgagtagg 780
ctggtaatgc tcttcgtagg tgtattgctg tcgcaaatcc tgcagtggag tatgaaactt 840
gctaatgcac tcttcatgtt ttatcctgtt ttattgttgt tgcgaactc 889

<210> SEQ ID NO 222
<211> LENGTH: 626
<212> TYPE: DNA
<213> ORGANISM: Oryza sativa

<400> SEQUENCE: 222
atccaccaca tcgacaacct cacgccgtcg acaactttcc agccaaaatg ggtcgtcttc 60
actccaaggg caagggcatt gcctcctcca ccctccccta ctcccgcact cctcctgcgt 120
ggctcaagac cacccccgac caggttgtcg accacatctg caagctggcc aagaagggtg 180
ccactccttc ccagatcggt gttgttctcc gtgactccca cggtgttgcc caggtcaaga 240
tcgtgaccgg taacaagatc ctccgtatcc tcaagtccaa cggcctcgcc cccgagcttc 300
ccgaggacct ttacttcctg atcaagaagg ccgtcgctgt ccgcaagcac cttgagcgta 360
accgcaagga caaggactcc aagttccgcc tcattctgat cgagtcccgt atccaccgtc 420
tgtcccgcta ctacaagacc gtcggtgtcc ttccccccac ctggcgctac gagtccgcca 480
ctgcctccac cctggtcgca taagcgaagg cgttggttgt ctgtggtcat ggagataggg 540
gcatgattga tattctgggc ttctgttcgg agtatctttc atgtgtgtta gatacgacca 600
ttaaaaaaga acttatgagt tatacc 626

<210> SEQ ID NO 223
<211> LENGTH: 757
<212> TYPE: DNA
<213> ORGANISM: Oryza sativa

<400> SEQUENCE: 223
atgggccgca tgcacagcag cgggaagggg atgtcctgct cggtgctccc ctacaggcgc 60
gccgctcccg cctgggtcaa gacgtccgcg tcggaggtgg aggagatgat cgtgcgcgtc 120
gccaagaagg gccagctgcc gtcgcagatc ggggcgatcc tccgcgacgc ccacgccgtc 180
ccgctcgccc agggcgtcac cggcggcaag atcctccgcg tgctcaagtc ccgcggcctc 240

```
gcgcccgagg tgcccgagga cctctacttc ctcatcaaga aggccgtcgc gatgaggaag    300

cacctcgaga ggaacaggaa ggacaaggac accaagttcc gcctcatcct cgtcgagagc    360

agggtgcacc gcctcacccg ctactaccgc ctcgccaaga agatccccgc cttcttcaag    420

tacgactcca ccaccgcgag cactctcgtg gcctgaagtg gaactgaagg tttcgttcgt    480

tttcagcttc ttttttgggc gacttgaatt ctcttgacag ccatggagtt ttgtttaatc    540

ttaagtaagt aggaatgctt ttgttggtgt aatgtgttaa atctacctcc tgcacctgaa    600

gagaagttgc ttactgagac tcgatctagg aatgcttttg ttggtgtaat gtgttaaatc    660

tacctcctgc acctgaagag aagttgctta ctgagactcg gatcagattt tattttcctg    720

aaagaaaggt tattcgcaat gatatgaagt tcaattt                             757
```

```
<210> SEQ ID NO 224
<211> LENGTH: 671
<212> TYPE: DNA
<213> ORGANISM: Triticum aestivum

<400> SEQUENCE: 224

cggcacgagg tccagtatca ccacgccaaa ccgacaagat gggccgtctt cacagcaagg     60

gaaagggcat ttctgcctcc gctctcccct actctcgatc ttcccctgcg tggttgaaga    120

ccacccccga gcaggttgtc gagcagatct ccaagctcgc ccgtaagggt gccacccctt    180

ctcagatcgg tgtcattctc cgtgactctc acggtattgc ccaggtcaag cacgtcactg    240

gtaaccgaat tctccgaatt ctcaagtcca gcggcctcgc ccccgagctc cccgaggatc    300

tgtacatgct tatcaagaag gctgttgccg tccgaaagca ccttgagcgc aaccgcaagg    360

acaaggactc caagttccgt ctcattctca ttgagtcccg aattcaccgt ctggcccgtt    420

actacaagac cgtcggtgtc cttcccccca cctggaagta cgagtccgct actgccagca    480

ccatcgtcgc ttaagcgaac ataaaaacga cggctggcca agttcggatg gaagtgatgg    540

tttcccggat cacggagtta gggacaaatt atggaaaaag cttgcattta gagccatgat    600

gcttatgcgc cctatctggg aggactgaca gcgaaatcga cggctcaaat agaaagcttt    660

tcgaccgctg c                                                         671
```

```
<210> SEQ ID NO 225
<211> LENGTH: 634
<212> TYPE: DNA
<213> ORGANISM: Hordeum vulgare

<400> SEQUENCE: 225

agtatcacca cgccaaaccg acaagatggg ccgtcttcac agcaagggaa agggcatttc     60

tgcctccgct ctcccctact ctcgatcttc ccctgcgtgg ttgaagacca cccccgagca    120

ggttgtcgag cagatctcca agctcgcccg taagggtgcc accccttctc agatcggtgt    180

cattctccgt gactctcacg gtattgccca ggtcaagcac gtcactggta accgaattct    240

ccgaattctc aagtccagcg gcctcgcccc cgagctcccc gaggatctgt acatgcttat    300

caagaaggct gttgccgtcc gaaagcacct tgagcgcaac cgcaaggaca aggactccaa    360

gttccgtctc attctcattg agtcccgaat tcaccgtctg gcccgttact acaagaccgt    420

cggtgtcctt ccccccacct ggaagtacga gtccgctact gccagcacca tcgtcgctta    480

agcgaacata aaaacgacgg ctggccaagt tcggatggaa gtgatggttt cccggatcac    540

ggagttaggg acaaattatg gaaaaagctt gcatttagag ccatgatgct tatgcgccct    600
```

atctgggagg actgacagcg aaatcgacgg ctca 634

<210> SEQ ID NO 226
<211> LENGTH: 623
<212> TYPE: DNA
<213> ORGANISM: Arabidopsis thaliana

<400> SEQUENCE: 226
gatccttatc cagtatcacc acgccaaacc gacaagatgg gccgtcttca cagcaaggga 60
aagggcattt ctgcctccgc tctcccctac tctcgatctt cccctgcgtg gttgaagacc 120
acccccgagc aggttgtcga gcagatctcc aagctcgccc gtaagggtgc caccccttct 180
cagatcggtg tcattctccg tgactctcac ggtattgccc aggtcaagca cgtcactggt 240
aaccgaattc tccgaattct caagtccagc ggcctcgccc ccgagctccc cgaggatctg 300
tacatgctta tcaagaaggc tgttgccgtc cgaaagcacc ttgagcgcaa ccgcaaggac 360
aaggactcca agttccgtct cattctcatt gagtcccgaa ttcaccgtct ggcccgttac 420
tacaagaccg tcggtgtcct tccccccacc tggaagtacg agtccgctac tgccagcacc 480
atcgtcgctt aagcgaacat aaaaacgacg gctggccaag ttcggatgga agtgatggtt 540
tcccggatca cggagttagg gacaaattat ggaaaaagct tgcatttaga gccatgatgc 600
ttatgcgccc tatctgagag gac 623

<210> SEQ ID NO 227
<211> LENGTH: 533
<212> TYPE: DNA
<213> ORGANISM: Hordeum vulgare
<220> FEATURE:
<221> NAME/KEY: misc_feature
<222> LOCATION: (528)..(528)
<223> OTHER INFORMATION: n is a, c, g, or t

<400> SEQUENCE: 227
ctattcaaga tgggacgcat gcacagtggt ggaaaaggta ttgcaaagtc ttctttgcct 60
tacagacgct ctcctccttc atggttgaaa gtgactgcta gtcaagttga ggaccatgtc 120
aataagcttg ccaaaagagg tttgactcct tcacagattg gtgtgattct tcgtgattcc 180
aatggaattg cgcaagtcaa gagtgtcaca ggaaataaaa ttcttcgtat cctgaagaaa 240
tcaggacttg cacctgccat ccctgaggat ttgtacatgt taattaaaaa ggccgtggct 300
gttagaaagc acttggaacg caacaagaaa gataaggact ccaaatttag attgatcttg 360
attgagagcc gcattcacag actggcgaga tactaccgcg cctcaagaaa gctggatgca 420
aactggaagt acgaatctgc caccgcttct gcccttgtgg cttaattgtc acggcaatac 480
catacctttg tcgatacttt tgtaactgct gctaaaacac cacaaatntt tta 533

<210> SEQ ID NO 228
<211> LENGTH: 1167
<212> TYPE: DNA
<213> ORGANISM: Saccharum officinarum

<400> SEQUENCE: 228
tcggtctcgc caccgccgcc aacttgtcac tcgctctccc tcctgctcgc cgccgcccac 60
cgctcgccgc aaccgccgcc atgggtcgca tgtacggccc cgggaagggc atgtcctcgt 120
cggtgctgcc ctacgctcgc gtcgcccctg gctgggtgag gtcgaccgct ggggaggtgg 180
aggagatgat cgtgcgcgcc gccaagaagg gccacctgcc gtcgcagatc ggtgcgctgc 240
tccgcgacac gcacggcgtc ccgctggtcc acggcgtcac gggcggcaag atcctgcgca 300

-continued

```
tgctcaaggc ccgcgggctc gcgccggagg tgcccgagga cctctacttc ctcatcaaga    360

aggccgtcgc gatcaggaag cacctggaca ggaaccggac ggacgtggac gccaagttcc    420

gcctcatcct cgtcgagagc agggtccacc gcctgatccg ctactaccgc cgcaccaaga    480

agatcgcccc caacttgaag tacgaatcca ccaccgcgag cgctctggtg gcgtgatggc    540

tgtgaattga ttctctagag ctttggagct tgtcttaatc ctaaggaagt tatgtgatag    600

tagtagtact ttatgatatg ttactatgtg aggtctttaa atttatctac ccgatgcacc    660

taggaagagg tatgtatctt gagatttgac agttatgaga ctggatcggg tttttgacct    720

ttgaaggtgc ataactcaaa atggtttgga gttgggctta accttgatta ggttggatgg    780

tgctctcatc aaaagttaag aatgaagcaa gagacttggt atttagtttc actttttttcc   840

gccctttcga tcttggtttc accaattggg tcatgttaaa gttttggtat agcttagcta    900

gtgagctact ctacattgtt tgagatttga ggagcctcca agaacacaat ggtacttatg    960

gatgtgggtt tccttatccc atagctcaaa tgatctgtgc gaagtgttat gtttggttgc   1020

ctatatcaag tttttggttt agttctagaa tcattcaggg cgcttcttag aaattttggg   1080

atgtaattcc aatttgaact aaatattaag gatttggatc ctgctgccca acaagtgtct   1140

ttgggtggta aggagcattc ctatgtc                                       1167
```

<210> SEQ ID NO 229
<211> LENGTH: 1812
<212> TYPE: DNA
<213> ORGANISM: Hordeum vulgare

<400> SEQUENCE: 229

```
ggcacgagcc gaggtaaggg gatttctgca tctgccctgc cttacaagag gactccacct     60

agttggttga agatctcctc tcaagatgtt gaggataaca tttgcaagtt tgctaagaag    120

ggtttgaccc catctcaaat tggtgtcatt ctacgagatt ctcatgggat tgctcacgtg    180

aagagtgtta ctggcagcaa gattctgcgc atactgaaag cccatggtct tgctcctgaa    240

atacccgagg atctgtacca cctgattaag aaagccgttg ccatcagaaa gcatcttgag    300

aggaaccgaa aagacaagga ttccaagttt aggttgatct tggttgagag caggatccac    360

cgactcgccc gctattataa gaagacaaag aagctgccac cagtgtggaa atatgagtct    420

actactgcca gcactcttgt ggcctagata aatcaaattt tgaactgtct tcctgtgctt    480

cgattgatat tcttctggat cggctaagag gagttggact ttttgtatta cgttctatta    540

atgccgtaaa agaactagtc cacttaattt gaagtggaga tacttaatgt gttaaatctt    600

atgtttagta tattggaata attcatctct catttcaaag aaaaatcggt ctcgccaccg    660

ccgccaactt gtcactcgct ctccctcctg ctcgccgccg cccaccgctc gccgcaaccg    720

ccgccatggg tcgcatgtac ggccccggga agggcatgtc ctcgtcggtg ctgccctacg    780

ctcgcgtcgc ccctggctgg gtgaggtcga ccgctgggga ggtggaggag atgatcgtgc    840

gcgccgccaa gaagggccac ctgccgtcgc agatcggtgc gctgctccgc gacacgcacg    900

gcgtcccgct ggtccacggc gtcacgggcg gcaagatcct gcgcatgctc aaggcccgcg    960

ggctcgcgcc ggaggtgccc gaggacctct acttcctcat caagaaggcc gtcgcgatca   1020

ggaagcacct ggacaggaac cggacggacg tggacgccaa gttccgcctc atcctcgtcg   1080

agagcagggt ccaccgcctg atccgctact accgccgcac caagaagatc gcccccaact   1140

tgaagtacga atccaccacc gcgagcgctc tggtggcgtg atggctgtga attgattctc   1200
```

tagagctttg gagcttgtct taatcctaag gaagttatgt gatagtagta gtactttatg 1260
atatgttact atgtgaggtc tttaaattta tctacccgat gcacctagga agaggtatgt 1320
atcttgagat ttgacagtta tgagactgga tcgggttttt gacctttgaa ggtgcataac 1380
tcaaaatggt ttggagttgg gcttaacctt gattaggttg gatggtgctc tcatcaaaag 1440
ttaagaatga agcaagagac ttggtattta gtttcacttt tttccgccct ttcgatcttg 1500
gtttcaccaa ttgggtcatg ttaaagtttt ggtatagctt agctagtgag ctactctaca 1560
ttgtttgaga tttgaggagc ctccaagaac acaatggtac ttatggatgt gggtttcctt 1620
atcccatagc tcaaatgatc tgtgcgaagt gttatgtttg gttgcctata tcaagttttt 1680
ggtttagttc tagaatcatt cagggcgctt cttagaaatt ttgggatgta attccaattt 1740
gaactaaata ttaaggattt ggatcctgct gcccaacaag tgtctttggg tggtaaggag 1800
cattcctatg tc 1812

<210> SEQ ID NO 230
<211> LENGTH: 769
<212> TYPE: DNA
<213> ORGANISM: Populus tremula x Populus tremuloides

<400> SEQUENCE: 230
caccaatcga acgagcgcgc tcctcagcag actttgggtc gtcttctatc tgaaccggcc 60
attcttcaac aaggaagaag tacctcaagc ctcacatcat gggtcgtatg cacaatcccc 120
acaagggtat cgccggttcg gcacttccct acaagcgaac tcctccaaga tggttgaagg 180
tcaccccgga ggaagtctct gagcagatct tcaagcttgc ccgtaagggt atgacccccct 240 ctcaaattgg tgttgtcctc cgagacagcc acggtattgc ccaagtcaag agtgtcaccg 300
gtgccaaaat tcttcgtatc ctcaagggta acggtcttgc ccctgagctc cccgaagatc 360
tttaccactt gatcaagaag gctgtttctg tccgaaagca tcttgaacga aaccgaaagg 420
acaaggactc caaattccgt ttgattctca ttgaatctcg aatccaccgt cttgtccgtt 480
actacaagac aaaatctcaa ctctcgcctt ccttcaaata cgagagtgca accgcctcca 540
ccattgtctc atgaagactc tatccatctg accatctcct ttgtggtctt ctctcatcgt 600
tcatgatcgt tatgggtttg ctaaatgcac caaccaatct tgttacatcc atgtgttctc 660
actatgcttc cctgatctcc atgtcccatg tccccgttca ttggaaatat caaactcctc 720
cagttggtcg tcatcaccga cttgcaagat aatctaaaca tgcacttta 769

<210> SEQ ID NO 231
<211> LENGTH: 559
<212> TYPE: DNA
<213> ORGANISM: Hordeum vulgare

<400> SEQUENCE: 231
ttaaattgta aattgtattt tttaaatgtc cgtacaaata acagtttact taagcaacca 60
aagcggaagc tgtactggac tcgtatctcc agttgggagc gatctttgat ttgcgtttgt 120
agtaccttgc caaacgatga atacgtgatt caaccaaaat caaacggaat ttggaatctc 180
tgtctttcct gttcctttcc aaatgttttc tgattgctac ggctttcttg atcaaatggt 240
acaaatcttc agggagacct ggagccaaac ccatagcttt catgatccta agaattttgt 300
ttccagtcac aaatcttact tgagcaacac catgggaatc tcgtaaaata acaccaattt 360
tagatggtgt caaacccttc ttggccaatt tgaaaatgtg gtccttgaca tcctcggacg 420
acgatttcag ccaggtggct acgctgcggc ggtatggaag agccgacttg gaaatacctt 480

-continued ttccgggtgt gtgcatccga cccatgttga cgtttttgtt ttacacttta agaacgataa 540
aaaaattatt ccacaatgc 559

<210> SEQ ID NO 232
<211> LENGTH: 779
<212> TYPE: DNA
<213> ORGANISM: Oryza sativa

<400> SEQUENCE: 232
aaccttccca atgtacatac tttacatatt agattgcaag gcatattaca aaaagtgctt 60
acagaaaggg gaagaatgcc cacttcaatc tgcttacaga aaggggaagg atgcacactc 120
caatctgttt caacaaacta atggtacaac aatatggcga gtagctgatt ctctggaaaa 180
aaactgccat agcctccaag atgttgctct aaggggaaaa tccccaaaaa atgctattta 240
cattgtattc ctgcgcctct ccatctcagc gcgtctcaat aaagttgcta gcacaacaat 300
ccattcctta aatttgacag aacacatgtg agcaacaagg aactcaacat caagccgact 360
ttgaagagta tccatttgaa gcgcaaagta ggtgggagct tctttgtgcg cttgtagtag 420
cggacgaggc ggtggatcct gctctcaaca agaataagcc tgaaacttga gtccttgtcc 480
ttcctgttcc tctccaaatg cttcctaata gcaacagcct tcttgatcag gaagtacagg 540
tcttccagga tcttcggtgc aagaccgtgg gccttgagga tgtgaagaat cttgctactg 600
gcgatgctct tgacgagggg gattccgtgc tggtgacgga gcacaacgcc aatctgcgac 660
gacatctgac ccatcttcgc ggccttcatg atcatctcct ccacattgga ggcggcgttc 720
ttgagcaagc tcgggggaat cctcttgcac ggcagcgccg acgacgagat acccttctc 779

<210> SEQ ID NO 233
<211> LENGTH: 674
<212> TYPE: DNA
<213> ORGANISM: Glycine max
<220> FEATURE:
<221> NAME/KEY: misc_feature
<222> LOCATION: (670)..(670)
<223> OTHER INFORMATION: n is a, c, g, or t
<220> FEATURE:
<221> NAME/KEY: misc_feature
<222> LOCATION: (673)..(673)
<223> OTHER INFORMATION: n is a, c, g, or t

<400> SEQUENCE: 233
accaggaact agtctcgagt ttttatcctt aattttttgt tctaggtcga agaaaatatc 60
tgcaagtttg cgaagaaagg tttgaccccg tctcagattg gtgtcattct cagagattct 120
cacggtattg ctcaggtcaa tagcgtcact ggcagcaaaa tccttcgcat cctcaaagct 180
cacggacttg cgcctgaaat tccagaggat ctgtaccatt tgattaagaa ggcagtttca 240
attaggaagc atcttgagag gaacaggaag gacaaggact ccaagttcag gttgattctt 300
gttgagagca gaatccaccg acttgctcgc tattacaaga agactaagaa gctcccacca 360
gtctggaagt acgaatcaac aactgctagc actctggttg cttagagaat gtatcaactt 420
tcatgggttt tgctaccttg cagtcgccgt tgagctagca atttgccata tcattttgat 480
gtgtatttga aggctggata agttatgtgg tcttaatttt tttaagaacc tataatttag 540
ctagttaagt caatttatca ttgtggtgtt ctttttcttt tagccgttgg aggttgttct 600
ttaaagagat gactatggtt tttggtttta ttttcaagta atatatatgc tgagaagatt 660
tgaggatcan aana 674

<210> SEQ ID NO 234
<211> LENGTH: 458
<212> TYPE: DNA
<213> ORGANISM: Populus tremula x Populus tremuloides

<400> SEQUENCE: 234
cacacttaca ataatgggtc gaatgcacag taatggtaaa ggtatgtcga agtcagcact 60
tccatacaag agaacaccac caagttggtt aaaaacaagc gcaaatgaag tttgtgacca 120
tgtttgtcga ttggcaaaga aaggtttaac accatcacaa attggtgttg ttcttcgaga 180
ttcacatgga attccacaag ttaaatcagt cacaaataac aaaattcttc gtattttgaa 240
ggcaaacgga tttgcacctg aattgcctga agatttatac catttgatca agaaagctgc 300
ttcaattcgt aaacatttaa aaagatctcg tcaagataaa gatgcaaagt tccatcttat 360
tcttgttgaa gccagaattc accgtgtttc acgatactac aaggaaagca aacacttacc 420
agcaaactgg agatacgaat caccaactgc tgcaactt 458

<210> SEQ ID NO 235
<211> LENGTH: 481
<212> TYPE: DNA
<213> ORGANISM: Nicotiana tabacum

<400> SEQUENCE: 235
acgccggtag ccaatcctca ctcgccatca tgggtcgcat gcacagtcgc ggtaagggta 60
tttcagcttc ggctcttcct tacaaaagaa ctcctcctag ttggctcaag atctccgctc 120
ctgatgttga ggacaacatt tgcaagtttg cgaagaaagg attgactcct tcacagattg 180
gtgtgattct tcgtgactca cacggaattg cacaagtcaa gagtgtcact ggcagcaaga 240
tcttgcgtat cctcaaggct cacgggcttg ctcctgagat accagaggat ctgtaccacc 300
tgattaagaa ggcagttgct attaggaagc atttggaaag ggacagaaag gataaggatt 360
ccaagttccg cttgatttag gtggagagca ggatccatcg tcttgctcgc tattacaaga 420
aaacaaagaa gctcccacct gtctggaaat acgaatcaac caatgctagc acgcttgtgg 480
c 481

<210> SEQ ID NO 236
<211> LENGTH: 717
<212> TYPE: DNA
<213> ORGANISM: Triticum aestivum
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (296)..(296)
<223> OTHER INFORMATION: n is a, c, g, or t
<220> FEATURE:
<221> NAME/KEY: misc_feature
<222> LOCATION: (299)..(299)
<223> OTHER INFORMATION: n is a, c, g, or t

<400> SEQUENCE: 236
atcacaatgt ctaattttcc ctcgataaat tggggatana ccctagggag gggggggatg 60
aattccaaaa ccaaaaatgg tggggggat tctccaagta aacataaaaa atttggtctc 120
ttgttcatct aaatcgctcc aaactcaaaa gcgttacatg aaattgataa tatgtagaac 180
aagaccatcc tgaagccggt aagagcacac cagatgaaga gccctcctaa gccaccaaaa 240
tgctcccggg gggggggggg ggcttccatt tatccgggaa cttcttcctc cccttntant 300

```
aacgggggggg acggtggatc ctgctctcaa caagaatgag cctgaatttg gagtctttgt    360

ccttcctgtt cctctcaaga tgcttcctaa tggcgacagc cttcttaatc aaaaagtaca    420

gatcctctgg gatttccgga gccaggccat gagccttgat gatgcggagg atcttgcttc    480

ccgtaacgct cttcacgagg gggataccgt gctggtcacg gaggagaacg ccgatctgcg    540

agggcatctg acccttcttc gcagccttcg tgatcaactc gtcgacatca gcgacggtgg    600

gtcttgaccc cacctcggag gagtcctctt gtacggcaac cccgacaacc atataccctt    660

cccgccggct gtcaatgccc cccattgcgt caggcgacgg gtttaacttc cgcccac       717
```

<210> SEQ ID NO 237
<211> LENGTH: 685
<212> TYPE: DNA
<213> ORGANISM: Brassica napus
<220> FEATURE:
<221> NAME/KEY: misc_feature
<222> LOCATION: (663)..(663)
<223> OTHER INFORMATION: n is a, c, g, or t

<400> SEQUENCE: 237

```
ggcagcagga actcatctca tcgagacagt gaaaggaaac cctaactttt caagatgggg     60

cgtatgcatt cgagaggaaa gggtatctct gcatctgcgt tgccgtacaa gcgttcacct    120

ccgacatggc tcaagaccac ggccctcgat gttgatgagt caatctgcaa gtttgcgaag    180

aagggttgac accatctcag attggtgtga ttcttcgtga ctctcacggt atccctcagg    240

tgaagagtgt taccggaaac aagatcttgc gtattctcaa agctcacggt cttgcacctg    300

agattcctga tgatctgtac catttgatca agaaggcagt tgctatccgc aagcatttgg    360

agaggaacag gaaggacaag gattccaagt ttaggctgat tcttgcggag agcaggatcc    420

accgtcttgc tcgttactac aagaagacca agaagcttcc tccagtctgg aagtacgagt    480

ctactactgc ttctactctt gtagcttaga gcacggtctt ctcttaaaag gcttcaagag    540

ccactactgt ttttttttt tgatgtctta tctctgaact tgaacttagt ttctatgttt    600

cgcagtactt ttgttttgtc aaggtacaat gatgttttga tgatttcatg gaaccaatgc    660

gtntaatcta ttgtcagaat tgcaa                                          685
```

<210> SEQ ID NO 238
<211> LENGTH: 447
<212> TYPE: DNA
<213> ORGANISM: Triticum aestivum
<220> FEATURE:
<221> NAME/KEY: misc_feature
<222> LOCATION: (369)..(369)
<223> OTHER INFORMATION: n is a, c, g, or t
<220> FEATURE:
<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (385)..(385)
<223> OTHER INFORMATION: n is a, c, g, or t
<220> FEATURE:
<221> NAME/KEY: misc_feature
<222> LOCATION: (417)..(417)
<223> OTHER INFORMATION: n is a, c, g, or t
<220> FEATURE:
<221> NAME/KEY: misc_feature
<222> LOCATION: (423)..(424)
<223> OTHER INFORMATION: n is a, c, g, or t
<220> FEATURE:
<221> NAME/KEY: misc_feature
<222> LOCATION: (435)..(435)

<223> OTHER INFORMATION: n is a, c, g, or t
<220> FEATURE:
<221> NAME/KEY: misc_feature
<222> LOCATION: (445)..(446)
<223> OTHER INFORMATION: n is a, c, g, or t

<400> SEQUENCE: 238
aagcgccagc tcgccgtcgt ccgaatagta cactctaacg ccgccatggg gcgtatgcac 60
agccgcggga agggtatctc gtcgtcggcg ctgccgtaca agaggacgcc tcctacctgg 120
ctgaagaccg ccgcctccga cgtggaggag atgatcacaa aggcagcgaa gaagggacag 180
atgccgtcgc agatcggcgt cctgctccgt gaccagcacg gtatcccccct tgtcaagagt 240 gtcaccggca gcaaaatcct ccgcatcctc aaggccatgg gctggaaccg aaatcccgga 300
ggactgtact ctcatcaaga agccgtggcg ataaggaaca ctttagagga acaagaagga 360
caaagatcna aatcaagntc atctngtcaa aacaggttca acgccttgcc cgtatanaac 420
gcnnaagaac ttcancactt gaatnna 447

<210> SEQ ID NO 239
<211> LENGTH: 608
<212> TYPE: DNA
<213> ORGANISM: Populus tremula x Populus tremuloides

<400> SEQUENCE: 239
cacagagcca ccaaggagct gagctaaagt gactgcaaaa gaagcagcga atctccacag 60
tcgttgccat gggtcgtatg cacagtaaag gcaagggtat ctcagcatct gctttgccat 120
acaagaggac ctcacctagt tggcttaaga tttctcctca agatgttgac gacaatatct 180
gcaagtttgc aaagaaaggt ttgacaccat ctcaaattgg tgttatcctt cgtgattctc 240
atggtattgc tcaagtgaaa actgttactg gcaaccagat tttgaggata ttgaaggccc 300
atgggcttgc acctgaaatt cctgaggatc tgtaccacct cattaagaaa gcagtttgct 360
atttaggaag catctagaga ggaacaggaa ggataaagat tcccaaattt aggtttgatt 420
ttggtcgaga gcaggatcca ccgcctttgc tcgctattac aagaagacca agaagcttcc 480
accagttctg ggaaatatga atccaccact gccagcaccc ctcgtggcat aggcaaagat 540
atccttggtt tttagttgtc agcacgtcct ttgaactcaa atcttggatg agctgatcag 600
ccttttga 608

<210> SEQ ID NO 240
<211> LENGTH: 701
<212> TYPE: DNA
<213> ORGANISM: Oryza sativa

<400> SEQUENCE: 240
acccttggtg gtttggctcc cccgggaatc gggcttatgg gcgggaagat gggtcagatg 60
tcgtcgcaga ttggcgttgt gctccgtcac agcacggaat ccccctcgtc aagagcatcg 120
ccagtagcaa gattcttcac atcctcaatg cccacggtct tgcaccgaag atcctggaag 180
acctgtactt cctgatcaag aaggctgttg ctattaggaa gcatttggag aggaacagga 240
aggacaagga ctcaagtttc aggcttattc ttgttgagag caggatccac cgcctcgtcc 300
gctactacaa gcgcacaaag aagctcccac ctactttacg gtcttggatt atttttctcg 360
agttttctac agttttctcc tgcagtagaa tgcttcaaat ggatactctt caaagtcggc 420
ttgatgttga gttccttgtt gctcacatgt gttctgtcaa atttaaggaa tgaattgttg 480
tgctagcaac tttattgaga cgcgctgagg tactgcctat ctttcacatg ttcaacaact 540
gtgcacacaa tttcagtaat actgttcttt tgactaactt gtggcaggct tctgcatctg 600
acaatgcagt gttttttctt attttgtttt ttggattttt accatgtatt gatcgtttaa 660
tgttttgtaa gaagcgtact catccttggt gctaaaaaaa a 701

<210> SEQ ID NO 241
<211> LENGTH: 565
<212> TYPE: DNA
<213> ORGANISM: Triticum aestivum
<220> FEATURE:
<221> NAME/KEY: misc_feature
<222> LOCATION: (498)..(498)
<223> OTHER INFORMATION: n is a, c, g, or t
<220> FEATURE:
<221> NAME/KEY: misc_feature
<222> LOCATION: (523)..(523)
<223> OTHER INFORMATION: n is a, c, g, or t

<400> SEQUENCE: 241
gctaggtttc cctctccgcc gccacagcag cttctcccca tctccctcct cgccgccgcc 60
ctccgctcgc cgctcgccgc catgggacgc atgcacagca acgggaaggg catgtcgtcc 120
tcggtgatcc cctacaagcg ggaggccccg acctgggtca agacgtccgc gccggacgtg 180
gaggagatca tcgtccgcgc cgccaagaag ggccagctgc cgtcgcagat cggcgccctg 240
ctccgcgacg gctacggcat cccgctgtcc aaggccgtca ccggcgccaa gatcgtgcgc 300
ctgctcaagg cgcgcgggct ggcgccggag atgccccgag gacctctact tcctcatcaa 360
gaaggccgtt gcgattcgga agcacctgga agaggaacaa gtcggacgtg gacgccaagt 420
tccgcctcat cctcgtcgag aacaaggtcc aacgcctcaa ccgctactac cgcctcaaca 480
agaagatgcc gccgcctngg aagtacgagt cacaccgcga agnatctcgt cgctgaatcg 540
gttaacctcg gttctttgac taatt 565

<210> SEQ ID NO 242
<211> LENGTH: 1052
<212> TYPE: DNA
<213> ORGANISM: Oryza sativa

<400> SEQUENCE: 242
gtggagacga gcgacctgag agagagagag agagaaggca agggaaggag gagaagaagg 60
gggacgaagc ggacgaggcg cgcgcgcgcc atctttgctt tgcttcctct ctcttccctc 120
tcctctcctc tcctccggtc gtcggcctcc ccggccggcc ggcgcctgcc cgtgcttgag 180
gcgcggcggc ggatacgggg ggtgacgaca tggccgacgg gggagagaag tgccgggacg 240
cggccggcga gggcggcggc ggcggcgacc tgtacgccgt gctcgggctc aagaaggagt 300
gctccgacgc cgacctcaag ctcgcgtacc ggaagctcgc catgagatgg catccggaca 360
aatgctcatc ctccagcagt gcaaagcaca tggaggaagc caaggagaag ttccaggaga 420
tccagggcgc ctattccgtc ctctcagact caaacaagcg gttcctctac gacgtggggg 480
tatatgatga tgacgacaat gacgatgaca acctgcaggg gatgggggac ttcattggtg 540
agatggccca gatgatgagc caggcacggc caacgaggca ggagagcttt aaagaactgc 600
agcagctatt cgtagacatg ttccaagctg atcttgattc gggtttctgc aatggaccct 660
caaagtgcta ccatacccag gcccaaagcc agactcgaac atcctcaacc tccccttcga 720
tgtcaccgtc tccaccgcct ccagtagcta ctgaggcaga atcgccatca tgtaatggta 780
ttaataagcg tggttcatca gcaatggact ctgggaagcc tccaagagcc agcgaagtca 840

-continued

```
gtgctggaca gagtcaatca gggttttgtt tcgggaagag tgatgctaaa caagcggcga    900

agacgcgaag cgggaacacg gccagccgga ggaggaacgg ccggaagcag aaggtgtcgt    960

cgaagcacga cgtctcgtct gaggacgaga tgccaggttc gcagtggcac ggcgtggcct   1020

gacctttgtt cgtgactggt ttggcccttg at                                 1052


<210> SEQ ID NO 243
<211> LENGTH: 1513
<212> TYPE: DNA
<213> ORGANISM: Hordeum vulgare
<220> FEATURE:
<221> NAME/KEY: misc_feature
<222> LOCATION: (1269)..(1269)
<223> OTHER INFORMATION: n is a, c, g, or t
<220> FEATURE:
<221> NAME/KEY: misc_feature
<222> LOCATION: (1273)..(1274)
<223> OTHER INFORMATION: n is a, c, g, or t
<220> FEATURE:
<221> NAME/KEY: misc_feature
<222> LOCATION: (1276)..(1278)
<223> OTHER INFORMATION: n is a, c, g, or t
<220> FEATURE:
<221> NAME/KEY: misc_feature
<222> LOCATION: (1281)..(1282)
<223> OTHER INFORMATION: n is a, c, g, or t
<220> FEATURE:
<221> NAME/KEY: misc_feature
<222> LOCATION: (1284)..(1285)
<223> OTHER INFORMATION: n is a, c, g, or t
<220> FEATURE:
<221> NAME/KEY: misc_feature
<222> LOCATION: (1287)..(1287)
<223> OTHER INFORMATION: n is a, c, g, or t
<220> FEATURE:
<221> NAME/KEY: misc_feature
<222> LOCATION: (1299)..(1299)
<223> OTHER INFORMATION: n is a, c, g, or t
<220> FEATURE:
<221> NAME/KEY: misc_feature
<222> LOCATION: (1302)..(1302)
<223> OTHER INFORMATION: n is a, c, g, or t
<220> FEATURE:
<221> NAME/KEY: misc_feature
<222> LOCATION: (1304)..(1305)
<223> OTHER INFORMATION: n is a, c, g, or t
<220> FEATURE:
<221> NAME/KEY: misc_feature
<222> LOCATION: (1307)..(1311)
<223> OTHER INFORMATION: n is a, c, g, or t
<220> FEATURE:
<221> NAME/KEY: misc_feature
<222> LOCATION: (1364)..(1364)
<223> OTHER INFORMATION: n is a, c, g, or t
<220> FEATURE:
<221> NAME/KEY: misc_feature
<222> LOCATION: (1495)..(1495)
<223> OTHER INFORMATION: n is a, c, g, or t

<400> SEQUENCE: 243

cggacgaggg gggcaggcag tgcgtggaga ggagcccaga cagccgagga gagagaaaga     60

gggaaacttc aggagcctcc tcctcctccc ccggcgcacc ctccggccgg cgacgcgcgc    120

ggcatggcca ccggcggcga cggggacccg gcggcgcccg gcggcggcga cctgtacgcc    180

gtgctggggc tcagcaagga gtgctccgac gccgacctca aggtcgccta ccggaagctc    240

gccatgaggt ggcatccgga caggtgctcg tcctccagcg gcaccaagca catggaggag    300

gccaaggaga agttccagga gatccagggc gcctattcgg tcctctccga cgccaacaag    360

cggttcctct acgacgtggg ggtgtaccaa gaagaagaag acagcgacga cagcatgcag    420

gggatggggg acttccttgg tgagatggcc catatgatga gccagacgcg gccagcgagg    480
```

caggagagct tcgaggagct gcagcagctg tttgtggaca tgttccagtc tgatattgac 540
tcgggatttt gcaatggacc tgccaagggc catcatgacc cgttccaaag acagactcaa 600
acattctcga cctccccttc ctcgccgcca tctccaccac ctccgctagc tacagaggca 660
gaagcagcct catgtaacgg cattaacaag cgtggctcat cagcaatggg ctctgggaag 720
cctccaagag ctgcggaagc gggtgcgggt tacggccagt ctgagttttg ttttgggacg 780
agtgatgcca agcaagcgcc aagggcgcga ggcgggaaca ccagcaggag acgaaacggg 840
cagaagcaga agctgtcgtc gaagcacgat gtctcgtccg aggacgagat gctgagcccg 900
cagcagccca gagtagtatg accctcgatg caaccatctg gtcccttgtc gccttatgtc 960
ctgaccatgt caatggtcac tcggtatcgc actgcagccg atagagcgcc agcgccggaa 1020
gctgttacga ggggggatgc ttcgtcgaag gctatgtagg ccccccttag aaggtttgta 1080
agagaaccta gtgtgtgaga ctcatcgatg ttaccgcatt ctttttctc ggtttgtgac 1140 gctatgttgt tgttgttgtt gttgttgtgg ttgttgttgg gcattgtact ctcgattgat 1200
tcagtgtcca ttgctgttat gatggaagaa gaaagctcct tgttgtggtg aaaaaaaaaa 1260
aaaaaaaana cannannnaa nnannanaaa aaaaaaaana anannannnn naaaaatacg 1320
tggggggggg gccccgcccc aattcccccct taaagggggg gagntaaccg ccgttactac 1380
tattttactg ccaccccccgc aactgccacc tagtcggcaa tcgaccccgt tattttgcct 1440
tcttgcgagt gcgaatgtgt ttgctggtcg ttgtatttcg gccgcttgta gcggnttgaa 1500
aaggaaatat ttg 1513

<210> SEQ ID NO 244
<211> LENGTH: 1257
<212> TYPE: DNA
<213> ORGANISM: Triticum aestivum

<400> SEQUENCE: 244
gcacgaggga gcgacctgag ccgagagaga gagagagaga gggaaggaaa cgccaggaac 60
ctcctcctcc ctcctctccg ctctcctcct cctcctcccc cgcgcatcct cgagcccccc 120
aggccggcgg cgcgggacgc ggcatggcca ccggcggcga cggctgcggc ggcggggagc 180
cggcggcgcc cggcggcggc gacctgtacg ccgtgctggg gctcagcaag gagtgctccg 240
acgccgacct caagctcgcc taccggaagc tggccatgag atggcatccg gacagatgct 300
cgtcctccag cggcaccaag cggatggagg aggccaagga gaagttccag gagatccagg 360
gcgcctattc cgtcctctcc gacgccaaca agcggttcct ctacgacgtg gggtgtacc 420 aagaagaaga agacagcgac gacagcatgc aggggatggg ggacttcctt ggtgagatgg 480
cccatatgat gagccagaca cggccagcga ggcaggagag ctttgaggag ctgcagcagc 540
tgtttgtgga catgtttcag tctgatattg actcggggtt ttgcaataga cctgccaagg 600
gccatcatga cccgttccaa acattctcga cctccccttc ctcgtcgcca tctccaccac 660
ctccagtagc tacagaggca gaagcagcct catgtaacgg cattaacaag cgtggctcat 720
cagcaatggg ctctgggaag cctccaagag ctggggaagc gggtgcgggt tacggccagc 780
ctgagttttg ttttgggacg agcgacgcca agcaagcgcc aaaggcgcga ggcaggaaca 840
ccagcaggag acggaacggg caaaagcaga agctgtcgtc gaagcacgac gtctcgtccg 900
aggacgagat gctgagcccg cagcagccca gagtagcatg accctcgatg caaccgtctg 960
gtcccttgtc accttatgtc ctgaccatgt ccttggtcac ccagtatcag tgcagccagc 1020

```
aagtagagcg ccagcgccgg aagctgttac aaggaggggg gattgcttcg tcgaaggcta   1080

tgtagccccc ccttagaagg tttgtaagag aacctatagc gcgtaagact cgtcgatgtc   1140

accacattgt tctttctcgg tttgtgccgc tgtgttgttg ttgttgttgt tgtaattggg   1200

cattggattc tcgattgatt cagtgttcat tgttgttatg atggagggac aaggctc      1257
```

<210> SEQ ID NO 245
<211> LENGTH: 1094
<212> TYPE: DNA
<213> ORGANISM: Zea mays

<400> SEQUENCE: 245

```
agtgcggcga cgcggcggca gagggcggag acctctacgc ggttctcggg ctaaaaaagg    60

agtgctccga ggccgagctt aaggtcgctt accggaagct cgccaagaaa tggcacccgg   120

acaaatgctc gtcctccagc agcgtgaagc acatggagga agccaaggag aagttccaag   180

agatccaggg cgcctattcc gtactctccg acgccaataa acggctcctc tacgatgtgg   240

gagtatatga cgatgaggac gacgaggaaa gcatgcaggg gatgggggac ttcatcggtg   300

agatggccca gatgatgagc caggcgcagc cgacgaggca agaaagcttt gaggagctgc   360

agcagctttt tgtggacatg tttcagtccg atattgattc aggattctgc aataggactg   420

ccaaggccca tcagtttcag gggccagcca aaagtagaac atgctcgacc tcaccttcat   480

catcaccgtc ccctcctcct accacagcaa aggatgcaga ggtgccatca tgtaatggct   540

tcaataagcg gggttcatca gctctggact cagggaagcc tccaaagcct gttgaaggtg   600

gtgcaggtca gaaccaggct ggattctgtt ttggggtgag cgacacgaag gaaacgccga   660

agctgccagg tcagaacgcc agccggagga ggaacggccg gaaacagaag ctgtcatcca   720

agcacgatgt ttcatctgaa gatgaaacgg cggccggttc gtagcacacc agcagtttga   780

cccattggct tcggtgatat atcattcgtt ggcccttggc tgtgcctagg ggccctagta   840

gctagcagca gcagcaggga cggcacatca tgccagctgc tgtgatctga agaggcgttt   900

agctcatcat atgcctcacc ttaggcctgt gggggatttt ccattgaaac tcgtcgatga   960

tactacatct ttctttctcc atctgtgtcg tttgtgttgt aagacagtga cttctgaagt  1020

ctgatcgtct cggttctttt tattaacatc tgatatacgt tactgcctgt tggtagtagc  1080

gaaagattaa aagg                                                    1094
```

<210> SEQ ID NO 246
<211> LENGTH: 851
<212> TYPE: DNA
<213> ORGANISM: Triticum aestivum
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t

<400> SEQUENCE: 246

```
attcggcacg aggnaacaag cggttcctct acgacgtagg ggtgtaccaa gnaagaagaa    60

gacagcgacg acagcatgca ggggatgggg gacttccttg gtgagatggc ccatatgatg   120

agccagacac ggccagcgag gcaggagagc tttgaggagc tgcagcagct gtttgtggac   180

atgttccagt ctgacattga ctcgggattt tgcaatggac ctgccaaggg ccatcatgac   240

ccgttccaaa cattctcgac cttcccttcc tcgtcgccat ctccaccacc tccgctagct   300
```

```
acagaggcag aagcagcctc atgtaacggc attaacaagc gtggctcatc agcaatgggc    360

tctgggaagc ctccaagaac tggggaagcg ggtgcgggtt acggccagcc tgagttttgt    420

tttgggagga gcgacgccaa gcaagcgcca aaggcgcgag gcgggaacac cagcaggaga    480

cgaaacgggc agaagcagaa gccgtcttcg aagcacgatg tctcgtccga ggacgagatg    540

ctgagcccgc agcagcccag agtagtatga ccctcgatgc gaccatctgg tcctttgtca    600

ccttatgtcc tgaccatgtc aatggtcact cagtatcaca ctgcagccgg caagtagagc    660

gccagcgccg gaagctgtta caacgagggg gggttgcttc gtcaaaggct atgtaggccc    720

cccttagaag gtttgtaaaa gaacctagcg tgtaagactc attgatgtta ccgcattctt    780

ctttctcggt ttgtgccgct gtgttgttgt aattgggcat tggattctcg attgattcag    840

tgttcattgt t                                                         851
```

<210> SEQ ID NO 247
<211> LENGTH: 859
<212> TYPE: DNA
<213> ORGANISM: Zea mays

<400> SEQUENCE: 247

```
aacaagatat acctcgaccg ctttcaagtc acgattgcct acaaaacata atgttcagaa     60

catcacaatc caagtactat tttcttggta atagttcaat acacacccaa tttttttaa    120

ttatcatggt atcaacttct ccagttaaaa aaatgaatag cttagaagtc actcactgtc    180

actggtagtg gtagtacaac acaaccggca cagatgggga aagaaaactg tagtatcatc    240

gacgagtttc aatggaaatc cctcttaggc ctgtagacgc tggttcggtt ttcgaagtac    300

ctttcaaccc taaagacctc tcaaaagact aaaggcatat gatgagctaa acgcctcttc    360

agatcacagc agctggcaga ggcgacatga tgtgccctcc ctactgctga catcaccaaa    420

gccaacggtc aaactgctac cgtgctgctg atgctaggaa ccggccgtat catcttcgga    480

tgtaacgtag tgcttgggga acagcttctg tttccggccg ttcctcttcc ggttggcgtt    540

cggacctcgc ggctttggcg tgtcgctcac cccaaaacaa aatccagcct ggctctgacc    600

tgcaccacat tcaacaggcc ttggaggctt tcctgagtcc attgctgatg aacccgctt    660

attgaagcca ttacatgatg acacctctgc ctcctttact atagtagtag gaggggaccg    720

tggtgagcat gttctacttt tggcttgccc ctgaacctga tggcccttag cagtcccatt    780

gcagaatcct gaatcaatat cagactggaa catgtcgaca aaaagctgct gcagctcctc    840

aaagctttcc tgcctcatc                                                 859
```

<210> SEQ ID NO 248
<211> LENGTH: 607
<212> TYPE: DNA
<213> ORGANISM: Triticum aestivum
<220> FEATURE:
<221> NAME/KEY: misc_feature
<222> LOCATION: (526)..(526)
<223> OTHER INFORMATION: n is a, c, g, or t
<220> FEATURE:
<221> NAME/KEY: misc_feature
<222> LOCATION: (551)..(551)
<223> OTHER INFORMATION: n is a, c, g, or t
<220> FEATURE:
<221> NAME/KEY: misc_feature
<222> LOCATION: (554)..(554)
<223> OTHER INFORMATION: n is a, c, g, or t
<220> FEATURE:
<221> NAME/KEY: misc_feature
<222> LOCATION: (561)..(561)

<223> OTHER INFORMATION: n is a, c, g, or t
<220> FEATURE:
<221> NAME/KEY: misc_feature
<222> LOCATION: (566)..(566)
<223> OTHER INFORMATION: n is a, c, g, or t
<220> FEATURE:
<221> NAME/KEY: misc_feature
<222> LOCATION: (586)..(587)
<223> OTHER INFORMATION: n is a, c, g, or t
<220> FEATURE:
<221> NAME/KEY: misc_feature
<222> LOCATION: (596)..(597)
<223> OTHER INFORMATION: n is a, c, g, or t

<400> SEQUENCE: 248
ccactcccac tccccatatt catatattct gtattcacaa cccacctcac atcactagtt 60
acatgttgca ataacaaact gactaacccg ccgaaccgat ctagcaagct agttggcaaa 120
cttatcgcat ggagccctcg tgctcccatc ccgttgttgt tcttgtgcag tcctctccga 180
tgccaacaag cggttcctct acgacgtggg ggtgtaccag gaagaagaag acagcgacga 240
cagtatgcag gggatggggg acttccttgg tgagatggcc catatgatga gccaggcgcg 300
gccagcgagg caggagagct ttgaggagct gcagcagctg tttgtggaca tgttccagtc 360
tgatattgac tcaggatttt gcaatggacc tgccaagggc catcatgacc cgttccaaac 420
attctcgacc tccccttcct cgtcgccatc tccaccacct ccgctagcta cagaggcaga 480
agcagcctca tgtaacggca ttaacaagcg tggctcatca gcaaangggc tctggggaaa 540
gcctccaaga nccnggggaa ncggtncggg ttacaaccag cctgannttt gttttnngga 600
ccaacga 607

<210> SEQ ID NO 249
<211> LENGTH: 1640
<212> TYPE: DNA
<213> ORGANISM: Zea mays

<400> SEQUENCE: 249
gattcggacg accgggacac ctgcctcctc cccttctccc atctctcccc ctctccctct 60
cgtggccacg actgccgctg ccgccctacg ccaggtgtcc aggtcatctc cggcccattc 120
gccggcgacg agcaccccac tagatcgacc gagatatgga cggcctgtgg catctggggg 180
acgagctccg cgggcagccc aaggtggtgg aggaccgcca gtggtcgctc atgacgtcca 240
agctggcaga gatcaccagg tccaggggcg agaggacgaa cgacctcgac tacgccagga 300
tgaacgccgc ccccgacgcc aagcggtggg gcaaggcggc gtcctaccag caccatgacg 360
agggcaggat ggaccaccac gtcggcctca gcctcaagat gaacgatctc aagatgaacg 420
aggccgccgc tgccgccgtc atgaagctcc ccttccgcgg cgtgccctac aacgtcaacc 480
cgatgtaccc caaggggagc aacgccaacg ccaatgtcaa cgcgttcaag atgaatgtcg 540
gggtgaacaa gtactccagc agcgcgaacg ggaaagactc cggcgggaaa agcagtggcg 600
gcagcaacaa caacagcggc ggcggaggca acggcaatgg gaccgccaac ggcagttccg 660
cagttgacaa gcgcttcaag acgttgccga cgagcgagat gctgccgaag aacgaagtcc 720
ttggtgggta catctttgtc tgcaacaacg ataccatgca ggaggacctc aagaggcagc 780
tttttggatt gccagcaaga tatcgtgatt cagtccgggc aattactcct ggcctgcctc 840
ttttcctcta taactacacc actcaccagc ttcatggggt atttgaggct gccagttttg 900
gtgggtctaa tattgatccc actgcatggg aggataagaa gtgtaaaggt gaatctagat 960
tcccagcgca ggtgaggatc cgcgttagga agctgtgcaa gccgttggaa gaggattcct 1020
tcaggccagt tttgcaccac tatgatggcc caaagtttcg cctcgagctc tccatcgcgg 1080
agaccctgtc cctgctagac ctatgcgaga aggaaggcat ctgagctgtt ggctgcctcg 1140
tgaggttcta gtaaatatca atcatccttg tatgttctgt ggatggtggt tggcaatgtt 1200
gtttattttt caagcgcaag ctgctgccgg tctcgttttc cctgtcctgg atggaagcaa 1260
agggacctgg tactttgaag gccccccctc aaacataagc tgtgagcctg tcagtgcacg 1320
tgtccgccgt tgtcgtcaag aaccaaacca aatcatgaaa tcttgcgccg acggagagtt 1380
ggagcgtgta tgttttgcta tctctatcta catgtctcag tagagtggat ataccctggg 1440
gtccccaaaa gatgggggcc tgtatgtaac actacgtgta atggttaagg tgaatgtgcc 1500
gtgaggcccc ccaaaagttg gagtgtgtat ttttgttgtc accttgaacc gactttgcgt 1560
atgctttttt ttagtgctgc taccttctgc gctgtgtttg gcttctggtt catgtttttg 1620
taatataagg tggcttgcgc 1640

<210> SEQ ID NO 250
<211> LENGTH: 1570
<212> TYPE: DNA
<213> ORGANISM: Triticum aestivum

<400> SEQUENCE: 250
ccacgcgtcc gggtggactc tgtgtgggcg gagcgaagtg ggagccaacg ccaagccagc 60
cgagccgact cctatcctcc tcttcccctt ccccgcagca gtttccccaa atccagcgcc 120
ctccccgccg gaatccggcg ccgaatcgag cagagagctt gaactgagct atggacaact 180
tgtggcatct cggagatgag ttccgtgggc aatcaaaggt ggtggaggac cgccaatggt 240
ctctcatgac atcaaagctt gctgagatca caaagtcaaa ggctgagagg atgaatgact 300
ttgagtatgc acggatgaac accgtccctg atgtcaagca atgggataag ctatcctacc 360
accaagaaga caacaagatg gaccacctca atcttggcct gatgaacctg gatcttaaga 420
tgaatgatct caagatgaac gaggctgcca tgaagtaccc tttccgcaac atggcctata 480
acatgaatcc gatgtacccc aagggaaaca acggtaatgt caattcgttc aagatgaatg 540
ttggggtcaa caaatatccc aataatcaga atgggaagga agcaaacggc aaacacaatg 600
gtggtaacaa caacaatgga ggcaacagca acaacaactc tgttgacaag cgcttcaaaa 660
cattgccaac aagcgagatg ctaccgagga atgaagttct tggtggatac atctttgtct 720
gcaacaatga taccatgcag gaggatctca agagacagct tttggcttg ccagcaagat 780 atcgtgattc agtccgagcc atcactcctg gtctacctct tttcctctac aactacacga 840
cccatcagct acatggggtg tttgaggctg ctagttttgg aggatcaaac attgatccca 900
ctgcttggga agataagaag tgcaaaggtg aatccagatt cccagcacag gtgaggatcc 960
gcattagaag gctttgcaag gccttggaag aggatgcttt caggccagtg ctgcaccact 1020
atgatggtcc taaattccgc ctcgagctct ccatagcaga gacactgtca ctgctagacc 1080
tgtgcaagac agaagacgcc tgatctgctt cggaacatgt ttgtggttgc tctgtggttc 1140
tttttagtaa atatcatccc tgtaagttgt ggaagatgtt ttcacaatga tctgtcccgt 1200
ccgtcgtcca tgaaagcgca agctgttggt tggtggttgc atttccccca gaaaggacct 1260
ggtactcgga agaagtaggc ctctaaagat gtgagcctgt ctgtgtcggt gccgtctgtc 1320
cgtaatctcg gtgatgtgta tgttcttctt catatttatg tatttgtagt gcagtatgcc 1380
cgccgccagc ggggaaaccc cgaaagacgg gggatactgt tgtgatgcat catgaatgcc 1440

-continued

```
ccaaagtgag ggcggttgat gttgggagtg tatcttgttg tctctgtacc ttaccttggt   1500

ttggaaagtt ggaaccttgc atttgacttg atgctgctgt ttctgtactg ctgccagtgt   1560

ggaaggttaa                                                          1570


<210> SEQ ID NO 251
<211> LENGTH: 1824
<212> TYPE: DNA
<213> ORGANISM: Hordeum vulgare

<400> SEQUENCE: 251

ttcggcacga ggcctcgtgc cgaattcggc acgaggccgt gtgcgcggag cgaagtggga     60

gccgagccaa gccgagtctc ctctccttcc ccttcctcgc agcgccctcc ccgtccgaat    120

tcggggccgg atcgagcagg cggagagctt gaactgagct atggacaact tgtggcatct    180

cggagatgag ttccgtggtc aatcaaaggt ggtggaggac cgccaatggt ctctcatgac    240

atcaaagctg gctgagatca caaagtcaaa ggctgagagg atgaatgact ttgagtatgc    300

aaggatgaac actgtccctg atgtgaagca atgggataag ctatcctacc accaagaaga    360

caacaagatg gaccacctca atcttggcct catgaacctg gatcttaaga tgaatgatct    420

caagatgaat gaggctgcca tgaagtaccc tttccgcaac atggcctata acatgaatcc    480

gatgtacccc aagggaaaca atggtaatgt caattcattc aagatgaatg ttggggtcaa    540

caaatatccc aataatcaaa atgggaagga agcaaacggc aaacacaatg gtggtaacaa    600

caacaatgga ggcaacagca acaactctgt tgacaagcgc ttcaaaacat tgccaacaag    660

cgagatgcta ccgaggaatg aagttcttgg tggatacatc tttgtctgca acaatgatac    720

catgcaggag gatctcaaga ggcagctttt tggcttgcca gcaagatatc gtgattcagt    780

ccgagcaatc actcccggtc tacctctttt cctctataac tacacgaccc atcaactcca    840

tggggtgttt gaggctgcta gttttggagg atcaaacatt gatcccaccg cctgggaaga    900

taaaaagtgc aaaggcgaat ccagattccc agcacaggtg agaatccgca ttagaaggct    960

gtgcaaggcc ttggaagagg atgcttttag gccagtgctg caccactatg atggtcctaa   1020

attccgcctt gagctctcca tagcagagac actgtcactg ctagaccttt gcaagtcaga   1080

agacgcctaa tctgcttcgg aacatgggtg tggttgctct gtggttcttt ttagtaaata   1140

tcatccctgt aagttgtgga agatgttttc acaatgttct gttctgtccg tcgtccatga   1200

aagcgcaagc tgttggttgg tggttgcatt tcccccagaa aggacctggt acttggaaga   1260

agtaggcctc taagatgtga gcctgtctct gtgttggtgc cgttcgtccg taatctcggt   1320

gatctgtatg ttctccttat ttatgtattt gtagtgcagt atgcccgccg ccagcgggga   1380

aacccccccg aaagatgggg gggatactgt tgtgatgcat catgaatgcc ccaaagtgag   1440

ggcggttttt gtatcatcat gctggagtgt atctgttgtc tttgtacctt ggttgggaaa   1500

gttggaacct tgcattttac ttggatgctg tttttgtact gcctgtgttg gaagttaaaa   1560

ccttgcaatt ttactggttg ctgctattga gatgctgtcg ctgtacacgc tcgtccatct   1620

tgctttcacg ttcaggaatg tagttatgta cttcctccgt tcacaaatac tccccccgtt   1680

tgtaaatata agtctttcta gagattccac aatatattta ggaacggagg aagtatatct   1740

tatacttctc cgtaccaaaa tataatcaat ttgaactgta aaagcctctt atattctggt   1800

atgaatataa tcaatttgaa ctgt                                          1824


<210> SEQ ID NO 252
<211> LENGTH: 1700
```

<212> TYPE: DNA
<213> ORGANISM: Oryza sativa

<400> SEQUENCE: 252
ccatgtgttg gaccgggaat tcggcattat gggcggggcc ttggcgtaaa ataaaagaga 60
aatctccccc cgtctcgtcg tctcctccgc tccttgcgcc tccccaagac gagtcgcggc 120
tgaacagaag agggggagta ggcggcgatc tccatctggc gactcgcgag cagagcaggg 180
gaggggatcc tgatctggaa gaagctctcc tcttaatttc agcgccttaa ccttaataca 240
agtaccagtt tgagtttgtt tgttcccaag ttggatccgg ccctgggtaa tttctttctt 300
gctgaaggtg gagagactga gctgagctat ggacaacttg tggcatctcg gggatgagtt 360
ccgtgggcag tcgaaggtag tggaggaccg tcagtggtct ctcatgacat cgaagttggc 420
tgagatcaac aagtccaagg cggagaggac gaatgagctt gactatgcgc ggatgaacac 480
catccctgat gtcaagcaat gggataaggt atcctaccac caagatgaga gcaagatgga 540
ccacctcaat cttggcctta tgaatctaga tcttaagatg aacgacatca ggatgaatga 600
cgcagctatg aagaatcctt tccgcggcat ggcctacaac atgaatcagc tgtaccccaa 660
gggaggcaat ggcaatgtta actcgttcaa gatgaatgtt ggggtcaaca aatatttgca 720
tagtccaaat ggcaaagatg tcaatggcaa aaacagtggt gccaacagca atggaagtaa 780
cagcagcggg aacaacagca gcaactctgc tgttgacaaa cgattcaaaa cattgccaac 840
aagtgagatg ctaccaagga atgaagtgct cggtggatat atctttgttt gcaacaatga 900
caccatgcag gaggatctca agaggcagct tttgggttg ccagcaagat atcgtgattc 960
agtccgagca attattcctg gtctacctct tttcctctat aactacacga cccatcagct 1020
tcatggggta tttgaggctt ctagttttgg aggatctaat attgatccca ctgcatggga 1080
agataagaag tgtaaaggtg aatctagatt cccagcgcag gtgaggatcc gcattagaaa 1140
gctctgcaag cctttggaag aggatgcttt cagaccagtg ctgcaccatt acgatggtcc 1200
aaagtttcgt cttgagctct ccatagctga gaccttatca ctgctagacc tttgtgagaa 1260
agaaggcgtc tgaactgttg aagaggtggt tgctttgagg ctttagtaca tatcgctctt 1320
gtatgttgtg gaaggtggtt cactatgttc tcatgttcgt taagcgcaag ctgttggttg 1380
ccccctgcaa ggacctggta cttgaaggcc tctaatacgt gtgcctgtct gtattgtgcc 1440
gtccgtaatc ttgaaaatgt gtatgttttg ctatttatgt attttggtag agtacaccca 1500
gaagggaacc ccaaaatggg gggatactgt aatgcatcat aatgccctaa ataagggcag 1560
ttgatgttca gagtgtattc gtgttgtatc ttaaaaacct tgcatttgcc ttaatgctgc 1620
tttgcacttc aaagttgtgt tttgctcaag ttttgcttag tagcaacgta gcatgccttt 1680
tatttactcc tcaaacaaaa 1700

<210> SEQ ID NO 253
<211> LENGTH: 1546
<212> TYPE: DNA
<213> ORGANISM: Zea mays

<400> SEQUENCE: 253
gccacctgcc ttctctcctt ccttccatcc attcctccct gtctccgccc tcttctgact 60
cccgtaggcc gtggtgccgc cgccgactgc tgggactgcc ctacaccaag tgcccaggtc 120
atcttcgggc cattcgccgg cgacgagcac caccaggtgt gccaggttga ccgagctatg 180
gacagcctgt ggcatcttgg ggacgagctc cgcgggcagc ccaaggtggt ggaggaccgc 240

-continued

```
cagtggtctc tcatgacgtc caagctggcg gagatcacca ggtccaaggg cgagaggatg    300

aacaccgtcc ctgacgccaa gcagtgggac aagacgtcct accagcttca cgacgacagc    360

aggatgggcc acatcaacct cggcctcatg aaccttgatc tcaagatgaa cgaggctgcc    420

gccatgaagc tccccttccg tggcatgccg tataacatga accagatgta cctcaagggg    480

agcaatgcca attccaatgt caatgcgttc aagatgaatg ttggggtcaa caagtactcc    540

aatagtccaa acgggaaaga cgccaatggg aaaaacaatg gcggcagtgg cggcaacaac    600

aacaatggga gcgccaacgg cacttctgtg gctgacaagc gcttcaagac attgccgacg    660

agtgagatgc taccgaggaa tgaagtcctt ggtggataca tctttgtctg caacaacgat    720

accatgcagg aggatctcaa gaggcagctt tttggtttgc cagcaagata tcgtgattca    780

gtccgagcaa tcactcctgg cttgcctctt ttcctctata actacacaac ccaccagctt    840

catggggtat ttgaggctgc cagttttggt gggtccaata tcgatcctac tgcatgggag    900

gataagaagt gtaaaggtga atctagattc ccagcgcagg tgaggatctg cattaggaag    960

ctgtgcaagc cgttggaaga ggattccttc aggccagttt tgcaccatta tgatgggcca   1020

aagttccgcc ttgagctctc catcgcggag acattgtcac tgctagacct atgcgggaag   1080

gaaggcatct gagctgtcga ggaggtggtg gtggttgcct tgtgagcttc tagtaaatac   1140

caatcatctt tgtatgtttt gtggatggtg gttggcaacg ttgtttattt atgcgcaagc   1200

tgctgctggt ttcgggatgg aaggaaagac ctggtccctg aaacaagctg cggagagtga   1260

gcctgtcagt gtattgtgtc tggcgtggtc aagaaccaaa tcaatgttgg accgaccgac   1320

tgagagtttg gagtgtgtat gttttgctat tactcttatc tctagtagag tgtgggtata   1380

cctgggcaga atgtgtcccc aaaagttggg ggcctgtctg tgtactgtgt gcgatggacg   1440

ccctaagtaa aaaaagggca ggtgatggtc gtgctccagg tttgtgtttt gtactctgtt   1500

gtaccttgaa cctcctttgc gttttgccta atcagagaat gaatcc                  1546


<210> SEQ ID NO 254
<211> LENGTH: 1031
<212> TYPE: DNA
<213> ORGANISM: Triticum aestivum
<220> FEATURE:
<221> NAME/KEY: misc_feature
<222> LOCATION: (14)..(14)
<223> OTHER INFORMATION: n is a, c, g, or t

<400> SEQUENCE: 254

cgtaccggtg gatnccgttg tcggcggagc gaagtgggag ccaacgccaa gccagccgag     60

cggactcctc tcctcctcgc agcagttcgc gattcgcccc caaatccagc gccctccccg    120

ccggaatccg gcgccgaatc ttgcagagag cttgaaccga gctatggaca acttgtggca    180

tctcggagat gagttccgtg ggcaatcaaa ggtggtggag gaccgccaat ggtctctcat    240

gacatcaaag ctggctgaga tcacaaagtc aaaggctgag aggatgaatg actttgagta    300

tgcacggatg aacaccgtcc ctgatgtgaa gcaatgggat aagctatcct accaccaaga    360

agacaacaag atggaccacc tcaatcttgg cctcatgaac ctggatctta agatgaacga    420

tctcaagatg aacgaggctg ccatgaagta ccctttccgc aacatggcct ataacatgaa    480

ccccatgtac cccaagggaa acaacggtaa tgtcaattca ttcaagatga atgtcggggt    540

caacaaatat ccgaataatc agaatgggaa ggaagcaaac ggcaaacaca atggtggtaa    600

caacaacaat ggaggcaaca gcaacaacaa ctctgttgac aagcgcttca aaacattacc    660

aacaagcgag atgctaccaa ggaatgaagt tcttggtgga tacatctttg tctgcaacaa    720
```

tgataccatg caggaggatc tcaagagaca gctttttggc ttgccagcaa gatatcgtga 780
ttcagtccga gccatcactc ctggtctacc tcttttcctc tacaactaca cgacccatca 840
gctacatggg gtgtttgagg ctgctagttt tggaggatca aacattgatc ccaccgcttg 900
ggaagataag aagtgcaaag gtgaatccag attcccagca caggtgagga tccgcattag 960
aaggctttgc aaggccttgg aagaggatgc ttttaggcca gtgctgcacc actatgatgg 1020
tcctaaattc c 1031

<210> SEQ ID NO 255
<211> LENGTH: 1385
<212> TYPE: DNA
<213> ORGANISM: Oryza sativa

<400> SEQUENCE: 255
gactggactg aaggagtaga aattggcgta aaataattga gaaatctccc cccgtctcgt 60
cgtctcctcc gctccttgcg cctccccaag acgagtcgcg gctgaacaga agagggggag 120
taggcggcga tctccatctg gcgactcgcg agcagagcag gggaggggat cctggtggag 180
agactgagct gagctatgga caacttgtgg catctcgggg atgagttccg tgggcagtcg 240
aaggtagtgg aggaccgtca gtggtctctc atgacatcga agttggctga gatcaacaag 300
tccaaggcgg agaggacgaa tgagcttgac tatgcgcgga tgaacaccat ccctgatgtc 360
aagcaatggg ataaggtatc ctaccaccaa gatgagagca agatggacca cctcaatctt 420
ggccttatga atctagatct taagatgaac gacatcagga tgaatgacgc agctatgaag 480
aatcctttcc gcggcatggc ctacaacatg aatcagctgt accccaaggg aggcaatggc 540
aatgttaact cgttcaagat gaatgttggg gtcaacaaat atttgcatag tccaaatggc 600
aaagatgtca atggcaaaaa cagtggtgcc aacagcaatg gaagtaacag cagcgggaac 660
aacagcagca actctgctgt tgacaaacga ttcaaaacat tgccaacaag tgagatgcta 720
ccaaggaatg aagtgctcgg tggatatatc tttgtttgca acaatgacac catgcaggag 780
gatctcaaga ggcagctttt tgggttgcca gcaagatatc gtgattcagt ccgagcaatt 840
attcctggtc tacctctttt cctctataac tacacgaccc atcagcttca tggggtatct 900
gaggcttcta gtttcggcgg ctctaatctc gatcccactg aatgggacga tacgacgtgt 960
aacggtgaat ctagattccc agctcaggtg acgctccgcc ttccaaagct ctgcaagcct 1020
ttggaagacg ctgcttccac accagtgctg caccattacg atggaccaca gtctcgtcta 1080
gacctctcca tagctgacaa cttatcactg ctacacctct gtgcccaaca acgcgtctga 1140
actgttgaag acgtgcttgc ctcgaggctt caccaactat cgctctcgta tgtagagcac 1200
cgaggcccct cacgtacacc ctatcgtcag cgcaaccgac cggtgccccc tgacagaaca 1260
gctacccgac agccccacca ggcagcgtac acaacggccg ccagcaacca aacccacgac 1320
tcacgacaac agcaacgcca acccccaacc ccaccaacag cccaacacca cacaaccccc 1380
aagaa 1385

<210> SEQ ID NO 256
<211> LENGTH: 785
<212> TYPE: DNA
<213> ORGANISM: Oryza sativa

<400> SEQUENCE: 256
ccaagacgag tcgccgttga acagaagagg gggagtaggc ggcgatctcc atctggcgac 60

-continued

```
tcgcgagcag agcaggggag gggatcctga tctggaagaa gctctcctct taatttcagc    120

gccttaacct taatacaagt accagtttga gtttgtttgt tcccaagttg gatccggccc    180

tgggtaattt ctttcttgct gaaggtggag agactgagct gagctatgga caacttgtgg    240

catctcgggg atgagttccg tgggcagtcg aaggtagtgg aggaccgtca gtggtctctc    300

atgacatcga agttggctga gatcaacaag tccaaggcgg agaggacgaa tgagcttgac    360

tatgcgcgga tgaacaccat ccctgatgtc aagcaatggg ataaggtatc ctaccaccaa    420

gatgagagca agatggacca cctcaatctt ggccttatga atctagatct taagatgaac    480

gacatcagga tgaatgacgc agctatgaag aatcctttcc gcggcatggc ctacaacatg    540

aatcagctgt accccaaggg aggcaatggc aatgttaact cgttcaagat gaatgttggg    600

gtcaacaaat atttgcatag tccaaatggc aaagatgtca atggcaaacg attcaaaaca    660

ttgccaacaa gtgagatgct accaaggaat gaagtgctcg gtggatatat ctttgtttgc    720

aacaatgaca ccatgcagga ggatctcaag aggcagcttt ttgggttgcc agcaagatat    780

cgtga                                                                785
```

```
<210> SEQ ID NO 257
<211> LENGTH: 1024
<212> TYPE: DNA
<213> ORGANISM: Gossypium hirsutum

<400> SEQUENCE: 257

cagaagaacg ttggggtcaa cggtgggttc aacaaaggga tctattccaa accagggaac     60

aacaacaata acttcaatgt taatttgaat gggaacaaga gcaaaggaga agaatatcat    120

ggaaccaaga gtgggaagaa gaacagcaac aagaaaaaac aataacaaca acgacaataa    180

caacgaaaac aaggatggga aaagtgctgc tgataaaagg tttaagacac tgccaccatc    240

tgaatcattg ccgagaaatg aaactgtcgg cggctatatt tttgtctgca acaacgatac    300

catggaggag aatctcagaa gacagctctt tggtttgcct ccacgttacc gtgattcagt    360

ccgggcaata actccgggcc tgcctctgtt cctctacaac tactccaccc accaactcca    420

tggtgttttt gaggctgcaa gctttggtgg aacaaacatt gacccaactg cctgggagga    480

caagaaatgc cctggcgaat ctcgattccc tgctcaggtt cgcgttatta caaggaaaat    540

ctgcgagcca cttgaagaag attcatttag gccaattctc catcactacg atggtccaaa    600

attccgcctt gaactcaaca tcccagaggc actttccctg ttggatatat ttgctgatca    660

acaagatact tgtatttctt aagcaacaag atgcttgagc aaaactaaaa cactaggcat    720

atcgatacaa atacagatac acacagagat aatgaagaga agagtttgaa gaataagtag    780

agaaaaatag aaattatatt tgtgaaagtg cctttgttag atgtaaaact ttttttttca    840

caggctttgc tgtgattgtt tttcttttct tttcttttt actgtttggc ttatacataa    900

ataatacctg aaactaagtg ataaacatcg acttattttg ggatgttact taatataagt    960

ttgagatttt gttgtattag aacttgtttt gaagctatga atctaaaact acaattattg   1020

gtct                                                                1024
```

```
<210> SEQ ID NO 258
<211> LENGTH: 943
<212> TYPE: DNA
<213> ORGANISM: Solanum tuberosum

<400> SEQUENCE: 258

aaaggggata aataggaaat ttggtaaagg attttttgaa gatgagcata aaagtgtgaa     60
```

-continued

```
gaagaataac aagagtgtta aagagagtaa caaggatgtt aatagtgaga aacagaatgg    120

tgttgataaa aggtttaaga ctttgccacc agcagaatct ttgccaagaa atgagacagt    180

tggtggatat atttttgttt gcaacaatga tactatggct gagaatctca aaagggagct    240

ctttggcttg cccccacgtt acagggactc agttaggcaa ataacacctg gattgcctct    300

ttttctgtac aactactcga cccatcagct tcacggtgtt tttgaggctg caagctttgg    360

tgggtcaaat attgatccat cggcctggga ggacaagaag aaccctggtg aatctcgctt    420

tcctgctcag gtccttgtcg tgacaaggaa agtctgtgaa ccacttgaag aggattcatt    480

caggccaatc cttcaccact acgacggccc taaattccgc ctcgagctaa acgttccaga    540

ggctatttct cttctagaca tttttgaaga gaacaagaac taaatgaatg ttcttgtttt    600

acaagcagag aatggacaat ataccattat aaaggaagaa aaaaaagagt tgattagaga    660

aaaagagtga aaaagagttt gcttctagta atactgaaga gagtttgcag agcagaaaaa    720

aaaactatct atctattgta tatagatata tacataaatg cagaatataa tgatctggaa    780

aaacactttt tgtgtggaga caaatattat tatatttact atattgtgta atccagcaag    840

aatttgctgt ataataataa gtgaaatatg agtaaaaaca agttatgttt ggttattact    900

acctattatt tcctctttgc tatatctaaa atgcatttgg tgt                      943
```

<210> SEQ ID NO 259
<211> LENGTH: 1236
<212> TYPE: DNA
<213> ORGANISM: Triticum aestivum
<220> FEATURE:
<221> NAME/KEY: misc_feature
<222> LOCATION: (1185)..(1185)
<223> OTHER INFORMATION: n is a, c, g, or t

<400> SEQUENCE: 259

```
cacacgtgcc gggactggag cacgaggaca ctgacatgga ctgaagcagt agaaaattca     60

agatcacttt tccgtgcact ttttttacc tcggagccac acagactctc accacatccc    120

aggaaccaga gcagcaagcc ttgtggagct cggctcgagc atggacacca agcatgcgga    180

ttcgttcgac gagcgcgacg tcgtcgtcga cgccggctgc gtccgcgccg tgctcgggga    240

gctggtcctc accttcctct tcgtcttcac cggagtcgcc gccgccatgg ccgccggggt    300

gccggagctg caaggcgcgg ctatgccgat ggcgacgttg gccggggttg ccctcgcgca    360

ggcgctggcg gcgggggtgc tggtgacggc gggcttccac gtgtcgggcg ggcacctcaa    420

cccggcggtg acggtggcgc tgctggcgcg cgggcacatc acggcgttca gggccgtgct    480

gtacgtggcg gcccagctgc tggcctcctc cctcgcctgc atcctcctcc gctacctctc    540

cggcggccag gctactccgg ttccggtcca caccctaggc gcaggcatag gccccatgca    600

agggctggtc atggaggtca tcctcacctt ctccctcctc ttcgtcgtgt acgcgaccat    660

catcgacccg cggaccacgg tgcccggcta cggtccgatg ctcaccggcc tcatcgtcgg    720

tgccaacaca attgccggcg gcaacttctc cggcgcttcc atgaacccag ctaggtcctt    780

cgggcccgcg ttggccactg gggtgtggac caaccactgg gtctactggg tcggcccgct    840

ggtcggcggc cccctcgccg ggttcgtcta tgaaacggtg ttcatggtga cgaagacgca    900

tgagcctcta cttggttggg acttttagaa aagcaggttg ctcgcatact tgcatttata    960

ttttgcgatg tataccagtg tgtataaggc aatcgatgtt gctgatagat tttcaggcaa   1020

tgtgaatcta gctaggtgtt gaaatggttt gtagggagca gcgactaaag tggctgtttt   1080
```

-continued tttggttgt taaaagcttt gattaaaagg ctaataatca gccgtgtaaa tatatttgtt 1140
tggaagacgt gaatttcaac ccattagagg tgtgattttt ctttngttct attagaggtg 1200
tgattggtgt tgcgaatcag ggacaaacct tttgtg 1236

<210> SEQ ID NO 260
<211> LENGTH: 1080
<212> TYPE: DNA
<213> ORGANISM: Triticum aestivum

<400> SEQUENCE: 260
cccacgcgtc cgttactttt aacctcggag ccgcacagac tctcgccaca tcccaagaac 60
cagagcggcg agcctcgtgg agctcagctc gagcatggac accaagcatg cggattcgct 120
cgacgagcgt gacgtcgtcg tcgtcgacgc cggctgcgtc cgcgccgtgc tgggggagct 180
ggtcctcacc ttcctcttcg tcttcaccgg agtcgccgcc gccatggccg ccggggtgcc 240
ggagctgcag ggcgcggcta tgccgatggc gacgctggcc ggggttgccc tcgcgcaggc 300
gctggcggcg ggggtgctgg tgacggcggg gttccatgtg tcgggcgggc acctcaaccc 360
ggcggtgacg gtggcgctgc tggcgcgcgg gcacatcacg gcgttcaggg cggtgctgta 420
cgtggcggcc cagctgctgg cctcctccct cgcctgcatc ctcctccgct acctctccgg 480
cggccaggcc actccggttc cggtgcacac cctgggcaca ggcataggcc ccatgcaagg 540
gctggtcatg gagatcatcc tcaccttctc cctcctcttt gtggtgtacg cgaccatcct 600
cgacccgcgg accacggtgc ccggctacgg accgatgctc accggtctca tcgtcggtgc 660
caacaccatt gccggcggca atttctccgg cgcttccatg aaccccgccc ggtccttcgg 720
gcccgcgttg gccactggag tgtggaccaa ccattgggtc tactgggtcg gcccgctggt 780
cggtggcccc ctcgccgggt tcgtctatga gacagtgttt atggtgacga agacgcatga 840
gcctctactt ggttgggact tttagaaaag caggttgctc gcatacttgc atttacattt 900
tgcgatgtat aatggtatgt ataagacaat cgatgtcgct gatagatttt tcaggcgaag 960
tgattctagg tagggtgtca gaaatggttt gtacggagct actacaatgc tgtgtaaata 1020
tatttgtttg gaagatgtga atttcaaccc cttagaggtg tgaaattttt tttgagttct 1080

<210> SEQ ID NO 261
<211> LENGTH: 1139
<212> TYPE: DNA
<213> ORGANISM: Hordeum vulgare
<220> FEATURE:
<221> NAME/KEY: misc_feature
<222> LOCATION: (12)..(12)
<223> OTHER INFORMATION: n is a, c, g, or t

<400> SEQUENCE: 261
ctcgtgccga anttcggcac gagccaactt ttcggtgcgc ttttgcatcg tcctgagctt 60
tcacccctct tccttccttc cttccatccc aagaacaaga gcgacgagtg tggtggagtt 120
cagtcccgcc atggccgcca ccaagcacgc ggattcgttc gacgagcgtg aagtcgccgt 180
cgtcgacacc ggctgcgtcc gcgccgtgct gggggagctg gtcctcacct tcctcttcgt 240
cttcaccgga gtcgccgccg ccatggccgc cggggtgccg gagctgccgg gcgcggctat 300
gccgatggcg acgttggccg gggttgcgct tgcgcaggcg ctggcagcgg gggtgttggt 360
gacggcgggg ttccatgtct ccggcgggca cctcaacccg gcggtgacgg tggcgctgct 420
ggcgcgcggg cacatcacgg cgttccgggc ggtgctgtac gtggtggccc agctgctggc 480
ctcctccctc gcctgcatcc tcctccggtg cctcaccggc ggccagccta caccggttcc 540
ggtgcacacc ctgggcgcag gcataggccc catgcaaggc ctggtcatgg agatcatcct 600
caccttctcc ctcctcttcg tcgtgtacgc caccatcctc gacccgcgga ccacggtgcc 660
cggctacgga ccgatgctca ccggccttat tgtcggtgcc aacaccattg cgggcggcaa 720
cttctctggg gcgtccatga accctgctcg gtctttcggg cctgcgttgg ctaccggggt 780
gtggaccaat cattggatct attgggttgg cccattggtc ggtggtccgt tggccggttt 840
tgtctatgag atggtcttca tggtgaagaa gacgcacgag cctctgcttg gttgggactt 900
ttaggaaagc aaattgctcg catacttgta attgcatttt gcaatgtata ccggtgtgta 960
taagacaatc aatgttgctg atagatttgt ttctagctat atatagtgtt caaatggttt 1020
gtaaggagca actacaaaag atgttttttt agagggatgg ggttagaagc tttgattaaa 1080
aggctaataa tcagctgtgt aaatatattt gtttggaaat cactggatct tttgggcca 1139

<210> SEQ ID NO 262
<211> LENGTH: 1369
<212> TYPE: DNA
<213> ORGANISM: Triticum aestivum

<400> SEQUENCE: 262
ctcagcctag gccttgtgaa gtcacttatt tgattactgc aggaatatca tttcatacct 60
ttggtactaa tcgtatcata tgttgccggg accgtaacat ggacagacag cggttacttg 120
acaaggccta ggctgaggat gccgaaggag gtatggggcc agtctttctc cttggcctta 180
gtcagcatgg ctctgcccca ggacttttcc gtgcactttt tttacctcgg agccacacgg 240
actactctca ccacatccca agaagcagag caacgagcct tgtaagcatg gacaccaagc 300
acgcggattc gttcgaggag cgtgacgtcg tcgtcgacgc cggctgcgtc cgcgccgtgc 360
tgggggagct ggtcctcacc ttcctcttcg tcttcaccgg agtcgccgcc gccatggccg 420
ccggggttcc ggagctgccg ggcgcggcta tgccgatggc gacgttggcc ggggttgccc 480
tcgcgcaggc gctggcggcg ggggtgctgg tgacggcggg cttccatgtg tcgggcgggc 540
acctcaaccc ggcggtgacg gtggcgttgc tggcgcgcgg gcacatcacg gcgttcaggg 600
cggtgctgta cgtggcggcc cagctgctgg cctcctccct cgcctgcatc ctcctccgct 660
acctctccgg cggccaggct actccggttc cagtgcacac cctgggcgca ggcataggcc 720
ccatgcaagg gctggtcatg gaggtcatcc tcaccttctc cctcctcttc gtcgtgtacg 780
cgaccatcat cgaccctcgg accacggtgc ccggctacgg tccgatgctc accggcctca 840
tcgtcggtgc caacaccatt gccggaggta acttctccgg tgcgtccatg aaccccgcta 900
ggtcctttgg tcccgcgttg gccatgggag tgtggaccaa ccactgggtc tactgggtcg 960
gtccgctggt cggtggcccc ctcgcggggt tcgtctacga gatggtgttc atggtgaaga 1020
aagacgcacg agcctctgct tggctgggac ttctagaaaa caggttgctc ccatacttgc 1080
atttacattt tgcgatgtat accagtgtgt ataaggcaat cgatgttgct ggtagatttt 1140
tcaggcccag tgattctagc tagggtgtcc aaatggtttg tagggaggta ctacggtgga 1200
tgtttttttt cttgggggag ggggggagat aggttttgtt caaagctttg attaaaaggc 1260
taataatcag ccgtgtaaat atattgggcg cttataggcg ccggcgcgcc ggccgaaccg 1320
ctcggccggt cgagccccag ccgcccgata tcatgaataa gagccgtcc 1369

<210> SEQ ID NO 263
<211> LENGTH: 1430
<212> TYPE: DNA

<213> ORGANISM: Oryza sativa

<400> SEQUENCE: 263

```
ggcacaaaca gtttcgcttt cttgatagcc atgtcgcagc cacagctttg tttgctagaa      60
tgagacaccc ctgattcctc agccacatac ttagattaag aaactaatca ccttcctcaa     120
tcttggttcc taatccgcta taaaaagcag aggaaagcag aggagacagg cagagcagag     180
gagagaaccc caccttggca aaaagaaaag aaaaataata tcatcgcact tttgctgcc     240
cttttcatcc cctcggatat tcacgaagca aatctctctg caattctttt cttttttttt     300
tttgatcttg cggatcttct ccattgagga aaggcgagag ctttgggatc gattccgggc     360
catggcgaag gaggtggatc cgtgcgacca cggcgaggtc gtcgacgccg ggtgcgtccg     420
cgccgtgctg gccgagctcg tcctcacctt cgtcttcgtc ttcaccggcg tcgccgccac     480
catggccgca ggggtgccgg aggtggcggg ggcggcgatg ccgatggcgg cgctggcggg     540
ggtggcgatc gcgacggcgc tggcggcggg ggtgctggtg acggcggggt tccacgtgtc     600
cggcgggcac ctgaacccgg cggtgacggt ggcgctgctg gcgcgggggc acatcacggc     660
gttcaggtcg gcgctctacg tcgccgccca gctgctggct tcctccctcg cctgcatcct     720
cctccgctac ctcaccggcg gcatggcgac cccggtgcac actctgggct cagggatagg     780
gcccatgcag ggcctggtca tggagatcat cctaaccttc tccctcctct tcgtcgtcta     840
cgcgaccatc cttgacccgc ggagctcggt cccgggcttc ggcccgctgc tcacgggcct     900
catcgtcggt gccaacacca tcgctggtgg caacttctcc ggcgcgtcaa tgaacccggc     960
ccggtcattt gggccggcgc tggccactgg agtgtggacc caccactgga tctactggct    1020
cgggccgctg attggcgggc ctctcgctgg gctggtctat gagtcattgt tcttggtcaa    1080
gaggacccat gagcctctgc tagataattc cttttagtag tctggtctct ttagatggtt    1140
tcatttgcag aatgcatata ttgccaggta gtaataagat gcttgtgcag cttgtaggcc    1200
tgtaagggct gtataattat tattttcttt ttgccctcga ggattttatc aacgttgata    1260
atcagccatg taaaaagatt gtttgggata tgattttttt gttagtataa aatgtagtcc    1320
ggtagttggt ctgttgtaaa tcggcgaatg ccatgtggtt ttgaaattag aatctatgta    1380
aacattttca aatgaattca gtaaaattca tttcaaatgg gtaaaaaaaa               1430
```

<210> SEQ ID NO 264
<211> LENGTH: 618
<212> TYPE: DNA
<213> ORGANISM: Saccharum officinarum
<220> FEATURE:
<221> NAME/KEY: misc_feature
<222> LOCATION: (597)..(597)
<223> OTHER INFORMATION: n is a, c, g, or t

<400> SEQUENCE: 264

```
cccacccgcc tcctcctcct cctcctcctg tcgttcaaaa tatctcgctg cgcttttccg      60
agtccttttc cctccaagga acaggaacaa ccggcgcttt taccccacca cccgctttcc     120
cctccccgcc aggaacagga gcgacaaggc tcctcctcgc aatagttcat tcattcatgg     180
cgaagctcgt gaacaagctg ctcgattcgt tcgaccacga cgacactacg ccggacgtcg     240
gctgcgtgcg cgccgtgctg gccgagctcg tcctcacctt cctcttcgtc ttcaccggcg     300
tctccgccgc catggccgcc gggtccggcg ggaagcccgg cgaggctatg ccgatggcga     360
cgctggcggc ggtggctatc gcgaacgcgc tggccgccgg cgtcctggtc acggccgggt     420
tccacgtctc cggcggccac ctcaaccccg ccgtgacggt ggggctcatg gtgtgccgcc     480
```

acatcaccaa gctccgcgcg gtgctctaca tcgccgcgca gctgctggcc tcctccctcg 540
cctgcattct cctccgctac ctcagcggcg gcatggtgac cccggtgcac gccctgngcg 600
ctggcatcaa gcccgatg 618

<210> SEQ ID NO 265
<211> LENGTH: 2695
<212> TYPE: DNA
<213> ORGANISM: Oryza sativa

<400> SEQUENCE: 265
ctttgaagtc ctagcctaaa agctcttcta ctcgcataaa gaaagatggt gaagcttgca 60
tttggaagct gcggcgactc tttcagtgcc tcgtccatca aggcctatgt cgcggagttc 120
attgccacac tcctctttgt gttcgccggc gtcggctccg ccattgccta cgggcaactg 180
acaaagggcg gcgcgctaga cccagctggt ctggtggcga tcgccatagc ccatgccttc 240
gcgctgttcg tcggagtttc catggccgcc aacatctccg gtggccactt gaaccccgtt 300
gtcaccttcg gcctcgccgt cggtggccac atcaccatcc tcaccggcat cttctactgg 360
gtcgctcagc tgctcggcgc gtccgtcgcg tgtctgctct gcagttctcc acccacggac 420
aggttggcta tcccgacgca cgccatcgcc ggaattagcg agatcgaggg catggtgatg 480
gagattgtga tcacgttcgc gctggtgtac acggggtacg ccacggcggc cgacccgaag 540
aagggttccc tcggcaccgt cgcgcccatg gacatcggct tcatcgtcgg tgccaacatc 600
ctggcggcgg ggccctttag cggcagttcc atgaaccctg cccgctcctt cggcccggcc 660
gtcgcggccg gcaacttcgc cggcaactgg gtgtactggg tcggcccact gatcggtggt 720
ggcctggccg ggctcgtcta cgacgacgtg ttcatcgcct cctaccagcc ggtgatgatc 780
ggattcactg ttattttatg tgaccggtct gaccaggctg tgtatgccgg tcagaccagc 840
ggtgatcgag cggtgactcc atgcctaggg agagtatttg cggtgatgga ccgggagtcg 900
gcttggtgta ggatgcaatc ttacattatg gctgagaatt atgatatttg gagaaaagtt 960
tctcatcctt atgtgattcc tgaagctatt aatactgctg ctgaaaaaac tgcttttgaa 1020
caaaattgca aagctcgcaa tattcttttg agtgggattt ctcgttcgga ttatgatcgt 1080
gttgctcatc ttcaaactgc tcatgagatt tggattgctt tgagtaattt tcatcaagga 1140
acaaataata ttaaagaact tcgtcgtgat cttttcaaaa aggagtatat taaatttgag 1200
atgaaacctg gagaagcttt ggatgactat ctttctaggt ttaataaaat tttgagtgat 1260
cttagatctg ttgattcttc ttatgatgct aattatccac aatctgagat ttctcgtcac 1320
tttttgaatg gtcttgacat gtctatttgg gagatgaaag ttacatctat tcaggagtct 1380
gttaacatgt ctactttgac tttggattcg ctttacacaa aattgaaaac tcatgagatg 1440
aatattcttg ctcgtaaagt tgattctaag tctagtgctt tggtttcttc ttcgacttct 1500
ttggatgttg gtgcttcttc atcgaagtct tctgttcttg ctttatttaa tgccatgtcc 1560
gatgatcaac tcgaacagtt cgaggaggag gacttggttt tgttatctaa caaattttct 1620
cgagctatga aaaatgttag gaacaggaaa agaggagaac cgaatcgttg ttttgagtgt 1680
ggagcacttg atcatcttcg ctcgcattgt cctaagcttg ggagaggcaa gaaggaagat 1740
gatggtagag tcaaagagga tgacgtgaac aagaagaaga acatgaagga gaaggagaag 1800
aagaagcatt gtatgcagtg gttaatccaa gaactcataa aagtttttga tgaatcggaa 1860
gatgaagatg agggcaaagg taagcaagtt gttgatctag cttttattgc tcgtaatgca 1920

-continued

```
agttctgatg ttgatgaatc tgatgatgat aatgaagaaa agcttagtta tgatcaatta   1980

gaatatgctg cttacaaatt tgctaagaaa cttcaaacat gttctattgt gcttgatgag   2040

aaggatcata ctattgagat tcttaatgct gaaattgcta gattaaaatc tttgattcct   2100

aatgatgata attgtcaatc ttgtgaagtt ttattttctg aaattaatgc tttgcgagat   2160

gtcaattctg ttaattgcaa gaaattggaa tttgagattg aaaaatctaa aaagttggaa   2220

tcttcttttg ctcttggatt tgctttacat gctcgtgttg ttgatgagtt gattttgaca   2280

aagaacgttt tgaaaaaaat acaaagttgc tttttgtgca agttctttgg tcaatgcttc   2340

atgtgcaaat aaggcaaaac aaaacaatgg tgttttgatt tctcaagatt gttcaaagtg   2400

tgttttgaat gagttgaagt tgaaagatgc tttagagcgt gttaaacaca tggaagaaat   2460

tattaaacaa gatgaggtgt tttcatgctc aacttgtaga aaacaaaaag gtcttttgga   2520

tgcttgtaaa aattgtgcta ttcttactca ggaggtttct tatttgaaaa gttctttgca   2580

aagattttct gatggtaaaa agaacctcaa catgattctt gatcaatcta acgttagcac   2640

acacaatcgt ggtttaggtt ttgattctta ttcaaaggac cttgatgtcg cctag        2695
```

<210> SEQ ID NO 266
<211> LENGTH: 1083
<212> TYPE: DNA
<213> ORGANISM: Glycine max
<220> FEATURE:
<221> NAME/KEY: misc_feature
<222> LOCATION: (24)..(24)
<223> OTHER INFORMATION: n is a, c, g, or t

<400> SEQUENCE: 266

```
attagttcga ttttgtagta agtnaggtgc caatatggtg aagatagctc ttggtacttt     60

ggatgactct tttagcgctg cctctcttaa agcttatttc gcagagttcc acgcaactct    120

gattttcgtg ttcgctggtg ttggatcagc catcgcttac aacgagctta caaaagatgc    180

agccttggat ccaacggggc tggtggcagt agctgtggca catgcatttg cactgtttgt    240

aggtgtctcc gtcgccgcca acatctcagg tggccatttg aacccagctg tcacttttgg    300

attggccatt ggaggcaaca tcactctcat cactggtttc ttatactgga ttgcccaatt    360

gttgggttct atagtcgcat gcctcctcct caatttgatc accgctaaga gcattccaag    420

ccactcgccg gctaatggtg tgaacgattt gcaagctgta gtgtttgaga ttgttatcac    480

atttgggttg gtttacactg tgtatgcaac tgcagtagac ccaaagaagg ggtcattggg    540

tatcattgca cccattgcta ttgggttcgt tgtgggtgcc aacatcttag cagcaggccc    600

attcagcggc ggttcaatga acccagctcg ctcattcggc ccagctgtgg tcagtggaga    660

cttggctgct aactggatct actgggttgg cccattgatt ggaggaggtt tggctggctt    720

gatttatgga gacgtcttca ttggttccta tgcccctgtc ccagcctctg aaacctaccc    780

ttgagcttca acttcacttg tgtgttcctt caagtttcat ctctgttcac cgtttcatgt    840

catgagcctc ttggcttctt gcattttaaa ctctacttta tctattatcc accgcttgca    900

ataattatgt aaattataat tcgaacttga tacatgaatt gttggaaggt ccccttgttt    960

ttcggttttc gtcctaccaa tgacagcgag ctagctagtg gtttttacgg atcagatctg   1020

cagttcattt ttcaactgta atcaatctcg gccaatattt aatagactaa cataattaaa   1080

aaa                                                                 1083
```

<210> SEQ ID NO 267
<211> LENGTH: 1146

<212> TYPE: DNA
<213> ORGANISM: Triticum aestivum
<220> FEATURE:
<221> NAME/KEY: misc_feature
<222> LOCATION: (1126)..(1126)
<223> OTHER INFORMATION: n is a, c, g, or t
<220> FEATURE:
<221> NAME/KEY: misc_feature
<222> LOCATION: (1133)..(1133)
<223> OTHER INFORMATION: n is a, c, g, or t

<400> SEQUENCE: 267
aggaattcgg cacgagggaa acattccgtc tcatcctccc cagctcggtt tttgggccat 60
tctaagccac catgcctgcc tccatcgcct tcggtcggtt cgatgactcc ttcagcttgg 120
cctctttcaa ggcctacatc gccgagttca tctccaccct catcttcgtc ttcgccggcg 180
tcggctctgc catcgcctac tccaaggtga gcggcggcgc gccgcttgac ccatccgggc 240
tgatcgccgt ggcgatctgc cacgggttcg ggctgttcgt cgcggtcgcc gtcggcgcca 300
acatctccgg cggccatgtg aaccctgccg tcaccttcgg cctcgccctc ggcggccaga 360
tcaccatcct caccggcatc ttctactggg ttgcccagct cctcggcgcc atcgtcggcg 420
ccttcctcgt ccagttctgc accggcgtgg cgacccctac acacgggctt tccggcgtgg 480
gcgccttcga gggcgtcgtg atggagatca tcgtcacctt cgggctcgtc tacaccgtgt 540
acgccaccgc cgccgacccc aagaaggggt ccctcggcac catcgctcca atcgccatcg 600
gcttcatcgt cggcgccaac atcctcgtcg ccggcccctt ctccggcggg tccatgaacc 660
ctgcacgctc cttcggcccc gccgttgcca gcggcgactt caccaacatc tggatctact 720
gggccggccc gctcatcggc ggtggcctcg ccggcgtcgt ctaccggtac ctgtacatgt 780
gcgacgacca caccgccgtc gccggcaacg actactaagc cagccatggg aagatcattc 840
ggtctttggt ttccataatg tcttcggcaa cataagaagt gcgtacgtgg tggtcactct 900
caggattgtc tggatgatgt gaggaacgtc atgttgtttg gttccgatcg aaagcccgcg 960
aggctgtggc acttggatga tgcatgtttc tgtatctgta ctgtgatgga tgttgtgaag 1020
ttgttggggt ttcaagattc ttcagttgag tttccttatg cgattcaata agagcatcat 1080
tgtttagtgc attcccatgc ccacggccaa acttctgggg tacatngtcg ttnacaacct 1140
ccactt 1146

<210> SEQ ID NO 268
<211> LENGTH: 1076
<212> TYPE: DNA
<213> ORGANISM: Triticum aestivum
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (954)..(954)
<223> OTHER INFORMATION: n is a, c, g, or t

<400> SEQUENCE: 268
attcctagga ttacgncgac ccacgcgtcc gtctacctct catcctccca gttctgttcc 60
tcggccattc tagccaccat gccgggctcc atcgccttcg gtcgcttcga tgactccttc 120
agcttggcct ctttcaaggc ctacatcgct gagttcatct ccaccctcat cttcgtcttc 180
gccggcgtcg gctctgccat cgcctacact aaggtgagcg gcggcgcgcc ccttgaccca 240
tccgggctga ttgccgtggc gatatgccac gggttcgggc tgttcgtcgc ggtcgccatc 300

-continued

```
ggcgccaaca tctccggcgg ccacgtgaac cctgccgtca ccttcggcct cgccctcggc    360

ggccagatca ccatcctcac cggcatcttc tattgggttg cccagctcct cggtgccatc    420

gtcggcgcct tcctcgtcca gttctgcacc ggcgtggcga cccctacaca cgggctttcc    480

ggcgtgggcg cctttgaggg cgtcgtgatg gagatcatcg tcaccttcgg gctcgtctac    540

accgtgtacg ccaccgccgc cgaccccaag aagggttccc tcggcaccat cgcccccatc    600

gccatcggct tcatcgtcgg cgccaacatc ctcgttgccg gccccttctc cggcgggtcc    660

atgaaccctg cacgctcctt cggccccgcc gttgccagcg gcgacttcac caacatctgg    720

atctactggg ccggcccgct catcggcggt ggcctcgccg gcgtcgtcta ccggtacgtg    780

tacatgtgcg acgaccacag ctccgtcgcc ggcaacgact actaagccag ccatgggaag    840

agtcgtcggg tccataatgc ctttcggcaa cataaaagtg cgtacgtggt gggcagtctc    900

acgaatggtc tcgatgatgt gaagaaccat cctgttgttt gggtcagatc gaanctgtta    960

cacctgggat atgcatgttc ttttatctgt aaatgtgatg tggtgaagtt gttggggttg   1020

agattcttca gtggagtttc cttatcgatt caatagaaca tattggttag gcatcc       1076
```

```
<210> SEQ ID NO 269
<211> LENGTH: 749
<212> TYPE: DNA
<213> ORGANISM: Solanum tuberosum

<400> SEQUENCE: 269

gatcacattg gcaagtgact taaaattgta ctttctttga tttaagcaca ttcttttgtg     60

agagccaaaa aaaaatggtg aagattgcct ttggtagcat tggtgactct ttaagtgttg    120

gatcattgaa ggcttactta gctgagttta ttgccactct actctttgta tttgctggtg    180

ttggatctgc tatagcttat aataagttga cttcagatgc agctcttgac ccagctggtc    240

tagtagcaat agctgtggct catgcatttg cattgtttgt tggggtttcc atggcagcca    300

atatctcggg tggacattta aatccagctg tcactttggg attggctgtt ggtggtaaca    360

tcaccatctt gactggctta ttctactggg ttgcccaatt acttggctcc acagttgctt    420

gcctcctcct taaatatgtc actaatggtt tggctgttcc aactcacgga gttgctgccg    480

ggatgaatgg agctgaggga gtagttatgg aaatagtcat tacctttgca cttgtctaca    540

ctgtttatgc cacagcagct gtcgttgctg gagacttttc tcagaactgg atttactggg    600

tcggaccact cattggtgga ggattggctg ggtttattta tggagatgtt ttcattggat    660

cccacacccc acttccaacc tcagaagact atgcttagaa caaagaagaa agaagaagtc    720

ttcaacaatg ttttcttttg tgtgttttc                                      749
```

```
<210> SEQ ID NO 270
<211> LENGTH: 729
<212> TYPE: DNA
<213> ORGANISM: Saccharum officinarum
<220> FEATURE:
<221> NAME/KEY: misc_feature
<222> LOCATION: (550)..(551)
<223> OTHER INFORMATION: n is a, c, g, or t
<220> FEATURE:
<221> NAME/KEY: misc_feature
<222> LOCATION: (679)..(679)
<223> OTHER INFORMATION: n is a, c, g, or t

<400> SEQUENCE: 270

cagctagcaa tttctcaagc tcagagcgct aagtcttcca gccgcgaaga gctaagaggg     60

aaagcaagat ggtgaagctc gcgttcggaa gcgtcggcga ctccttcagc gccacctcca    120
```

```
tcaaggccta cgtctctgag ttcatcgcca ccctcctctt cgtcttcgcc ggcgtcggtt    180

ccgccatcgc ctacggacaa ctgaccaacg atggcgcgct cgaccctgcc ggtctggtgg    240

cgatcgcgat cgcgcacgcg ctggccctct tcgtgggcgt ctccatcgcc gcgaacatct    300

ccggcggcca cctgaacccg gccgtgacgt tcggcctggc cgtgggcggc cacatcacca    360

tcctcacggg cctcttctac tgggtggccc agctgctggg cgcgtccgtg gcgtgcctgc    420

tcctcaagtt cgtgacccac ggcaaggcga tcccgaccca cggcgtgtcc gggatcagcg    480

agctggaagg cgtggtgttc gagatcgtca tcaccttcgc gctcgtgtac accgtgtacg    540

ccaccgccgn ncgaccccaa gaagggctcc ctcggcacca tcgcgcccat cgccatcggc    600

ttcatcgtcg gcgccaacat cctcgccgcg gggcccttca gccgcggctc catgaacccg    660

gcccgtcctt cgggcccgnc gtcgcccgcg gcaacttcgc cggcaactgg gtctactggg    720

tccgcccat                                                            729
```

```
<210> SEQ ID NO 271
<211> LENGTH: 1269
<212> TYPE: DNA
<213> ORGANISM: Populus tremula x Populus tremuloides
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t
<220> FEATURE:
<221> NAME/KEY: misc_feature
<222> LOCATION: (46)..(46)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (97)..(98)
<223> OTHER INFORMATION: n is a, c, g, or t
<220> FEATURE:
<221> NAME/KEY: misc_feature
<222> LOCATION: (181)..(181)
<223> OTHER INFORMATION: n is a, c, g, or t

<400> SEQUENCE: 271

gaaatatcat gncgaactac acatngccct gatnacatac nttggnttct atctcatnnt     60

cagtcgcttc tcccattttc cagagctccc ctttagnnct gttctttcaa agatggctgg    120

aattgccttt ggtcgctttg atgattcttt cagtttaggg tcttttaagg gcctatcttg    180

nctgaattca tctcaacttt gctctttgtt tttgctggtg ttggttcagc catggcttac    240

aataagctga caggtgatgc agctcttgat cctgctgggc tagtagccat tgcggtttgc    300

catggatttg ctctcttcgt tgcagtttct gtaggtgcca acatctccgg tggccatgtt    360

aaccctgctg tcacttttgg cttggctctt ggtggccaaa tcaccatcct cactggcatc    420

ttctactgga ttgcccagct cctgggctcc attgtcgcat gctaccttct caaagttgcc    480
```

-continued

```
actggaggct tggtaattaa gatcgatata tattttgcct cttattatat attgaatcac     540

tctactggga cgacctccta atacatatat gaaaatctcc atgcattttt tttcttctga     600

actcttcttc ttttatggta agaagtatgt tttcatgaga aatgtgattt atttattaat     660

tttcccttaa gcttgactct ctatatgatt acctggtttc aacaggcagt ccccatccac     720

agtgttgcag ctggagtagg agccattgaa ggagtcgtca tggagatcat catcacattt     780

gccttggttt acactgtcta tgcaactgct gctgacccca agaagggatc cctcggcacc     840

atagctccca tagccatcgg tttcattgtg ggtgccaaca tcttggctgc aggcccattc     900

tctggtggat ccatgaaccc agcccgatca tttggcccag ctgtggctag tggtgatttc     960

catgacaact ggatctactg ggctgggcct cttgttggtg gtgggattgc tggacttatc    1020

tatggaaacg tgttcatcac tgatcatact cctttgtccg gagacttcta ataacttcac    1080

ttggccacat ttgtctttgt aataaagaaa ggggtagcag attatgctct tctttctttt    1140

ctttgctctc tctctctctt taaacaattt catcaagtct atcttgttgt aaagctttgt    1200

tgtcaaaaac catttgcttt tatgaaaatg aatggagtgt gcagcctcag ccaagtctct    1260

tttggaggc                                                            1269
```

<210> SEQ ID NO 272
<211> LENGTH: 1132
<212> TYPE: DNA
<213> ORGANISM: Solanum tuberosum

<400> SEQUENCE: 272

```
agtgacttaa aattgtactt tctttgattt aagcacattc ttttgtgata gccaaaaaaa      60

aatatggtga agattgcctt tggtagcatt ggtgactctt taagtgttgg atcattgaag     120

gcttacttag ctgagtttat tgccactcta ctctttgtat ttgctggtgt tggatctgct     180

atagcttata ataagttgac ttcagatgca gctcttgacc cagctggtct agtagcaata     240

gctgtggctc atgcatttgc attgtttgtt ggggtttcca tggcagccaa tatctcgggt     300

ggacatttaa atccagctgt cactttggga ttggctgttg gtagaaacat caccatcttg     360

actggcttat tctactgggt tgcccaatta cttggctcca cagttgcttg cctcctcctt     420

aaatatgtca ctaatggttt ggtatattgt ttcactatta acatactatt aagttaatta     480

aatcctatta ttagtctaat tagaggttgg gcgaccatgt tgtactaaag cttataagct     540

gatcaaatta tgatcaattt ttcagctact tttaatcggc taaccaaacg ggctcgttat     600

tggatttttg caggctgttc caactcatgg agttgctgct gggatgagtg gagctgaggg     660

agtagttatg gaaatagtca tcacctttgc acttgtttac actgtttatg ccacagcagc     720

agatcccaaa aagggctcac ttggaaccat tgcacccatg gcaattgggt tcattgtggg     780

agccaacatt ttggcagctg gcccattcag tggtgggtca atgaacccag cacgatcatt     840

tgggccagct gttgttgcag gagacttttt tcagaactgg atttactggg ttggaccact     900

cattggtgga ggattggctg ggtttattta tggagatgtt ttcattggat cccccccccc     960

ccttccaacc tcagaagatt atgcttagaa caaagaagaa agaagaagtt tttaacaatg    1020

ttttcttttt gtgtgttttc aaaaatgcaa tgttgatttt aatttaagtt ttgtttattg    1080

tgttatgcaa gaagtttgtt tccaatgaaa tatcctgttt ggttcatttt gt            1132
```

<210> SEQ ID NO 273
<211> LENGTH: 713
<212> TYPE: DNA
<213> ORGANISM: Glycine max
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(43)
<223> OTHER INFORMATION: n is a, c, g, or t

<400> SEQUENCE: 273
atgtcacagg aggctttcca actccaatcc acagtgtnnc nnntggggtt ggagctgttg 60
aaggagttgt gaccgagatc atcatcacat ttggtttggt gtacacagtg tatgccacag 120
cagcagaccc taagaaggga tcattgggaa ccattgcacc aattgccatt ggtttcattg 180
ttggtgccaa catcttggca gcagggccat tctctggcgg ctcgatgaac ccagcacgct 240
ccttcgggcc tgcagttgtt agtggtgact tccatgacaa ctggatctac tgggttggac 300
ctctcattgg tggtggtttg gctggcctta tctatggcaa tgtcttcatt cgctctgacc 360
atgcacctct ttccagtgaa ttttgatttg gttcaagtca tggcatgtgt aattcatgtt 420
tcttgatgat aaaaggagga aaaagcagtt cttgcttttc tttctttttc tatctctctt 480
ttttctctct ctccattcta tgcttttttt ttcttctctt aatttatttg taaagtgtgc 540
tactactgtt taatttggtg agaattcaag aggttggtgg tgtgcagaag tgctttatat 600
ataattatct ggggtttact tttttggctt tccttttaat tttggatccc gtgcatgagg 660
actattgtac cactggcatt tatcattatg gagaagttca cacttcctaa cct 713

<210> SEQ ID NO 274
<211> LENGTH: 1100
<212> TYPE: DNA
<213> ORGANISM: Solanum tuberosum

<400> SEQUENCE: 274
tttctctcta agtctattat tagtagttaa ttaaattatt ttttatagtg aaaatggctg 60
gcggcgtagc tattggaagt tttagtgatt cattcagcgt tgtgtctctt aaggcctatc 120
ttgctgaatt catctccaca ctcatctttg tcttcgccgg agttggttcc gccattgctt 180
acagcaagtt gacagcaaat gctgcacttg atccggctgg gctcgtagct attgcagttt 240
gccatggatt tgctctattt gtggccgttt cagtttcagc taacatctct ggtggccatg 300
ttaaccctgc tgtcacctgc ggattaacct tcggcggcca tattaccttt attactggct 360
ccttctacat gtttgctcaa cttaccggcg ccgctgtagc ttgcttcctc ctcaaattcg 420
tcaccggagg atgtgtaagc ccttcaattt ttacctattt atcgcgtaaa catgaccgat 480
tttatttttt ttagattact aatttcactt tttacgacga tctcaggcta ttccaaccca 540
tggagtggga gctggtgtgg ggataattga aggacttgtg atggaaataa ttatcacatt 600
tggtttagtg tacactgtat tcgcaacagc cgctgacccg aagaagggtt cattgggcac 660
aattgcaccg attgctattg gtttcattgt tggagctaat atttggctg ctggtccatt 720 ttccggcgga tcaatgaacc cagctcgttc atttggacct gcaatggcta ctggtaactt 780
tgagggtttc tggatctact ggattggtcc attagttggt ggtagtttgg ctggtcttat 840
ttacaccaat gtgttcatgc aacaagaaca tgctcctcta tccaatgagt tctaaattga 900
atttgtttga gtttgatttg tgggtctaaa aaaagcccat ttgaatttcg tttttttttt 960
taaaaaaagg gaaggaaaag caatattttt tgttgtttct ttctttgttt tttccggaat 1020
tgttgttttg tttttctagt tattggtttg cagctgtata tgcattatct tttggtgaga 1080

```
tgttcttgtc atgatgctct                                               1100


<210> SEQ ID NO 275
<211> LENGTH: 1110
<212> TYPE: DNA
<213> ORGANISM: Zea mays
<220> FEATURE:
<221> NAME/KEY: misc_feature
<222> LOCATION: (820)..(820)
<223> OTHER INFORMATION: n is a, c, g, or t
<220> FEATURE:
<221> NAME/KEY: misc_feature
<222> LOCATION: (824)..(824)
<223> OTHER INFORMATION: n is a, c, g, or t
<220> FEATURE:
<221> NAME/KEY: misc_feature
<222> LOCATION: (982)..(983)
<223> OTHER INFORMATION: n is a, c, g, or t
<220> FEATURE:
<221> NAME/KEY: misc_feature
<222> LOCATION: (1000)..(1000)
<223> OTHER INFORMATION: n is a, c, g, or t

<400> SEQUENCE: 275

caccagatct tcttctctga attccagtcc aagggccgga ataccgtcag agggagtggg     60

agagggggggg aaaaaagatg gtgaagctcg catttggaag ctttcgcgac tctttgagcg    120

ccgcgtcgct caaggcctat gtggccgagt tcattgccac gctgctcttc gtgttcgccg    180

gcgtcgggtc cgccattgcc tactcgcaat tgacgaaggg cggcgctctg gaccccgccg    240

gcctggtggc catcgccatc gcccatgcgt tcgcgctctt cgtcggcgtc tccatggccg    300

ccaacatctc cggcggccac ctgaaccccg ccgtcacctt cggcccccttc gacggcgcgt   360

ccatgaaccc ggcccgctcc ttcggccccg ccgtggcggc cggtaacttc gccggcaact    420

gggtgtactg ggtcggcccc ctcgtcggcg gtggcctggc ggggctcgtc tacggcgacg    480

tgttcatcgc ctcctaccag ccggtcggcc agcaggagta cccatgaaag tccggatgag    540

ctagcccgat cgatccgtct gtgttgattt caccatcgtc gtcgtcgtgt catctggcgc    600

ttcgtgctgt gatcatgttt tgtcctgttt gcatttccca acgtctggtt ttcatttcca    660

ttcaccaacg gtgccaagat gccgtaagca agcgagagaa gtgttcggtc tgtatctgta    720

taaatgcaat gcacagttcg gcgtttccaa aaaaaaaaaa aaaaacctcg ggggggggccc   780

cggaccccaa tccccccctat aggagtgaaa ataaaaaacn ccgntgttag cgaccgtctg   840

catgtattac aatatgcgtc tatttatctt cccgcagtat ttaaataacc ctcgcgagca    900

cggggaagga gcaaagagag atcagtaaga gggaggcaag tgcgcgacag aaaagaagaa    960

aggaagatcc cacgcgaaat cnntgaataa aacaactgtn taatttatac atgaattcta   1020

ataggacaaa gcccgcaccc gccgaccata tacattacct cagatgaaaa gggaggcaaa   1080

gagatcagga cagacaagca acaatattaa                                    1110


<210> SEQ ID NO 276
<211> LENGTH: 1110
<212> TYPE: DNA
<213> ORGANISM: Zea mays
<220> FEATURE:
<221> NAME/KEY: misc_feature
<222> LOCATION: (820)..(820)
<223> OTHER INFORMATION: n is a, c, g, or t
<220> FEATURE:
<221> NAME/KEY: misc_feature
<222> LOCATION: (824)..(824)
<223> OTHER INFORMATION: n is a, c, g, or t
<220> FEATURE:
<221> NAME/KEY: misc_feature
```

<222> LOCATION: (982)..(983)
<223> OTHER INFORMATION: n is a, c, g, or t
<220> FEATURE:
<221> NAME/KEY: misc_feature
<222> LOCATION: (1000)..(1000)
<223> OTHER INFORMATION: n is a, c, g, or t

<400> SEQUENCE: 276
caccagatct tcttctctga attccagtcc aagggccgga ataccgtcag agggagtggg 60
agaggggggg aaaaaagatg gtgaagctcg catttggaag ctttcgcgac tctttgagcg 120
ccgcgtcgct caaggcctat gtggccgagt tcattgccac gctgctcttc gtgttcgccg 180
gcgtcgggtc cgccattgcc tactcgcaat tgacgaaggg cggcgctctg gaccccgccg 240
gcctggtggc catcgccatc gcccatgcgt tcgcgctctt cgtcggcgtc tccatggccg 300
ccaacatctc cggcggccac ctgaaccccg ccgtcacctt cggccccttc gacggcgcgt 360
ccatgaaccc ggcccgctcc ttcggccccg ccgtggcggc cggtaacttc gccggcaact 420
gggtgtactg ggtcggcccc ctcgtcggcg gtggcctggc ggggctcgtc tacggcgacg 480
tgttcatcgc ctcctaccag ccggtcggcc agcaggagta cccatgaaag tccggatgag 540
ctagcccgat cgatccgtct gtgttgattt caccatcgtc gtcgtcgtgt catctggcgc 600
ttcgtgctgt gatcatgttt tgtcctgttt gcatttccca acgtctggtt ttcatttcca 660
ttcaccaacg gtgccaagat gccgtaagca agcgagagaa gtgttcggtc tgtatctgta 720
taaatgcaat gcacagttcg gcgtttccaa aaaaaaaaaa aaaaacctcg gggggggccc 780
cggaccccaa tcccccctat aggagtgaaa ataaaaaacn ccgntgttag cgaccgtctg 840
catgtattac aatatgcgtc tatttatctt cccgcagtat ttaaataacc ctcgcgagca 900
cggggaagga gcaaagagag atcagtaaga gggaggcaag tgcgcgacag aaaagaagaa 960
aggaagatcc cacgcgaaat cnntgaataa aacaactgtn taatttatac atgaattcta 1020
ataggacaaa gcccgcaccc gccgaccata tacattacct cagatgaaaa gggaggcaaa 1080
gagatcagga cagacaagca acaatattaa 1110

<210> SEQ ID NO 277
<211> LENGTH: 1223
<212> TYPE: DNA
<213> ORGANISM: Oryza sativa

<400> SEQUENCE: 277
atcacatcct ctcctcctta tacctctgct cactcagctc tcccccgcgc gcgtcaccgt 60
cgtcgccatg tcgggcaaca tcgccttcgg ccgcttcgat gactccttca gcgcggcctc 120
cctcaaggcc tacgtcgccg agttcatctc caccctcgtc ttcgtcttcg ccggcgtcgg 180
ctccgccatc gcctacagtg agtaaatcga tggcaccatg gcgcatgcaa acgtacgatg 240
aacggtgcga ttaattgtga tttacgatcg aattgcagcc aagttgaccg gcggcgcgcc 300
gcttgacccg gccgggctgg tcgccgtggc ggtgtgccac gggttcgggc tgttcgtggc 360
ggtggccatc ggcgccaaca tctccggcgg ccacgtcaac ccggccgtca ccttcggcct 420
cgccctcggc ggccagatca ccatcctcac cggcgtcttc tactggatcg cccagctcct 480
cggcgccatc gtcggcgccg tcctcgtcca gttctgcacc ggcgtggtaa gccttctttc 540
ttgcatgcac ctcaccgcca gagctgagct ctcagcctga tccgtcactc actcactgac 600
gccgccgtgg gtggccgttg gtttgcaggc gacaccgacg cacgggctgt ccggcgtggg 660
cgcgttcgag ggcgtggtga tggagatcat cgtcaccttc gggctggtgt acaccgtgta 720

-continued

```
cgccaccgcc gccgacccca agaaggggtc gctcggcacc atcgcgccca tcgccatcgg    780

cttcatcgtc ggcgccaaca tcctcgtcgc cggccccttc tccggcggct ccatgaaccc    840

ggcgcgctcc ttcggccccg ccgtcgccag cggcgactac accaacatct ggatctactg    900

ggtcggcccc ctcgtcggcg gcggcctcgc cggcctcgtc taccggtacg tctacatgtg    960

cggcgaccac gcccccgttg ccagcagcga gttctaatta cccatttcgc catcggcaac   1020

acgcataaaa atggtggtca ctccatcgtc agaatcttgt gaggatgtgt tgtgaaggac   1080

tgatttggtt cagatgggga agaaggcttt tgttgcgagg atgtgacact tgggtgatga   1140

tcgatccatg tttagtttct tcttgattaa tttgtaatgt gatcagtgtg gagcaagttg   1200

gatgagatgc atgtttaaga tcg                                           1223
```

<210> SEQ ID NO 278
<211> LENGTH: 606
<212> TYPE: DNA
<213> ORGANISM: Lycopersicon esculentum

<400> SEQUENCE: 278

```
ctaacatctc cggtggtcat gttaaccctg cggtcacctg tggattaacc ttcggcggac     60

atattacctt tatcactggc tccttctaca tgcttgctca acttaccggc gccgctgtag    120

cttgcttcct cctcaaattc gtcaccggag gatgtgtaag tccttcaatt tttacgaccg    180

atttttattt tgttttagat tactaatttc actttttacg acgatctcag gctattccaa    240

cccatggagt gggagctggt gtgagcatac tagaaggact cgtgatggaa ataataatca    300

catttggttt agtttatact gtgttcgcaa ccgccgctga cccgaagaag ggttcattgg    360

gcacaattgc accgattgca attggtctca ttgttggagc taatattttg gctgccggac    420

cattctccgg tggatcaatg aacccagctc gttcatttgg acctgcaatg gttagtggta    480

actttgaggg tttctggatc tactggattg gtccattagt tggtggtagt ttggctggtc    540

ttatttacac aaatgtgttc atgacacaag aacatgctcc tttatccaat gagttctaaa    600

ttgaat                                                               606
```

<210> SEQ ID NO 279
<211> LENGTH: 540
<212> TYPE: DNA
<213> ORGANISM: Capsicum annuum

<400> SEQUENCE: 279

```
atttctctc taattaagtc tattcttctt cctttagctt ctattaaatt tattattctt     60

cttttatagt gatcaaaaaa atggctggca ttgcttttgg acgtgttgat gattcattca    120

gtgctgggtc tcttaaggcc tatcttgctg aattcatctc cactttgctc tttgtcttcg    180

ctggtgttgg ctccgccatt gcttacaaca agttgacagt aaatgctgca cttgacccgg    240

ctgggctcgt agctattgca gtttgccatg gattcggtct cttcgtggct gtttcaattg    300

ctgctaacat ctctggtggt catgttaacc ctgctgtcac cttcggattg gcccttggtg    360

gtcaaattac ccttcttact ggcctttttt tacaccattg ctcaactttt gggctccatt    420

gtagcttgca tcctcctcaa attcgtcacc ggaggattgg ctattccaac tcatggagtg    480

gcagctggtg tgggtgccat tgaaggagtt gtgatggaaa taattgtcac ctttgctttg    540
```

<210> SEQ ID NO 280
<211> LENGTH: 1019
<212> TYPE: DNA
<213> ORGANISM: Hordeum vulgare
<220> FEATURE:
<221> NAME/KEY: misc_feature
<222> LOCATION: (994)..(994)
<223> OTHER INFORMATION: n is a, c, g, or t

<400> SEQUENCE: 280
ggccgggtcg gccggtccgc ctcacggcga gcaccgacct actcgaccct tcggccggca 60
tcgcgctcct agccttaatt ggccgggtcg tgttttcggc atcgttactt tgaagaaatt 120
agagtgctca aagcaagcca tcgctctgga tacattagca tgggataaca tcataggatt 180
ccggtcctat tgtgttggcc ttcgggatcg gagtaatgat taatagggac agtcgggggc 240
attcgtattt catagtcaga ggtgaaattc ttggatttat gaaagacgaa caactgcgaa 300
agcatttgcc aaggatgttt tcattaatca agaacgaaag ttgggggctc gaagacgatc 360
agataccgtc ctagtctcaa ccataaacga tgccgaccag ggatcggcgg atgttgctta 420
taggactcca ccggcacctt cgggctcacc ggcatcggcg cgtgggaggc ggtggtcctg 480
gagatcgtca tgaccttcgg gctggtgtac acggtgtacg ccaccgccgt cgaccccaag 540
aagggcagcc tgggcaccat cgcgcccatc gccatcggct tcatcgtcgg cgccaacatc 600
ctcgtcggcg gcgccttctc cggcgcgtcc atgaaccccg ccgtctcctt cggccccgcc 660
ctcgtcagct gggagtgggg gtaccagtgg gtgtactggg tcggccccct catcggcggc 720
ggcctcgccg gcgtcatcta cgagctgctc ttcatctccc gcacccacga gcagctcccc 780
accaccgact actaagctca ccgccgcctg ccccccgccc gcccgtccgt ccgtgtggtc 840
gatcgcgtct cccccttgctt cccagacatg agtcgtttaa gtttgctttg aatgaatgaa 900
tccatcccat tcccagggtc gatcggtcca tcagtttgtg gtgctgtgaa acctgtgacg 960
atcgaccctg tcaatttgct tgtgtaaaac ctgnaattcg tccgcccgag aatttcaag 1019

<210> SEQ ID NO 281
<211> LENGTH: 779
<212> TYPE: DNA
<213> ORGANISM: Gossypium hirsutum

<400> SEQUENCE: 281
acccgctttt gggttgtcat caggtggggg ggtgtttaac gcattggttt tcgaaatggt 60
gatgcccttc ggattggtgt acccagtgta cgccccagcc gttgatccca aaaagggaag 120
cttgggaaca atcgccccat tggcaattgg tttcatcgtg ggggccaaca ttttggcagg 180
aggtgccttc gatggagcct caatgaaccc agctgtttca tttggaccac ccttggttag 240
ctggacatgg gacaacccct ggatttattg ggtgggaccc cttatcggtg gtgggctcgc 300
tggtttcatt taggagttca ttttcatcag caacacccag gagcagttcc caacccccga 360
ttattaagcc taatcagggt ttaattgatt tgtttgtccc tttgaaaccg gatttttttcc 420 gatttcattt gagtttccta tttctttcct tgttttttgt gtttaatttg gggcccgtcg 480
attttgttta cttttttttc attccccatc ctttttcatg atcatcatgc atggcagatg 540
ttgtttacaa ttgcatgccc tgaaaaaatg gtatatgagt gactccctgt aagttttttt 600
ttttatatta ttcaaaacca gcatcagggc tgtaaatgtg actttttttcc ttcccttttc 660 cttgttttta tcatgggcat ttcctattca cttttccctt ttcttaagta agattgtaca 720
ggtggcatgt ttcatttaga cagaatattt aagataatga aaaaaaagga gttttttttt 779

<210> SEQ ID NO 282
<211> LENGTH: 1118
<212> TYPE: DNA

<213> ORGANISM: Oryza sativa

<400> SEQUENCE: 282
accgccccga atccgccccc aaatctcctc gcgacctcga aaccctagcc tcctccggcc 60
accgtcgccg gccacggtga gcggccccac ccccccgcag ccatggcctc cccggagggc 120
tccacgtggg tcttcgactg ccctctgatg gacgacctcg ccgccgccgc cggcttcgac 180
gccgcccccg ccggaggctt ctactggacg acgcccgctc ctccgcaggc ggcgctacag 240
ccgccgccgc cgcagcagca gcccgtcgcc cctgccaccg cggctccgaa cgcctgtgct 300
gaaatcaatg gctctgtgga ctgtgaacat ggcaaagaac agccaacaaa taaacgtccg 360
agatcagaaa gtggcactcg accaagctcc aaagcatgca gggaaaaagt aagaagggac 420
aagttgaacg agaggttctt ggaactgggt gctgtcctgg aaccagggaa gacacccaaa 480
atggacaaat cgtctatatt gaacgatgct attcgtgtaa tggctgagct gcgtagtgag 540
gcacagaagt tgaaggaatc aaatgagagt ctccaagaga aaatcaaaga gttgaaggct 600
gagaaaaacg agctgcgtga tgagaagcaa aagctgaagg cagagaaaga gagcctggag 660
cagcagataa agttcctgaa tgctcgacca agcttcgtac cacaccctcc ggttatccca 720
gccagtgcat tcactgctcc tcaagggcaa gctgccgggc agaagctgat gatgcctgtg 780
attggctacc caggatttcc gatgtggcag ttcatgccgc cttctgatgt tgataccaca 840
gatgacacca agtcatgccc tcctgttgca taagtcaaag caaagatcaa tttgcctcgc 900
cttgtaggaa agaggtgaaa ctgccttcca ttcaagccca gtttggtcgt cagtgtttaa 960
actacctagc taatcccagg attaaaccga agcttcgctg tatcgaagta tcaaccggtg 1020
acatgtgaac tgacgaaaga tgacaccgtt gtatattaca tattagtaaa taaattccat 1080
ctgtccaatt aaatgagaat tagaggccaa aaaattat 1118

<210> SEQ ID NO 283
<211> LENGTH: 1203
<212> TYPE: DNA
<213> ORGANISM: Triticum aestivum

<400> SEQUENCE: 283
cgttccggac tctctcagtt gtccgtactc gttaacctcg tgctcccccc tctgcttgat 60
ccttatctcg gcgccggagc ccacgaccgc ttccccccctt tccctcccct ccccctcacc 120
accccaaccc cgaaatatcc cccaattccg acgcgaccgc gaaaccctag ccccccggca 180
atcttcgctg gacccggaga gccgctccgg cgccatggca tccccggaag gatcaaactg 240
ggtattcgac tgccccctca tggacgacct tgctgccgcc gacttcgccg cggcatccgc 300
aggaggcttc tactggaccc cgccgatgca gccgcagatg cacactcttg cgcaggccgt 360
ctccgccacc ccggctccca atccctgtgc tgaaatcaat agctctgttt cggtggactg 420
ggaccatgcc aaaggacaac cgaaaaataa acgtcctagg tcagaaactg gtgctcaacc 480
tagctccaaa gcatgcaggg agaaagtgag aagggacaag ctaaacgaga ggttcttgga 540
attgggtgct gtcttggatc cggggaaaac acctaaaatc gacaaatgtg ctatattaaa 600
tgatgctatc cgtgcagtaa ctgaattgcg tagtgaagca gagaagttga aggattccaa 660
tgagtctctc caagagaaga ttagagagct aaaggctgag aagaatgagc tacgagatga 720
gaagcaaaag ttgaaggcgg agaaagagag cctggagcag cagattaagt tcatgaatgc 780
ccgtcagagc ctcgtaccac acccttctgt catcccagct gctgcattcg ctgccgccca 840
aggccaagcg gcagggcaca agctgatgat gcctgtaatg agctacccag gatttcccat 900
gtggcagttc atgccgcctt cagatgttga tacctccgat gaccccaagt catgccctcc 960
ggttgcataa gccagcaaaa atcatttgcc tcatctatct catggggaag gatggctaaa 1020
aagccgtccg ttaaagtata tcttactagt cgtcagtgtt actatgcaga agccgtttag 1080
tgttactata tgtagttaaa ccaagaaccg aactgaagcg tcgtcgttgt atcacccggg 1140
gacatttgat tatcttgtga caccgttgta tattgttagt aaataaatac catccgttga 1200
agc 1203

<210> SEQ ID NO 284
<211> LENGTH: 1077
<212> TYPE: DNA
<213> ORGANISM: Hordeum vulgare

<400> SEQUENCE: 284
gccccaaccc cgaaatatcc cccaactccg acgcgaccgc gaaaccctag tcccccggca 60
accttcgctg gacccgggga gccgctccgg cgccatggca tccccggaag gatcaaactg 120
ggtcttcgac tgccccctca tggacgacct tgctgccgcc gacttcgccg cggtacccgc 180
aggaggcttc tactggaacc cgccgatgcc gccgcagatg cacactctgg cgcaggccgt 240
ctccgccacc ccggctccca atccctgtgc tgaaatcaat agctctgttt cggtggactg 300
ggaccatgcc aaaggacaac cgaaaaataa acgtcctaga tcagaaactg gtgctcaacc 360
tagctccaaa gcatgcaggg agaaagttag aagggacaag ctaaatgaga ggttcttgga 420
attgggtgct gtcttggacc cggggaaaac acctaaaatc gacaaatgtg ctatattaaa 480
tgatgctatc cgtgcggtaa ctgaattgcg tagtgaagca gagaagttga aggattcaaa 540
tgagtctctc caagagaaga ttagagagct gaaggctgag aagaatgagc tgcgagatga 600
gaagcaaaag ctgaaggcgg aaaaagagag cctggagcag cagattaagt tcatgaatgc 660
ccgtcagaga ctcgtaccac acccttctgt catcccagct actgcattcg ctgccgccca 720
aggccaagcg gcagggcata agcttatgat gcctgtaatg agctacccag gatttcccat 780
gtggcagttc atgccgcctt cagatgttga tacctcggat gaccctaagt catgccctcc 840
tgttgcataa gccagcgaaa atcatttgcc tcatctatct catggggaag gatggctaaa 900
cagccttccg ttaaagtata ttttagttgt cagtgttact atgtagttaa actaagaacc 960
gaactgaagc atcgtcgttg tatcacctgg ggacatttga ttatcttgtg gcactgctgt 1020
atattgttag taaataaatg ccgtctgtcg aaggaaatgc tgattggacg ccatagc 1077

<210> SEQ ID NO 285
<211> LENGTH: 2595
<212> TYPE: DNA
<213> ORGANISM: Oryza sativa

<400> SEQUENCE: 285
gaccgccccg aatccgcccc caaatctcct cgcgacctcg aaaccctagc ctcctccggc 60
caccgtcgcc ggccacggtg agcggcccca cccccccgca gccatggcct ccccggaggg 120
ctccacgtgg gtcttcgact gccctctgat ggacgacctc gccgccgccg ccggcttcga 180
cgccgccccc gccggaggct tctactggac gacgcccgct cctccgcagg cggcgctaca 240
gccgccgccg ccgcagcagc agcccgtcgc ccctgccacc gcggctccga acgcctggta 300
attgcggggt ttacggcctc cgatcgcgct ccagccagcc ctggctgggc ccggtgccgt 360
ggtctggggt gctacatttt tttttcgtcc tgatttgtcg cggcagcgtg ttagtgcgta 420

-continued

```
agttgagact gggtatatcg tgatcgttgc tattgattgt tcgattggag gtcgatagaa    480
gcgtatcata tcagactatc agtgggattc ggatcagggg attagtcgtg tgtctgaaca    540
tttagaacta gttacatact ccctccgttt tctaaaatat gatgctgttg actttttaaa    600
atacatctga tcatcttatt caaaaaaatt atataatttt tatttatttt attgtgactt    660
gattcatcat tcatcgtcaa atattcttta ggcatgactt aaaaattttt tatatttgca    720
caaaaatttt gaagatgacg aatagtcaaa cgtttatcag aaagtcaacg acgtcataca    780
ttaaaaaaca gaagtagtat aacctagtag gagccgtcag cctgttttac tgaacagagg    840
gctcaattcc tggttatatt gaattgtcag cttcattttc aaatctattt atttgtgtgc    900
atacgtaatg tatttaaacc taatttaggg cctcttcatg atttataatt ctcattttaa    960
ttgtgatgca aatgctgcat agcatagcat atatagtttg ctaagcatgc attgtgtcat   1020
gtttatctgg tgtcatgtca tgggatagtt gaactgaaga aaacatacac cataattgat   1080
gatgtttatg atgccactat tgtacaagat tcagtttgcc gtgtaatatt acaatataag   1140
aactgataac aagtaaacca aatggtgtca aattggcgtg gtggtgggag ggtggatggt   1200
tgtgatttgc tgtaggtcca actgtctgag ataccagatt ttaaaatttt ttgtatctat   1260
atgcaagtaa attgcattga catgatattt tgagccaggt attgagattt gtcctgagct   1320
ttccagtgga tttttcaatg aatgatctat gaaggatcag aaacggggtg agagaagtgg   1380
ttaatctgta tcacttgggt tccagcacga agcttactgt ggaatggaaa tttattgaag   1440
aacgtgttca tgttaggata ttgtttactg caactctttg atttaagagt attcttttat   1500
ttatgatacc ttgtagtctt gtggtgctag tacattttct ttatgcacca ggaagtcatc   1560
tcatgtgttt ttaaatctgt cctggttttt gacttgtgct tccaccttct ggtgccatag   1620
gttgtggtgt tatgaaccac acagtgcatc ttaactgatg tattgttctg ttgtgttaaa   1680
tttgcttgat tcttttgttg tcattgtata gtttttttatg tacttattgc tgtatattat   1740
cgtgacatat ggcatactga agtacaagtt tattttttttc actagtgctg aaatcaatgg   1800
ctctgtggac tgtgaacatg gcaaagaaca gccaacaaat aaacgtccga gatcagaaag   1860
tggcactcga ccaagctcca aagcatgcag ggaaaaagta agaagggaca agttgaacga   1920
gaggttcttg gaactgggtg ctgtcctgga accagggaag acacccaaaa tggacaaatc   1980
gtctatattg aacgatgcta ttcgtgtaat ggctgagctg cgtagtgagg cacagaagtt   2040
gaaggaatca aatgagagtc tccaagagaa aatcaaagag ttgaaggctg agaaaaacga   2100
gctgcgtgat gagaagcaaa agctgaaggc agagaaagag agcctggagc agcagataaa   2160
gttcctgaat gctcgaccaa gcttcgtacc acaccctccg gttatcccag ccagtgcatt   2220
cactgctcct caaggtcaag ctgccgggca gaagctgatg atgcctgtga ttggctaccc   2280
aggatttccg atgtggcagt tcatgccgcc ttctgatgtt gataccacag atgacaccaa   2340
gtcatgccct cctgttgcat aagtcaaagc aaagatcaat ttgcctcgcc ttgtaggaaa   2400
gaggtgaaac tgccttccat tcaagcccag tttggtcgtc agtgtttact acctagctaa   2460
acccaggatt aaaccgaagc ttcgctgtat cgaagtatca accggtgaca tgtgaactga   2520
cgaaagatga caccgttgta tattacatat tagtaaataa attccatctg tccaattaaa   2580
tgagaattag atgcc                                                    2595
```